US010953369B2

(12) United States Patent
Finn et al.

(10) Patent No.: US 10,953,369 B2
(45) Date of Patent: Mar. 23, 2021

(54) SPIROCENTRIC COMPOUNDS AND POLYMERS THEREOF

(71) Applicants: Georgia Tech Research Corporation, Atlanta, GA (US); ExxonMobil Research and Engineering Company, Annandale, NJ (US)

(72) Inventors: M. G. Finn, Atlanta, GA (US); Craig McKay, Atlanta, GA (US); Nicholas Bruno, Atlanta, GA (US); Kirstie Thompson, Atlanta, GA (US); Huaxing Zhou, Furlong, PA (US)

(73) Assignees: Georgia Tech Research Corporation, Atlanta, GA (US); ExxonMobil Research & Engineering Company, Annandale, NJ (US)

(*) Notice: Subject to any disclaimer, the term of this patent is extended or adjusted under 35 U.S.C. 154(b) by 0 days.

(21) Appl. No.: 16/295,910

(22) Filed: Mar. 7, 2019

(65) Prior Publication Data

US 2019/0276454 A1 Sep. 12, 2019

Related U.S. Application Data

(60) Provisional application No. 62/753,470, filed on Oct. 31, 2018, provisional application No. 62/640,253, filed on Mar. 8, 2018.

(51) Int. Cl.
| | | |
|---|---|---|
| *C07D 221/20* | (2006.01) |
| *C07D 311/96* | (2006.01) |
| *C07D 471/10* | (2006.01) |
| *C07D 487/10* | (2006.01) |
| *B01D 67/00* | (2006.01) |
| *B01D 71/82* | (2006.01) |
| *C08J 3/24* | (2006.01) |
| *C08G 65/26* | (2006.01) |
| *B01D 69/08* | (2006.01) |
| *B01J 31/04* | (2006.01) |

(52) U.S. Cl.
CPC ......... *B01D 67/0006* (2013.01); *B01D 69/08* (2013.01); *B01D 71/82* (2013.01); *C07D 221/20* (2013.01); *C07D 311/96* (2013.01); *C07D 471/10* (2013.01); *C07D 487/10* (2013.01); *C08G 65/266* (2013.01); *C08J 3/246* (2013.01); *B01D 2323/30* (2013.01); *B01J 31/04* (2013.01); *C08G 2650/50* (2013.01); *C08J 2371/00* (2013.01)

(58) Field of Classification Search
CPC .................. C07D 221/20; C07D 311/96
See application file for complete search history.

(56) References Cited

U.S. PATENT DOCUMENTS

| | | |
|---|---|---|
| 7,410,525 B1 | 8/2008 | Liu et al. |
| 7,449,146 B2 | 11/2008 | Rakow et al. |
| 7,485,173 B1 | 2/2009 | Liu et al. |
| 7,690,514 B2 | 4/2010 | McKeown et al. |
| 7,758,751 B1 | 7/2010 | Liu et al. |
| 7,943,543 B1 | 5/2011 | Liu et al. |
| 8,378,694 B2 | 2/2013 | Moses et al. |
| 8,459,200 B2 | 6/2013 | Battiato et al. |
| 8,575,414 B2 | 11/2013 | Liu et al. |
| 8,623,928 B2 | 1/2014 | Du et al. |
| 8,686,104 B2 | 4/2014 | Du et al. |
| 8,821,621 B2 | 9/2014 | Dwyer et al. |
| 8,835,180 B2 | 9/2014 | Gryska et al. |
| 8,858,692 B2 | 10/2014 | Dwyer et al. |
| 8,969,628 B2 | 3/2015 | Priske et al. |
| 9,018,270 B2 | 4/2015 | McKeown et al. |
| 9,212,261 B2 | 12/2015 | McKeown et al. |
| 9,244,008 B2 | 1/2016 | Kang et al. |
| 9,279,792 B2 | 3/2016 | Palazzotto et al. |
| 9,291,484 B2 | 3/2016 | Rakow |
| 9,296,668 B2 | 3/2016 | Wendland |
| 2005/0003215 A1 | 1/2005 | Hacker et al. |
| 2005/0282053 A1 | 12/2005 | Kurano et al. |
| 2007/0155953 A1 | 7/2007 | Li et al. |
| 2007/0209505 A1 | 9/2007 | Liu et al. |
| 2008/0070320 A1 | 3/2008 | Palazzoto et al. |
| 2008/0203281 A1 | 8/2008 | Sanders et al. |
| 2009/0069613 A1 | 3/2009 | Rice et al. |
| 2009/0069617 A1 | 3/2009 | Shecterle et al. |
| 2009/0069618 A1 | 3/2009 | Rice |
| 2010/0019658 A1 | 1/2010 | Lin et al. |
| 2010/0058926 A1 | 3/2010 | Yates et al. |
| 2010/0130634 A1 | 5/2010 | Fritsch |
| 2010/0130796 A1 | 5/2010 | Combes et al. |

(Continued)

FOREIGN PATENT DOCUMENTS

| | | |
|---|---|---|
| CN | 103566777 | 2/2014 |
| EP | 1965197 | 3/2008 |

(Continued)

OTHER PUBLICATIONS

SARSAH. Journal of Organic Chemistry, 2013, 78, 2051-2058 (Year: 2013).*
Search Report and Written Opinion from PCT application No. PCT/US19/21236 dated Jun. 26, 2019.
Hart & Colina, "Ionomers of Intrinsic Microporosity: In Silico Development of Ionic-Functionalized Gas-Separation Membranes," Langmuir 2014, vol. 30, pp. 12039-12048.
Sprick, et al., (N-Heterocyclic carbene)Pd(triethylamine) Cl2 as Precatalyst for the Synthesis of Poly(triarylamine)s, O. Polym. Chem. 2013, vol. 51 pp. 4904-4911.

(Continued)

*Primary Examiner* — Noble E Jarrell
(74) *Attorney, Agent, or Firm* — Troutman Pepper Hamilton Sanders LLP; John A. Morrissett; Scott A. Bergeson

(57) ABSTRACT

The present invention is directed to novel functionalized spirocentric compounds and polymers thereof that produce hyper-rigid cross-linked membranes.

17 Claims, 2 Drawing Sheets

(56) References Cited

U.S. PATENT DOCUMENTS

| | | |
|---|---|---|
| 2010/0280216 A1 | 11/2010 | Antonietti et al. |
| 2010/0331437 A1 | 12/2010 | Liu et al. |
| 2013/0085191 A1 | 4/2013 | Laskoski |
| 2013/0146538 A1 | 6/2013 | Liu et al. |
| 2013/0186177 A1 | 7/2013 | Palazzotto et al. |
| 2013/0217799 A1 | 8/2013 | Visser et al. |
| 2013/0239805 A1 | 9/2013 | Husain |
| 2013/0247756 A1 | 9/2013 | Li et al. |
| 2014/0251897 A1 | 9/2014 | Livingston et al. |
| 2014/0255636 A1 | 9/2014 | Odeh et al. |
| 2015/0194681 A1 | 7/2015 | Liu et al. |
| 2015/0239806 A1 | 8/2015 | Wendland |
| 2016/0035986 A1 | 2/2016 | Chung et al. |
| 2016/0082429 A1 | 3/2016 | Wendland |
| 2016/0367948 A1 | 12/2016 | Song et al. |
| 2017/0338414 A1 | 11/2017 | Mujica-Fernaud et al. |

FOREIGN PATENT DOCUMENTS

| | | |
|---|---|---|
| EP | 2397218 | 12/2011 |
| WO | WO2005113121 | 12/2005 |
| WO | WO2009001065 | 12/2008 |
| WO | WO2009045733 | 4/2009 |
| WO | WO2009103070 | 8/2009 |
| WO | WO2010002404 | 1/2010 |
| WO | WO2010124359 | 11/2010 |
| WO | WO2011026541 | 3/2011 |
| WO | WO2011057384 | 5/2011 |
| WO | WO2011130818 | 10/2011 |
| WO | WO2012035327 | 3/2012 |
| WO | WO2012035328 | 3/2012 |
| WO | WO2012050686 | 4/2012 |
| WO | WO2012044419 | 5/2012 |
| WO | WO2012082537 | 6/2012 |
| WO | WO2012141883 | 10/2012 |
| WO | WO2012174099 | 12/2012 |
| WO | WO2013057492 | 4/2013 |
| WO | WO2013090188 | 6/2013 |
| WO | WO2014052021 | 4/2014 |
| WO | WO2014078914 | 5/2014 |
| WO | WO2014186094 | 11/2014 |
| WO | WO2014207559 | 12/2014 |
| WO | WO2015001422 | 1/2015 |
| WO | WO2015015299 | 2/2015 |
| WO | WO2015047750 | 4/2015 |
| WO | WO2015088844 | 6/2015 |
| WO | WO2015095026 | 6/2015 |
| WO | WO2015095034 | 6/2015 |
| WO | WO2015095038 | 6/2015 |
| WO | WO2015129925 | 9/2015 |
| WO | WO2015130550 | 9/2015 |
| WO | WO2016009273 | 1/2016 |
| WO | WO2016148869 | 9/2016 |
| WO | WO2016161367 | 10/2016 |
| WO | WO2016187670 | 12/2016 |
| WO | WO2016195977 | 12/2016 |
| WO | WO2016206008 | 12/2016 |
| WO | WO2017060863 | 4/2017 |
| WO | WO2017085601 | 5/2017 |
| WO | WO2017091357 | 6/2017 |
| WO | WO2017146466 | 8/2017 |

OTHER PUBLICATIONS

Rabindranath, et al., "Purple red and Luminescent Polyiminoarylenes Containing the 1,4-diketo-3,6-diphenylpyrrolo [3,4-c]pyrrole (DPP) Chromophore," Polymer 2009 vol. 50 pp. 1637-1644.

Search Report and Written Opinion from PCT application No. PCT/US19/21238 dated Jul. 1, 2019 (16 pages).

\* cited by examiner

SPIROCENTRIC COMPOUNDS AND POLYMERS THEREOF

RELATED APPLICATIONS

This application claims the benefit of priority to U.S. Provisional Patent Application No. 62/753,470, filed 31 Oct. 2018, and titled "FUNCTIONALIZED MEMBRANES AND METHODS OF PRODUCTION THEREOF," and also claims the benefit of priority to U.S. Provisional Patent Application No. 62/640,253, filed 8 Mar. 2018, and titled "SPIROCENTRIC COMPOUNDS AND POLYMERS THEREOF," both of which are incorporated herein by reference in their entireties.

FIELD OF INVENTION

The present invention relates to novel functionalized spirocentric compounds and polymers thereof and their use for making hyper-rigid cross-linked membranes.

BACKGROUND OF THE INVENTION

Microporous hyper rigid polymeric membranes have emerged as energy efficient molecular separation platforms relative to traditional energy intensive processes. These membranes combine porosity and rigidity, allowing for high permeability and good selectivity. A known polymer of intrinsic microporosity is PIM-1, which has been studied for gas separation and with solvent nanofiltration. PIM-1 is solution-processable, which has enabled the development of a variety of membrane morphologies including dense flat sheet, thin composite materials, and hollow fiber membranes. While PIM-1 has a relatively high membrane permeability for many gases in gas separation due to the "molecular ladder" structure of its polymer chains, it has only a low-to-moderate selectivity.

A variety of methods for covalent derivatization or modification of PIM-1 structures have been described, including tetrazole and methyl tetrazole formation, thioamide formation, amideoxime formation, partial nitrile hydrolysis, nitrile reduction, direct amide formation, and ortho aryl sulfonation. However, the resulting polymers often display poor solubility in solvents that would be used for making membranes, and thus are not practical for further development. To bypass the poor solubility of modified PIM polymers, functionalization directly on the PIM-1 thin film membrane has been reported. However, to reveal the full potential of PIM structures, crosslinkable polymers that are solution processable are required, after which cross-linking could be used to generate insoluble hyper-rigid cross-linked PIM networks. While intermolecular interactions have been used to cross-link PIM-1, examples of covalent cross-linking of PIM-1 rely on aggressive conditions of heat to induce non-specific decarboxylative cross-linking, oxidative cross-linking, and azide decomposition to nitrene for C—H insertion cross-linking. These approaches are nonspecific and generate very low levels of cross-linking.

Thus, despite their potential success, current approaches for polymers of intrinsic microporosity for chemical separations are limited by (1) solution processability; (2) ability to maintain well-defined pore sizes in solvent due to swelling and aging; (3) limited tunability of pore sizes; and (4) limited functional group tolerance.

Thus, there exists an unmet need for monomers and corresponding polymers thereof that are solution-processable at mild conditions and yield highly specific, hyper-rigid cross-linked membranes that have both high membrane permeability and high selectivity for molecular separations.

SUMMARY OF THE INVENTION

Various non-limiting aspects and embodiments of the invention are described below.

In one aspect, the present invention provides a spirocentric compound according to Formula I:

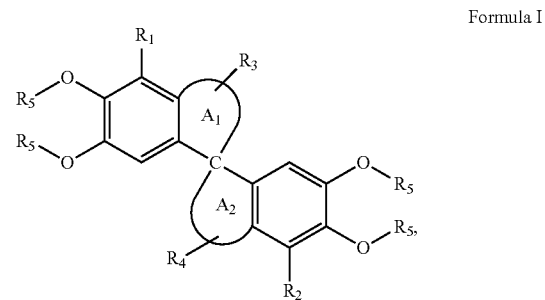

Formula I wherein:
in all structures the carbon indicated by "C" denotes a spiro-carbon;
$A_1$ and $A_2$ are each independently selected from:

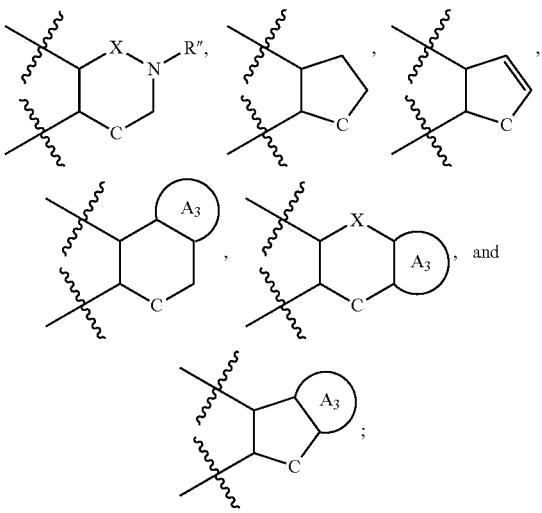

$A_3$ is a selected from substituted or unsubstituted $C_5$-$C_6$ aryl, substituted or unsubstituted $C_5$-$C_6$ heteroaryl, substituted or unsubstituted $C_5$-$C_6$ cycloalkyl and substituted or unsubstituted $C_5$-$C_6$ cyclic heterocycloalkyl;

X is —$CR_6$, —O—, —S—, $NR_6$, —C=O, —C=$NR_6$, —C=N—N($R_6$)$_2$, and C=N—$OR_6$;

$R_1$, $R_2$, $R_3$, and $R_4$ are each independently selected from H and Y—Z, wherein at least one of $R_1$, $R_2$, $R_3$, and $R_4$ is Y—Z;

$R_5$ is independently at each occurrence H, Si(O$R_6$)$_3$, or Si($R_6$)$_3$;

$R_6$ is independently at each occurrence selected from H, substituted or unsubstituted alkyl, substituted or unsubstituted heteroalkyl, substituted or unsubstituted aryl, and substituted or unsubstituted heteroaryl;

Y is independently absent or selected from substituted or unsubstituted alkyl, substituted or unsubstituted heteroalkyl, substituted or unsubstituted aryl, substituted or unsubstituted heteroaryl, —NH—(C=O)—; =NO—C$_{1-6}$ alkyl-; and —(C=O)-phenyl-;

Z is independently selected from —N$_3$, —C≡CH, C≡C—R', —C≡N, —(C=O)—H, —SH, —CH=CH$_2$, halide, —SO$_3$R$_6$, —B(OR$_6$)$_2$, Sn(R$_6$)$_3$, and Zn(R$_6$)$_2$;

R' is selected from substituted or unsubstituted alkyl, substituted or unsubstituted heteroalkyl, substituted or unsubstituted aryl, substituted or unsubstituted heteroaryl, —CN, —CO$_2$R$_6$, —(C=O)—N(R$_6$)$_2$, and —(C=O)—R$_6$; and R" is selected from R$_3$ and R$_4$.

In another aspect, the present invention provides a spiro-centric compound according to Formula II:

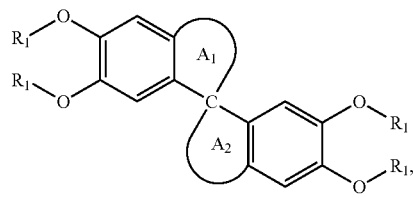

Formula II wherein: in all structures the carbon indicated by "C" denotes a spiro-carbon;

A$_1$ is selected from

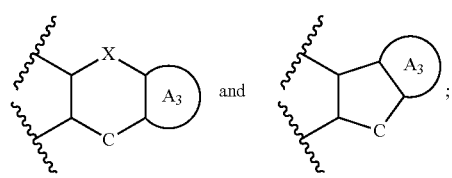

A$_2$ is

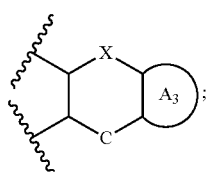

X is independently at each occurrence selected from O, or N—R$_2$;

R$_1$ is independently at each occurrence H or alkyl;

R$_2$ is selected from H, substituted or unsubstituted alkyl, and substituted or unsubstituted aryl; and A$_3$ is a selected from substituted or unsubstituted C$_5$-C$_6$ aryl, substituted or unsubstituted C$_5$-C$_6$ heteroaryl, substituted or unsubstituted C$_5$-C$_6$ cycloalkyl and substituted or unsubstituted C$_5$-C$_6$ cyclic heterocycloalkyl.

In another aspect, the present invention provides a compound according to Formula III:

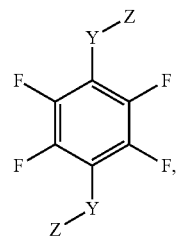

Formula III wherein:

Z is independently selected from —N$_3$, —C≡CH, C≡C—R', —C≡N, —(C=O)—H, —SH, —CH=CH$_2$;

Y is independently at each occurrence absent, or selected from

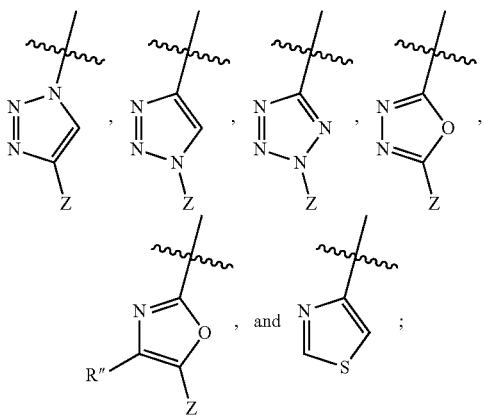

R' is selected from H, substituted or unsubstituted alkyl, substituted or unsubstituted heteroalkyl, substituted or unsubstituted aryl, substituted or unsubstituted heteroaryl, —CN, —CO$_2$R", —(C=O)—N(R")$_2$, and —(C=O)—R"; and R" is selected from H, substituted or unsubstituted alkyl, substituted or unsubstituted heteroalkyl, substituted or unsubstituted aryl, and substituted or unsubstituted heteroaryl.

In yet another aspect, the present invention provides a polymer according to Formula IV:

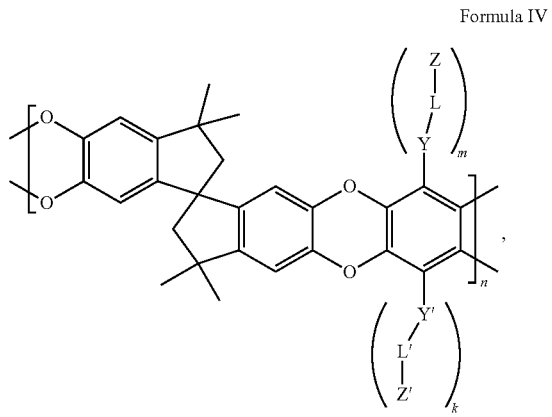

Formula IV wherein:

Y is absent or selected from tetrazole and thiazole;

L is absent or selected from substituted or unsubstituted $C_{1-12}$ alkyl, substituted or unsubstituted benzyl, and $C_{1-12}$ alkylcarbamate;

Z is absent or selected from —$N_3$, —C≡CH, C≡C—R', —C≡—N, —(C=O)—H, —SH, and —CH=$CH_2$; wherein when Y and L are both absent, Z is not absent;

Y' is absent or selected from hydrogen, tetrazole and thiazole;

L' is absent or selected from substituted or unsubstituted $C_{1-12}$ alkyl, substituted or unsubstituted benzyl, and $C_{1-12}$ alkylcarbamate;

Z' is absent or selected from —$N_3$, —C≡CH, C≡C—R', —C≡N, —(C=O)—H, —SH, and —CH=$CH_2$; wherein when Y' and L' are both absent, Z' is not absent;

R' is independently at each occurrence selected from substituted or unsubstituted alkyl, substituted or unsubstituted heteroalkyl, substituted or unsubstituted aryl, substituted or unsubstituted heteroaryl, —CN, —$CO_2R''$, —(C=O)—$N(R'')_2$, and —(C=O)—R'';

R'' is selected from H, substituted or unsubstituted alkyl, substituted or unsubstituted heteroalkyl, substituted or unsubstituted aryl, and substituted or unsubstituted heteroaryl;

the ratio of m to n is from 0 to 1;

the ratio of k to n is from 0 to 1; and n is an integer from 5 to 100,000;

provided that when Z is absent, Y is not absent or hydrogen, and when Z' is absent, Y' is not absent or hydrogen.

In yet another aspect, the present invention provides a polymer according to Formula V:

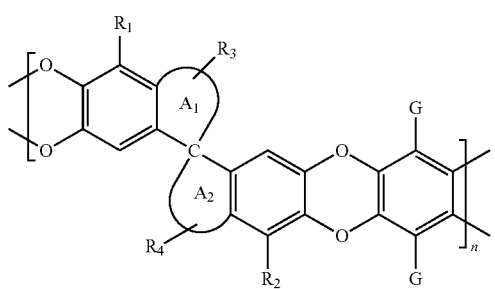

Formula V wherein: in all structures the carbon indicated by "C" denotes a spiro-carbon;

$A_1$ is selected from

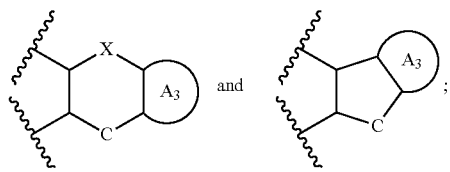

$A_2$ is

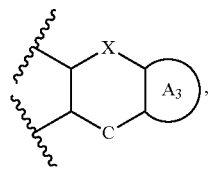

X is independently at each occurrence selected from O, or N—$R_5$;

$R_1$, $R_2$, $R_3$, and $R_4$ are each independently selected from H and Y—Z, $R_5$ is selected from H, substituted or unsubstituted alkyl, and substituted or unsubstituted aryl;

$A_3$ is a selected from substituted or unsubstituted $C_5$-$C_6$ aryl, substituted or unsubstituted $C_5$-$C_6$ heteroaryl, substituted or unsubstituted $C_5$-$C_6$ cycloalkyl and substituted or unsubstituted $C_5$-$C_6$ cyclic heterocycloalkyl;

Y is independently absent or selected from substituted or unsubstituted alkyl, substituted or unsubstituted aryl, —NH—(C=O)—; =NO—$C_{1-6}$ alkyl-; and —(C=O)-phenyl-;

Z is independently absent or selected from —$N_3$, —C≡CH, C≡C—R', —C≡N, —(C=O)—H, —SH, and —CH=$CH_2$;

R' is independently at each occurrence selected from substituted or unsubstituted alkyl, substituted or unsubstituted heteroalkyl, substituted or unsubstituted aryl, substituted or unsubstituted heteroaryl, —CN, —$CO_2R''$, —(C=O)—$N(R'')_2$, and —(C=O)—R'';

R'' is selected from H, substituted or unsubstituted alkyl, substituted or unsubstituted heteroalkyl, substituted or unsubstituted aryl, and substituted or unsubstituted heteroaryl;

G is selected from halogen, —CN, substituted or unsubstituted aryl, and substituted or unsubstituted heteroaryl; and n is an integer from 5 to 100,000.

In yet another aspect, the present invention provides a polymer according to Formula VI:

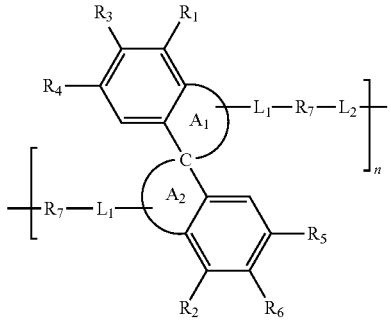

Formula VI wherein:

the carbon indicated by "C" denotes a spiro-carbon;

$A_1$ and $A_2$ are independently at each occurrence selected from:

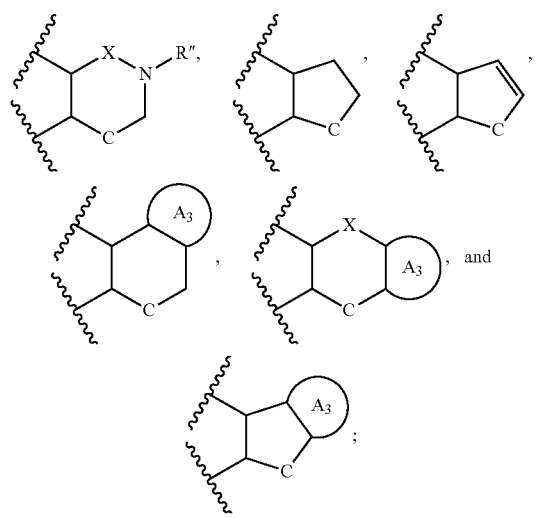

X is —CR$_2$", —O—, —S—, NR", —C=O, —C=NR", —C=N—N(R")$_2$, and C=N—OR";

R$_1$, R$_2$, R$_3$, R$_4$, R$_5$, R$_6$ are independently selected from H, —OR", —OSi(R")$_3$, Si(R")$_3$, substituted or unsubstituted alkyl, substituted or unsubstituted heteroalkyl, substituted or unsubstituted aryl, substituted or unsubstituted heteroaryl, substituted or unsubstituted cycloalkyl and substituted or unsubstituted heterocycloalkyl, wherein at least one of R$_1$, R$_2$, R$_3$, R$_4$, R$_5$, R$_6$, is further substituted with Z;

R$_7$ is absent or selected from substituted or unsubstituted aryl, substituted or unsubstituted heteroaryl; substituted or unsubstituted arylamine, and imido;

A$_3$ is a selected from substituted or unsubstituted C$_5$-C$_6$ aryl, substituted or unsubstituted C$_5$-C$_6$ heteroaryl, substituted or unsubstituted C$_5$-C$_6$ cycloalkyl and substituted or unsubstituted C$_5$-C$_6$ cyclic heterocycloalkyl;

Z is independently selected from —N$_3$, —C≡CH, C≡C—R', —C≡N, —(C=O)—H, —SH, and —CH=CH$_2$;

R' is selected from substituted or unsubstituted alkyl, substituted or unsubstituted heteroalkyl, substituted or unsubstituted aryl, substituted or unsubstituted heteroaryl, —CN, —CO$_2$R$_6$, —(C=O)—N(R")$_2$, and —(C=O)—R";

R" is independently at each occurrence selected from H, substituted or unsubstituted alkyl, substituted or unsubstituted heteroalkyl, substituted or unsubstituted aryl, and substituted or unsubstituted heteroaryl; and L$_1$ and L$_2$ are independently selected from a bond, substituted or unsubstituted alkyl, substituted or unsubstituted cycloalkyl, substituted or unsubstituted alkynyl, substituted or unsubstituted aryl, and substituted or unsubstituted heteroaryl.

In yet another aspect, the present invention provides a polymer according to Formula VII:

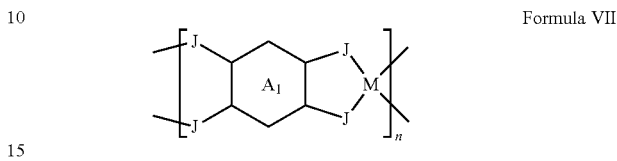

Formula VII wherein:

M is selected from —C—, —Si—, —Sn—, —Ti—, and —Zr—;

J is selected from —O— and —CH$_2$;

A$_1$ is a selected from substituted or unsubstituted aryl and substituted or unsubstituted heteroaryl, and n is an integer from 5 to 100,000.

In yet another aspect, the present invention provides a polymer according to Formula VIII:

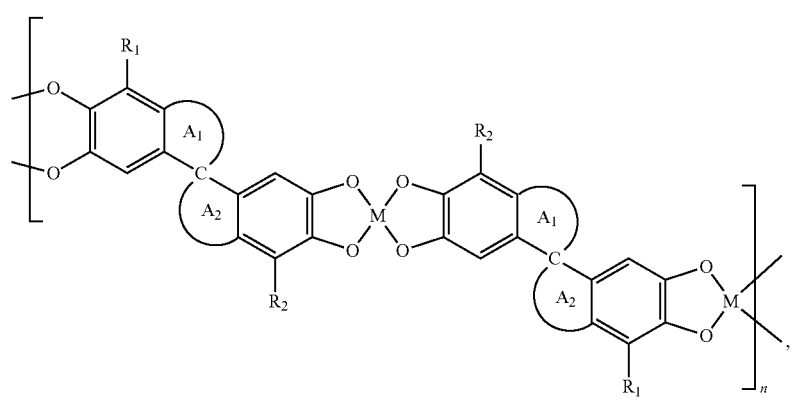

Formula VIII wherein: in all structures the carbon indicated by "C" denotes a spiro-carbon;

M is selected from —C—, —Si—, —Sn—, —Ti—, and —Zr—;

A$_1$ and A$_2$ are each independently selected from:

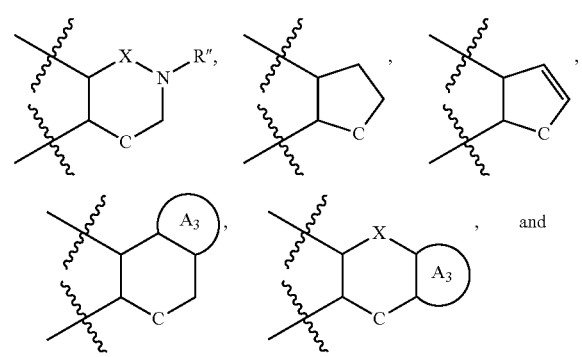

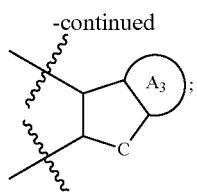

$A_3$ is a selected from substituted or unsubstituted $C_5$-$C_6$ aryl, substituted or unsubstituted $C_5$-$C_6$ heteroaryl, substituted or unsubstituted $C_5$-$C_6$ cycloalkyl and substituted or unsubstituted $C_5$-$C_6$ cyclic heterocycloalkyl;

X is —CR", —O—, —S—, NR", —C=O, —C=NR", —C=N—N(R")$_2$, and C=N—OR";

$R_1$, and $R_2$ are independently selected from H, substituted or unsubstituted alkyl, substituted or unsubstituted heteroalkyl, substituted or unsubstituted aryl, substituted or unsubstituted heteroaryl, substituted or unsubstituted cycloalkyl and substituted or unsubstituted heterocycloalkyl, wherein at least one of $R_1$, and $R_2$, is further substituted with Z;

Z is independently selected from —N$_3$, —C≡CH, C≡C—R', —C≡N, —(C=O)—H, —SH, and —CH=CH$_2$;

R' is selected from substituted or unsubstituted alkyl, substituted or unsubstituted heteroalkyl, substituted or unsubstituted aryl, substituted or unsubstituted heteroaryl, —CN, —CO$_2$R", —(C=O)—N(R")$_2$, and —(C=O)—R";

R" is independently at each occurrence selected from H, substituted or unsubstituted alkyl, substituted or unsubstituted heteroalkyl, substituted or unsubstituted aryl, and substituted or unsubstituted heteroaryl.

In yet another aspect, the present invention provides a polymer according to the formula:

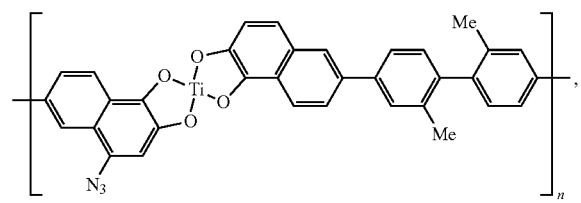

wherein n is an integer from 5 to 100,000.

In yet another aspect, the present invention provides a polymer according to the formula:

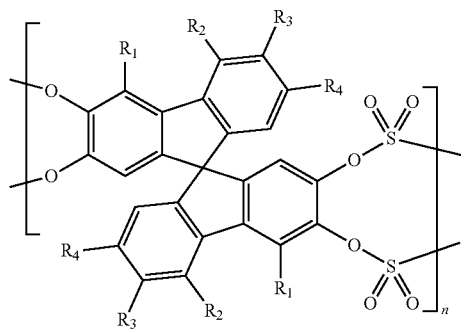

wherein:

$R_1$, $R_2$, $R_3$, and $R_4$ are independently selected from H, substituted or unsubstituted alkyl, substituted or unsubstituted heteroalkyl, substituted or unsubstituted aryl, substituted or unsubstituted heteroaryl, —OR', —SR', N(R")$_2$, wherein at least one of $R_1$, $R_2$, $R_3$, and $R_4$ is further substituted with Z;

Z is independently selected from —N$_3$, —C≡CH, C≡C—R', —C≡N, —(C=O)—H, —SH, and —CH=CH$_2$;

R' is selected from substituted or unsubstituted alkyl, substituted or unsubstituted heteroalkyl, substituted or unsubstituted aryl, substituted or unsubstituted heteroaryl, —CN, —CO$_2$R", —(C=O)—N(R")$_2$, and —(C=O)—R";

R" is independently at each occurrence selected from H, substituted or unsubstituted alkyl, substituted or unsubstituted heteroalkyl, substituted or unsubstituted aryl, and substituted or unsubstituted heteroaryl; substituted or unsubstituted arylamine, and imido, and n is an integer from 5 to 100,000.

These and other aspects of the present invention will become apparent to those skilled in the art after a reading of the following detailed description of the invention, including the appended claims.

BRIEF DESCRIPTION OF THE DRAWINGS

FIG. 2A shows the azide-alkyne coupling reaction scheme for the two monomers of the invention. FIG. 2B depicts FT-IR spectra before and after Cu(II)-catalyzed cross-linking reaction, indicating triazole formation as evidenced by the disappearance of the alkyne IR peak.

DETAILED DESCRIPTION

Figure 1:
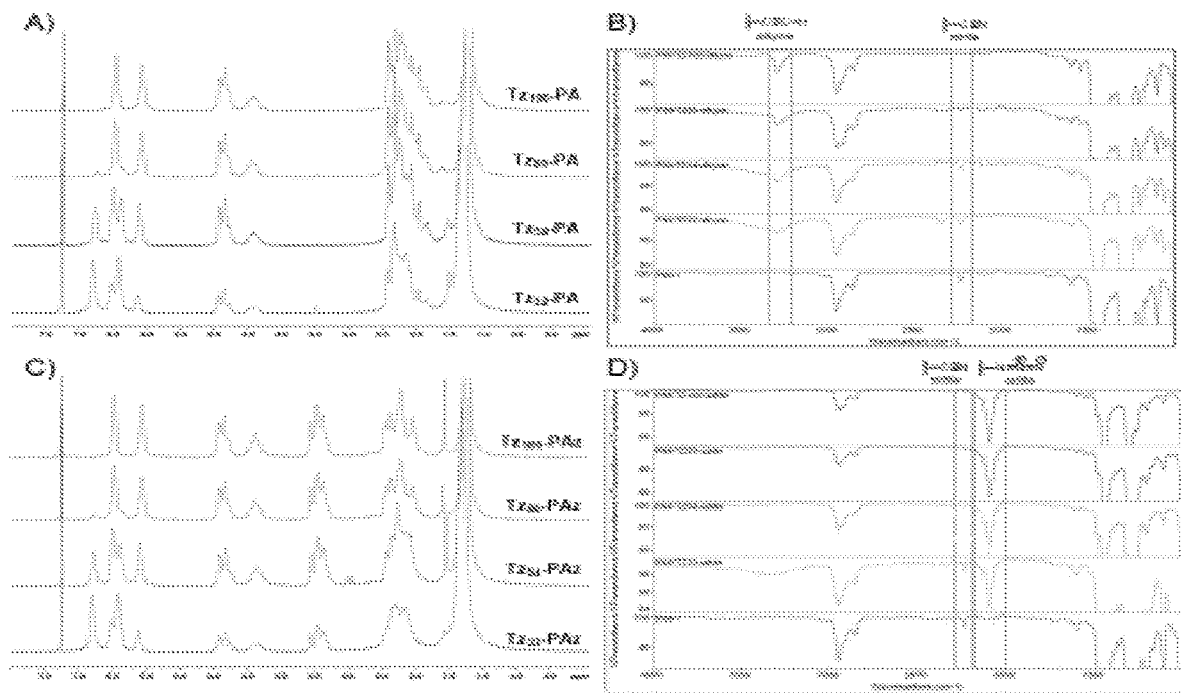
FIG. 1 depicts $^1$H NMR (FIG. 1A and FIG. 1C) and FT-IR (FIG. 1B and FIG. 1D) spectra for alkylation reaction of select monomers of the invention with short chain azide or alkyne linkers, giving rise to an average of 32, 54, 81 and 100 percent of the nitrile groups converted to alkylated tetrazoles bearing either azide or alkyne groups.

Detailed embodiments of the present invention are disclosed herein; however, it is to be understood that the disclosed embodiments are merely illustrative of the invention that may be embodied in various forms. In addition, each of the examples given in connection with the various embodiments of the invention is intended to be illustrative, and not restrictive. Therefore, specific structural and functional details disclosed herein are not to be interpreted as limiting, but merely as a representative basis for teaching one skilled in the art to variously employ the present invention.

Unless defined otherwise, all technical and scientific terms used herein have the same meaning as commonly understood by one of ordinary skill in the art to which this invention belongs.

As used in this specification and the appended claims, the singular forms "a", "an", and "the" include plural references unless the context clearly dictates otherwise. Thus, for example, a reference to "a method" includes one or more methods, and/or steps of the type described herein and/or which will become apparent to those persons skilled in the art upon reading this disclosure.

Ranges can be expressed herein as from "about" or "approximately" one particular value and/or to "about" or "approximately" another particular value. When such a range is expressed, another embodiment includes from the one particular value and/or to the other particular value.

By "comprising" or "containing" or "including" is meant that at least the named compound, element, particle, or method step is present in the composition or article or method, but does not exclude the presence of other compounds, materials, particles, or method steps, even if the other such compounds, material, particles, or method steps have the same function as what is named.

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon, bicyclic hydrocarbon, or tricyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-30 aliphatic carbon atoms. In some embodiments, aliphatic groups contain 1-20 aliphatic carbon atoms. In other embodiments, aliphatic groups contain 1-10 aliphatic carbon atoms. In still other embodiments, aliphatic groups contain 1-6 aliphatic carbon atoms, and in yet other embodiments, aliphatic groups contain 1, 2, 3, or 4 aliphatic carbon atoms. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "cycloaliphatic," as used herein, refers to saturated or partially unsaturated cyclic aliphatic monocyclic, bicyclic, or polycyclic ring systems, as described herein, having from 3 to 14 members, wherein the aliphatic ring system is optionally substituted as defined above and described herein. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, norbornyl, adamantyl, and cyclooctadienyl. In some embodiments, the cycloalkyl has 3-6 carbons. The terms "cycloaliphatic," may also include aliphatic rings that are fused to one or more aromatic or nonaromatic rings, such as decahydronaphthyl or tetrahydronaphthyl, where the radical or point of attachment is on the aliphatic ring. In some embodiments, a carbocyclic group is bicyclic. In some embodiments, a 'carbocyclic group is tricyclic. In some embodiments, a carbocyclic group is polycyclic. In some embodiments, "cycloaliphatic" (or "carbocycle" or "cycloalkyl") refers to a monocyclic $C_3$-$C_6$ hydrocarbon, or a $C_8$-$C_{10}$ bicyclic hydrocarbon that is completely saturated or that contains one or more units of unsaturation, but which is not aromatic, that has a single point of attachment to the rest of the molecule, or a $C_9$-$C_{16}$ tricyclic hydrocarbon that is completely saturated or that contains one or more units of unsaturation, but which is not aromatic, that has a single point of attachment to the rest of the molecule.

As used herein, the term "alkyl" is given its ordinary meaning in the art and may include saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 1-20 carbon atoms in its backbone (e.g., $C_1$-$C_{20}$ for straight chain, $C_2$-$C_{20}$ for branched chain), and alternatively, about 1-10 carbon atoms, or about 1 to 6 carbon atoms. In some embodiments, a cycloalkyl ring has from about 3-10 carbon atoms in their ring structure where such rings are monocyclic or bicyclic, and alternatively about 5, 6 or 7 carbons in the ring structure. In some embodiments, an alkyl group may be a lower alkyl group, wherein a lower alkyl group comprises 1-4 carbon atoms (e.g., $C_1$-$C_4$ for straight chain lower alkyls).

As used herein, the term "alkenyl" refers to an alkyl group, as defined herein, having one or more double bonds.

As used herein, the term "alkynyl" refers to an alkyl group, as defined herein, having one or more triple bonds.

The term "heteroalkyl" is given its ordinary meaning in the art and refers to alkyl groups as described herein in which one or more carbon atoms is replaced with a heteroatom (e.g., oxygen, nitrogen, sulfur, and the like). Examples of heteroalkyl groups include, but are not limited to, alkoxy, poly(ethylene glycol)-, alkyl-substituted amino, tetrahydrofuranyl, piperidinyl, morpholinyl, etc.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, binaphthyl, anthracyi and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone of as part of a larger moiety, e.g., "heteroaralkyl," or "heteroaralkoxy," refer to groups having 5 to 10 ring atoms (i.e., monocyclic or bicyclic), in some embodiments 5, 6, 9, or 10 ring atoms. In some embodiments, such rings have 6, 10, or 14 it electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. In some embodiments, a heteroaryl is a heterobiaryl group, such as bipyridyl and the like. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be monocyclic, bicyclic, tricyclic, tetracyclic, and/or otherwise polycyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen.

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be monocyclic, bicyclic, tricyclic, tetracyclic, and/or otherwise polycyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring.

The term "unsaturated," as used herein, means that a moiety has one or more units of unsaturation.

The term "halogen" means F, Cl, Br, or I; the term "halide" refers to a halogen radical or substituent, namely —F, —Cl, —Br, or —I.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

The term "spiro compound" refers to a chemical compound that presents a twisted structure of two or more rings, in which at least 2 rings are linked together by one common atom, e.g., a carbon atom. When the common atom is located in the center of the compound, the compound is referred to as a "spirocentric compound." The common atom that connects the two or more rings is referred to as the "spiro-atom." When such common atom is a carbon atom, it is referred to as the "spiro-carbon."

As used herein, ring fusions, including without limitation aliphatic and aromatic ring fusions, are represented by wavy bond connections, such as shown below.

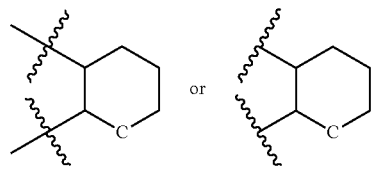 [SMILES: *C1CCCCC1* ; *C1CCCCC1*]

The connecting bonds may themselves be single or multiple (e.g., aromatic, double, triple, etc.) bonds. By way of non-limiting example, a spirocentric compound containing a spiro-carbon linking two bicyclic rings is shown below.

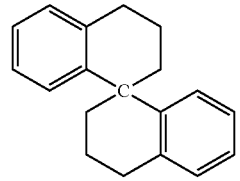 [SMILES: c1ccc2c(c1)CCCC21CCCc2ccccc21]

This compound may be schematically represented as follows:

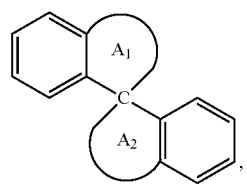

wherein $A_1$ and $A_2$ are

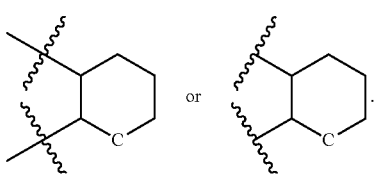 [SMILES: *C1CCCCC1* ; *C1CCCCC1*]

In the above example, the connecting bonds, represented by wavy bond connections, are aromatic bonds.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention.

Unless otherwise stated, all tautomeric forms of the compounds of the invention are within the scope of the invention.

Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{11}$C- or $^{13}$C- or $^{14}$C-enriched carbon are within the scope of this invention.

It is also to be understood that the mention of one or more method steps does not preclude the presence of additional method steps or intervening method steps between those steps expressly identified. Similarly, it is also to be understood that the mention of one or more components in a device or system does not preclude the presence of additional components or intervening components between those components expressly identified.

In one aspect, the present invention provides spirocentric compounds functionalized with reactive groups for subsequent polymerization. In some embodiments, the spirocentric compounds of the invention comprise one or more of the following groups: —N$_3$, —C≡CH, C≡C—R', —C≡N, —(C=O)—H, —(C=O)—OH, —(C=O)—OR$_6$, —(C=O)—R$_6$, —(C=O)—N(R$_6$)$_2$, —SH, —CH=CH$_2$, halide, —SO$_3$R$_6$, —B(OR$_6$)$_2$, Sn(R$_6$)$_3$, and Zn(R$_6$)$_2$, wherein R$_6$ is independently at each occurrence selected from H, substituted or unsubstituted alkyl, substituted or unsubstituted heteroalkyl, substituted or unsubstituted aryl, and substituted or unsubstituted heteroaryl.

In one aspect, the present invention provides spirocentric compounds according to Formula I:

Formula I

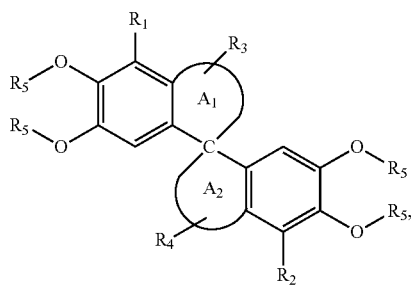

In all structures the carbon indicated by "C" denotes a spiro-carbon.

In one embodiment, A$_1$ and A$_2$ are each independently selected from:

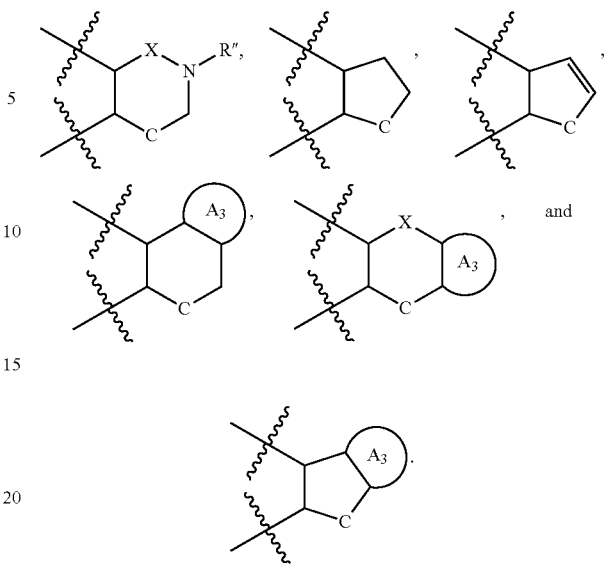

In one embodiment, A$_3$ is a selected from substituted or unsubstituted C$_5$-C$_6$ aryl, substituted or unsubstituted C$_5$-C$_6$ heteroaryl, substituted or unsubstituted C$_5$-C$_6$ cycloalkyl and substituted or unsubstituted C$_5$-C$_6$ cyclic heterocycloalkyl.

In one embodiment, X is selected from —CR$_6$, —O—, —S—, NR$_6$, —C=O, —C=NR$_6$, —C=N—N(R$_6$)$_2$, and C=N—OR$_6$.

In one embodiment, R$_1$, R$_2$, R$_3$, and R$_4$ are each independently selected from H and Y— Z, wherein at least one of R$_1$, R$_2$, R$_3$, and R$_4$ is Y— Z.

In one embodiment, R$_5$ is independently at each occurrence H, Si(OR$_6$)$_3$, or Si(R$_6$)$_3$.

In one embodiment, R$_6$ is independently at each occurrence selected from H, substituted or unsubstituted alkyl, substituted or unsubstituted heteroalkyl, substituted or unsubstituted aryl, and substituted or unsubstituted heteroaryl.

In one embodiment, Y is independently absent or selected from substituted or unsubstituted alkyl, substituted or unsubstituted heteroalkyl, substituted or unsubstituted aryl, substituted or unsubstituted heteroaryl, —NH—(C=O)—; =NO—C$_{1-6}$ alkyl-; and —(C=O)-phenyl-.

In one embodiment, Z is independently selected from —N$_3$, —C≡CH, C≡C—R', —C≡N, —(C=O)—H, —SH, —CH=CH$_2$, halide, —SO$_3$R$_6$, —B(OR$_6$)$_2$, Sn(R$_6$)$_3$, and Zn(R$_6$)$_2$.

In another embodiment, Z is independently selected from —N$_3$, —C≡CH, C≡C—R', —C≡N, —(C=O)—H, —SH, and —CH=CH$_2$.

In one embodiment, R' is selected from substituted or unsubstituted alkyl, substituted or unsubstituted heteroalkyl, substituted or unsubstituted aryl, substituted or unsubstituted heteroaryl, —CN, —CO$_2$R$_6$, —(C=O)—N(R$_6$)$_2$, and —(C=O)—R$_6$.

In one embodiment, R" is selected from R$_3$ and R$_4$.

In one embodiment, the compound of Formula I may have A$_1$ and A$_2$ each independently selected from:

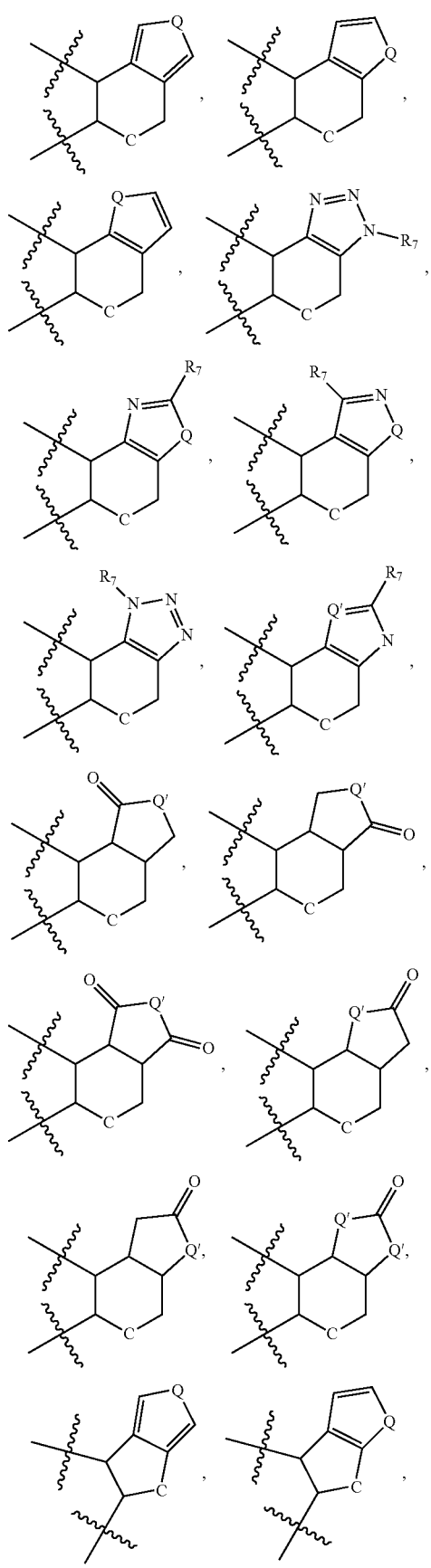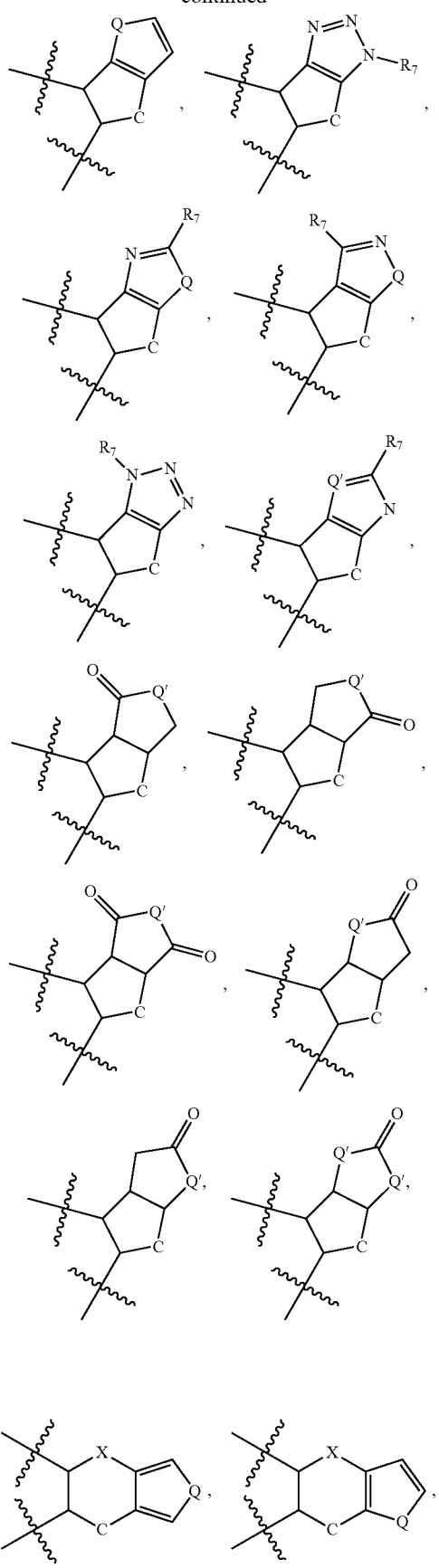

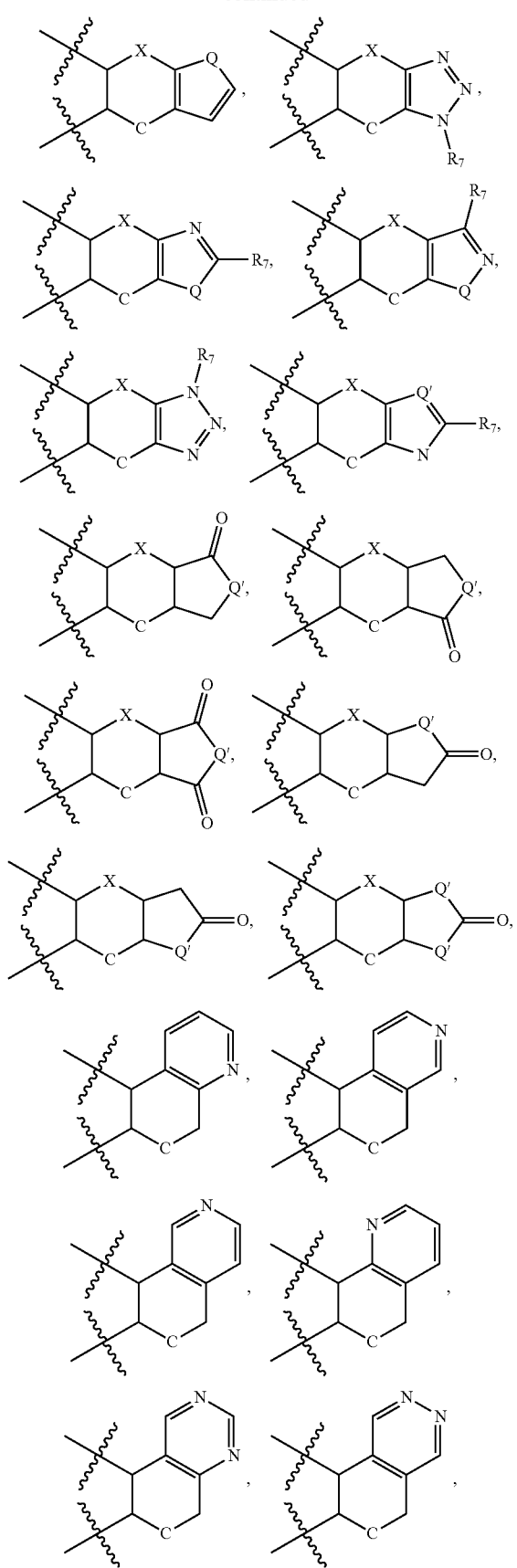
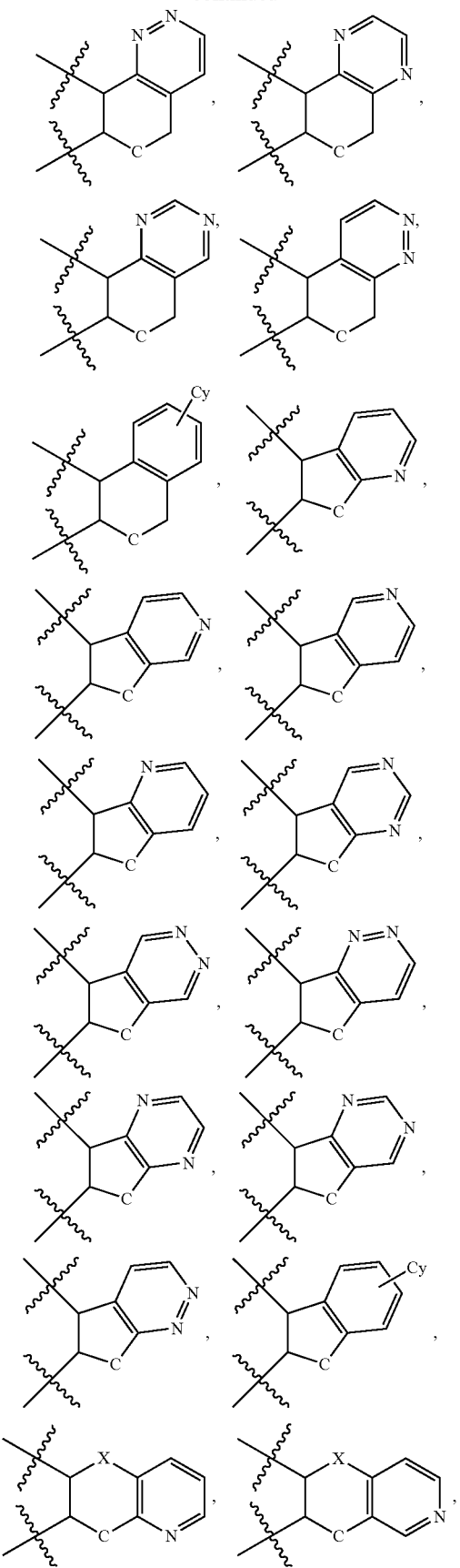

-continued

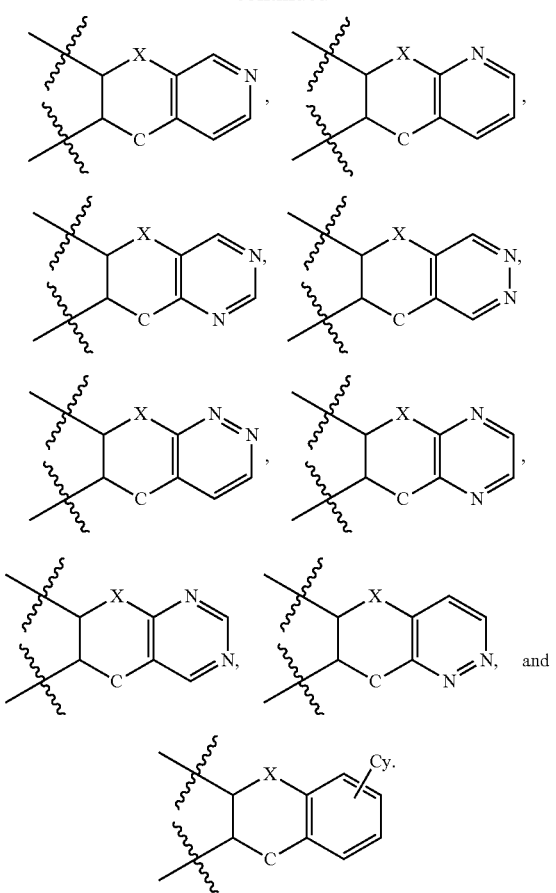

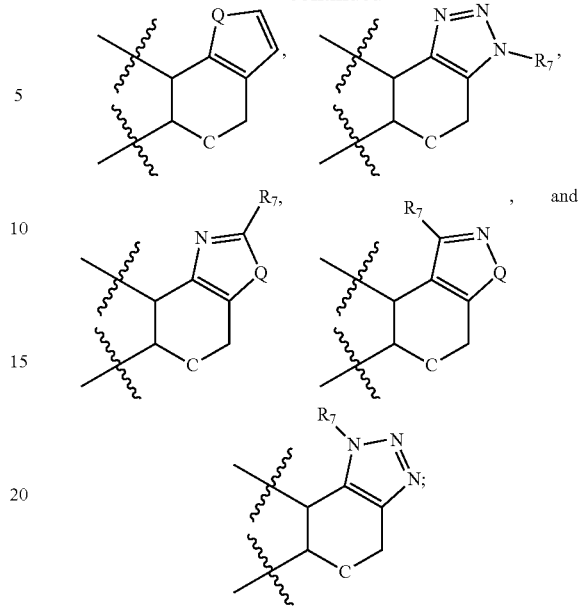

In one embodiment, X is selected from —CR$_6$, —O—, —S—, NR$_6$, —C=O, —C=NR$_6$, —C=N—N(R$_6$)$_2$, and C=N—OR$_6$.

In one embodiment, C$_y$ is selected from substituted or unsubstituted C$_5$-C$_6$ aryl, substituted or unsubstituted C$_5$-C$_6$ heteroaryl, substituted or unsubstituted C$_5$-C$_6$ cycloalkyl and substituted or unsubstituted C$_5$-C$_6$ cyclic heterocycloalkyl.

In one embodiment, Q is selected from —O—, —S—, —N—R$_7$, —C=O, —C=NR$_7$, —C=N—N(R$_7$)$_2$, and —C=N—OR$_7$.

In one embodiment, Q' is independently at each occurrence selected from —O—, —S—, and —N—R$_7$.

In one embodiment, R$_7$ is independently at each occurrence selected from R$_3$ and R$_4$.

In one embodiment, the compound of Formula I may have A$_1$ and A$_2$ each

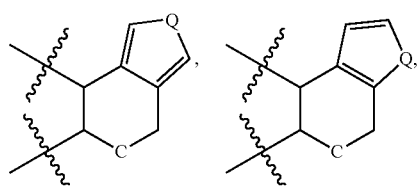

In one embodiment, Z is independently selected from —N$_3$, —C≡CH, C≡C—R', —C≡N, —(C=O)—H, —SH, and —CH=CH$_2$.

In one embodiment, Q is selected from —O—, —S—, —N—R$_7$, —C=O, —C=NR, —C=N—N(R$_7$)$_2$, and —C=N—OR$_7$.

In one embodiment, R' is selected from substituted or unsubstituted alkyl, substituted or unsubstituted heteroalkyl, substituted or unsubstituted aryl, substituted or unsubstituted heteroaryl, —CN, —CO$_2$R$_6$, —(C=O)—N(R$_6$)$_2$, and —(C=O)—R$_6$.

In one embodiment, R$_6$ is independently at each occurrence selected from H, substituted or unsubstituted alkyl, substituted or unsubstituted heteroalkyl, substituted or unsubstituted aryl, and substituted or unsubstituted heteroaryl.

In one embodiment, R$_7$ is independently at each occurrence selected from R$_3$ and R$_4$.

In one embodiment, the compound of Formula I may have A$_1$ and A$_2$ each

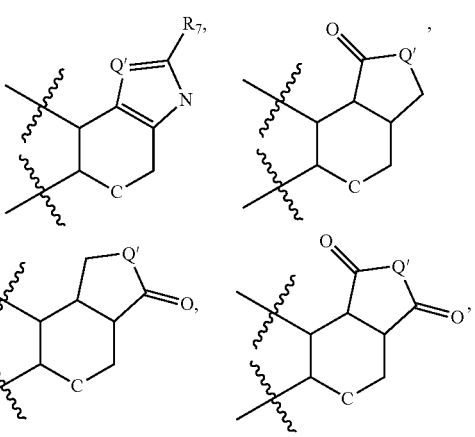

-continued

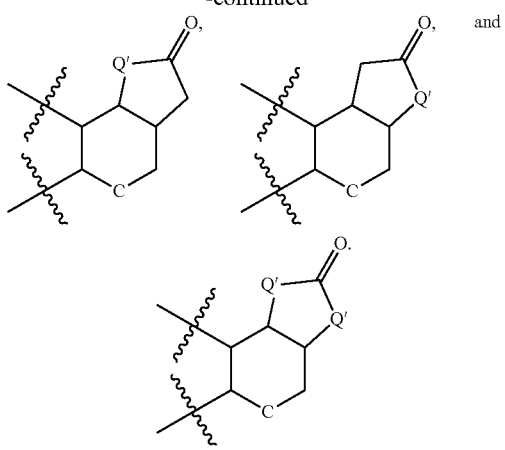

In another embodiment, Z is independently selected from —$N_3$, —C≡CH, C≡C—R', —C≡N, —(C=O)—H, —SH, and —CH=$CH_2$.

In one embodiment, Q' is independently at each occurrence selected from —O—, —S—, and —N—$R_7$.

In one embodiment, R' is selected from substituted or unsubstituted alkyl, substituted or unsubstituted heteroalkyl, substituted or unsubstituted aryl, substituted or unsubstituted heteroaryl, —CN, —$CO_2R_6$, —(C=O)—$N(R_6)_2$, and —(C=O)—$R_6$.

In one embodiment, $R_6$ is independently at each occurrence selected from H, substituted or unsubstituted alkyl, substituted or unsubstituted heteroalkyl, substituted or unsubstituted aryl, and substituted or unsubstituted heteroaryl.

In one embodiment, $R_7$ is independently at each occurrence selected from $R_3$ and $R_4$.

In one embodiment, the compound of Formula I may have $A_1$ and $A_2$ each

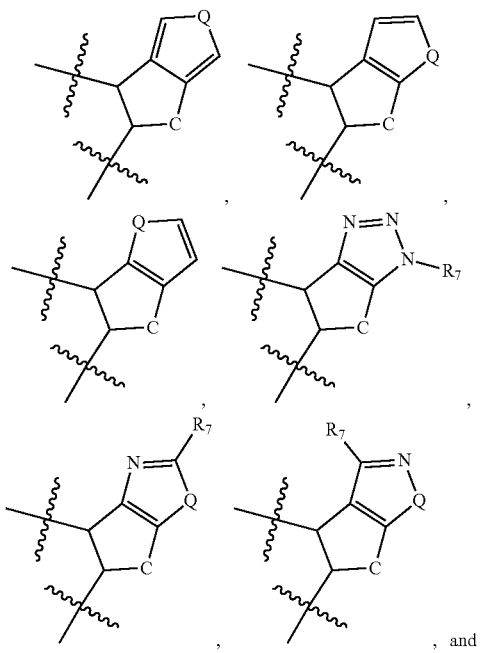

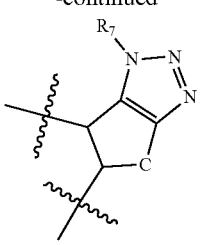

In another embodiment, Z is independently selected from —$N_3$, —C≡CH, C≡C—R', —C≡N, —(C=O)—H, —SH, and —CH=$CH_2$.

In one embodiment, Q is selected from —O—, —S—, —N—$R_7$, —C=O, —C=$NR_7$, —C=N—$N(R_7)_2$, and —C=N—$OR_7$.

In one embodiment, R' is selected from substituted or unsubstituted alkyl, substituted or unsubstituted heteroalkyl, substituted or unsubstituted aryl, substituted or unsubstituted heteroaryl, —CN, —$CO_2R_6$, —(C=O)—$N(R_6)_2$, and —(C=O)—$R_6$.

In one embodiment, $R_6$ is independently at each occurrence selected from H, substituted or unsubstituted alkyl, substituted or unsubstituted heteroalkyl, substituted or unsubstituted aryl, and substituted or unsubstituted heteroaryl.

In one embodiment, $R_7$ is independently at each occurrence selected from $R_3$ and $R_4$.

In one embodiment, the compound of Formula I may have $A_1$ and $A_2$ each

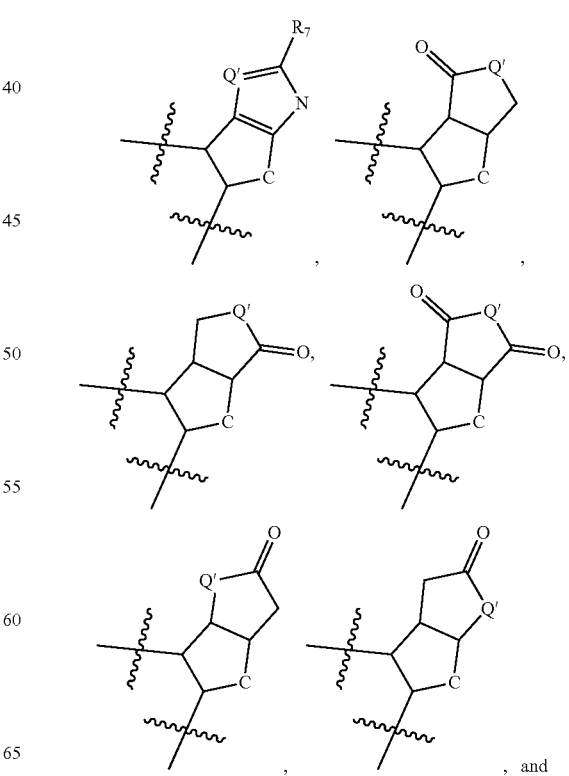

-continued

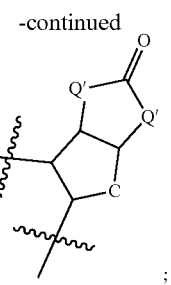

In another embodiment, Z is independently selected from —N$_3$, —C≡CH, C≡C—R', —C≡N, —(C═O)—H, —SH, and —CH═CH$_2$.

In one embodiment, Q' is independently at each occurrence selected from —O—, —S—, and —N—R$_7$.

In one embodiment, R' is selected from substituted or unsubstituted alkyl, substituted or unsubstituted heteroalkyl, substituted or unsubstituted aryl, substituted or unsubstituted heteroaryl, —CN, —CO$_2$R$_6$, —(C═O)—N(R$_6$)$_2$, and —(C═O)—R$_6$.

In one embodiment, R$_6$ is independently at each occurrence selected from H, substituted or unsubstituted alkyl, substituted or unsubstituted heteroalkyl, substituted or unsubstituted aryl, and substituted or unsubstituted heteroaryl.

In one embodiment, R$_7$ is independently at each occurrence selected from R$_3$ and R$_4$.

In one embodiment, the compound of Formula I may have A$_1$ and A$_2$ each

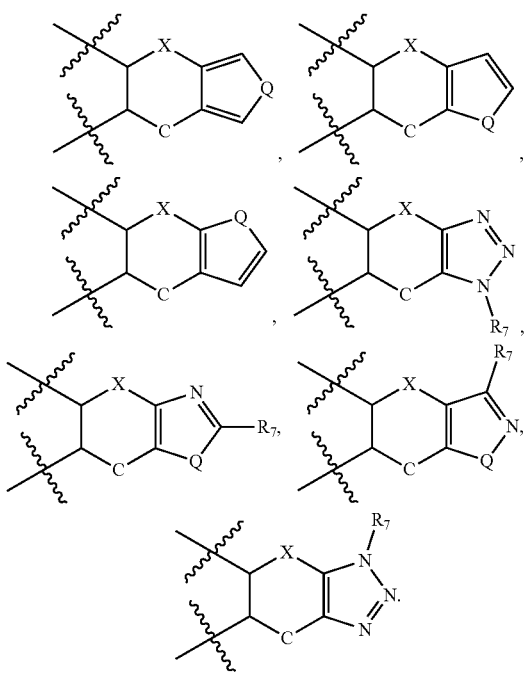

In another embodiment, Z is independently selected from —N$_3$, —C≡CH, C≡C—R', —C≡N, —(C═O)—H, —SH, and —CH═CH$_2$.

In one embodiment, X is independently selected from —CR$_6$, —O—, —S—, NR$_6$, —C═O, —C═NR$_6$, —C═N—N(R$_6$)$_2$, and C═N—OR$_6$.

In one embodiment, Q' is independently at each occurrence selected from —O—, —S—, and —N—R$_7$.

In one embodiment, R' is selected from substituted or unsubstituted alkyl, substituted or unsubstituted heteroalkyl, substituted or unsubstituted aryl, substituted or unsubstituted heteroaryl, —CN, —CO$_2$R$_6$, —(C═O)—N(R$_6$)$_2$, and —(C═O)—R$_6$.

In one embodiment, R$_6$ is independently at each occurrence selected from H, substituted or unsubstituted alkyl, substituted or unsubstituted heteroalkyl, substituted or unsubstituted aryl, and substituted or unsubstituted heteroaryl.

In one embodiment, R$_7$ is independently at each occurrence selected from R$_3$ and R$_4$.

In one embodiment, the compound of Formula I may have A$_1$ and A$_2$ each

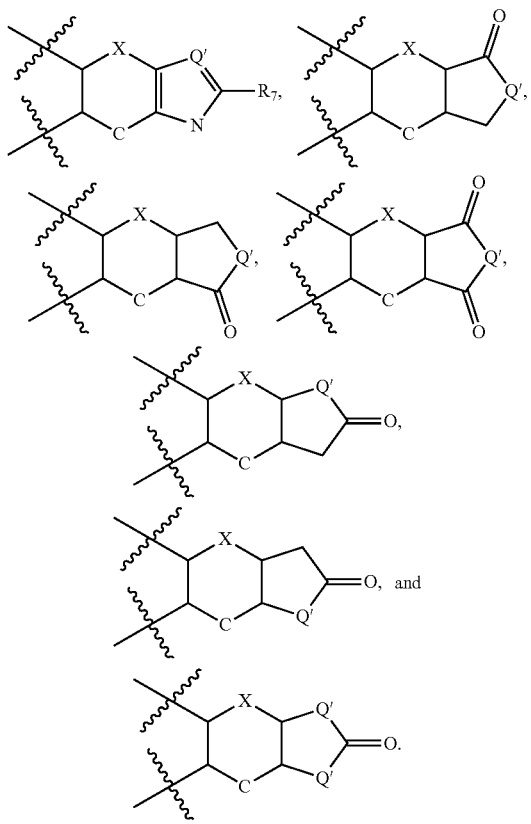

In another embodiment, Z is independently selected from —N$_3$, —C≡CH, C≡C—R', —C≡N, —(C═O)—H, —SH, and —CH═CH$_2$.

In one embodiment, X is independently selected from —CR$_6$, —O—, —S—, NR$_6$, —C═O, —C═NR$_6$, —C═N—N(R$_6$)$_2$, and C═N—OR$_6$.

In one embodiment, Q' is independently at each occurrence selected from —O—, —S—, and —N—R$_7$.

In one embodiment, R' is selected from substituted or unsubstituted alkyl, substituted or unsubstituted heteroalkyl, substituted or unsubstituted aryl, substituted or unsubstituted heteroaryl, —CN, —CO$_2$R$_6$, —(C═O)—N(R$_6$)$_2$, and —(C═O)—R$_6$.

In one embodiment, R$_6$ is independently at each occurrence selected from H, substituted or unsubstituted alkyl, substituted or unsubstituted heteroalkyl, substituted or unsubstituted aryl, and substituted or unsubstituted heteroaryl.

In one embodiment, $R_7$ is independently at each occurrence selected from $R_3$ and $R_4$.

In one embodiment, the compound of Formula I may have $A_1$ and $A_2$ each

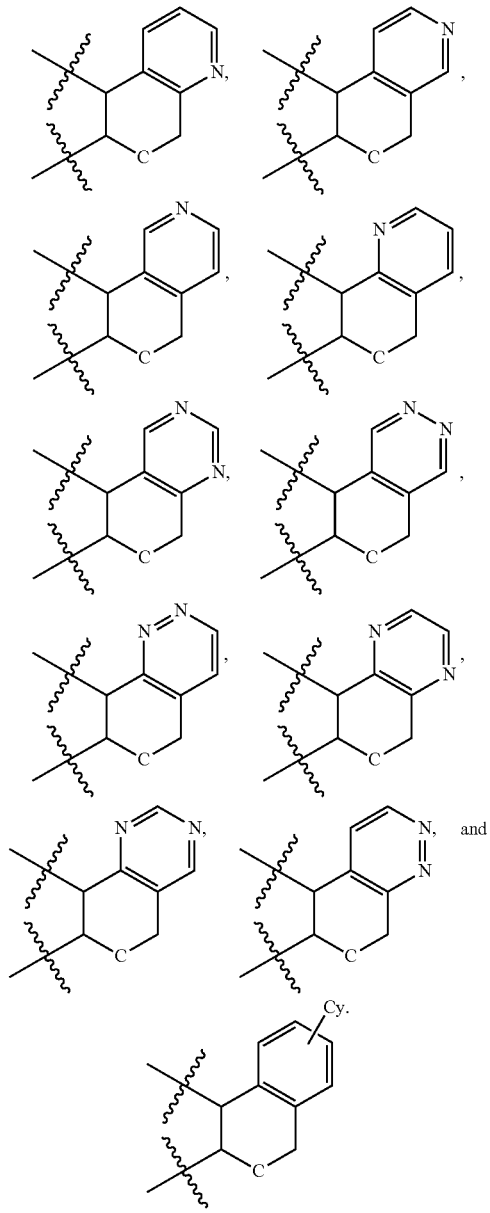

In another embodiment, Z is independently selected from —$N_3$, —C≡CH, C≡C—R', —C≡N, —(C=O)—H, —SH, and —CH=CH$_2$.

In one embodiment, R' is selected from substituted or unsubstituted alkyl, substituted or unsubstituted heteroalkyl, substituted or unsubstituted aryl, substituted or unsubstituted heteroaryl, —CN, —CO$_2$R$_6$, —(C=O)—N(R$_6$)$_2$, and —(C=O)—R$_6$.

In one embodiment, $R_6$ is independently at each occurrence selected from H, substituted or unsubstituted alkyl, substituted or unsubstituted heteroalkyl, substituted or unsubstituted aryl, and substituted or unsubstituted heteroaryl.

In one embodiment, $C_y$ is selected from substituted or unsubstituted $C_5$-$C_6$ aryl, substituted or unsubstituted $C_5$-$C_6$ heteroaryl, substituted or unsubstituted $C_5$-$C_6$ cycloalkyl and substituted or unsubstituted $C_5$-$C_6$ cyclic heterocycloalkyl.

In one embodiment, the compound of Formula I may have $A_1$ and $A_2$ each

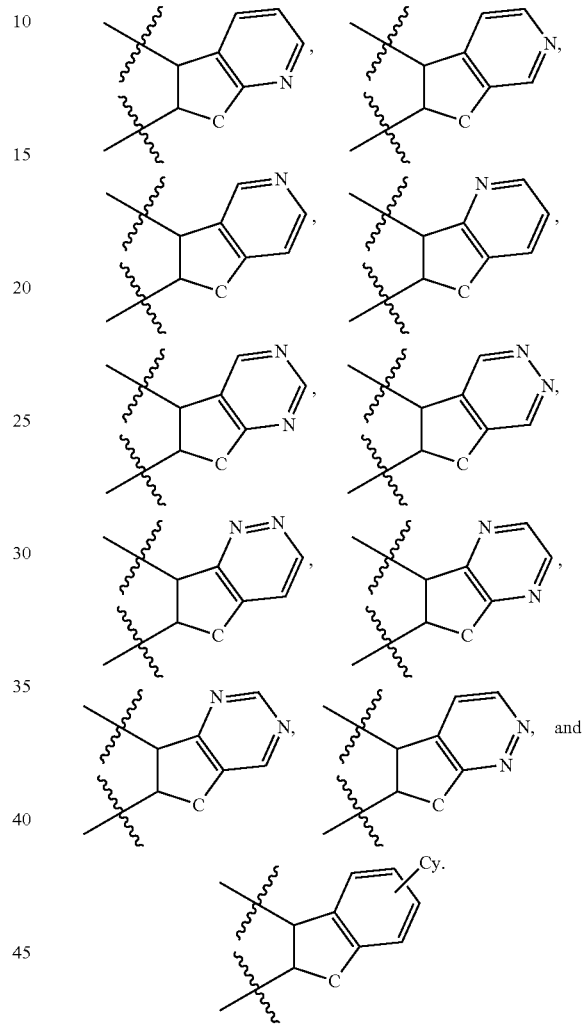

In another embodiment, Z is independently selected from —$N_3$, —C≡CH, C≡C—R', —C≡N, —(C=O)—H, —SH, and —CH=CH$_2$.

In one embodiment, R' is selected from substituted or unsubstituted alkyl, substituted or unsubstituted heteroalkyl, substituted or unsubstituted aryl, substituted or unsubstituted heteroaryl, —CN, —CO$_2$R$_6$, —(C=O)—N(R$_6$)$_2$, and —(C=O)—R$_6$.

In one embodiment, $R_6$ is independently at each occurrence selected from H, substituted or unsubstituted alkyl, substituted or unsubstituted heteroalkyl, substituted or unsubstituted aryl, and substituted or unsubstituted heteroaryl.

In one embodiment, $C_y$ is selected from substituted or unsubstituted $C_5$-$C_6$ aryl, substituted or unsubstituted $C_5$-$C_6$ heteroaryl, substituted or unsubstituted $C_5$-$C_6$ cycloalkyl and substituted or unsubstituted $C_5$-$C_6$ cyclic heterocycloalkyl.

In one embodiment, the compound of Formula I may have $A_1$ and $A_2$ each

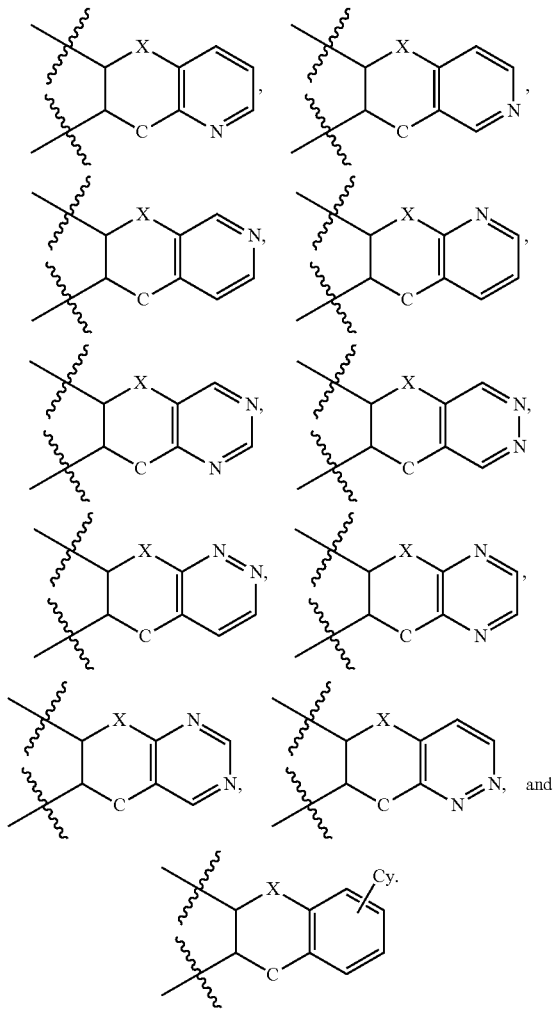

In one embodiment, X is selected from —$CR_6$, —O—, —S—, $NR_6$, —C=O, —C=$NR_6$, —C=N—$N(R_6)_2$, and C=N—$OR_6$;

In another embodiment, Z is independently selected from —$N_3$, —C≡CH, C≡C—R', —C≡N, —(C=O)—H, —SH, and —CH=$CH_2$.

In one embodiment, R' is selected from substituted or unsubstituted alkyl, substituted or unsubstituted heteroalkyl, substituted or unsubstituted aryl, substituted or unsubstituted heteroaryl, —CN, —$CO_2R_6$, —(C=O)—$N(R_6)_2$, and —(C=O)—$R_6$.

In one embodiment, $R_6$ is independently at each occurrence selected from H, substituted or unsubstituted alkyl, substituted or unsubstituted heteroalkyl, substituted or unsubstituted aryl, and substituted or unsubstituted heteroaryl.

In one embodiment, $C_y$ is selected from substituted or unsubstituted $C_5$-$C_6$ aryl, substituted or unsubstituted $C_5$-$C_6$ heteroaryl, substituted or unsubstituted $C_5$-$C_6$ cycloalkyl and substituted or unsubstituted $C_5$-$C_6$ cyclic heterocycloalkyl.

In one embodiment, a compound of Formula I may have the structure:

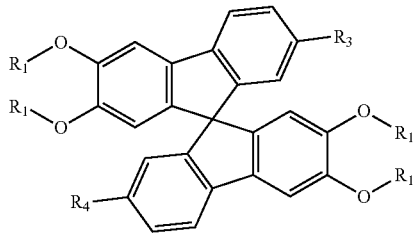

In one embodiment, $R_1$ is independently at each occurrence H or alkyl.

In one embodiment, $R_3$ and $R_4$ are each independently selected from halide and —$B(OR_6)_2$.

In one embodiment, $R_6$ is independently at each occurrence selected from H, substituted or unsubstituted alkyl, substituted or unsubstituted heteroalkyl, substituted or unsubstituted aryl, and substituted or unsubstituted heteroaryl.

In one aspect, the present invention provides spirocentric compounds according to Formula II:

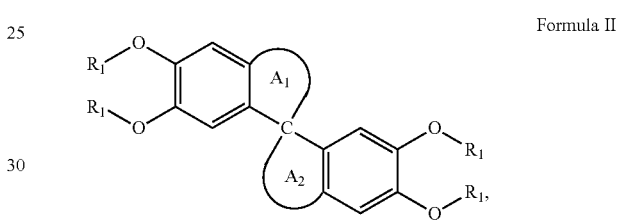

Formula II

In all structures the carbon indicated by "C" denotes a spiro-carbon.

In one embodiment, $A_1$ is selected from

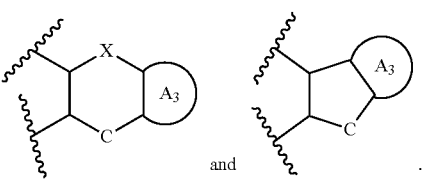

and

In one embodiment, $A_2$ is

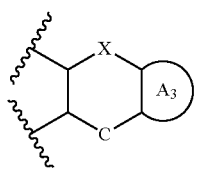

In one embodiment, X is independently at each occurrence selected from O, or N—$R_2$.

In one embodiment, $R_1$ is independently at each occurrence H or alkyl.

In one embodiment, $R_2$ is selected from H, substituted or unsubstituted alkyl, and substituted or unsubstituted aryl.

In one embodiment, $A_3$ is a selected from substituted or unsubstituted $C_5$-$C_6$ aryl, substituted or unsubstituted $C_5$-$C_6$ heteroaryl, substituted or unsubstituted $C_5$-$C_6$ cycloalkyl and substituted or unsubstituted $C_5$-$C_6$ cyclic heterocycloalkyl.

In one embodiment, the compound of Formula II may have $A_1$ and $A_2$ each independently selected from:
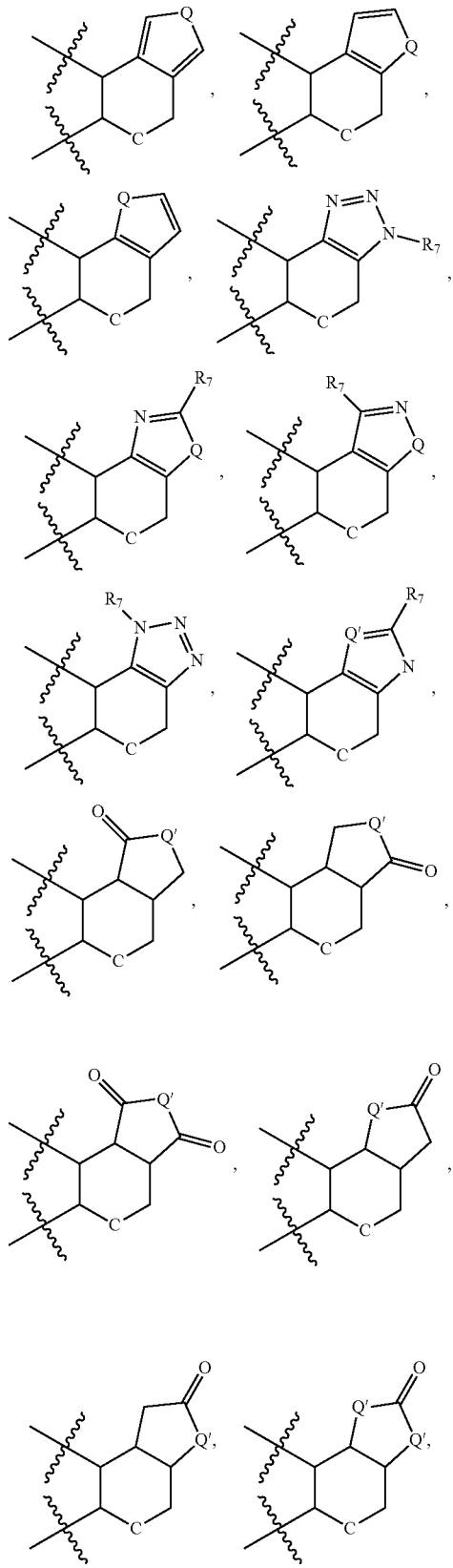
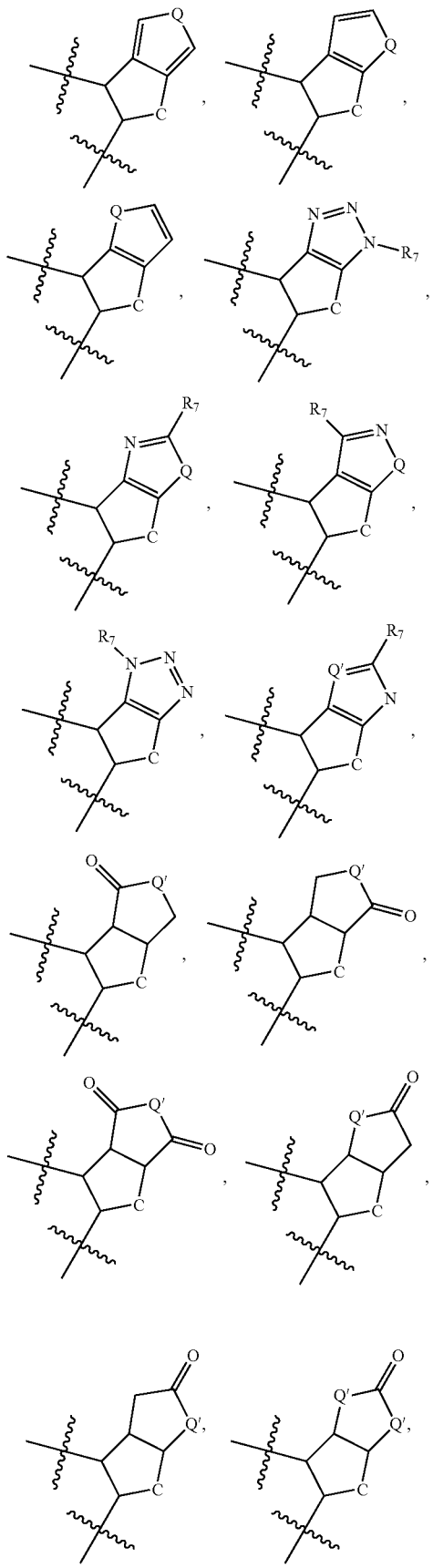

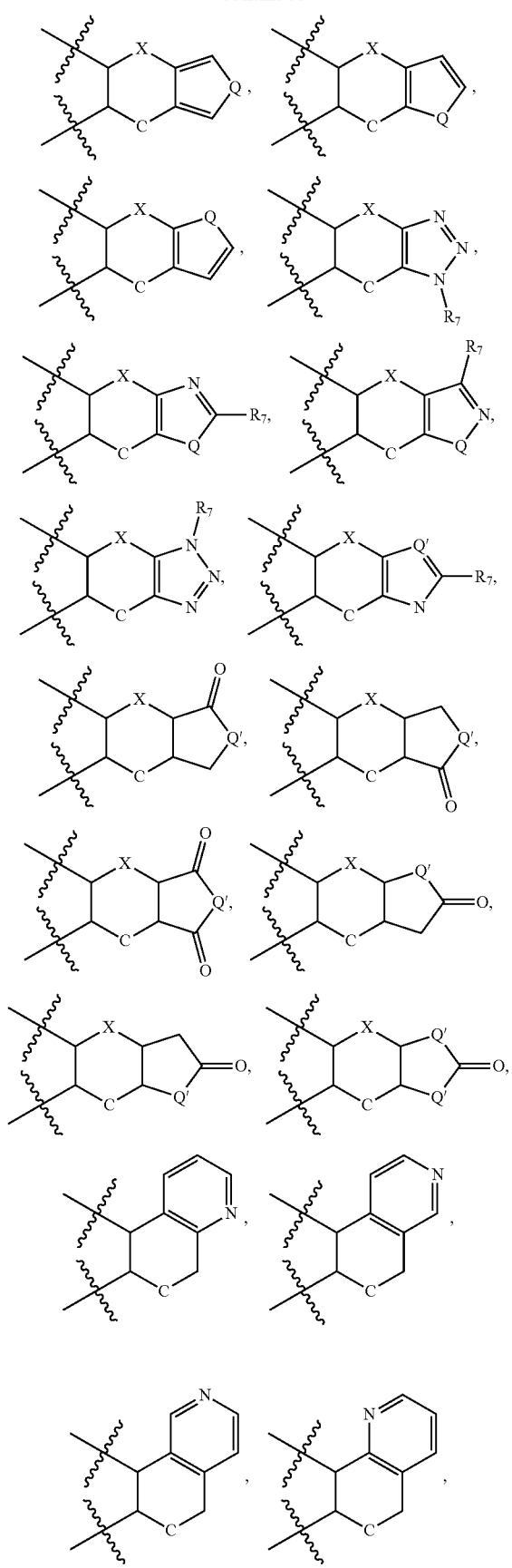
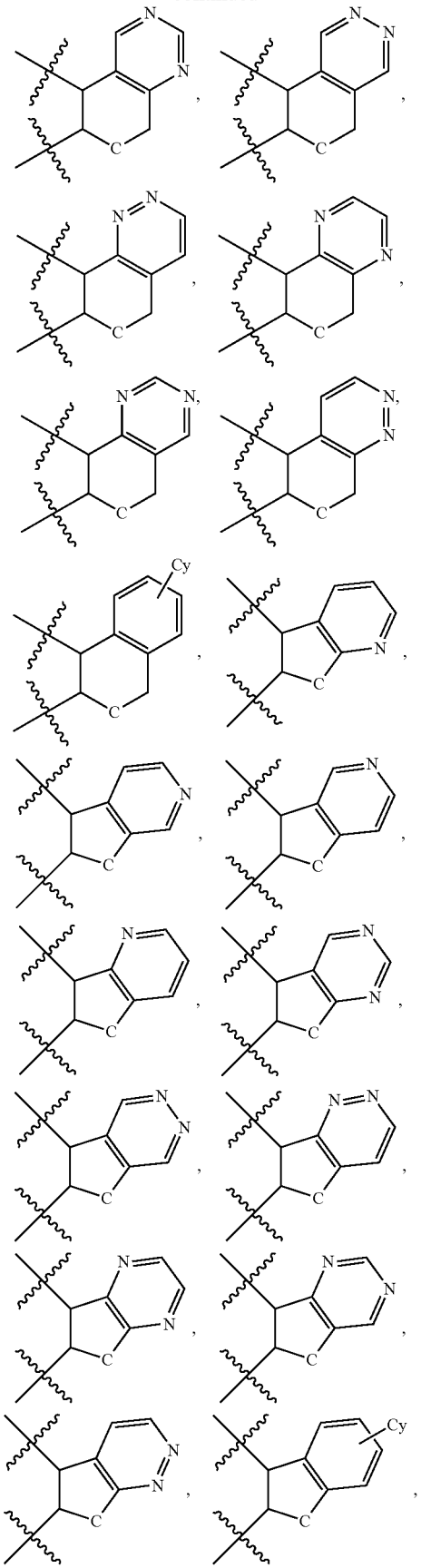

-continued

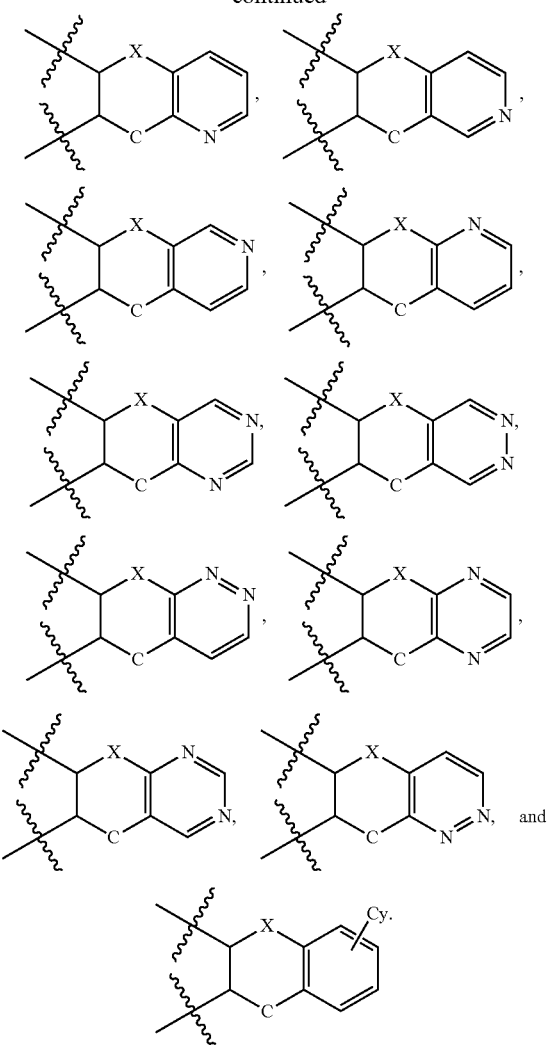

In one embodiment, X is selected from —CR$_6$—, —O—, —S—, NR$_6$, —C═O, —C═NR$_6$, —C═N—N(R$_6$)$_2$, and C═N—OR$_6$.

In one embodiment, C$_y$ is selected from substituted or unsubstituted C$_5$-C$_6$ aryl, substituted or unsubstituted C$_5$-C$_6$ heteroaryl, substituted or unsubstituted C$_5$-C$_6$ cycloalkyl and substituted or unsubstituted C$_5$-C$_6$ cyclic heterocycloalkyl.

In one embodiment, Q is selected from —O—, —S—, —N—R$_7$, —C═O, —C═NR$_7$, —C═N—N(R$_7$)$_2$, and —C═N—OR$_7$.

In one embodiment, Q' is independently at each occurrence selected from —O—, —S—, and —N—R$_7$.

In one embodiment, R$_6$ is independently at each occurrence selected from H, substituted or unsubstituted alkyl, substituted or unsubstituted heteroalkyl, substituted or unsubstituted aryl, and substituted or unsubstituted heteroaryl.

In one embodiment, R$_7$ is independently at each occurrence selected from R$_3$ and R$_4$.

In one aspect, the present invention provides spirocentric compounds according to Formula III:

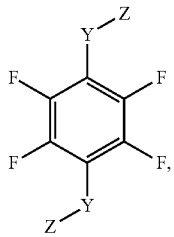

Formula III

In another embodiment, Z is independently selected from —N$_3$, —C≡CH, C≡C—R', —C≡N, —(C═O)—H, —SH, and —CH═CH$_2$.

In another embodiment, Z is selected from —N$_3$, —C≡CH, and C≡C—R'.

In one embodiment, Y is independently at each occurrence absent, or selected from

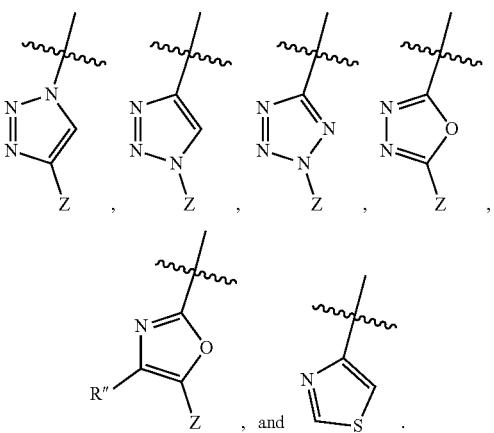

In one embodiment, R' is selected from substituted or unsubstituted alkyl, substituted or unsubstituted heteroalkyl, substituted or unsubstituted aryl, substituted or unsubstituted heteroaryl, —CN, —CO$_2$R", —(C═O)—N(R")$_2$, and —(C═O)—R".

In one embodiment, R" is selected from H, substituted or unsubstituted alkyl, substituted or unsubstituted heteroalkyl, substituted or unsubstituted aryl, and substituted or unsubstituted heteroaryl.

In one embodiment, the spirocyclic monomeric compounds according to Formula I may have the following structural formulas:

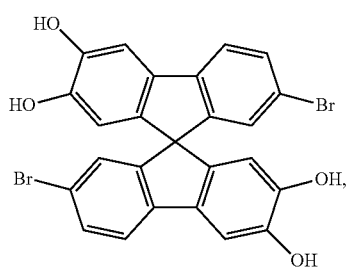

37
-continued
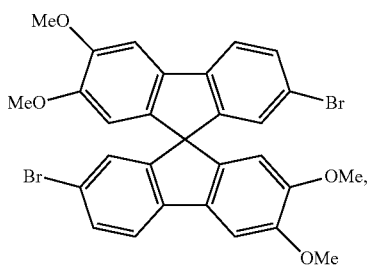
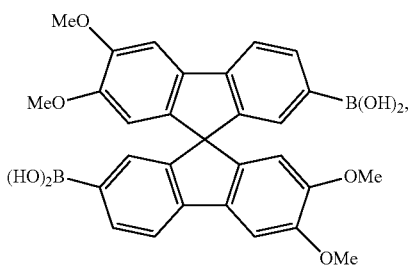
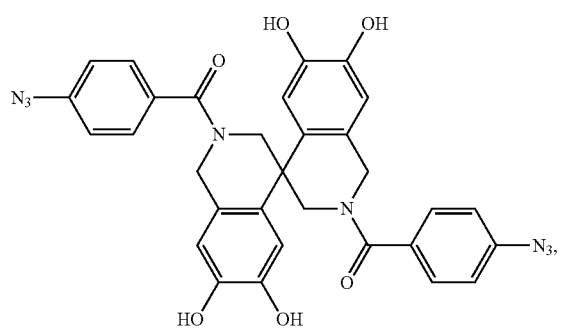
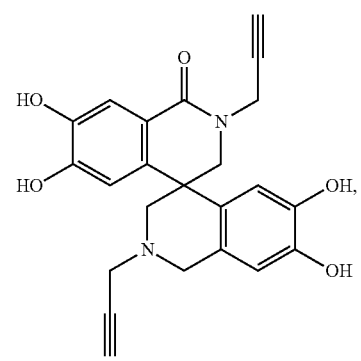
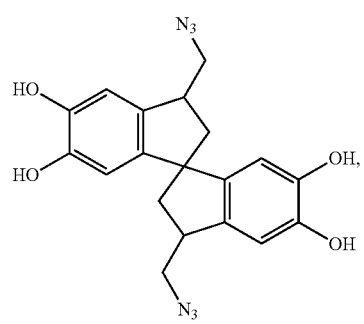
38
-continued
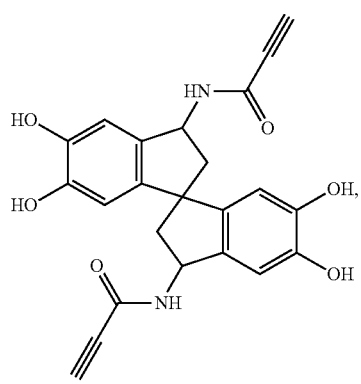
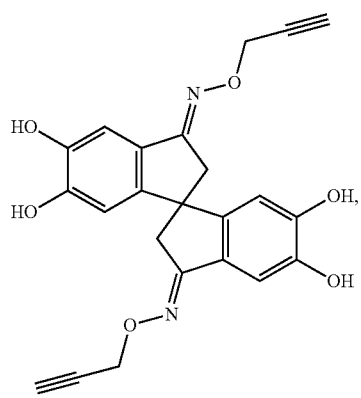
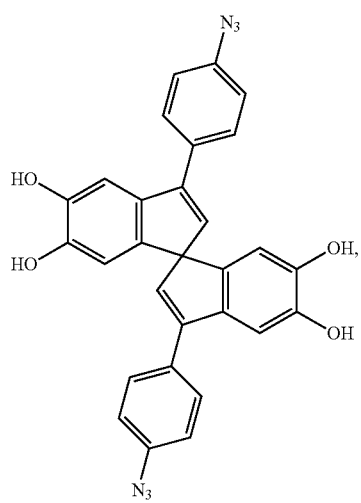

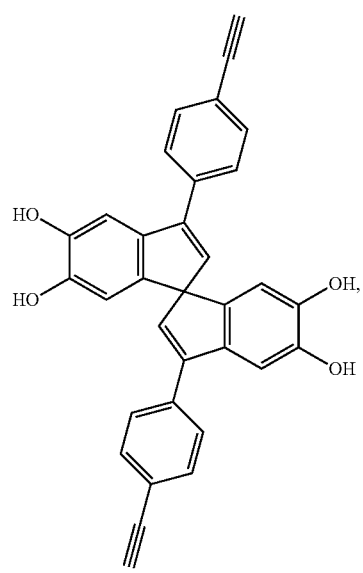
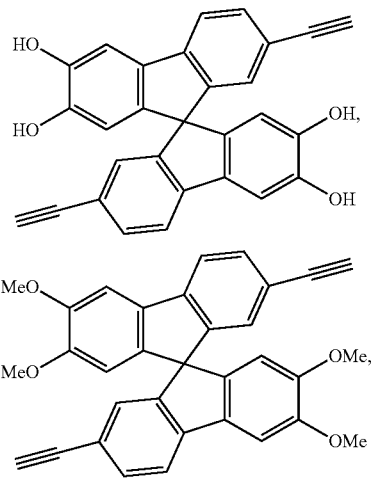
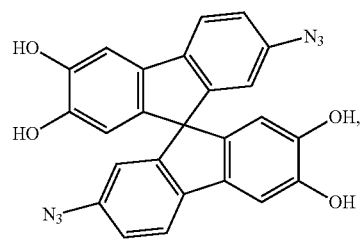
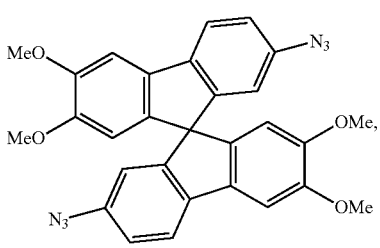
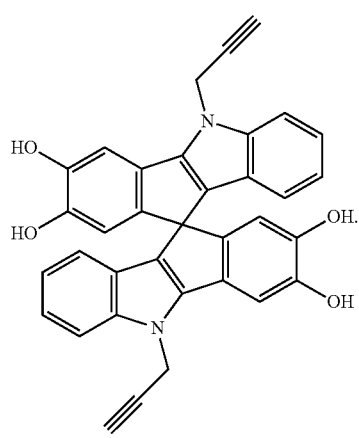 [SMILES: C#CCn1c2c(c3ccccc31)C1(c3cc(O)c(O)cc3-2)c2cc(O)c(O)cc2-c2c1c1ccccc1n2CC#C]
In one embodiment, the spirocyclic monomeric compounds according to Formula II may have the following structural formulas:
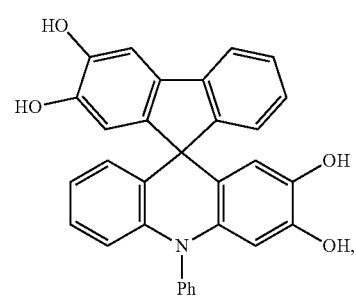
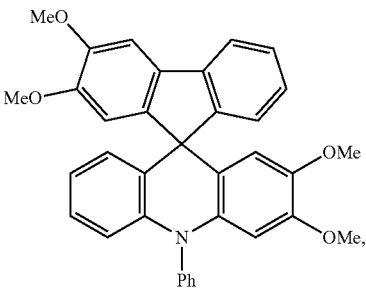
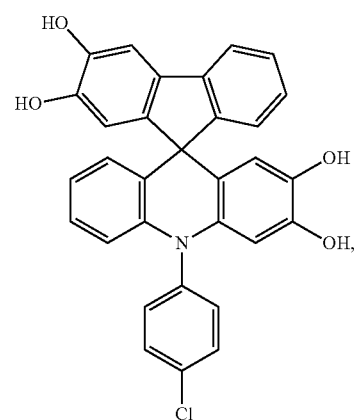

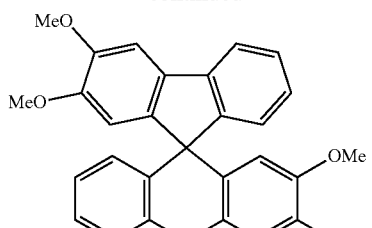
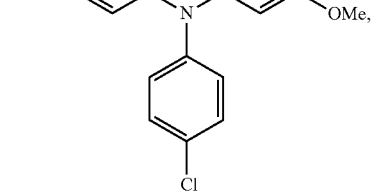
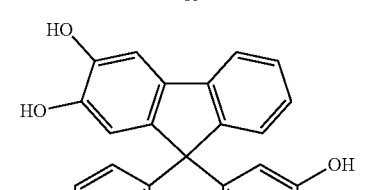
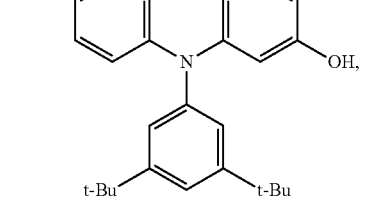
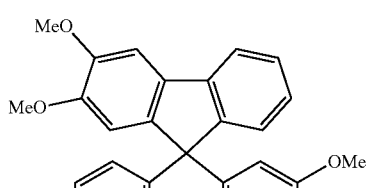
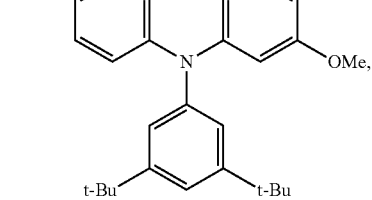
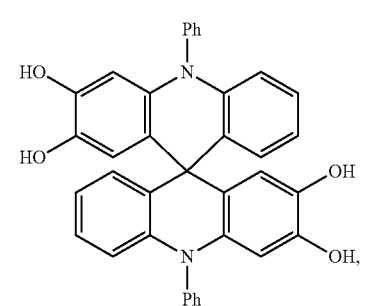
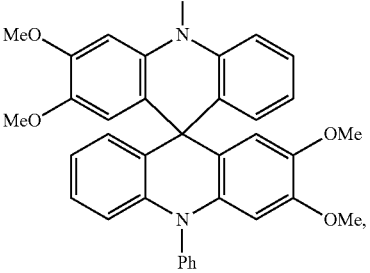
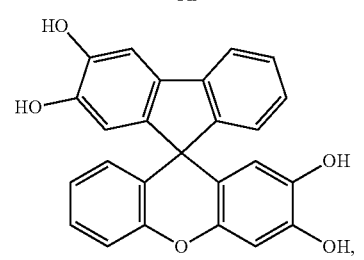
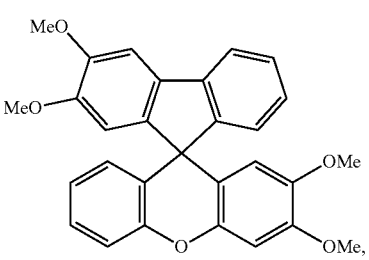
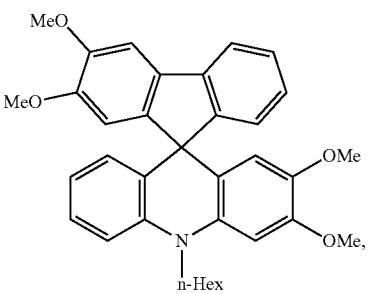
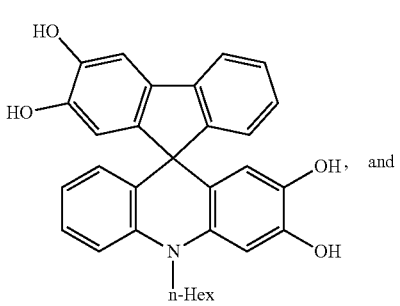

-continued

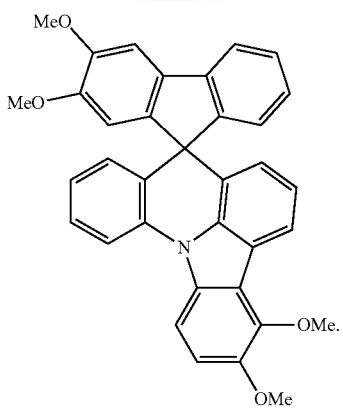

In one embodiment, the spirocyclic monomeric compounds according to Formula III may have the following structural formulas:

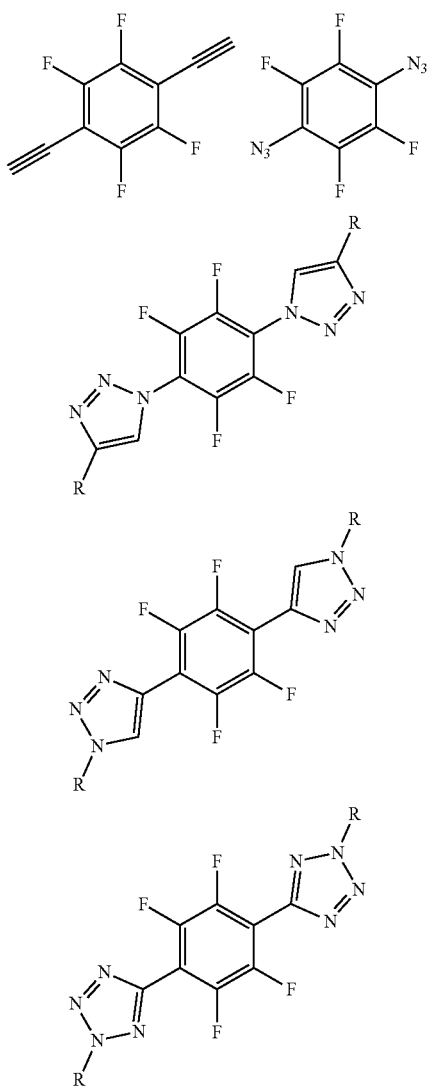

-continued

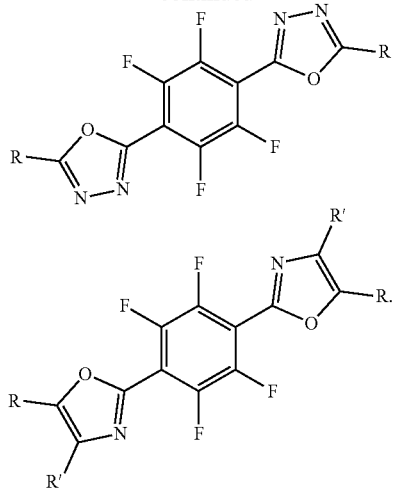

In one embodiment, R and R' are independently at each occurrence selected from substituted or unsubstituted alkyl, substituted or unsubstituted heteroalkyl, substituted or unsubstituted aryl, substituted or unsubstituted heteroaryl, —CN, —CO$_2$R", —(C═O)—N(R")$_2$, and —(C═O)—R", and where R and R' may be optionally substituted with Z.

In one embodiment, R" is selected from H, substituted or unsubstituted alkyl, substituted or unsubstituted heteroalkyl, substituted or unsubstituted aryl, and substituted or unsubstituted heteroaryl.

In one embodiment, Z is independently selected from —N$_3$, —C≡CH, C≡C—R', —C≡N, —(C═O)—H, —SH, and —CH═CH$_2$.

In one embodiment, the spirocyclic monomeric compounds according to the invention may be polymerized to yield polymers thereof. Many polymerization reactions of organic compounds may be suitable for producing polymers according to the invention. Some non-limiting examples are provided below.

In one embodiment, wherein one spirocentric compound of the invention comprises one or more —B(OR$_6$)$_2$ groups, it may be coupled with another compound, (e.g., but not limited to, another spirocentric compound of the invention) comprising a halide, e.g., a —Br, via, e.g., a palladium(0)-catalyzed Suzuki coupling reaction according to methods known in the art.

In one embodiment, wherein the compounds of the invention comprise more than one —B(OR$_6$)$_2$ groups and more than one —Br groups, the Suzuki coupling reaction may result in a polymerization reaction producing a polymer.

In another embodiment, wherein one spirocentric compound of the invention comprises one or more azide (—N$_3$) groups, it may be coupled with another compound, (e.g., but not limited to, another spirocentric compound of the invention) comprising a terminal alkyne via a copper(II)-catalyzed azide-alkyne cycloaddition reaction. In one embodiment, wherein the compounds of the invention comprise more than one azide groups and more than one terminal alkyne groups, the copper(II)-catalyzed azide-alkyne cycloaddition reaction may result in a polymerization reaction producing a polymer.

In another embodiment, wherein one spirocentric compound of the invention comprises one or more azide (—N$_3$) groups, it may be coupled with another compound, (e.g., but not limited to, another spirocentric compound of the invention) comprising a nitrile group via a Zn(II)-catalyzed cyclization reaction. In one embodiment, wherein the compounds of the invention comprise more than one azide groups and more than one nitrile groups, the zinc(II)-catalyzed azide-nitrile cycloaddition reaction may result in a polymerization reaction producing a polymer.

In another embodiment, wherein one spirocentric compound of the invention comprises one or more halide (e.g., —Br) groups, it may be coupled with another compound, (e.g., but not limited to, another spirocentric compound of the invention) comprising an amine, via, e.g., a Buchwald-Hartwig palladium(0)-catalyzed amination reaction. In one embodiment, wherein the compounds of the invention comprise more than one halide groups and more than one amine, the amination reaction may result in a polymerization reaction producing a polymer.

In the various polymer aspects presented below, n represents the number of repeating monomer units. As such, in some embodiments, n is an integer from 5 to 100,000. In another embodiment, n is from 10 to 50,000, or from 100 to 20,000, or from 1,000 to 20,000.

In one aspect, the present invention provides polymers according to Formula IV:

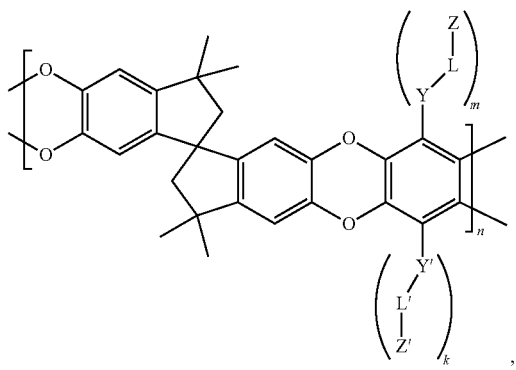

Formula IV

In one embodiment, Y is absent or selected from tetrazole and thiazole.

In one embodiment, L is absent or selected from substituted or unsubstituted $C_{1-12}$ alkyl, substituted or unsubstituted benzyl, and $C_{1-12}$ alkylcarbamate.

In one embodiment, Z is absent or selected from —$N_3$, —C≡CH, C≡C—R', —C≡N, —(C=O)—H, —SH, and —CH=$CH_2$ wherein when Y and L are both absent, Z is not absent.

In one embodiment, Z is absent or selected from —$N_3$ and —C≡CH.

In one embodiment, when Z is absent, Y is not absent or hydrogen.

In one embodiment, Y' is absent or selected from hydrogen, tetrazole, thiazole, and thioamide.

In one embodiment, Y' is selected from tetrazole, thiazole, and thioamide.

In one embodiment, L' is absent or selected from substituted or unsubstituted $C_{1-12}$ alkyl, substituted or unsubstituted benzyl, and $C_{1-12}$ alkylcarbamate.

In one embodiment, L' is selected from unsubstituted $C_{1-12}$ alkyl and unsubstituted benzyl.

In one embodiment, Z' is absent or selected from —$N_3$, —C≡CH, C≡C—R', —C≡N, —(C=O)—H, —SH, and —CH=$CH_2$ wherein when Y' and L' are both absent, Z' is not absent.

In one embodiment, Z' is absent. In one embodiment, when Z' is absent, Y' is not absent or hydrogen.

In one embodiment, R' is independently at each occurrence selected from substituted or unsubstituted alkyl, substituted or unsubstituted heteroalkyl, substituted or unsubstituted aryl, substituted or unsubstituted heteroaryl, —CN, —$CO_2R''$, —(C=O)—N(R'')$_2$, and —(C=O)—R''.

In one embodiment, R'' is selected from H, substituted or unsubstituted alkyl, substituted or unsubstituted heteroalkyl, substituted or unsubstituted aryl, and substituted or unsubstituted heteroaryl.

In one embodiment, the ratio of m to n is from about 0:1 to about 1:1. When the ratio of m to n is 0:1, none of the monomer units have Y-L-Z groups. When the ratio of m to n is 1:1, all monomer units bear a Y-L-Z group. When the ratio of m to n is between 0:1 and 1:1, some monomer units bear a Y-L-Z group. By way of non-limiting example, a ratio of m to n of 0.81:1 indicates that 81% of all monomer units have a Y-L-Z group, while 19% do not.

In one embodiment, when a monomer unit does not have a Y-L-Z group, a Z group takes its place, i.e., when the ratio of m to n is between 0:1 and 1:1, some monomer units bear a Y-L-Z group, and the rest bear a Z group. By way of non-limiting example, a ratio of m to n of 0.81:1 indicates that 81% of all monomer units have a Y-L-Z group, while 19% have a Z group.

In one embodiment, the ratio of m to n is about 0:1, or about 0.1:1, or about 0.2:1, or about 0.3:1, or about 0.4:1, or about 0.5:1, or about 0.6:1, or about 0.7:1, or about 0.8:1, or about 0.9:1, or about 1:1.

In one embodiment, the ratio of m to n is about 0:1 to 1:1, or 0.1:1 to 1:1, or 0.2:1 to 1:1, or 0.3:1 to 1:1, or 0.4:1 to 1:1, or 0.5:1 to 1:1, or 0.6:1 to 1:1, or 0.7:1 to 1:1, or 0.8:1 to 1:1, or 0.9:1 to 1:1, or 0:1 to 0.9:1, or 0:1 to 0.8:1, or 0:1 to 0.7:1, or 0:1 to 0.6:1, or 0:1 to 0.5:1, or 0:1 to 0.4:1, or 0:1:1 to 0.3:1, or 0:1 to 0.2:1, or 0:1 to 0.1:1. In one embodiment, the ratio of m to n is about 0:1 to 0.9:1, or 0:1 to 0.8:1, or 0:1 to 0.7:1, or 0:1 to 0.6:1, or 0:1 to 0.5:1, or 0:1 to 0.4:1, or 0:1 to 0.3:1, or 0:1 to 0.2:1, or 0:1 to 0.1:1.

In one embodiment, the ratio of m to n is about 0.1:1 to about 0.9:1, or about 0.2:1 to about 0.8:1, or about 0.3:1 to about 0.7:1, or about 0.4:1 to about 0.6:1. In one embodiment, the ratio of m to n is about 0.3:1 to about 1:1. In one embodiment, the ratio of m to n is about 0.1 to about 0.9. In one embodiment, the ratio of m to n is about 0.32:1, or about 0.54:1, or about 0.81:1.

In one embodiment, the ratio of k to n is from 0:1 to 1:1. When the ratio of k to n is 0:1, none of the monomer units have Y'-L'-Z' groups. When the ratio of k to n is 1:1, all monomer units bear a Y'-L'-Z' group. When the ratio of k to n is between 0:1 and 1:1, some monomer units bear a Y'-L'-Z' group. By way of non-limiting example, a ratio of k to n of 0.81:1 indicates that 81% of all monomer units have a Y'-L'-Z' group, while 19% do not.

When a monomer unit does not have a Y'-L'-Z' group, a Z' group takes its place, i.e., when the ratio of m to n is between 0:1 and 1:1, some monomer units bear a Y'-L'-Z' group, and the rest bear a Z' group. By way of non-limiting example, a ratio of m to n of 0.81:1 indicates that 81% of all monomer units have a Y'-L'-Z' group, while 19% have a Z' group.

In one embodiment, the ratio of k to n is about 0:1, or about 0.1:1, or about 0.2:1, or about 0.3:1, or about 0.4:1, or about 0.5:1, or about 0.6:1, or about 0.7:1, or about 0.8:1, or about 0.9:1, or about 1:1.

In one embodiment, the ratio of k to n is about 0:1 to 1:1, or 0.1:1 to 1:1, or 0.2:1 to 1:1, or 0.3:1 to 1:1, or 0.4:1 to 1:1, or 0.5:1 to 1:1, or 0.6:1 to 1:1, or 0.7:1 to 1:1, or 0.8:1 to 1:1, or 0.9:1 to 1:1, or 0:1 to 0.9:1, or 0:1 to 0.8:1, or 0:1 to 0.7:1, or 0:1 to 0.6:1, or 0:1 to 0.5:1, or 0:1 to 0.4:1, or 0:1:1 to 0.3:1, or 0:1 to 0.2:1, or 0:1 to 0.1:1. In one embodiment, the ratio of k to n is about 0:1 to 0.9:1, or 0:1 to 0.8:1, or 0:1 to 0.7:1, or 0:1 to 0.6:1, or 0:1 to 0.5:1, or 0:1 to 0.4:1, or 0:1 to 0.3:1, or 0:1 to 0.2:1, or 0:1 to 0.1:1.

In one embodiment, the ratio of k to n is about 0.1:1 to about 0.9:1, or about 0.2:1 to about 0.8:1, or about 0.3:1 to about 0.7:1, or about 0.4:1 to about 0.6:1. In one embodiment, the ratio of m to n is about 0.3:1 to about 1:1. In one embodiment, the ratio of k to n is about 0.1 to about 0.9. In one embodiment, the ratio of m to n is about 0.32:1, or about 0.54:1, or about 0.81:1.

In one embodiment, the ratio of k to n is about 0:1 to about 0.7:1. In one embodiment, the ratio of k to n is about 0.1:1 to about 0.9:1.

In one embodiment, n is an integer from 5 to 100,000. In another embodiment, n is from 10 to 50,000, or from 100 to 20,000, or from 1,000 to 20,000.

In one embodiment, when Z' is absent, Y' is not absent or hydrogen.

In one aspect, the present invention provides polymers according to Formula V:

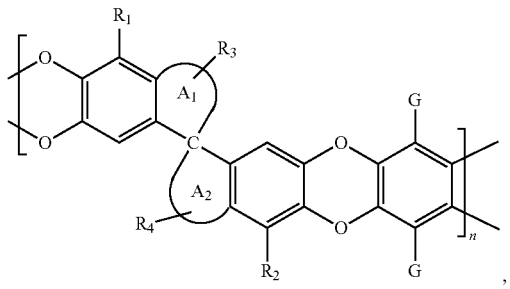

Formula V in all structures the carbon indicated by "C" denotes a spiro-carbon.

In one embodiment, $A_1$ is selected from

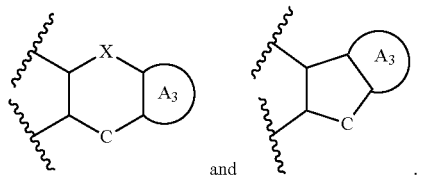

and

In one embodiment, $A_2$ is

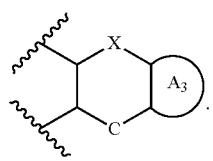

In one embodiment, X is independently at each occurrence selected from $-CR_6-$, $-O-$, $-S-$, $-N(R_6)_2$, $-C=O$, $-C=NR_6$, $-C=N-N(R_6)_2$, and $C=N-OR_6$.

In one embodiment, $R_1$, $R_2$, $R_3$, and $R_4$ are each independently selected from H and Y—Z.

$R_6$ is independently at each occurrence selected from H, substituted or unsubstituted alkyl, substituted or unsubstituted heteroalkyl, substituted or unsubstituted aryl, and substituted or unsubstituted heteroaryl, In one embodiment, $A_3$ is a selected from substituted or unsubstituted $C_5$-$C_6$ aryl, substituted or unsubstituted $C_5$-$C_6$ heteroaryl, substituted or unsubstituted $C_5$-$C_6$ cycloalkyl and substituted or unsubstituted $C_5$-$C_6$ cyclic heterocycloalkyl.

In one embodiment, Y is independently absent or selected from substituted or unsubstituted alkyl, substituted or unsubstituted aryl, $-NH-(C=O)-$; $=NO-C_{1-6}$ alkyl-; and $-(C=O)$-phenyl-.

In one embodiment, Z is independently absent or selected from $-N_3$, $-C\equiv CH$, $-C\equiv N$, and $-(C=O)-H$, $-SH$, and $-CH=CH_2$.

In one embodiment, G is selected from halogen, $-CN$, substituted or unsubstituted aryl, and substituted or unsubstituted heteroaryl.

In one embodiment, n is an integer from 5 to 100,000. In another embodiment, n is from 10 to 50,000, or from 100 to 20,000, or from 1,000 to 20,000.

In one embodiment, the polymer of Formula V may have $A_1$ and $A_2$ each independently selected from:

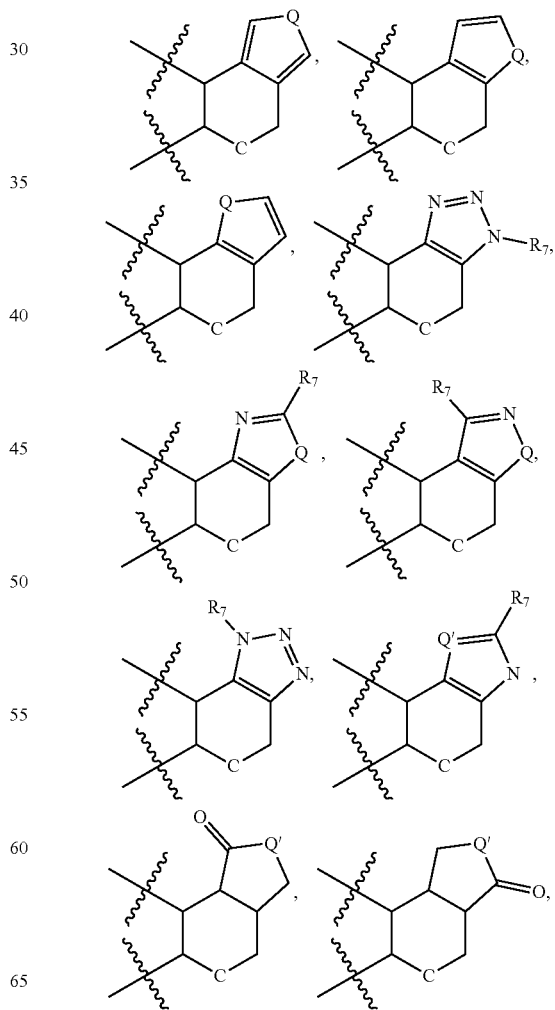

-continued
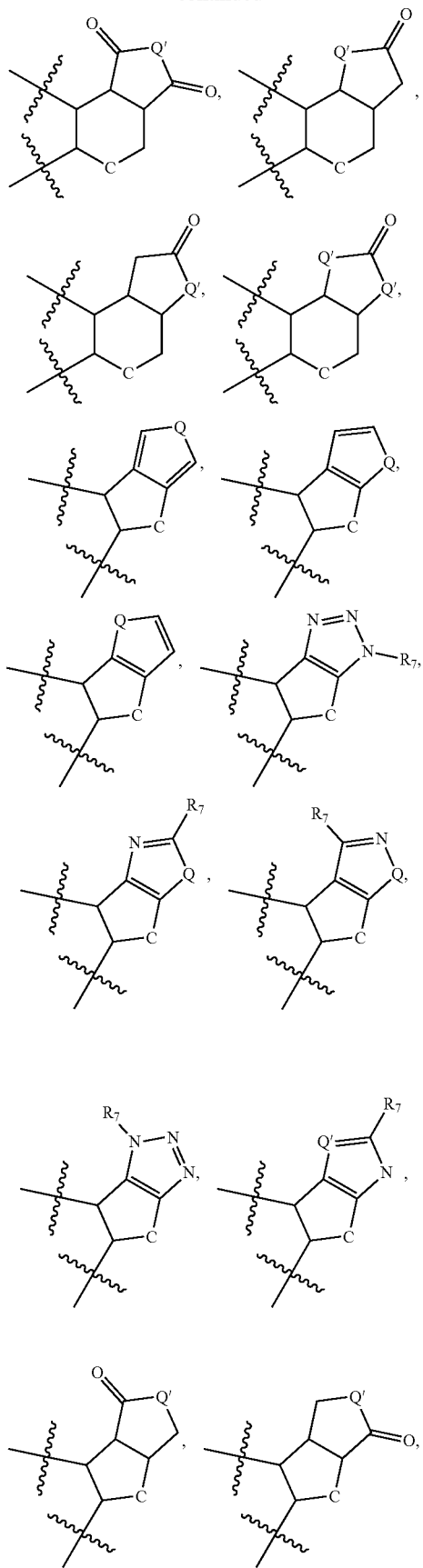
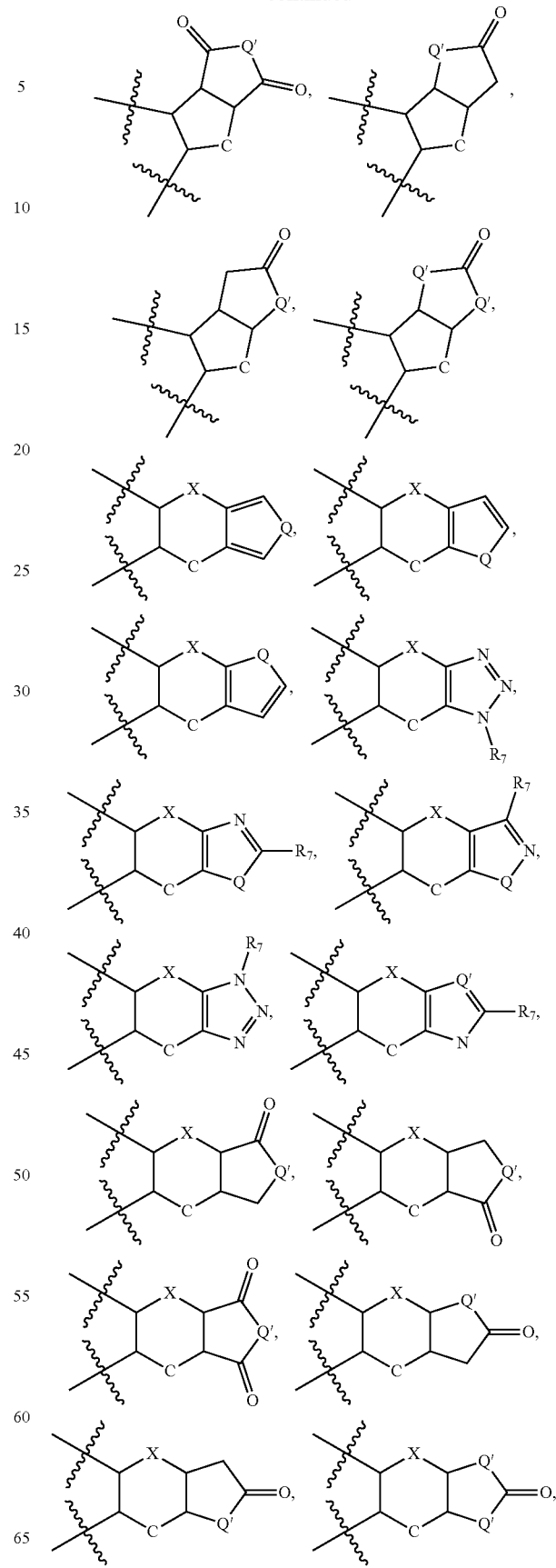

-continued
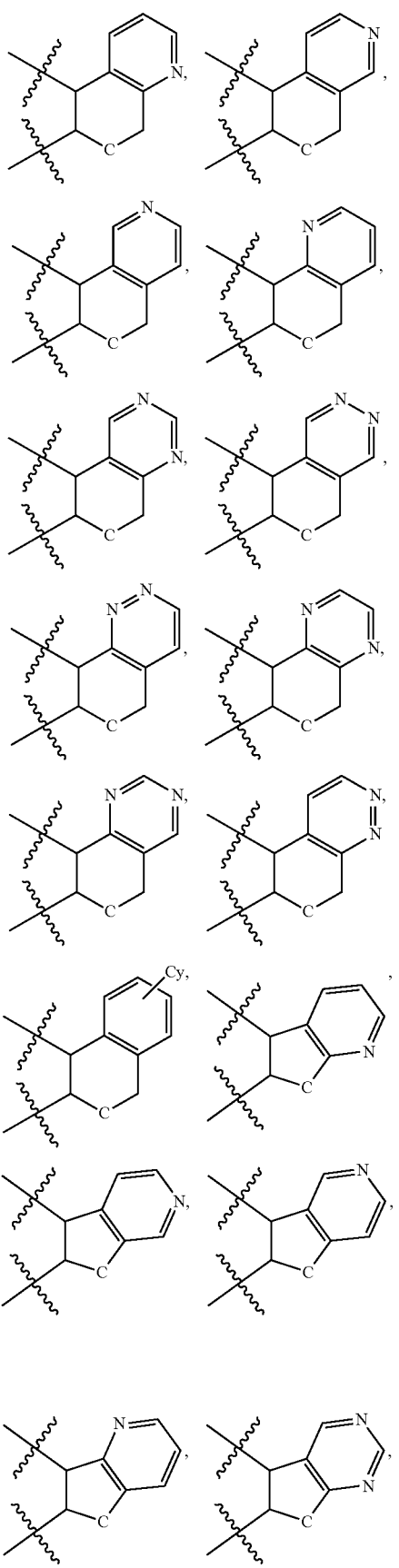
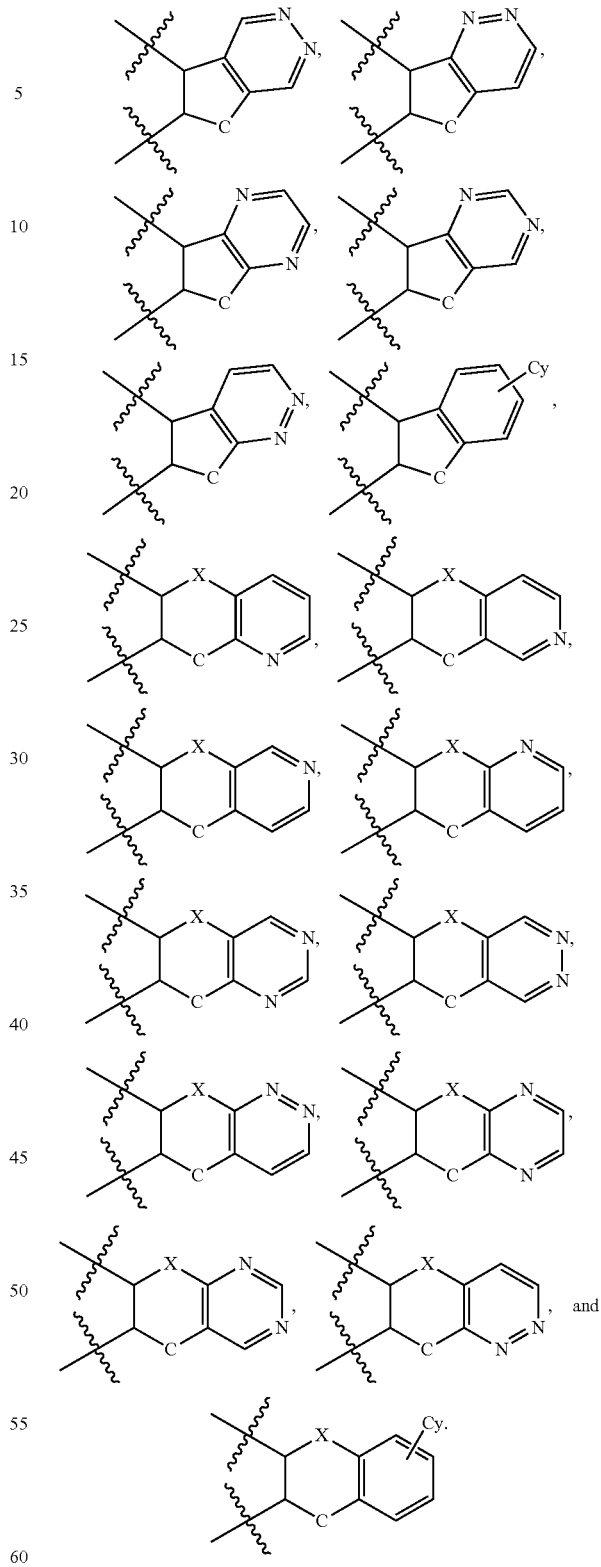
In one embodiment, X is selected from —CR$_6$, —O—, —S—, N(R$_6$)$_2$, —C=O, —C=NR$_6$, —C=N—N(R$_6$)$_2$, and C=N—OR$_6$.
In one embodiment, C$_y$ is selected from substituted or unsubstituted C$_5$-C$_6$ aryl, substituted or unsubstituted C$_5$-C$_6$ heteroaryl, substituted or unsubstituted $C_5$-$C_6$ cycloalkyl and substituted or unsubstituted $C_5$-$C_6$ cyclic heterocycloalkyl.

In one embodiment, Q is selected from —O—, —S—, —N—$R_7$, —C=O, —C=$NR_7$, —C=N—N($R_7$)$_2$, and —C=N—O$R_7$.

In one embodiment, Q' is independently at each occurrence selected from —O—, —S—, and —N—$R_7$.

$R_6$ is independently at each occurrence selected from H, substituted or unsubstituted alkyl, substituted or unsubstituted heteroalkyl, substituted or unsubstituted aryl, and substituted or unsubstituted heteroaryl.

In one embodiment, $R_7$ is independently at each occurrence selected from $R_3$ and $R_4$.

In one embodiment, the polymer of Formula V may have the structure selected from:

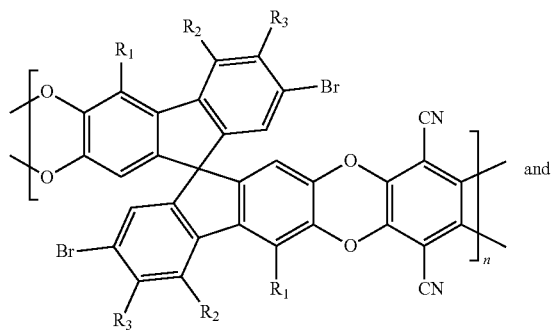

and

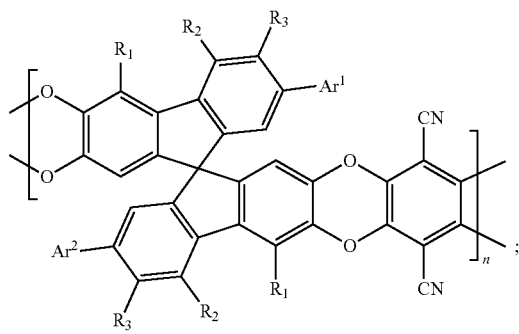

In one embodiment, at least one of $R_1$, $R_2$, and $R_3$ is substituted with Z.

In one embodiment, Z is independently absent or selected from —$N_3$, —C≡CH, C≡C—R', —C≡N, and —(C=O)—H, —SH, and —CH=$CH_2$.

In one embodiment, $Ar^1$ and $Ar^2$ are independently selected from substituted and unsubstituted aryl. In one aspect, the present invention provides polymers according to Formula VI:

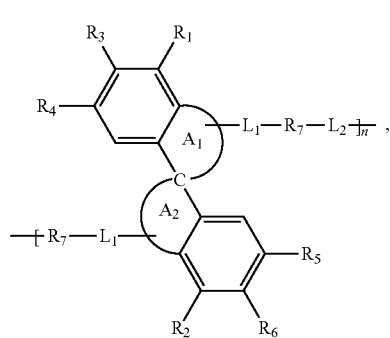

Formula VI in all structures the carbon indicated by "C" denotes a spiro-carbon.

In one embodiment, $A_1$ and $A_2$ are independently at each occurrence selected from:

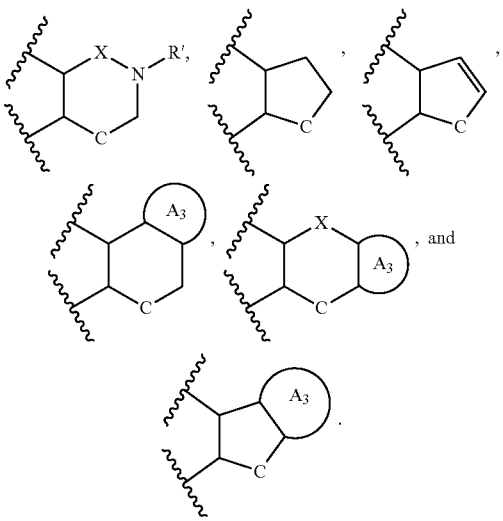

In one embodiment, X is —$CR_2"$—, —O—, —S—, N(R")$_2$, —C=O, —C=NR", —C=N—N(R")$_2$, and C=N—OR".

In one embodiment, $R_1$, $R_2$, $R_3$, $R_4$, $R_5$, $R_6$ are independently selected from H, —OR", —OSi(R")$_3$, Si(R")$_3$, substituted or unsubstituted alkyl, substituted or unsubstituted heteroalkyl, substituted or unsubstituted aryl, substituted or unsubstituted heteroaryl, substituted or unsubstituted cycloalkyl and substituted or unsubstituted heterocycloalkyl, wherein at least one of $R_1$, $R_2$, $R_3$, $R_4$, $R_5$, $R_6$, is further substituted with Z.

In one embodiment, $R_7$ is absent or selected from substituted or unsubstituted aryl, substituted or unsubstituted heteroaryl; substituted or unsubstituted arylamine, and imido.

In one embodiment, $A_3$ is a selected from substituted or unsubstituted $C_5$-$C_6$ aryl, substituted or unsubstituted $C_5$-$C_6$ heteroaryl, substituted or unsubstituted $C_5$-$C_6$ cycloalkyl and substituted or unsubstituted $C_5$-$C_6$ cyclic heterocycloalkyl.

In one embodiment, Z is independently selected from —$N_3$, —C≡CH, C≡C—R', —C≡N, —(C=O)—H, —SH, and —CH=$CH_2$.

In one embodiment, R' is selected from substituted or unsubstituted alkyl, substituted or unsubstituted heteroalkyl, substituted or unsubstituted aryl, substituted or unsubstituted heteroaryl, —CN, —CO$_2$R$_6$, —(C=O)—N(R")$_2$, and —(C=O)—R".

In one embodiment, R is independently at each occurrence selected from H, substituted or unsubstituted alkyl, substituted or unsubstituted heteroalkyl, substituted or unsubstituted aryl, and substituted or unsubstituted heteroaryl.

In one embodiment, L$_1$ and L$_2$ are independently selected from a bond, substituted or unsubstituted alkyl, substituted or unsubstituted cycloalkyl, substituted or unsubstituted alkynyl, substituted or unsubstituted aryl, and substituted or unsubstituted heteroaryl.

In one embodiment, the polymer of Formula VI may have A$_1$ and A$_2$ each independently selected from:

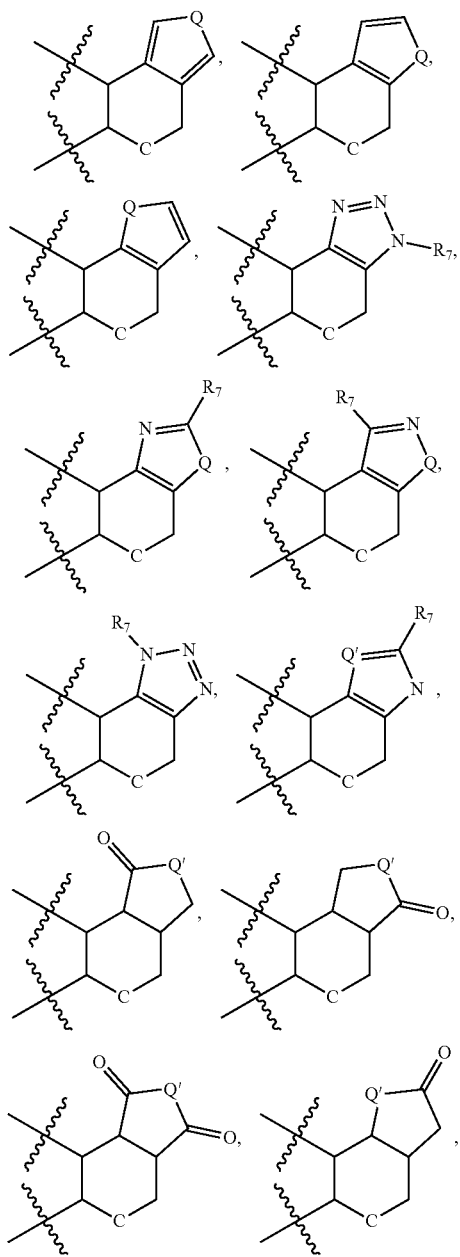

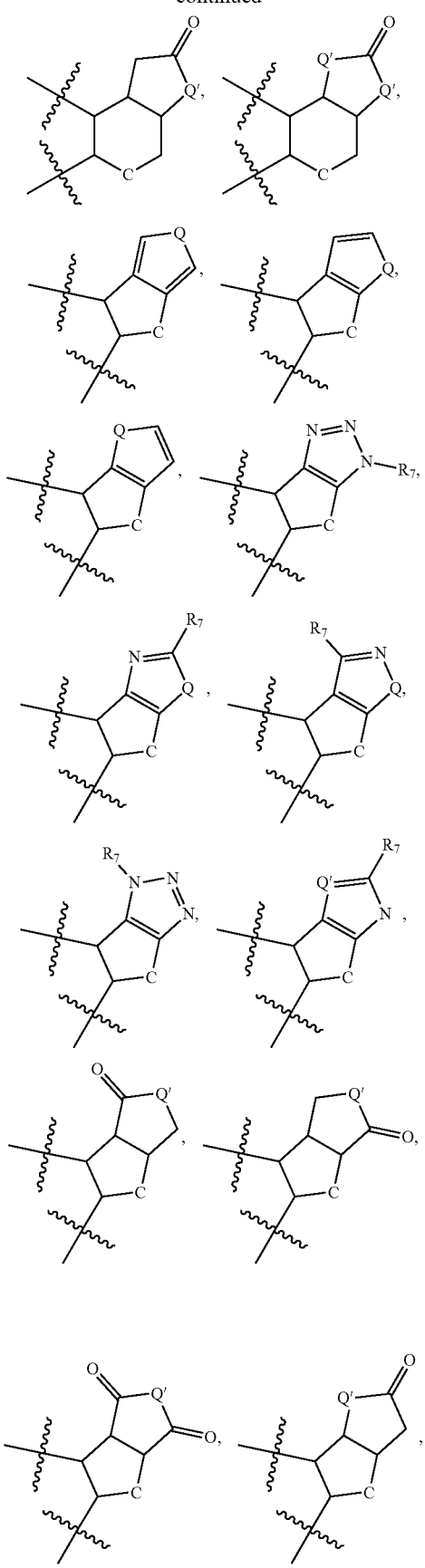

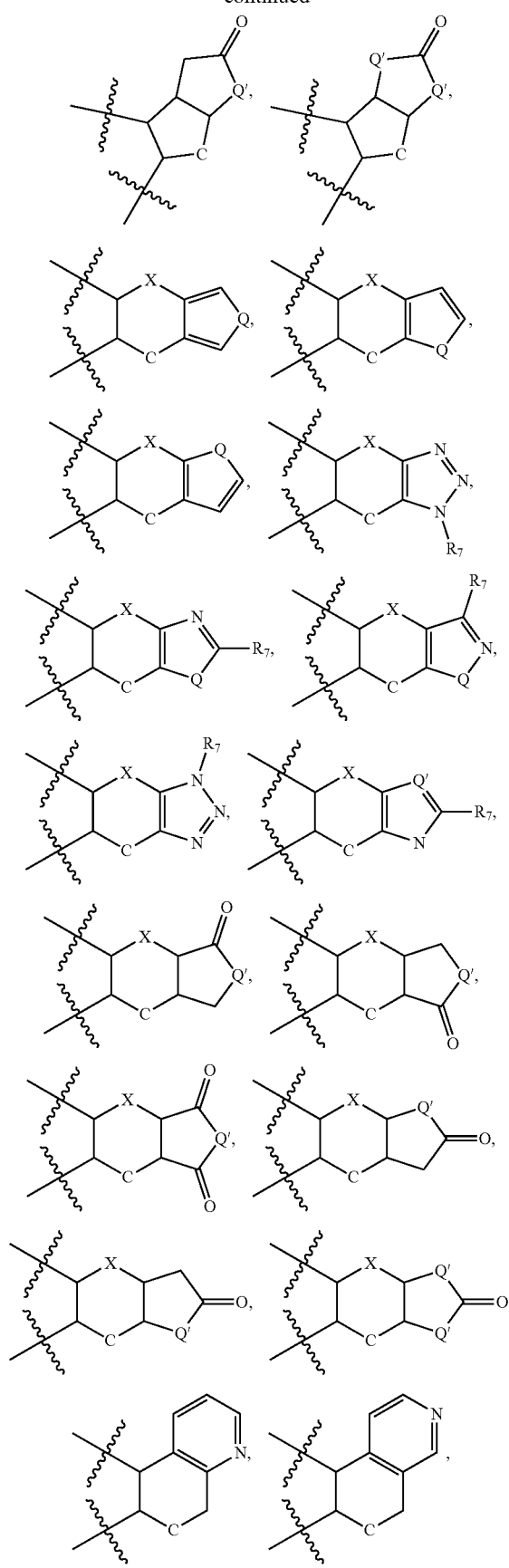
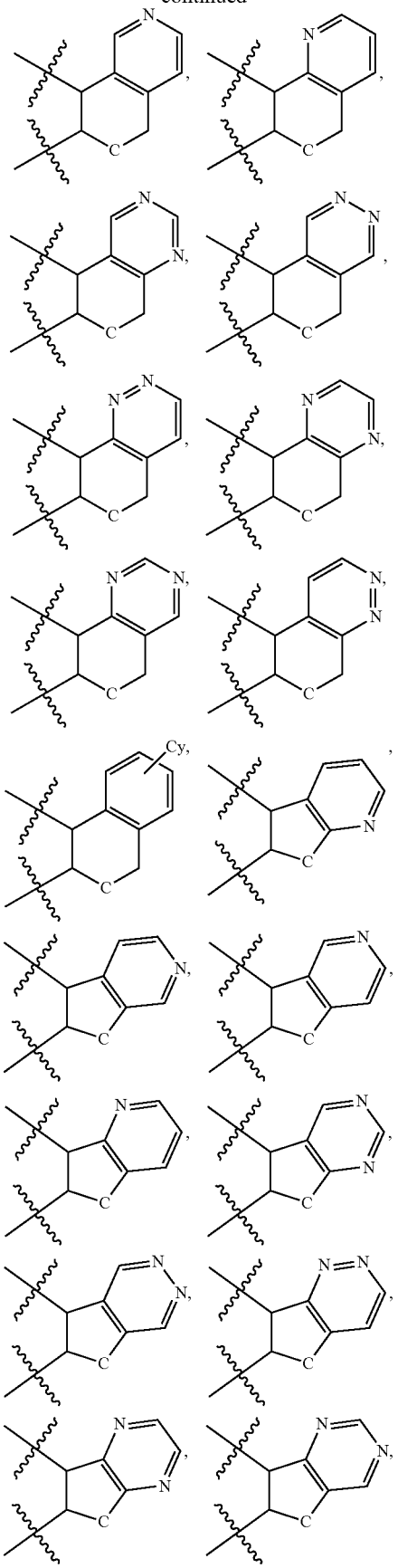

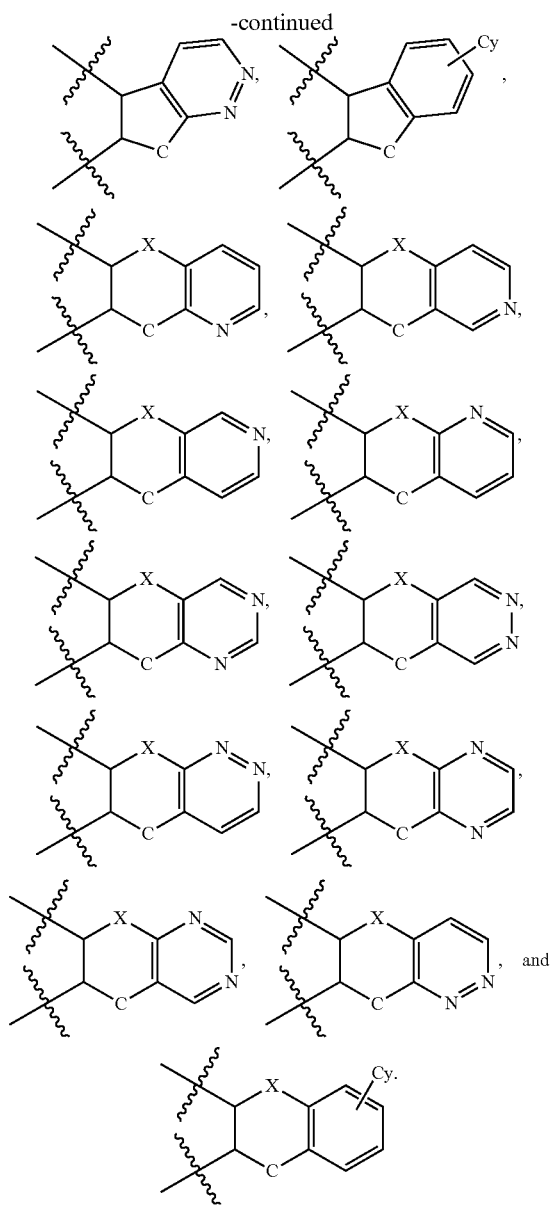

In one aspect, the present invention provides polymers according to Formula VII:

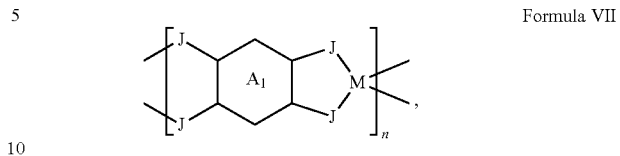

In one embodiment, M is selected from —C—, —Si—, —Sn—, —Ti—, and —Zr—.

In one embodiment, J is selected from —O— and —CH$_2$.

In one embodiment, A$_1$ is a selected from substituted or unsubstituted aryl and substituted or unsubstituted heteroaryl.

In one embodiment, n is an integer from 5 to 100,000.

In one embodiment, the polymers according to Formula VII may have the structure selected from

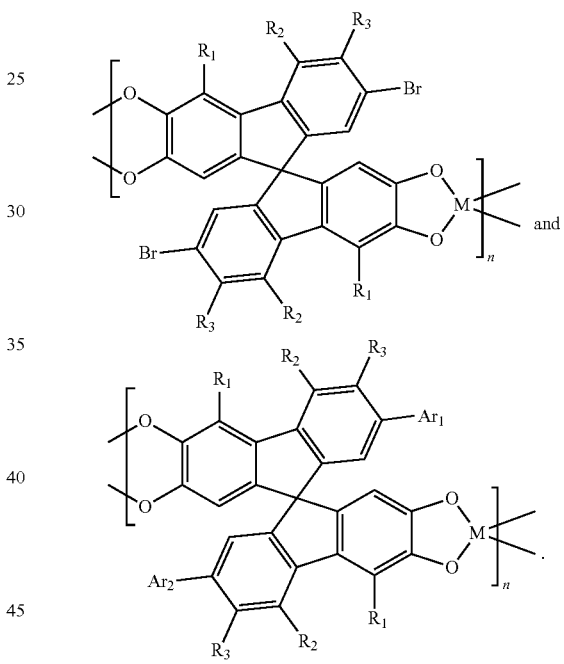

In one embodiment, X is selected from —CR", —O—, —S—, NR", —C═O, —C═NR", —C═N—N(R")$_2$, and C═N—OR".

In one embodiment, C$_y$ is selected from substituted or unsubstituted C$_5$-C$_6$ aryl, substituted or unsubstituted C$_5$-C$_6$ heteroaryl, substituted or unsubstituted C$_5$-C$_6$ cycloalkyl and substituted or unsubstituted C$_5$-C$_6$ cyclic heterocycloalkyl.

In one embodiment, Q is selected from —O—, —S—, —N—R$_7$, —C═O, —C═NR$_7$, —C═N—N(R$_7$)$_2$, and —C═N—OR$_7$.

In one embodiment, Q' is independently at each occurrence selected from —O—, —S—, and —N—R$_7$.

In one embodiment, R$_7$ is independently at each occurrence selected from R$_3$ and R$_4$.

In one embodiment, R" is independently at each occurrence selected from H, substituted or unsubstituted alkyl, substituted or unsubstituted heteroalkyl, substituted or unsubstituted aryl, and substituted or unsubstituted heteroaryl.

In one embodiment, R$_1$, R$_2$, and R$_3$ are independently selected from H, substituted or unsubstituted alkyl, substituted or unsubstituted heteroalkyl, substituted or unsubstituted aryl, substituted or unsubstituted heteroaryl, substituted or unsubstituted cycloalkyl and substituted or unsubstituted heterocycloalkyl, —OR', —SR', N(R")$_2$, and wherein at least one of R$_1$, R$_2$, and R$_3$ is substituted with Z; Z is independently selected from —N$_3$, —C≡CH, C≡C—R', —C≡N, —(C═O)—H, —SH, and —CH═CH$_2$.

In one embodiment, R' is selected from substituted or unsubstituted alkyl, substituted or unsubstituted heteroalkyl, substituted or unsubstituted aryl, substituted or unsubstituted heteroaryl, —CN, —CO$_2$R", —(C═O)—N(R")$_2$, and —(C═O)—R".

In one embodiment, R" is independently at each occurrence selected from H, substituted or unsubstituted alkyl, substituted or unsubstituted heteroalkyl, substituted or unsubstituted aryl, and substituted or unsubstituted heteroaryl.

In one embodiment, Ar¹ and Ar² are independently selected from substituted and unsubstituted aryl.

In one aspect, the present invention provides polymers according to Formula VIII:

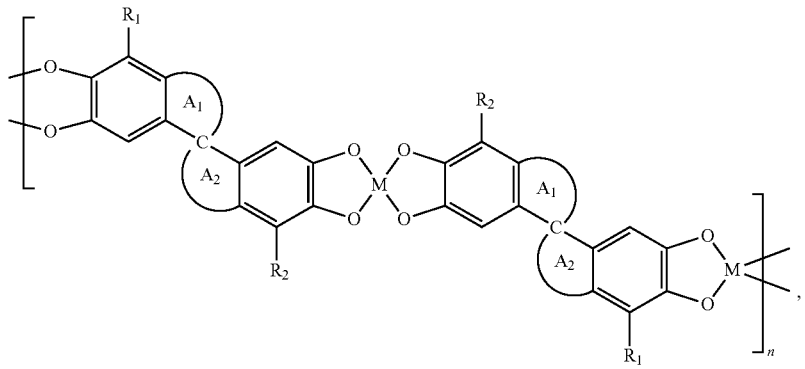

Formula VIII in all structures the carbon indicated by "C" denotes a spiro-carbon.

In one embodiment, M is selected from —C—, —Si—, —Sn—, —Ti—, and —Zr—.

In one embodiment, $A_1$ and $A_2$ are each independently selected from:

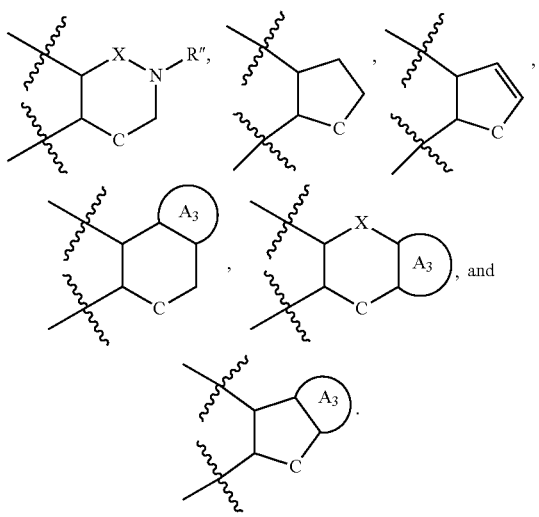

In one embodiment, $A_3$ is a selected from substituted or unsubstituted $C_5$-$C_6$ aryl, substituted or unsubstituted $C_5$-$C_6$ heteroaryl, substituted or unsubstituted $C_5$-$C_6$ cycloalkyl and substituted or unsubstituted $C_5$-$C_6$ cyclic heterocycloalkyl.

In one embodiment, —CR", —O—, —S—, NR", —C═O, —C═NR", —C═N—N(R")$_2$, and C═N—OR"—.

In one embodiment, Z is independently selected from —N$_3$, —C≡CH, C≡C—R', —C≡N, —(C═O)—H, —SH, and —CH═CH$_2$.

In one embodiment, R$_1$ and R$_2$, are independently selected from H, substituted or unsubstituted alkyl, substituted or unsubstituted heteroalkyl, substituted or unsubstituted aryl, substituted or unsubstituted heteroaryl, substituted or unsubstituted cycloalkyl and substituted or unsubstituted heterocycloalkyl, wherein at least one of R$_1$, and R$_2$, is further substituted with Z.

In one embodiment, R' is selected from H, substituted or unsubstituted alkyl, substituted or unsubstituted heteroalkyl, substituted or unsubstituted aryl, substituted or unsubstituted heteroaryl, —CN, —CO$_2$R", —(C═O)—N(R")$_2$, and —(C═O)—R".

In one embodiment, R" is selected from H, substituted or unsubstituted alkyl, substituted or unsubstituted heteroalkyl, substituted or unsubstituted aryl, and substituted or unsubstituted heteroaryl.

In one embodiment, n is an integer from 5 to 100,000.

In one embodiment, the polymer of Formula VIII may have $A_1$ and $A_2$ each

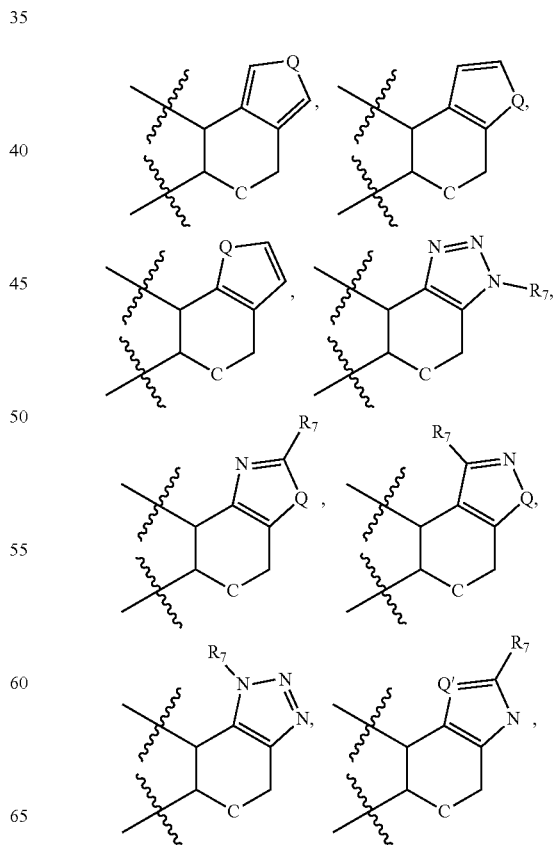

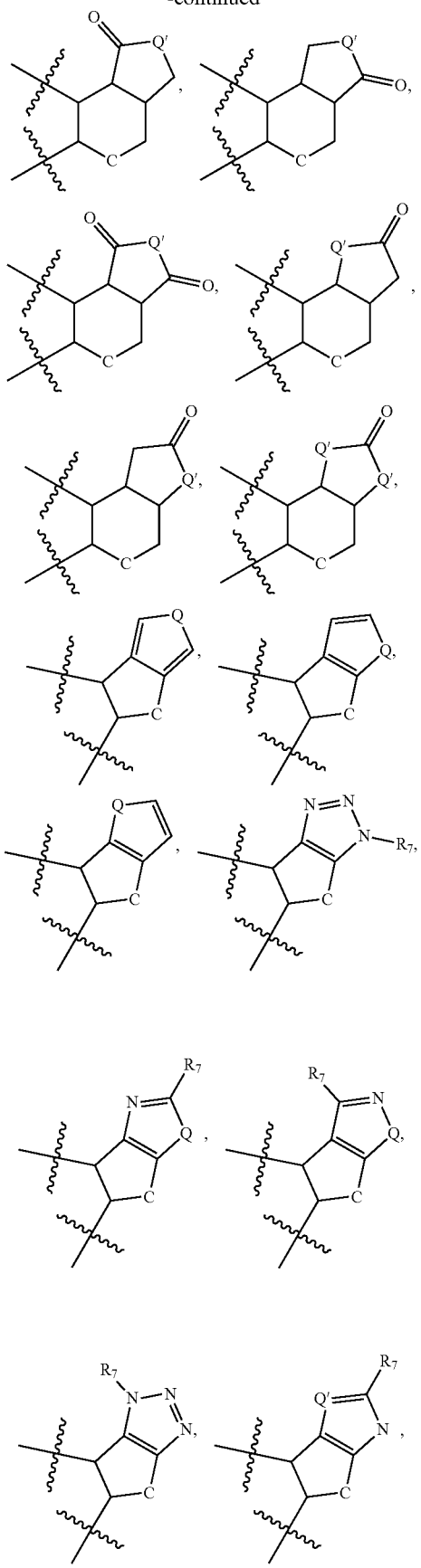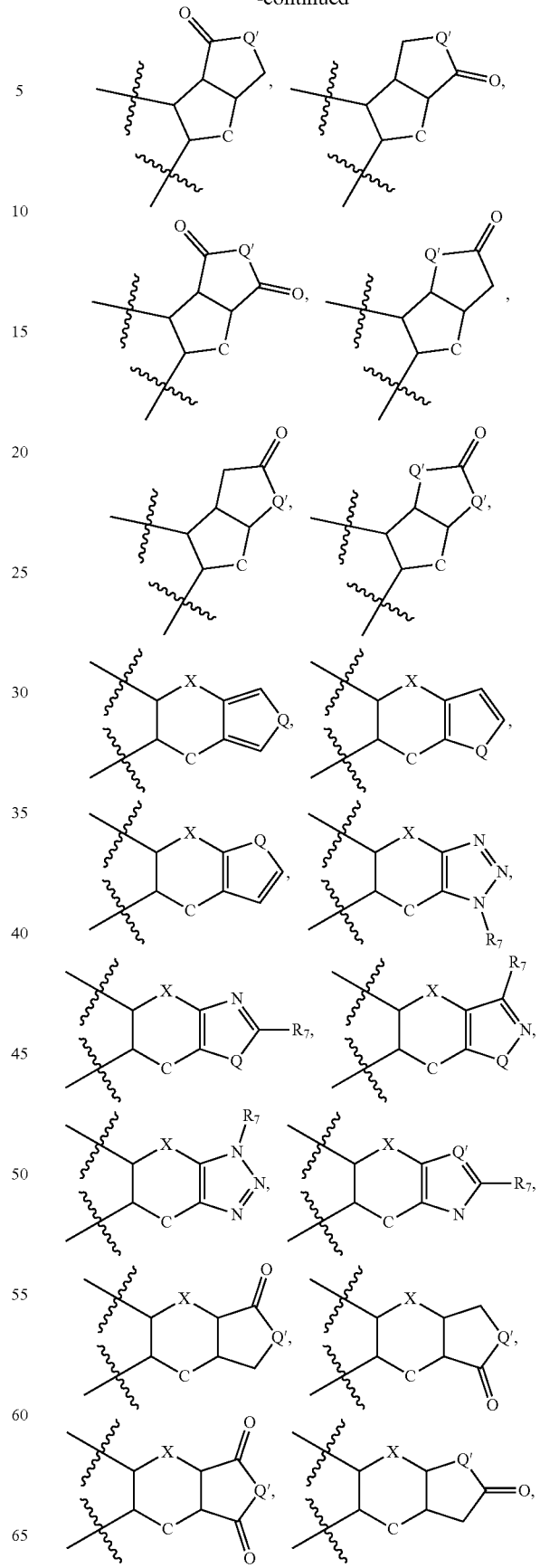

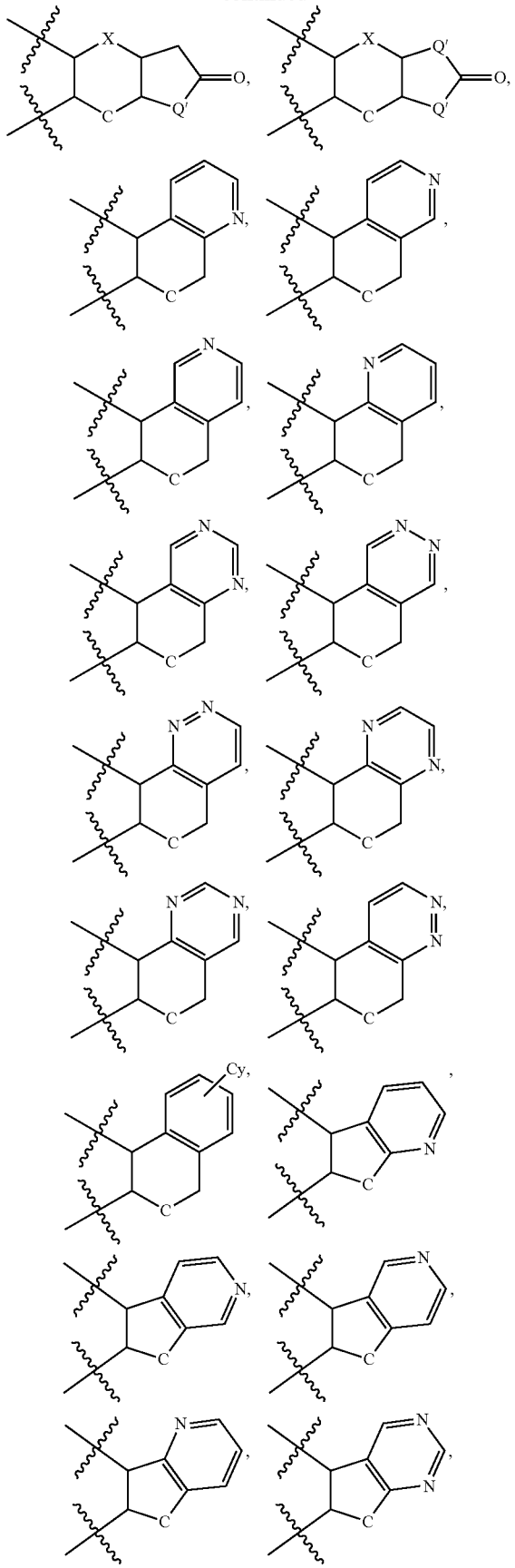
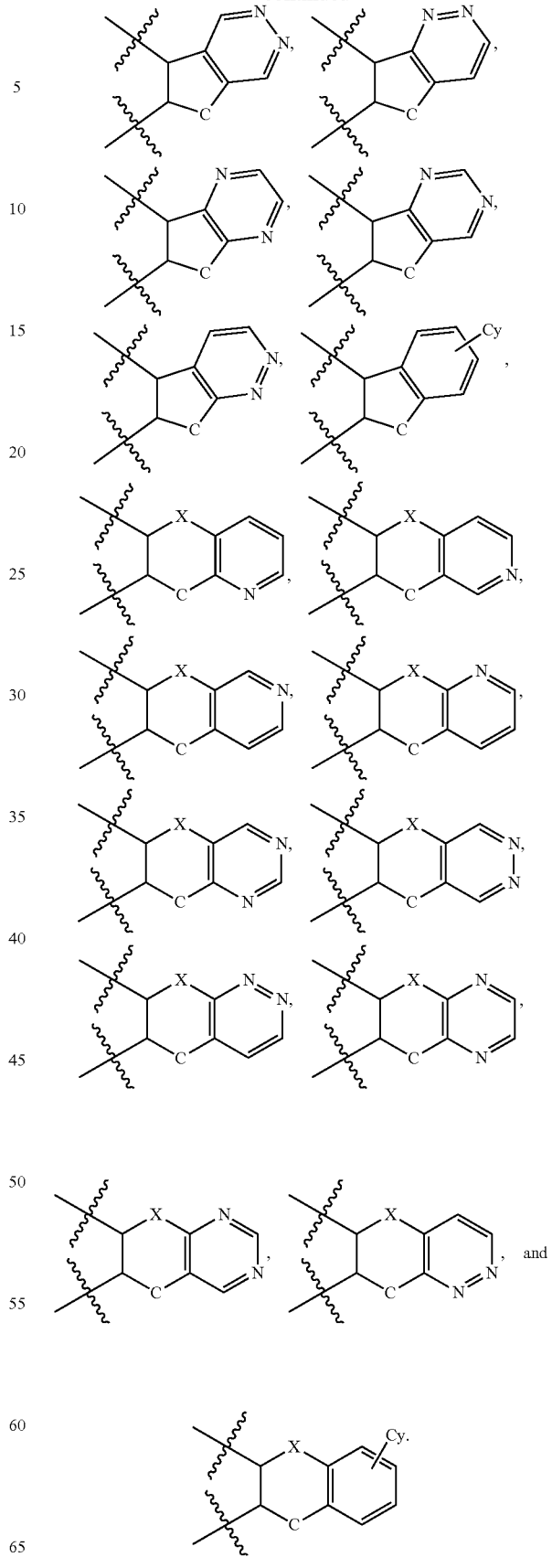

In one embodiment, X is selected from —CR", —O—, —S—, NR", —C=O, —C=NR", —C=N—N(R")$_2$, and C=N—OR".

In one embodiment, C$_y$ is selected from substituted or unsubstituted C$_5$-C$_6$ aryl, substituted or unsubstituted C$_5$-C$_6$ heteroaryl, substituted or unsubstituted C$_5$-C$_6$ cycloalkyl and substituted or unsubstituted C$_5$-C$_6$ cyclic heterocycloalkyl.

In one embodiment, Q is selected from —O—, —S—, —N—R$_7$, —C=O, —C=NR$_7$, —C=N—N(R$_7$)$_2$, and —C=N—OR$_7$.

In one embodiment, Q' is independently at each occurrence selected from —O—, —S—, and —N—R$_7$.

In one embodiment, R" is independently at each occurrence selected from H, substituted or unsubstituted alkyl, substituted or unsubstituted heteroalkyl, substituted or unsubstituted aryl, and substituted or unsubstituted heteroaryl.

In one embodiment, R$_7$ is independently at each occurrence selected from R$_3$ and R$_4$.

In one aspect, the present invention provides polymers according to the following formula:

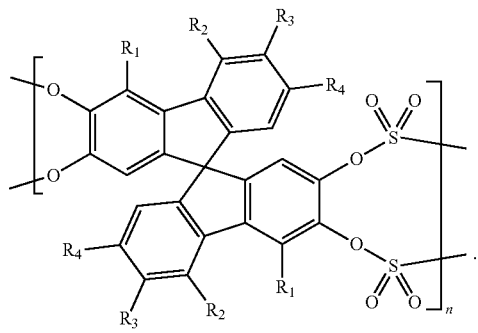

In one embodiment, R$_1$, R$_2$, R$_3$, and R$_4$ are independently selected from H, substituted or unsubstituted alkyl, substituted or unsubstituted heteroalkyl, substituted or unsubstituted aryl, substituted or unsubstituted heteroaryl, —OR', —SR', N(R")$_2$, wherein at least one of R$_1$, R$_2$, R$_3$, and R$_4$ is further substituted with Z.

In one embodiment, Z is independently selected from —N$_3$, —C≡CH, C≡C—R', —C≡N, —(C=O)—H, —SH, and —CH=CH$_2$.

In one embodiment, R' is selected from substituted or unsubstituted alkyl, substituted or unsubstituted heteroalkyl, substituted or unsubstituted aryl, substituted or unsubstituted heteroaryl, —CN, —CO$_2$R$_6$, —(C=O)—N(R")$_2$, and —(C=O)—R".

In one embodiment, R" is independently at each occurrence selected from H, substituted or unsubstituted alkyl, substituted or unsubstituted heteroalkyl, substituted or unsubstituted aryl, and substituted or unsubstituted heteroaryl.

In one embodiment, n is an integer from 5 to 100,000.

In one embodiment, the polymers of the invention may have the following structural formulas:

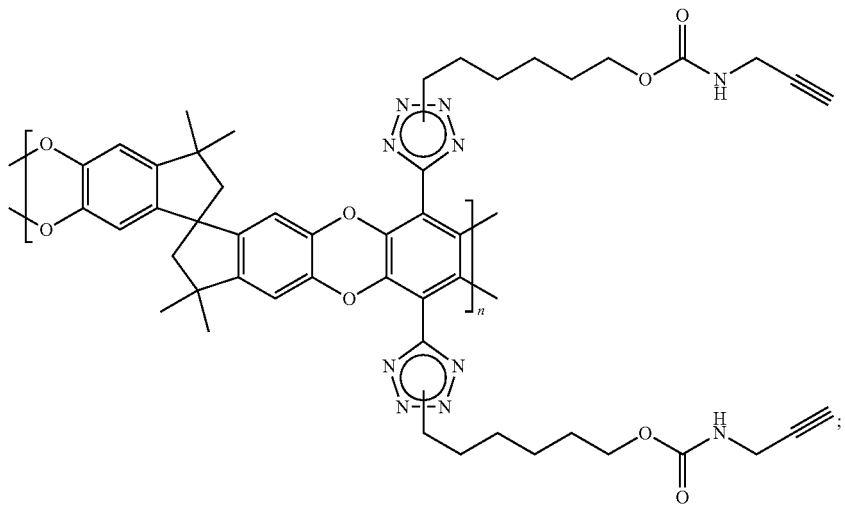

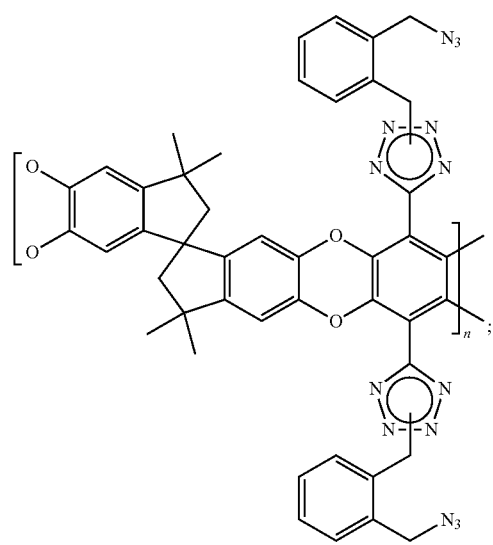
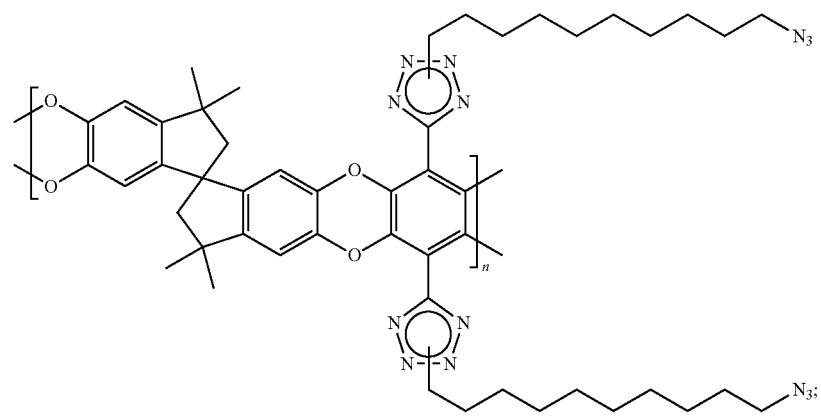
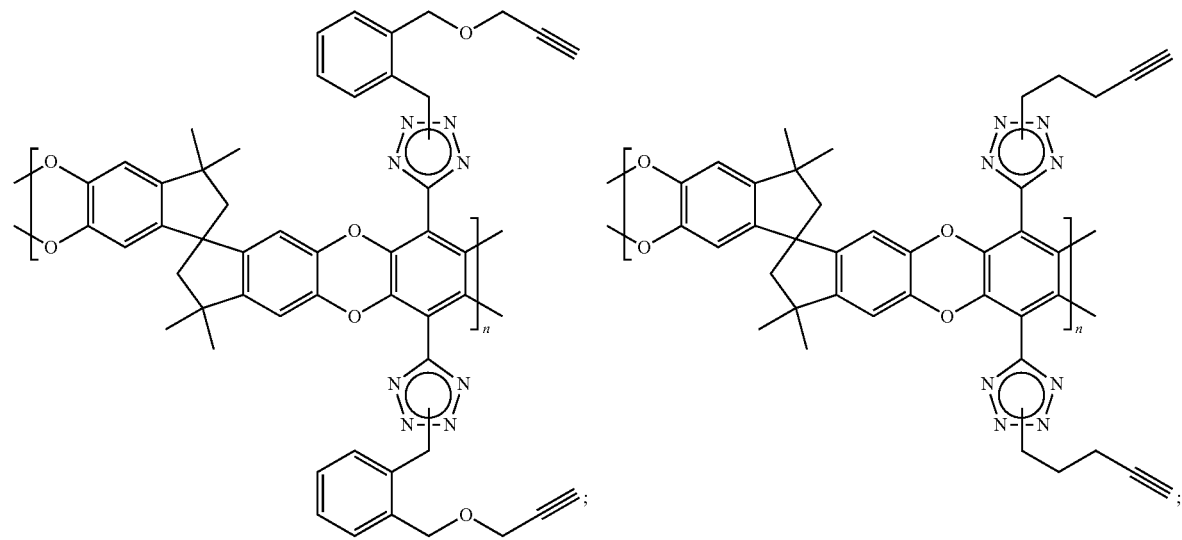

-continued
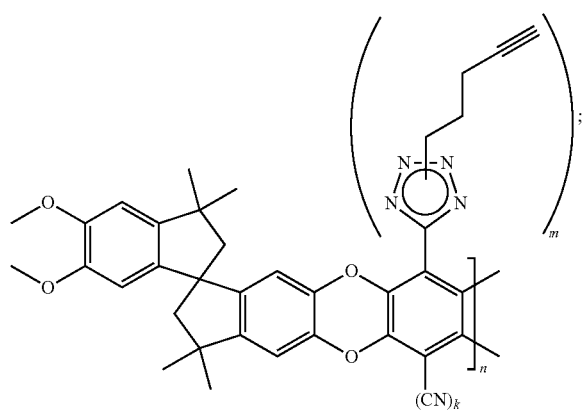
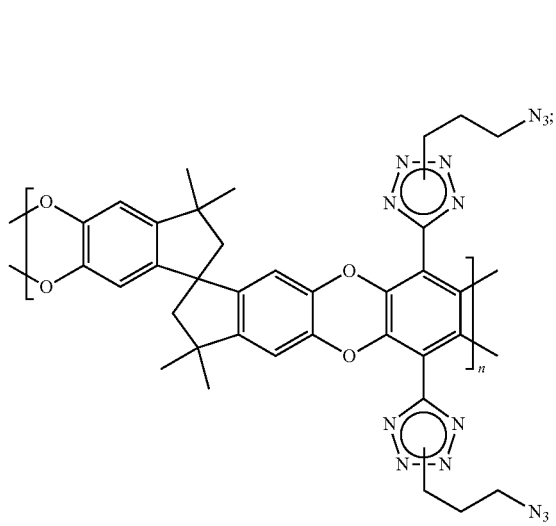
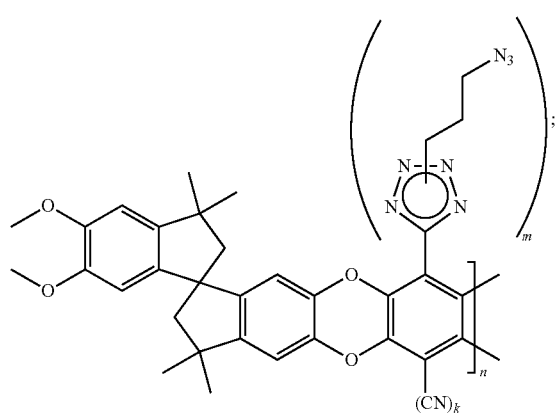
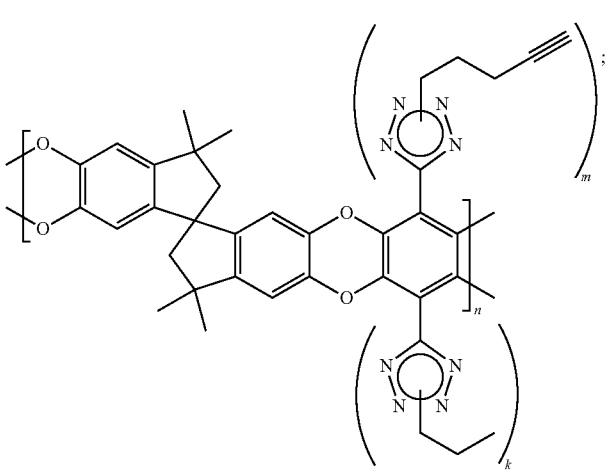
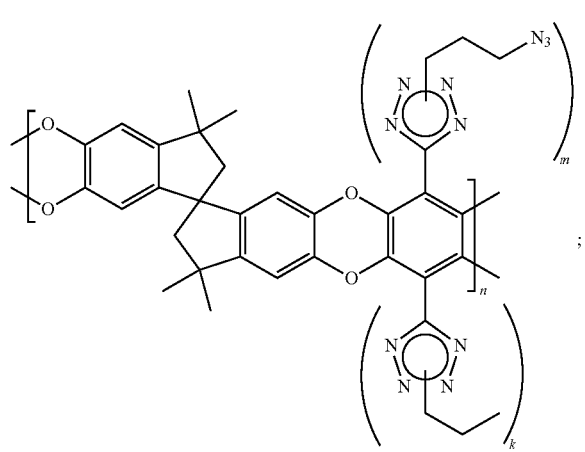
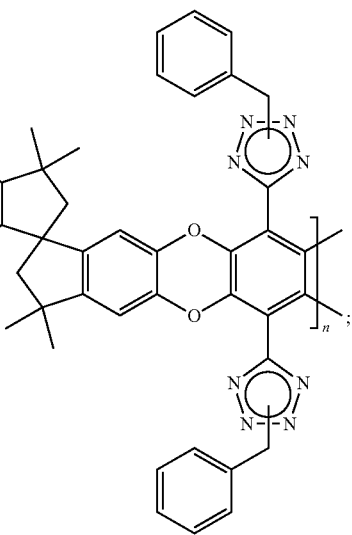

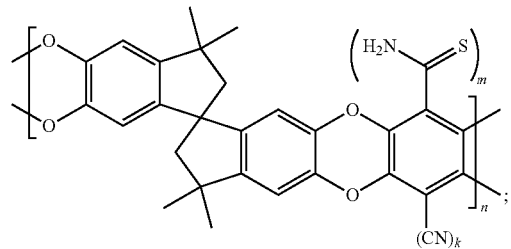
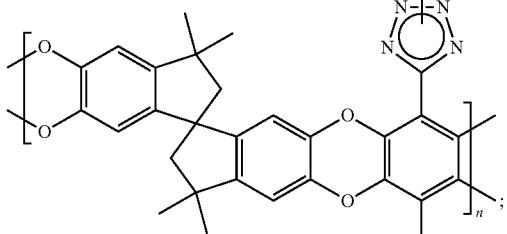
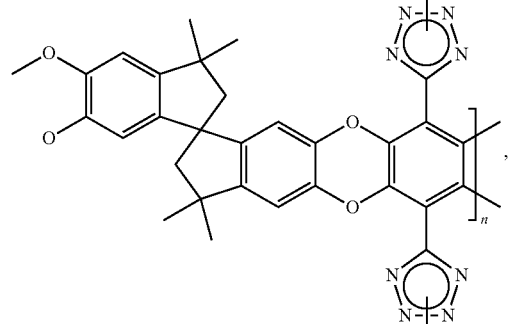
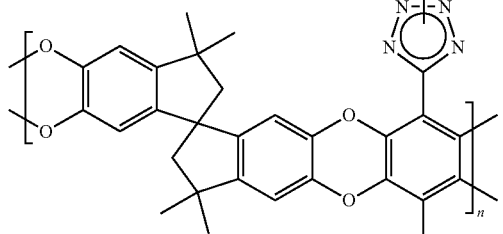
; and
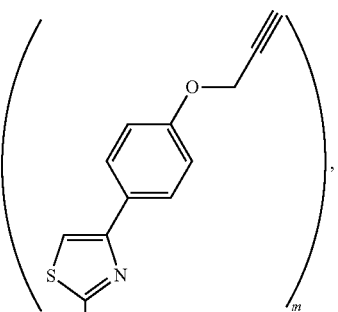

wherein the ratio of m to n is from about 0.1:1 to about 0.9:1; and the ratio of k to n is from about 0.1:1 to about 0.9:1.
In one embodiment, the polymers of the invention may have the following structural formulas:
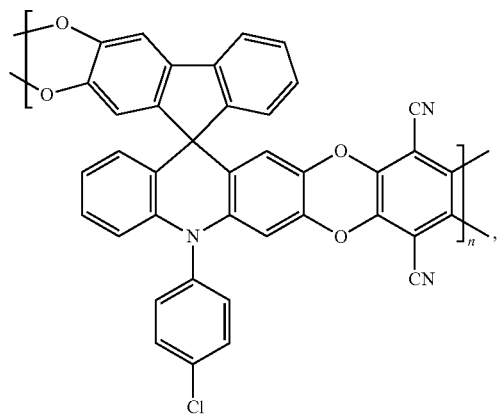
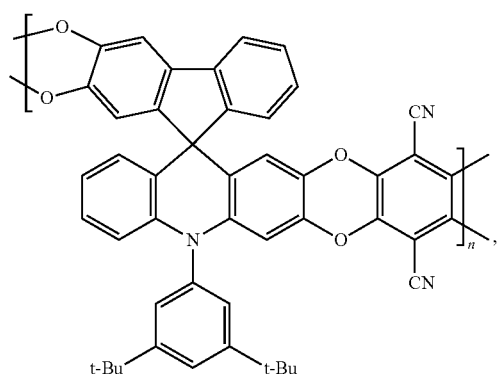
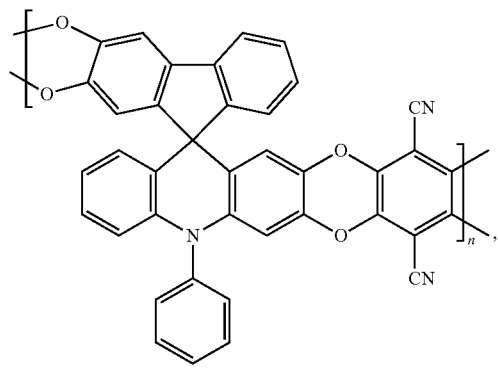
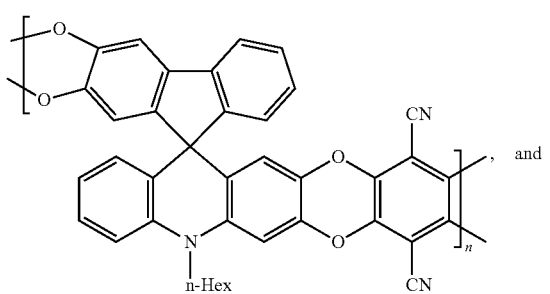
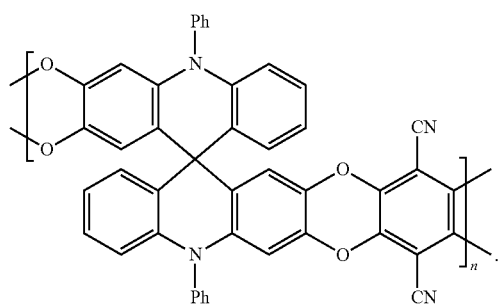
In one embodiment, the polymers of the invention may have the following structural formulas:
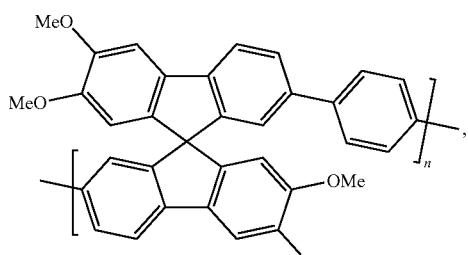
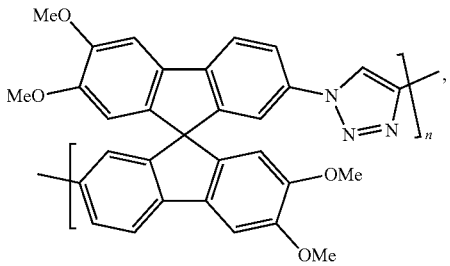
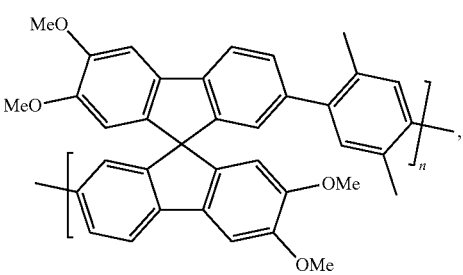
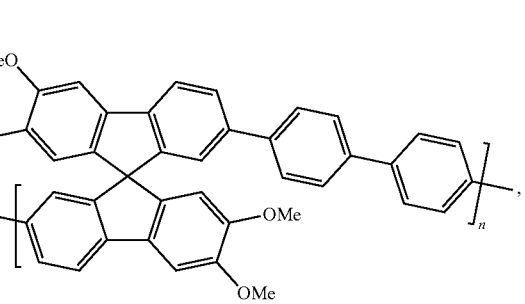

-continued

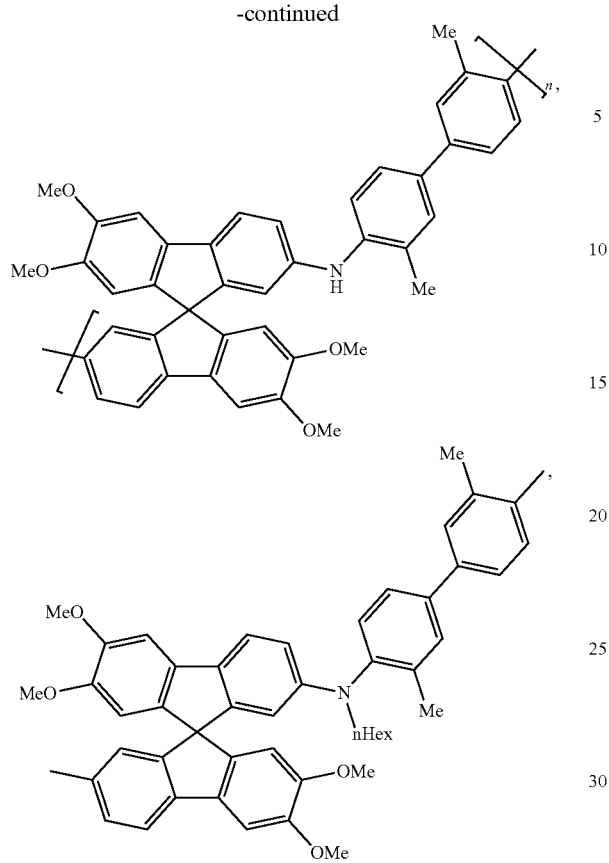

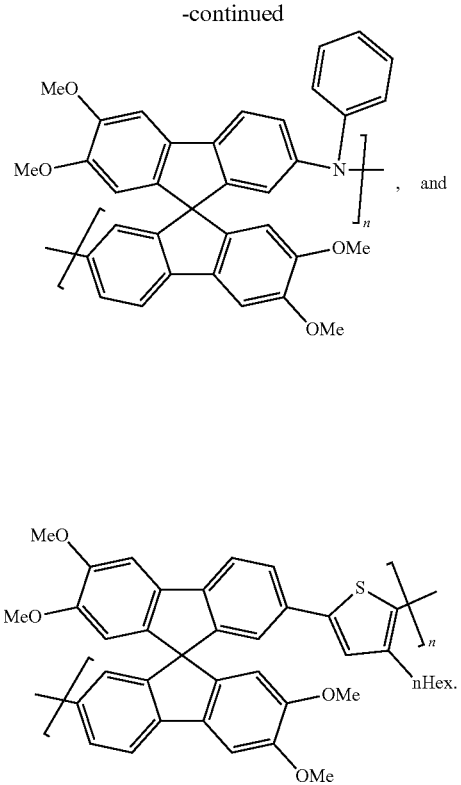

, and

In one embodiment, the polymers of the invention may have the following structural formula:

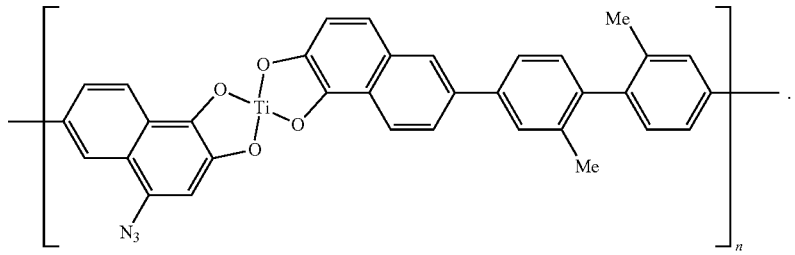

EXAMPLES

The following examples illustrate specific aspects of the instant description. The examples should not be construed as limiting, as the examples merely provide specific understanding and practice of the embodiments and their various aspects.

Reagents

Reagents were purchased at the highest commercial quality and used without further purification, unless otherwise stated. Reactions were monitored by thin layer chromatography (TLC) carried out on EMD Millipore® TLC Silica gel 60 F254 coated glass plates using short-wave UV light as the visualizing agent and KMnO4 and heat as developing agent. Flash column chromatography was performed using Silicycle® Siliaflash silica gel (60 Å pore diameter, 40-63 m particle size).

Instrumentation $^{1}H$ and $^{13}C$ NMR spectra were recorded on either a Bruker-AMX-400 or AVIIIHD-500 spectrometer that was calibrated using residual non-deuterated solvent as an internal reference (CHCl₃ at 7.26 ppm $^1$H NMR and 77.16 ppm $^{13}$C NMR; CH₃OH at 3.31 ppm $^1$H NMR and 49.0 ppm $^{13}$C NMR; DMSO at 2.50 ppm $^1$H NMR and 39.52 $^{13}$C NMR). The following abbreviations were used to explain NMR peak multiplicities: s=singlet, d=doublet, t=triplet, q=quartet, quint=quintet, m=multiplet, br s=broad singlet. Low resolution ESI mass spectra was obtained using an Advion high performance compact mass spectrometer (CMS) with mobile phase composed of 9:1/CH₃CN:H₂O+ 0.1% HCO₂H. High-resolution mass spectrometry (HRMS) of small molecules and intermediates was recorded on an Agilent 6200 Series Accurate-Mass Time-of-Flight (ESI-TOF) mass spectrometer. Attenuated total reflectance ATR FT-IR spectra was obtained using a Nicolet 6700 spectrometer containing a ZnSe crystal.

The following Examples 1 through 8 illustrate the syntheses of representative monomers according to embodiments of the present invention. It should be understood that these examples are merely illustrative and non-limiting, and other monomers according to the invention may be produced in a similar fashion.

Example 1: Synthesis of an Exemplary Spirocentric Monomer According to the Following Structural Formula

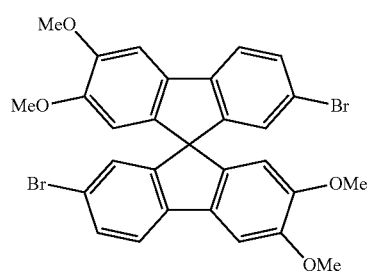 [SMILES: COc1cc2c(cc1OC)C1(c3cc(Br)ccc3-2)c2cc(Br)ccc2-c2cc(OC)c(OC)cc21]

The above-referenced intermediate was prepared using commercially available starting materials and reagents, according to methods known in the art, summarized in Reaction Scheme 1. Percentages indicate % yield for each corresponding step.

Reaction Scheme 1

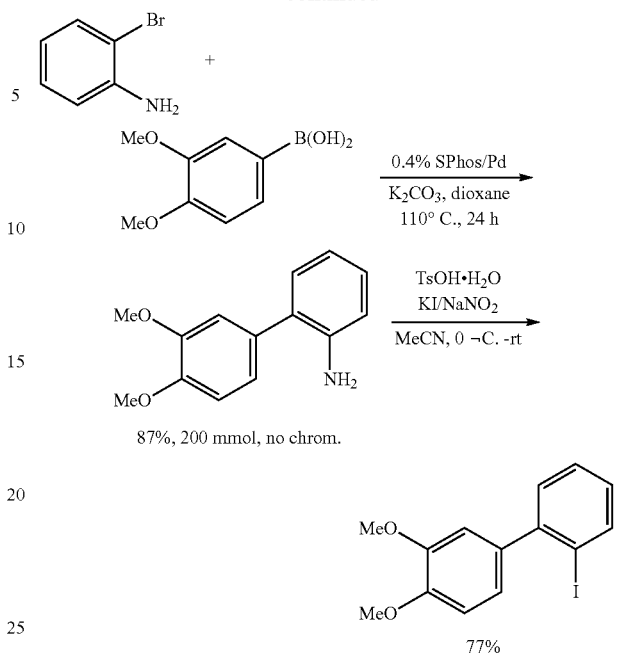

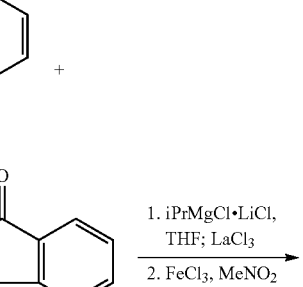

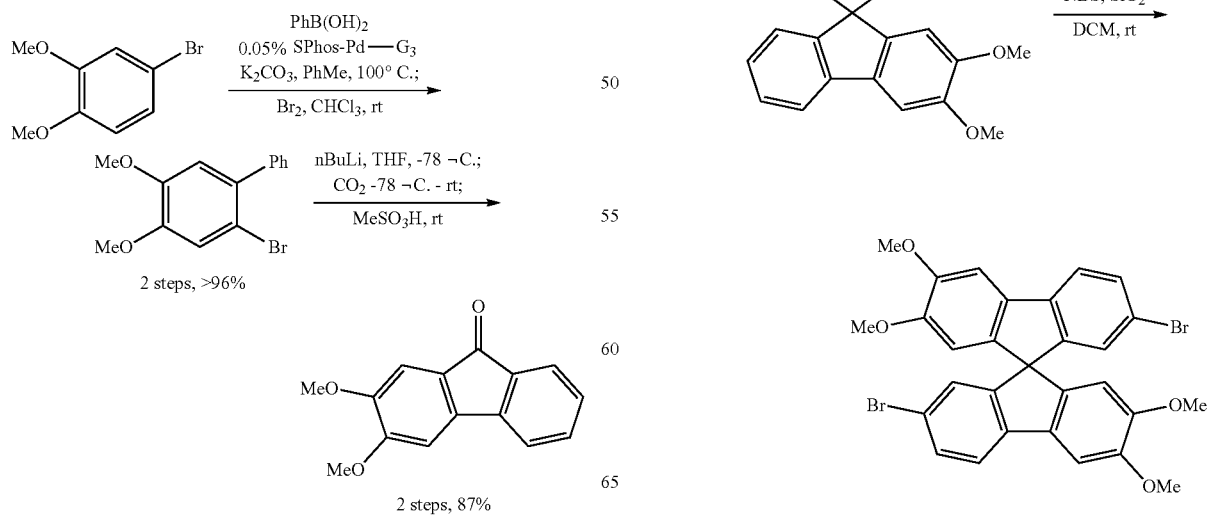

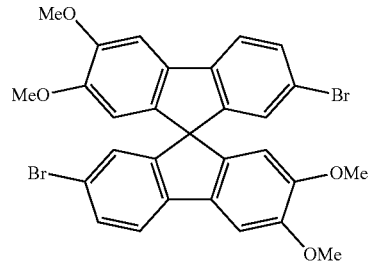

Example 2: Synthesis of an Exemplary Spirocentric Monomer According to the Following Structural Formula

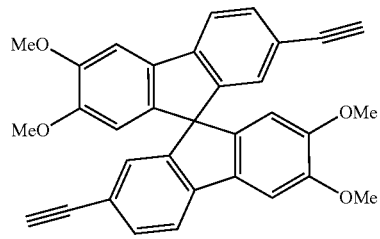 [SMILES: C#Cc1ccc2c(c1)C1(c3cc(C#C)ccc3-c3cc(OC)c(OC)cc31)c1cc(OC)c(OC)cc1-2]

The above-referenced monomer was prepared using commercially available starting materials and reagents, according to methods known in the art, summarized in Reaction Scheme 2. Percentages indicate % yield for each corresponding step.

Reaction Scheme 2

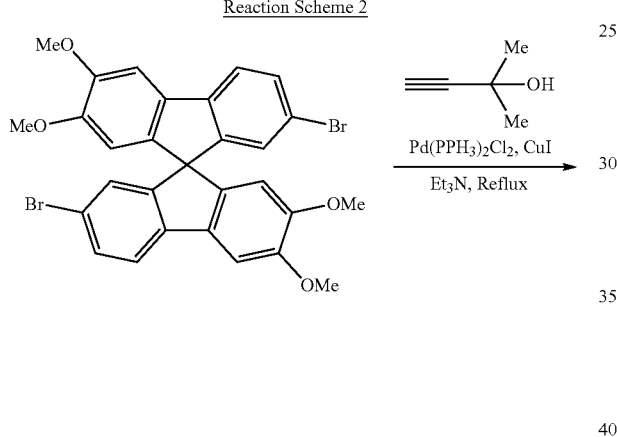

-continued

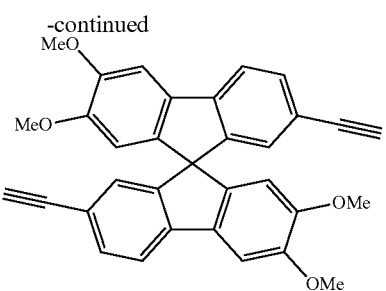

Example 3: Synthesis of an Exemplary Spirocentric Monomer According to the Following Structural Formula

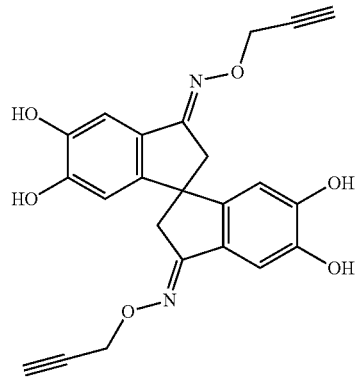 [SMILES: C#CCO/N=C1\CC2(C/C(=N\OCC#C)c3cc(O)c(O)cc32)c2cc(O)c(O)cc21]

The above-referenced monomer was prepared using commercially available starting materials and reagents, according to methods known in the art, summarized in Reaction Scheme 3. Percentages indicate % yield for each corresponding step.

Reaction Scheme 3

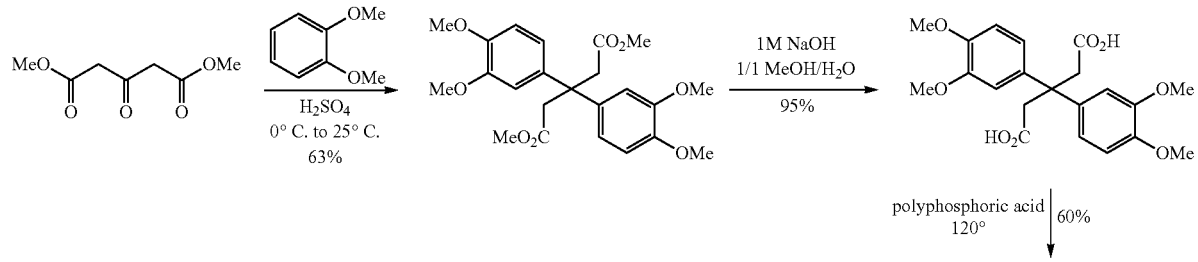

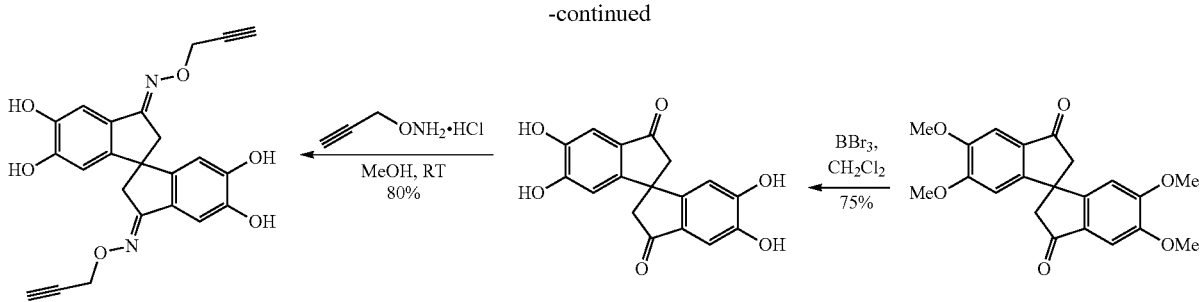
Example 4: Synthesis of an Exemplary Spirocentric Monomer According to the Following Structural Formula
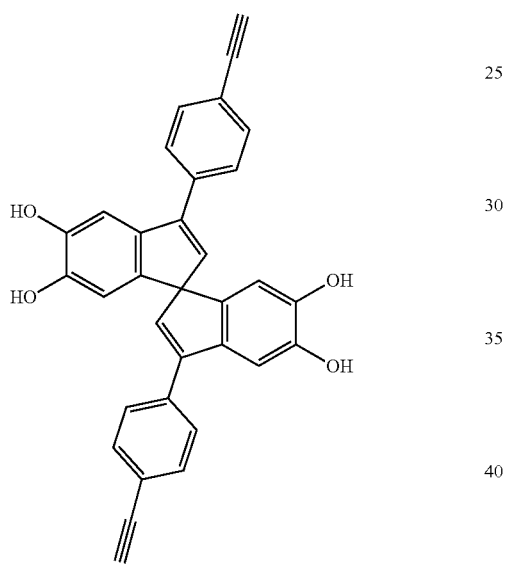
The above-referenced monomer was prepared using commercially available starting materials and reagents, according to methods known in the art, summarized in Reaction Scheme 4. Percentages indicate % yield for each corresponding step.
Reaction Scheme 4
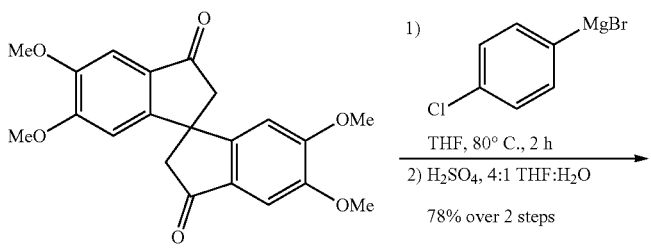

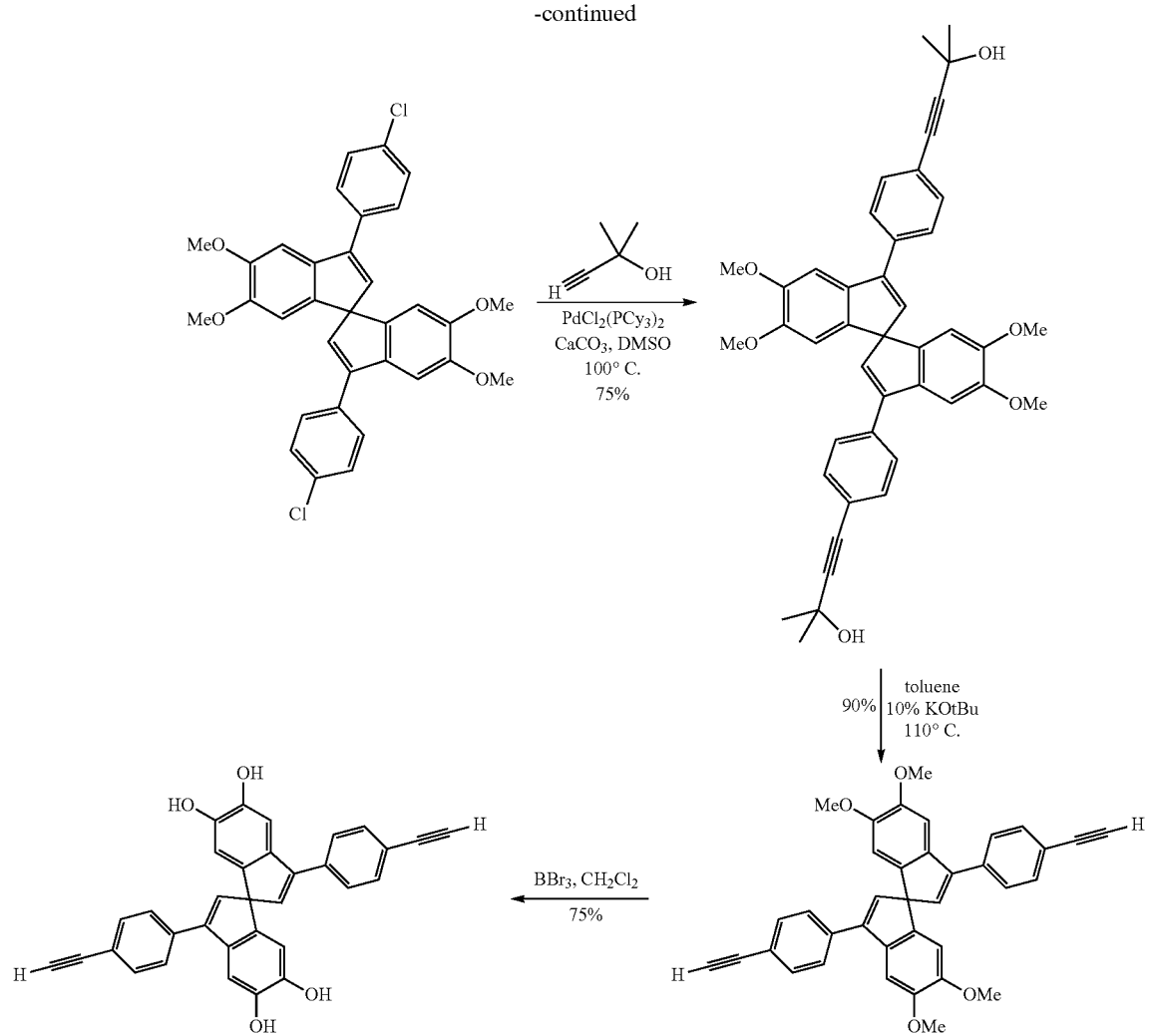
Example 5: Synthesis of an Exemplary Spirocentric Monomer According to the Following Structural Formula
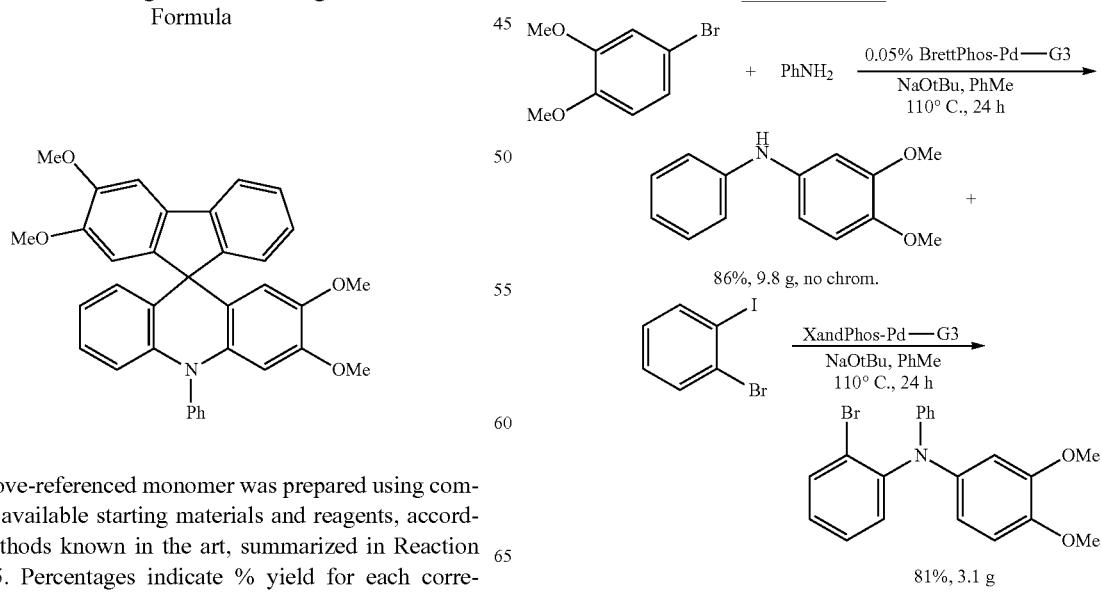
The above-referenced monomer was prepared using commercially available starting materials and reagents, according to methods known in the art, summarized in Reaction Scheme 5. Percentages indicate % yield for each corresponding step.

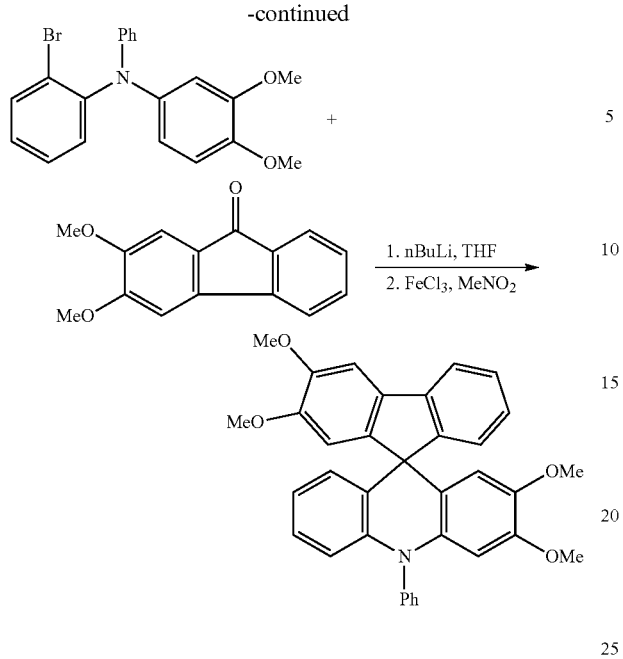
Example 6: Synthesis of an Exemplary Spirocentric Monomer According to the Following Structural Formula
The above-referenced monomer was prepared using commercially available starting materials and reagents, according to methods known in the art, summarized in Reaction Scheme 6. Percentages indicate % yield for each corresponding step.
Reaction Scheme 6
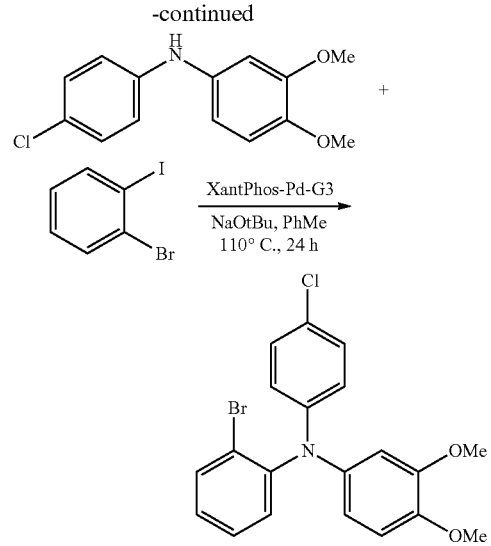
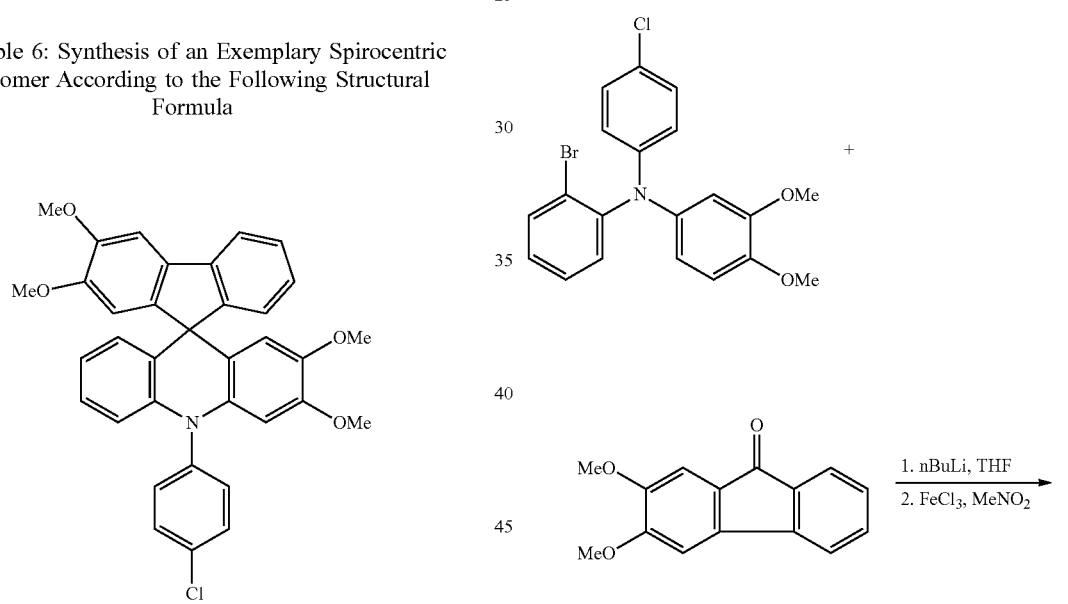
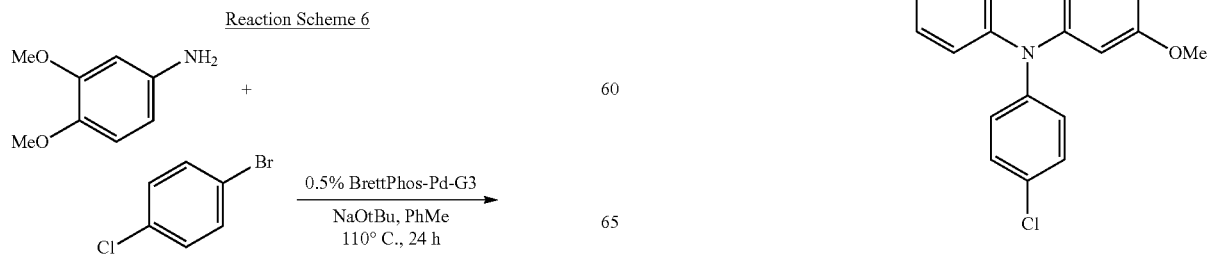

Example 7: Synthesis of an Exemplary Spirocentric Monomer According to the Following Structural Formula

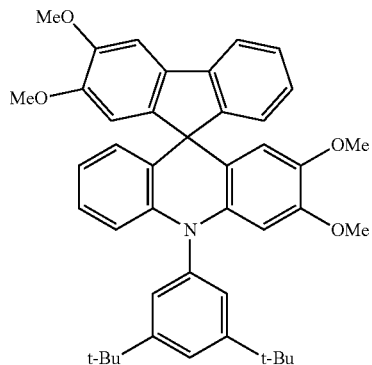 [SMILES: COc1cc2c(cc1OC)C1(c3ccccc3-2)c2ccccc2N(c2cc(C(C)(C)C)cc(C(C)(C)C)c2)c2cc(OC)c(OC)cc21]

The above-referenced monomer was prepared using commercially available starting materials and reagents, according to methods known in the art, summarized in Reaction Scheme 7. Percentages indicate % yield for each corresponding step.

Reaction Scheme 7

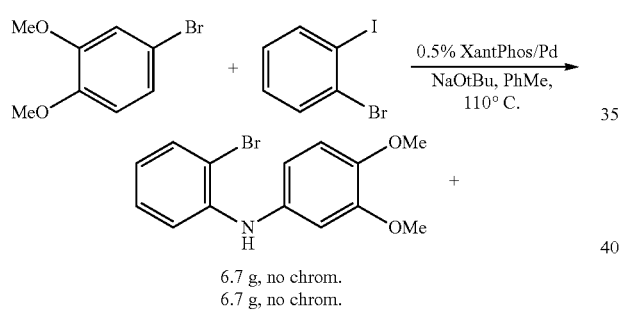

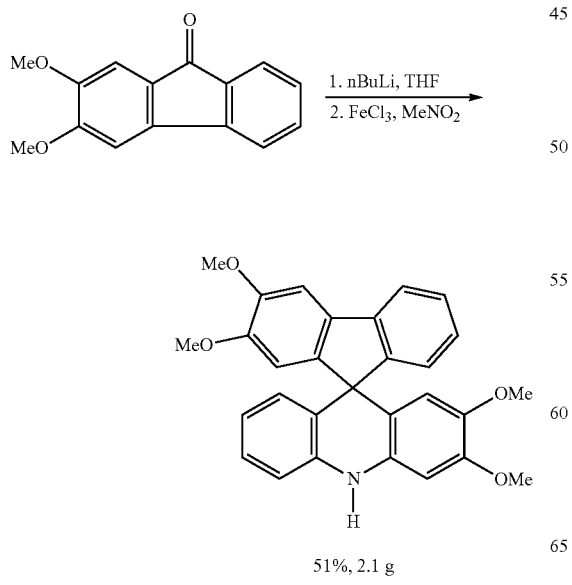

51%, 2.1 g

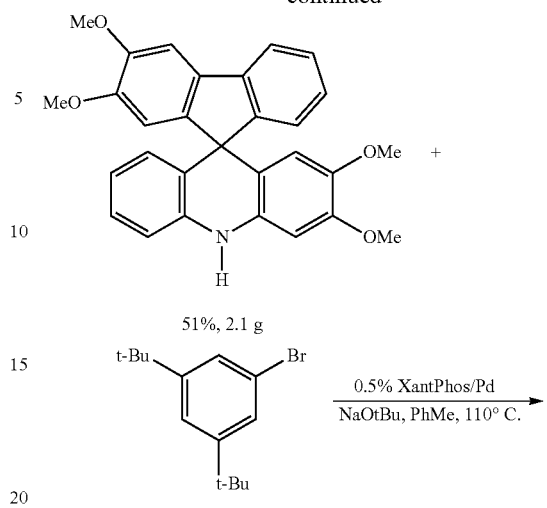

51%, 2.1 g

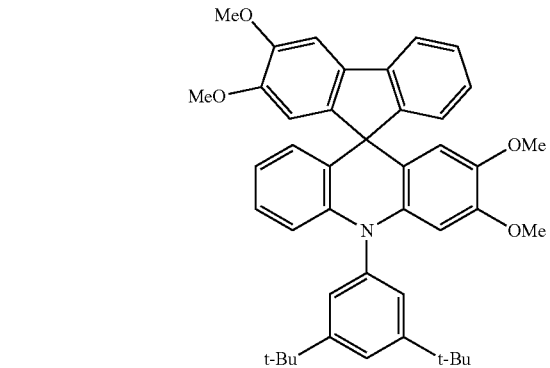

Example 8: Synthesis of an Exemplary Spirocentric Monomer According to the Following Structural Formula

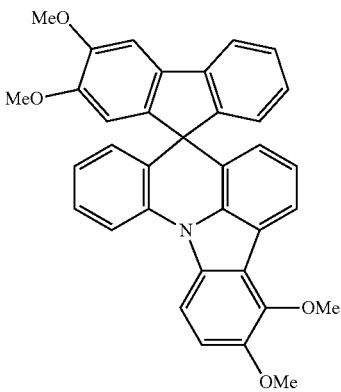 [SMILES: COc1cc2c(cc1OC)C1(c3ccccc3-2)c2ccccc2-n2c3ccc(OC)c(OC)c3c3cccc1c32]

The above-referenced monomer was prepared using commercially available starting materials and reagents, according to methods known in the art, summarized in Reaction Scheme 8. Percentages indicate % yield for each corresponding step.

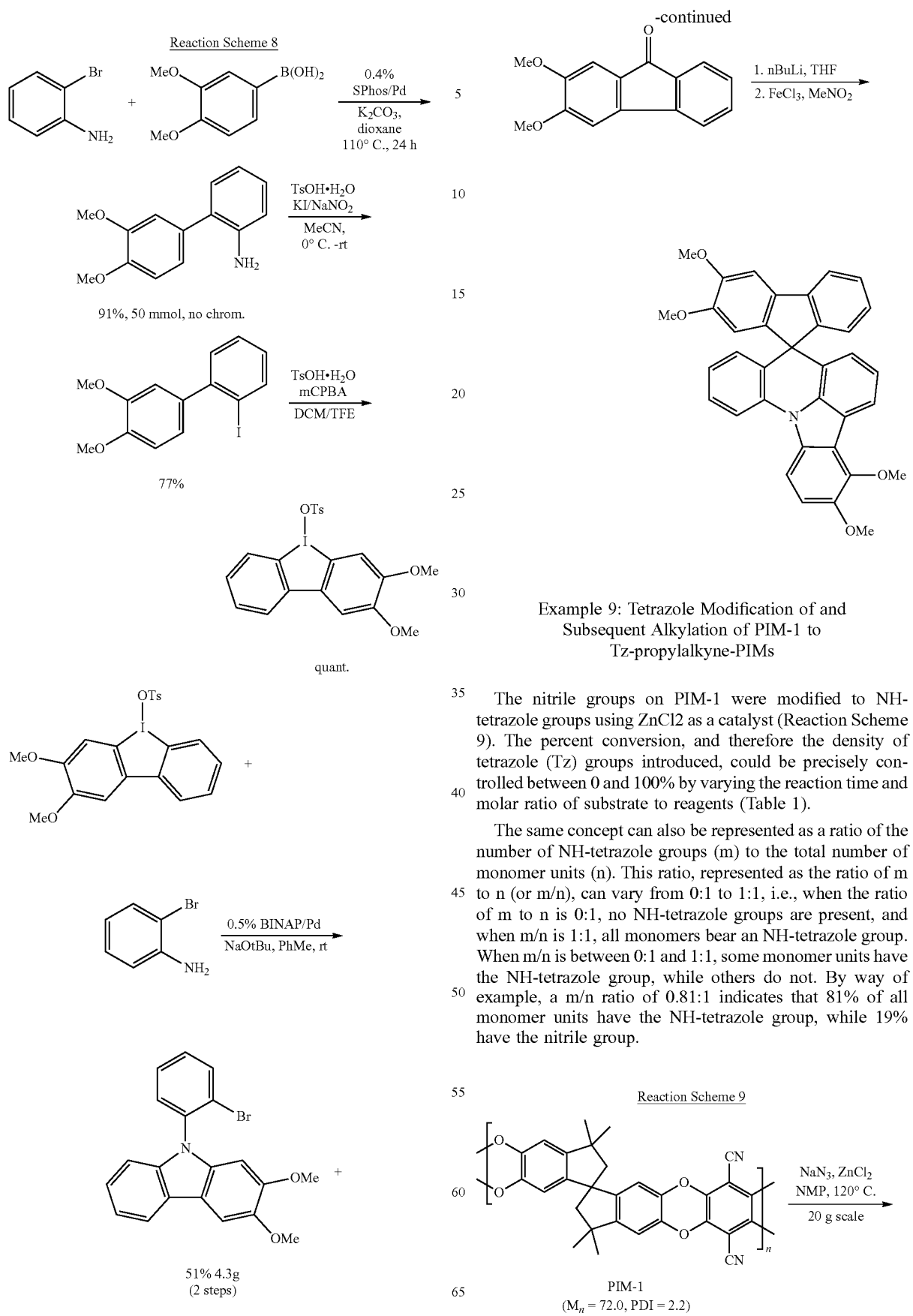

Example 9: Tetrazole Modification of and Subsequent Alkylation of PIM-1 to Tz-propylalkyne-PIMs The nitrile groups on PIM-1 were modified to NH-tetrazole groups using ZnCl2 as a catalyst (Reaction Scheme 9). The percent conversion, and therefore the density of tetrazole (Tz) groups introduced, could be precisely controlled between 0 and 100% by varying the reaction time and molar ratio of substrate to reagents (Table 1).

The same concept can also be represented as a ratio of the number of NH-tetrazole groups (m) to the total number of monomer units (n). This ratio, represented as the ratio of m to n (or m/n), can vary from 0:1 to 1:1, i.e., when the ratio of m to n is 0:1, no NH-tetrazole groups are present, and when m/n is 1:1, all monomers bear an NH-tetrazole group. When m/n is between 0:1 and 1:1, some monomer units have the NH-tetrazole group, while others do not. By way of example, a m/n ratio of 0.81:1 indicates that 81% of all monomer units have the NH-tetrazole group, while 19% have the nitrile group.

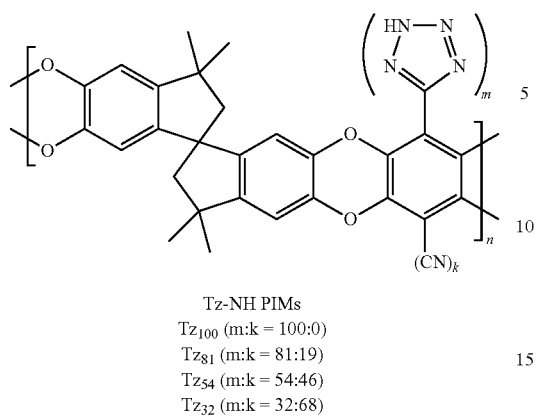

Tz-NH PIMs
Tz$_{100}$ (m:k = 100:0)
Tz$_{81}$ (m:k = 81:19)
Tz$_{54}$ (m:k = 54:46)
Tz$_{32}$ (m:k = 32:68)

TABLE 1

Time course tetrazole modification of nitriles present in PIM-1.

| Product | PIM-1 (eq.) | NaN$_3$ (eq.) | ZnCl$_2$ (eq.) | Time (h) | % Tetrazole | m/n Ratio |
|---|---|---|---|---|---|---|
| Tz$_{100}$-PA/Az | 1 | 8 | 8 | 168 | 100 | 1:1 |
| Tz$_{81}$-PA/Az | 1 | 8 | 4 | 96 | 81 | 0.81:1 |
| Tz$_{54}$-PA/Az | 1 | 8 | 4 | 5 | 54 | 0.54:1 |
| Tz$_{32}$-PA/Az | 1 | 8 | 4 | 0.5 | 32 | 0.32:1 |

As the number of NH tetrazoles incorporated was increased, the solubility of the corresponding Tz-PIM decreased substantially in membrane processing solvents such as THF and CHCl3. Tetrazole alkylation was expected to enhance solubility and allow characterization by 1H NMR. This was done with n-propylazides and alkynes bearing halide or tosylate leaving groups, as shown in Reaction Scheme 9.

Example 10: Subsequent Alkylation of Tetrazole-Modified PIM-1 to Tz-propylalkyne-PIMs or Tz-propylazide-PIMs Alkylation with short chain azide/alkyne linker was found to be complete, giving rise to an average of 32, 54, 81 and 100 percent of the nitrile groups converted to alkylated tetrazoles bearing either azide or alkyne groups, as measured using $^1$H NMR and FT-IR (FIG. 1). These are designated Tz$_{\#}$-PA or Tz$_{\#}$-PAz, where # is the percentage of tetrazole groups compared to starting nitriles, and "PA" or "PAz" denote alkyne and azide functionality, respectively. For comparison, a modified PIM was prepared in which azide and alkyne groups were incorporated into the same polymer using an equimolar ratio of azide and alkyne tosylates in the alkylation reaction. Interestingly, the resulting Tz$_{100}$-PA$_{50}$PAz$_{50}$ material underwent spontaneous cross-linking in the absence of catalyst at room temperature, presumably due to their high relative local concentration.

Reaction Scheme 10.

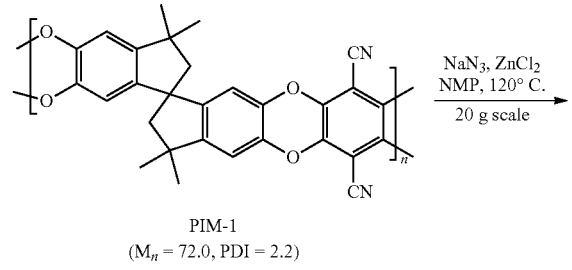

PIM-1
($M_n$ = 72.0, PDI = 2.2)

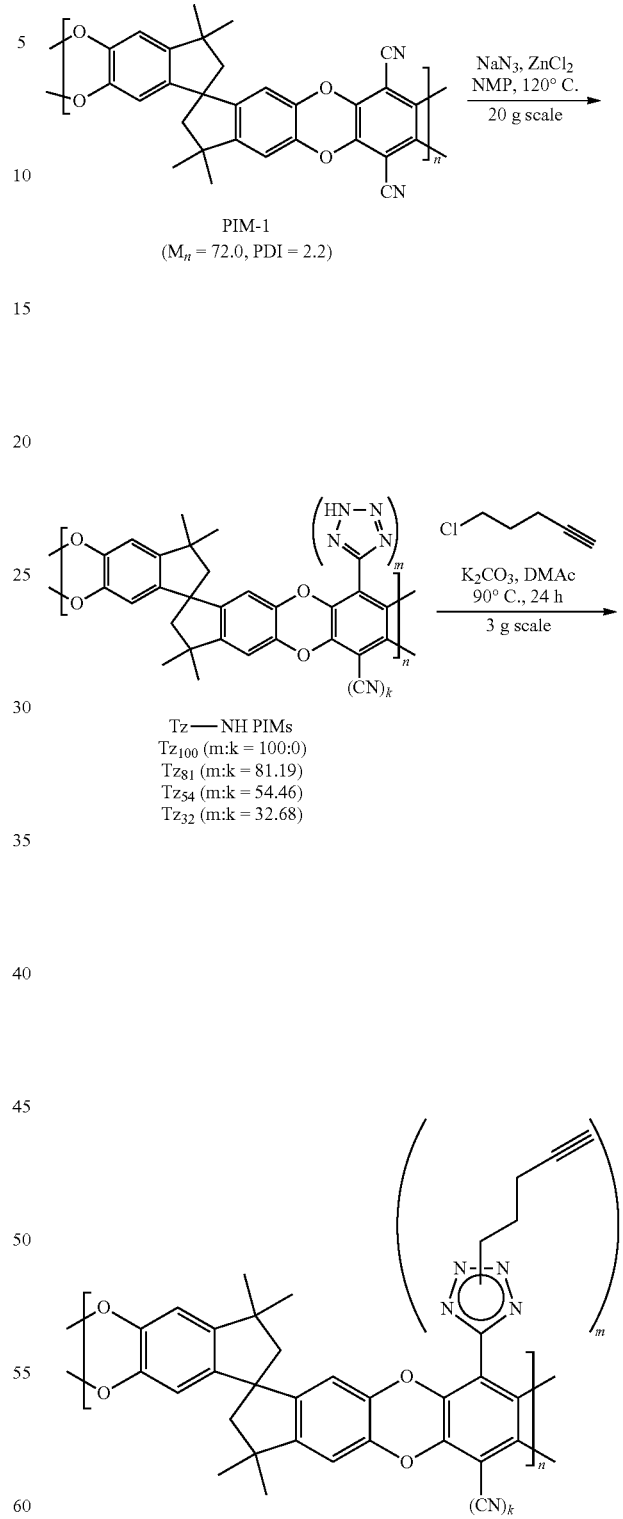

Tz—NH PIMs
Tz$_{100}$ (m:k = 100:0)
Tz$_{81}$ (m:k = 81:19)
Tz$_{54}$ (m:k = 54.46)
Tz$_{32}$ (m:k = 32.68)

Tz-propylalkyne-PIMs
Tz$_{100}$—PA (m:k = 100:0)
Tz$_{80}$—PA (m:k = 81:19)
Tz$_{54}$—PA (m:k = 54:46)
Tz$_{32}$—PA (m:k = 32:68)

Reaction Scheme 11.
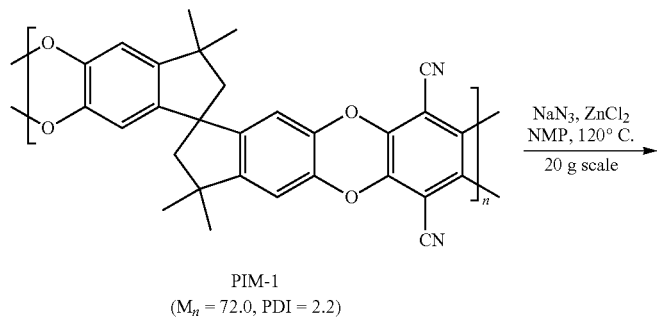
PIM-1
($M_n$ = 72.0, PDI = 2.2)
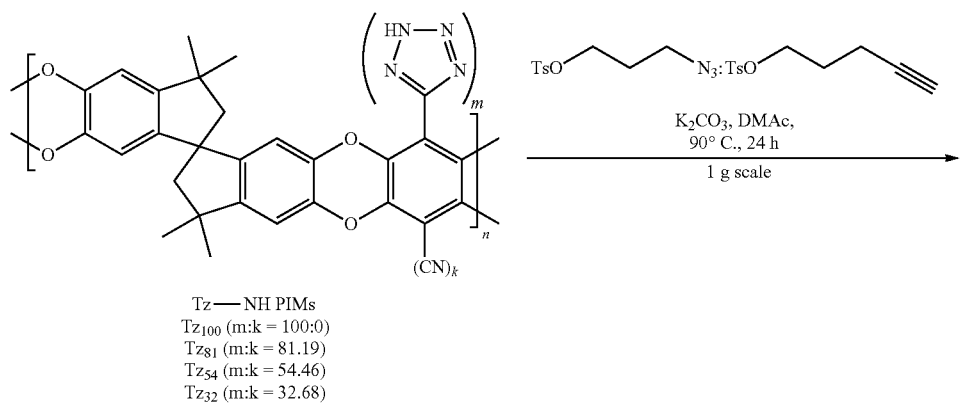
Tz—NH PIMs
$Tz_{100}$ (m:k = 100:0)
$Tz_{81}$ (m:k = 81.19)
$Tz_{54}$ (m:k = 54.46)
$Tz_{32}$ (m:k = 32.68)
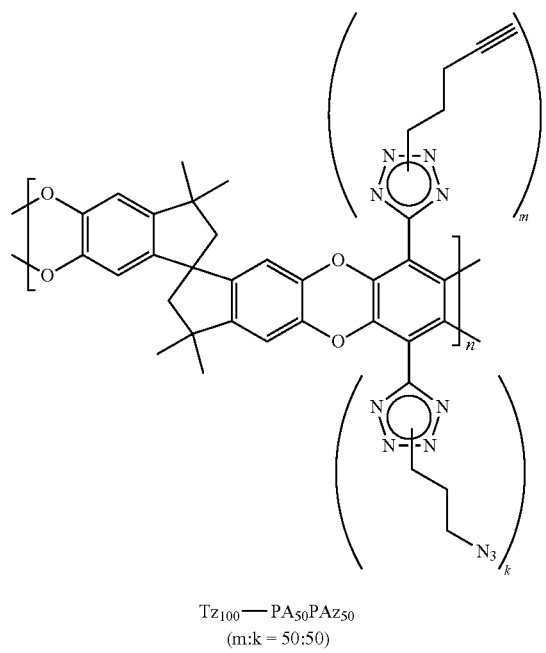
$Tz_{100}$—$PA_{50}PAz_{50}$
(m:k = 50:50)

Reaction Scheme 12.

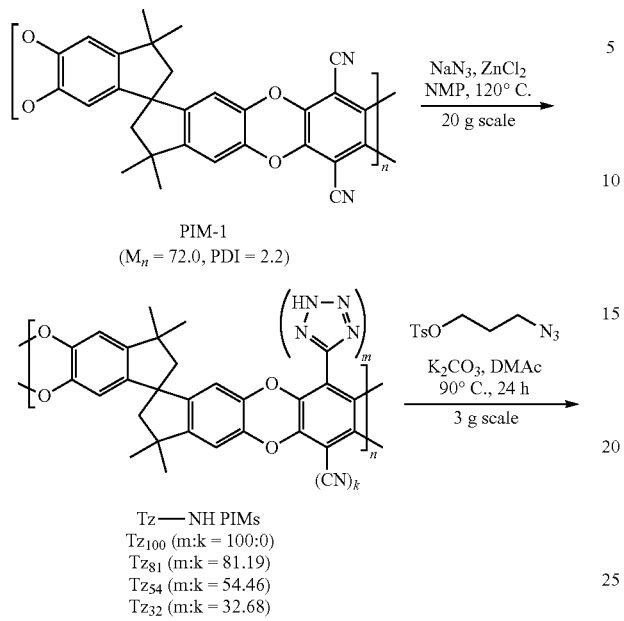

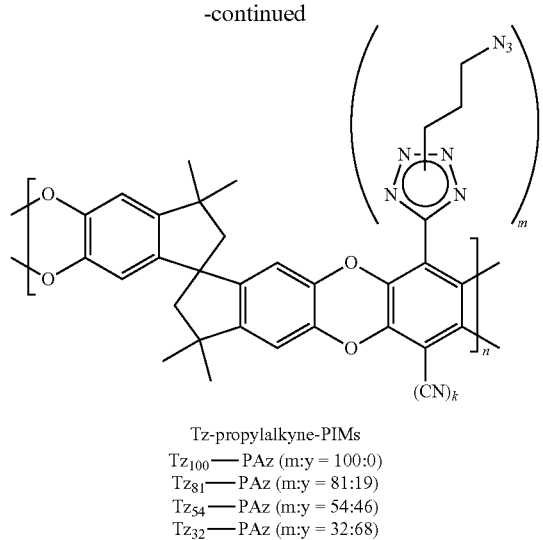

Tz-propylalkyne-PIMs
Tz$_{100}$—PAz (m:y = 100:0)
Tz$_{81}$—PAz (m:y = 81:19)
Tz$_{54}$—PAz (m:y = 54:46)
Tz$_{32}$—PAz (m:y = 32:68)

The number of cross-linker groups could also be controlled by full alkylation of TZ100-PIM (the PIM-1 derivative in which all the nitrile groups had been converted to NH-tetrazole) with differing mixtures of functionalized and non-functional alkyl halide (Reaction Scheme 13). These alkylated products all displayed improved solubility in THF and CHCl3. This route was also used to vary the linker length and rigidity to test the effects of these parameters on membrane performance.

Reaction Scheme 13.

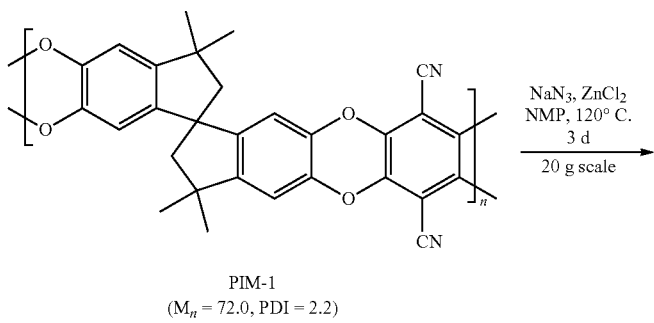

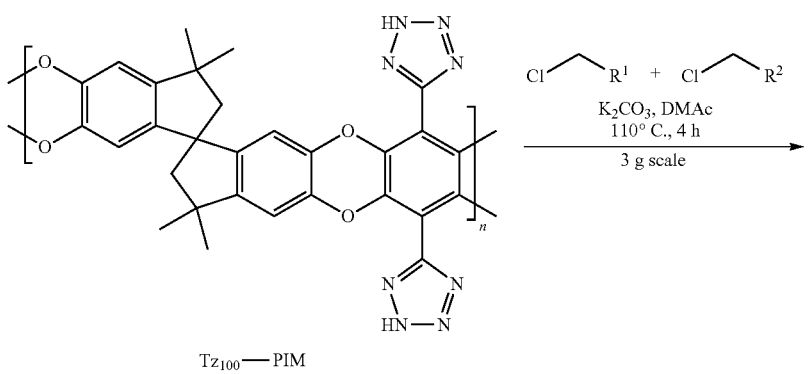

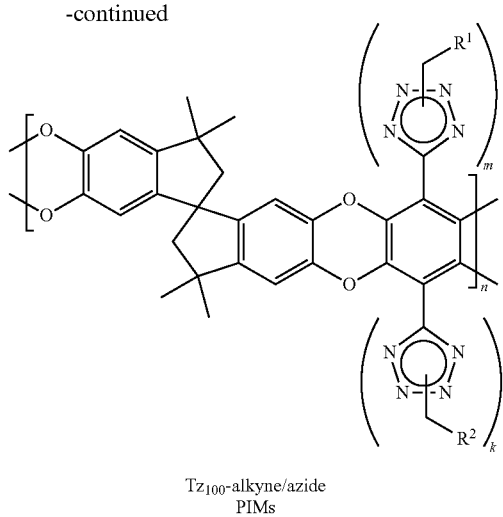

Tz<sub>100</sub>-alkyne/azide PIMs

Figure 2:
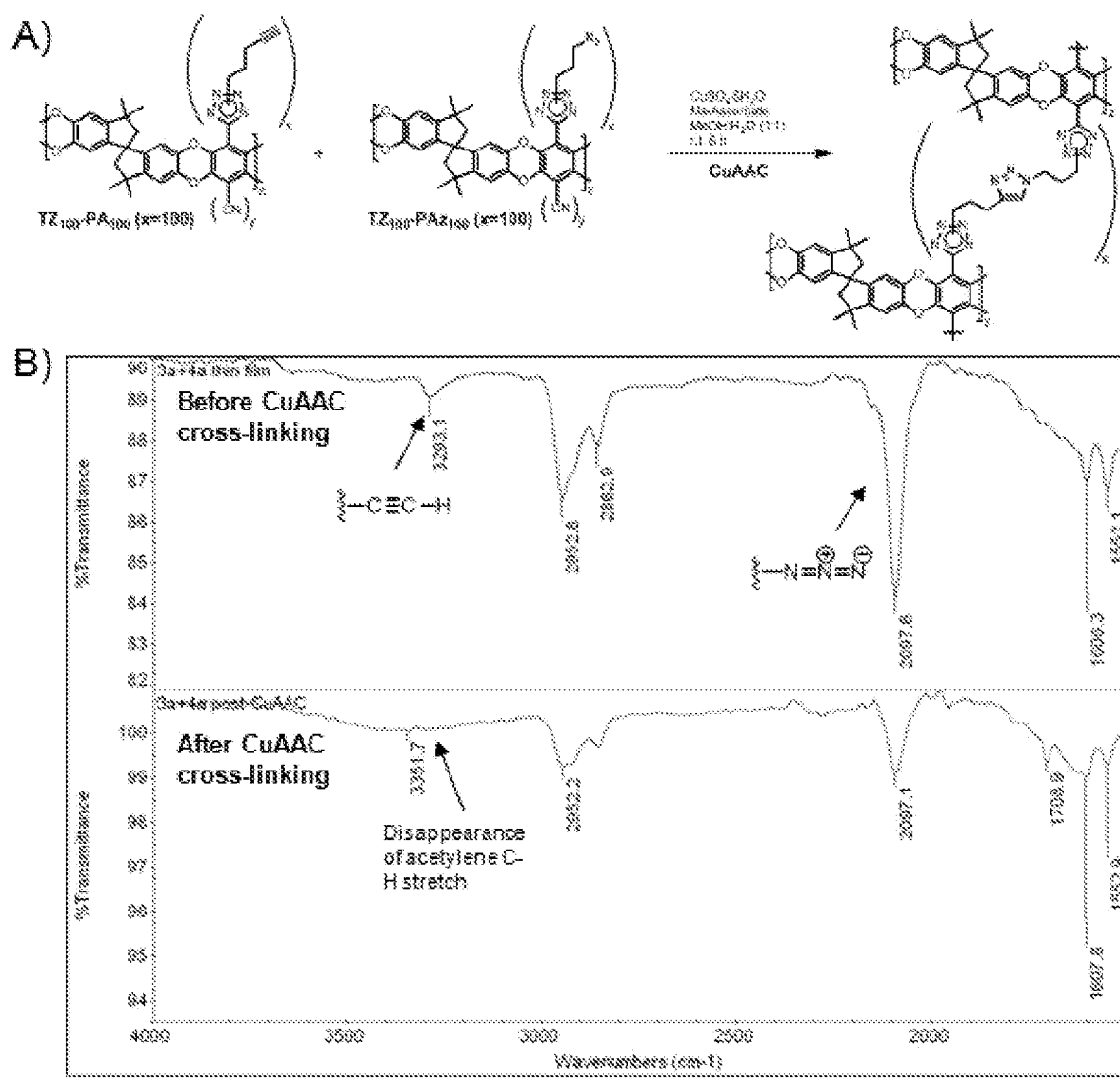
FIG. 2 depicts film casting and crosslinking of azide- and alkyne-functionalized PIM polymers.

Example 11: Film Casting and Crosslinking of Azide- and Alkyne-Functionalized PIM Polymers The facile crosslinking of azide- and alkyne-functionalized PIMS was demonstrated as shown in FIG. 2. Equimolar solutions of $Tz_{100}$-PA and $Tz_{100}$-PAz were mixed and immediately cast into thin films. After drying, the resulting films were suspended in aqueous methanol, and treated with $CuSO_4$ and sodium ascorbate to initiate the CuAAC crosslinking reaction. After 30 minutes at room temperature, FT-IR analysis showed substantial disappearance of characteristic stretching vibrations of both alkyne and azide groups, as expected for conversion to triazoles.

The following examples provide characterization data for select compounds and polymers according to the invention.

Example 12: TZ100-HpC100 PIM

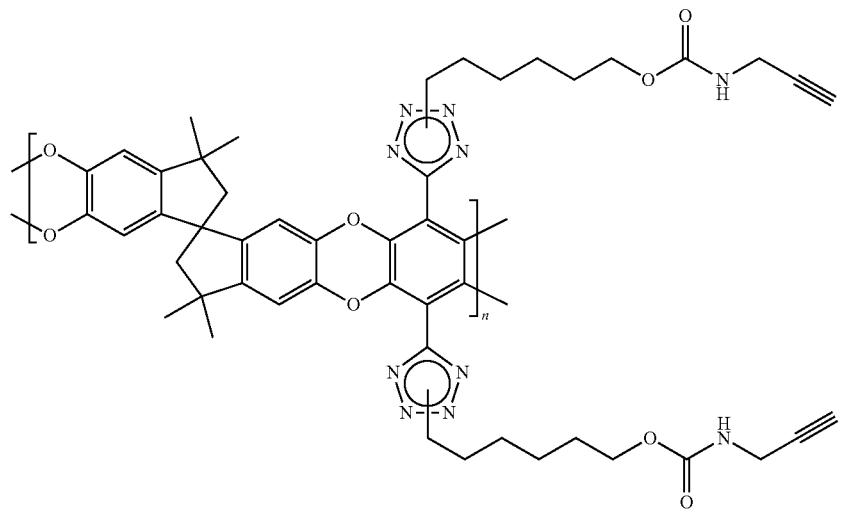

$TZ_{100}$-$HpC_{100}$ PIM: A vigorously stirred mixture of finely ground $Tz_{100}$-NH PIM (2 g, 4.2 mmol) in anhydrous DMAc (100 mL) was added 8-chlorohexyl N-(prop-2-yn-1-yl)carbamate (3.7 g, 16.8 mmol) and anhydrous $K_2CO_3$ (4.6 g, 33.6 mmol) and under $N_2$, the reaction was heated at 100° C. for 15 hrs. Added additional 8-chlorooctyl N-(prop-2-yn-1-yl)carbamate (3.7 g, 16.8 mmol) and allowed to stir at 100° C. for an additional 24 hrs. Upon completion, the reaction was cooled to r.t. then was added $H_2O$ (150 mL), the resulting light brown precipitate was collected by vacuum filtration. The filter cake was washed with $H_2O$ (3×50 mL), followed by MeOH (1×50 mL). The crude was re-dissolved in a minimum volume of $CHCl_3$, filtered over a plug of celite, then poured into MeOH. The resulting pale yellow precipitate was filtered, and washed with MeOH. The product was purified by a second round of re-precipitation from $CHCl_3$/MeOH. The solid was dried thoroughly in a vacuum oven at 60° C. for 3 hrs yielding a pale yellow solid (1.82 g). $^1H$ NMR ($CDCl_3$, 500 MHz, 323 K): δ 6.46 (s, 2H), 6.07 (s, 2H), 5.50-3.10 (m, 14H), 2.57-0.98 (m, 34H). $^{13}C$ NMR ($CDCl_3$, 100 MHz, 323 K): δ 156.3 (C), 149.0 (C), 146.3 (C), 140.4 (C), 139.7 (C), 136.8 (C), 112.0 (CH), 110.1 (CH), 108.5 (CH), 107.3 (CH), 80.2 (C), 71.5 (CH), 65.4 ($CH_2$), 59.3 ($CH_2$), 57.3 (C), 53.6 ($CH_2$), 48.2 ($CH_2$), 43.4 (C), 31.5 ($CH_2$), 31.0 ($CH_2$), 30.1 ($CH_2$), 29.0 ($CH_2$), 26.4 ($CH_2$), 26.3 ($CH_2$), 26.1 ($CH_3$), 25.8 ($CH_3$).

Example 13: TZ$_{100}$-o-AzBn$_{100}$ PIM

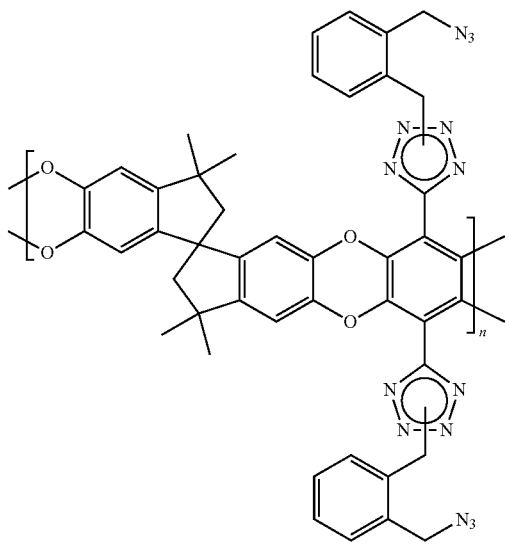

TZ$_{100}$-o-AzBn$_{100}$ PIM: A suspension of finely ground Tz$_{100}$-NH PIM (3 g) in anhydrous NMP (75 mL) was added 1-(azidomethyl)-2-(chloromethyl)benzene (3.4 g, 18.7 mmol) and anhydrous K$_2$CO$_3$ (3.9 g, 28.2 mmol) and the reaction was stirred under N$_2$, with heating at 110° C. for 16 hrs. Added additional 1-(azidomethyl)-2-(chloromethyl)benzene (1.7 g, 9.4 mmol) and stirring was continued at 110° C. for an additional 4 hrs. Upon completion, the reaction was cooled to r.t., then added H$_2$O (150 mL), the resulting red-brown precipitate was collected by vacuum filtration. The filter cake was washed with H$_2$O (3×50 mL), followed by MeOH (1×50 mL). The crude was re-dissolved in a minimum volume of CHCl$_3$, filtered over a plug of celite, then poured into MeOH. The precipitate was filtered, and washed with MeOH and dried under vacuum. The product was further purified by a second round of re-precipitation from CHCl$_3$/MeOH. The solid was dried thoroughly in a vacuum oven at 60° C. for 3 hrs yielding a pale yellow solid (2.5 g). $^1$H NMR (CDCl$_3$, 400 MHz, 323 K): δ 7.52-7.12 (m, 8H), 6.40 (s, 2H), 6.05-5.58 (s, 6H), 4.68-4.32 (m, 4H), 2.23-2.03 (m, 4H), 1.28 (s, 6H), 1.24 (s, 6H). $^{13}$C NMR (CDCl$_3$, 100 MHz, 323 K): δ 156.9 (C), 148.8 (C), 146.6 (C), 140.2 (C), 139.7 (C), 136.4 (C), 134.5 (C), 132.3 (C), 130.8 (CH), 130.3 (CH), 129.3 (CH), 127.7 (CH), 111.9 (CH), 110.1 (CH), 108.4 (CH), 107.0 (CH), 104.3 (CH), 102.9 (CH), 60.4 (CH$_2$), 59.1 (CH$_2$), 57.3 (C), 54.2 (C), 52.9 (CH$_2$), 49.5 (CH$_2$), 43.5 (C), 31.5 (CH$_3$), 30.1 (CH$_3$).

Example 14: TZ$_{100}$-DAz$_{100}$ PIM

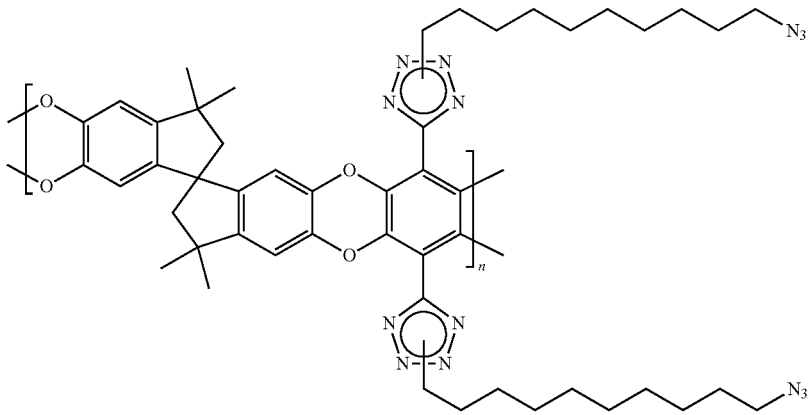

TZ$_{100}$-DAz$_{100}$ PIM: A suspension of finely ground Tz$_{100}$-NH PIM (3 g, 6.3 mmol) in anhydrous NMP (75 mL) was added 1-azido-10-bromodecane (4.9 g, 28.2 mmol) and anhydrous K$_2$CO$_3$ (3.9 g, 28.2 mmol) and the reaction was stirred under N$_2$, with heating at 85° C. for 16 hrs. Added additional slug of 1-azido-10-bromodecane (2.5 g, 14.1 mmol) and stirring was continued at 85° C. for an additional 4 hrs. Upon completion, the reaction was cooled to r.t., then added H$_2$O (150 mL), the resulting light brown precipitate was collected by vacuum filtration. The filter cake was washed with H$_2$O (3×50 mL), followed by MeOH (1×50 mL). The crude was re-dissolved in a minimum volume of CHCl$_3$, filtered over a plug of celite, then poured into MeOH. The resulting pale yellow precipitate was filtered, and washed with MeOH. The product was further purified by a second round of re-precipitation from CHCl$_3$/MeOH. The solid was dried thoroughly in a vacuum oven at 60° C. for 3 hrs yielding a pale yellow solid (2.4 g). $^1$H NMR (CDCl$_3$, 400 MHz, 323 K): δ 6.45 (s, 2H), 6.07 (s, 2H), 4.93-4.54 (m, 2H), 4.49-4.05 (m, 2H), 3.30-3.13 (m, 4H), 2.44-1.74 (8H), 1.69-0.95 (m, 40H). $^{13}$C NMR (CDCl$_3$, 100 MHz, 323 K): δ 156.4 (C), 148.8 (C), 146.3 (C), 140.3 (C), 136.9 (C), 112.0 (CH), 110.1 (CH), 108.5 (CH), 107.2 (CH), 59.2 (C), 57.3 (C), 53.6 (CH$_2$), 51.6 (CH$_2$), 48.2 (CH$_2$), 43.4 (C), 31.5 (CH$_3$), 30.1 (CH$_3$), 29.5 (CH$_2$), 29.4 (CH$_2$), 29.2 (CH$_2$), 29.1 (CH$_2$), 28.3 (CH$_2$), 27.0 (CH$_2$), 26.8 (CH$_2$), 26.5 (CH$_2$), 26.4 (CH$_2$).

Example 15: TZ$_{100}$-o-pgBn$_{100}$ PIM

TZ$_{100}$-o-pgBn$_{100}$ PIM: A vigorously stirred mixture of finely ground Tz$_{100}$-NH PIM (3 g) in anhydrous DMAc (75 mL) was added 1-(chloromethyl)-2-[(prop-2-yn-1-yloxy)methyl]benzene (5.5 g, 28.2 mmol) and anhydrous K$_2$CO$_3$ (3.9 g, 28.2 mmol) and under N$_2$, the reaction was heated at 100° C. for 15 hrs. Upon completion, the reaction was cooled to r.t. then was added H$_2$O (150 mL), the resulting light brown precipitate was collected by vacuum filtration. The filter cake was washed with H$_2$O (3×50 mL), followed by MeOH (1×50 mL). The crude was re-dissolved in a minimum volume of CHCl$_3$, filtered over a plug of celite, then poured into MeOH. The resulting pale yellow precipitate was filtered, and washed with MeOH. The product was purified by a second round of re-precipitation from CHCl$_3$/MeOH. The solid was dried thoroughly in a vacuum oven at 60° C. for 3 hrs yielding a pale yellow solid (3.26 g). $^1$H NMR (CDCl$_3$, 400 MHz, 323 K): δ 7.54-6.77 (m, 8H), 6.39 (s, 2H), 6.11-5.41 (m, 6H), 4.93-3.83 (m, 8H), 2.56-1.83 (m, 4H), 1.28 (s, 6H), 1.23 (s, 6H). $^{13}$C NMR (CDCl$_3$, 100 MHz, 323 K): δ 156.3 (C), 148.7 (C), 146.3 (C), 140.3 (C), 136.8 (C), 136.4 (C), 136.1 (C), 135.8 (C), 135.5 (C), 133.1 (C), 132.4 (C), 130.4 (CH), 129.9 (CH), 129.1 (CH), 128.9 (CH), 111.9 (CH), 110.1 (CH), 108.4 (CH), 107.1 (CH), 104.3 (CH), 103.1 (CH), 79.5 (C), 75.4 (CH), 69.9 (CH$_2$), 69.6 (CH$_2$), 59.2 (CH$_2$), 57.5 (C), 54.1 (C), 49.3 (CH$_2$), 43.4 (C), 31.6 (CH$_3$), 30.2 (CH$_3$).

Example 16: TZ$_{100}$-PA$_{100}$ PIM

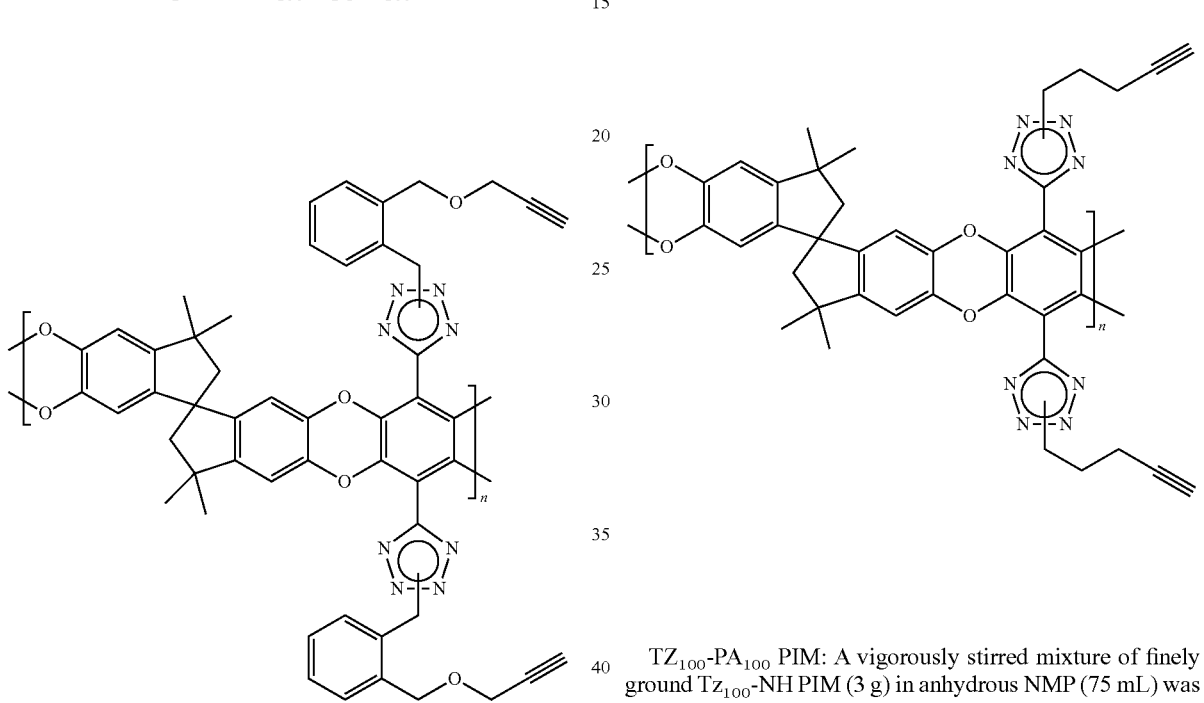

TZ$_{100}$-PA$_{100}$ PIM: A vigorously stirred mixture of finely ground Tz$_{100}$-NH PIM (3 g) in anhydrous NMP (75 mL) was added 5-chloro-1-pentyne (4 mL, 37.6 mmol) and anhydrous K$_2$CO$_3$ (5.2 g, 37.6 mmol) and under N$_2$, the reaction was heated at 85° C. for 16 h. A light brown milky solution resulted over the course of the reaction. Added a second round of 5-chloropentyne (2 mL, 18.8 mmol) and allowed to stir at 85° C. for an additional 6 h. Upon completion, the reaction was diluted with H$_2$O (200 mL), the resulting precipitate was collected by vacuum filtration over a Buchner funnel. The filter cake was washed with H$_2$O (3×200 mL), followed by MeOH (1×200 mL). The crude solid was dried thoroughly, then was redissolved in a minimum volume of CHCl$_3$, and filtered over a plug of celite, then poured into MeOH to induce precipitation. The resulting beige precipitate was filtered, and washed with MeOH. The Filter cake was re-precipitated from CHCl$_3$/MeOH. The light beige solid was dried thoroughly in a vacuum oven at 60° C., yielding an off-white solid (2.8 g). $^1$H NMR (CDCl$_3$, 400 MHz, 323 K): δ 6.48 (s, 2H), 6.09 (s, 2H), 4.86 (m, 2H), 4.44 (m, 2H), 2.42-1.86 (m, 14H), 1.24 (s, 6H), 1.21 (s, 6H). $^{13}$C NMR (CDCl$_3$, 100 MHz, 323 K): δ 156.6 (C), 148.8 (C), 148.4 (C), 146.5 (C), 140.8 (C), 140.5 (C), 136.9 (C), 112.0 (CH), 110.1 (CH), 108.4 (CH), 107.2 (CH), 82.0 (C), 70.3 (CH), 59.3 (CH$_2$), 57.3 (C), 52.2 (CH$_2$), 46.7 (CH$_2$), 43.4 (C), 31.5 (CH$_3$), 30.2 (CH$_3$), 28.3 (CH$_2$), 16.0 (CH$_2$), 15.9 (CH$_2$).

Example 17: TZ₈₂-PA₈₂

Example 18: TZ₃₃-PA₃₃

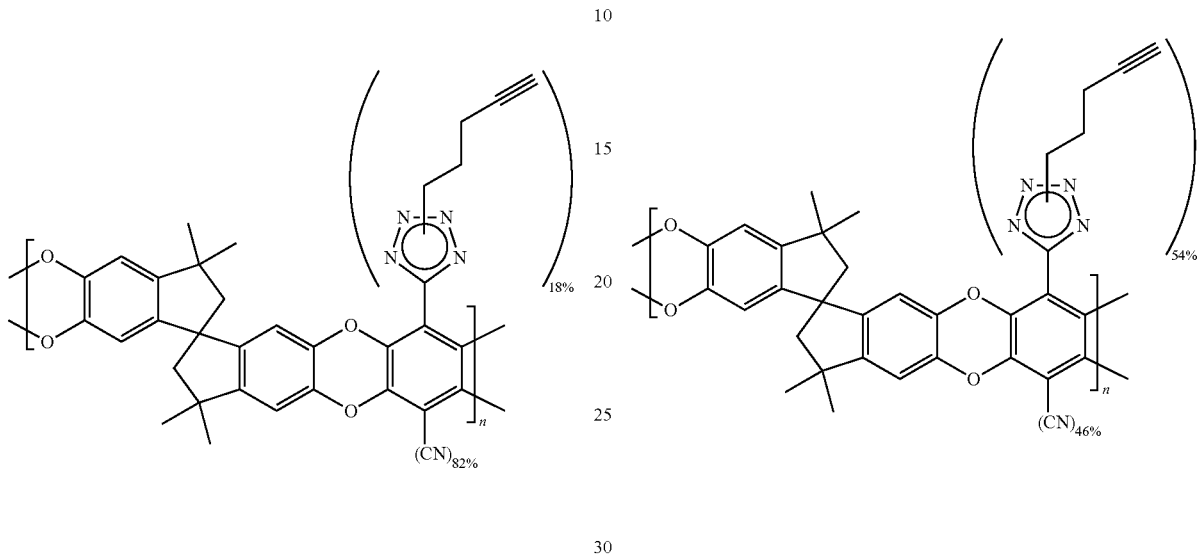

TZ$_{82}$-PA$_{82}$: A vigorously stirred mixture of finely ground Tz$_{82}$-NH PIM (3 g) in anhydrous DMAc (100 mL) was added 5-chloro-1-pentyne (4 mL, 37.6 mmol) and anhydrous K$_2$CO$_3$ (5.2 g, 37.6 mmol) and under N$_2$ the reaction was heated at 85° C. for 16 h. A light brown milky solution had formed over the course of the reaction. Upon completion, the reaction was diluted with H$_2$O (200 mL), the resulting precipitate was collected by vacuum filtration over a Buchner funnel. The filter cake was washed with H$_2$O (3×100 mL), followed by MeOH (1×50 mL). The crude solid was dried thoroughly, then was redissolved in a minimum volume of CHCl$_3$, filtered over a plug of celite, then poured into MeOH. The resulting beige precipitate was filtered, and washed with MeOH. The filter cake was purified a second time by re-precipitation from CHCl$_3$/MeOH. The light beige solid was dried thoroughly in a vacuum oven at 60° C. for 3 hrs. The title compound was isolated as a light beige/off-white solid (2.8 g). TZ$_{82}$-PA$_{82}$: $^1$H NMR (CDCl$_3$, 500 MHz, 323 K): δ 6.75 (s, 2H), 6.48 (s, 2H), 6.43 (s, 2H), 6.09 (s, 2H), 4.86 (m, 2H), 4.44 (m, 2H), 2.42-1.86 (m, 14H), 1.24 (s, 6H), 1.21 (s, 6H). $^{13}$C NMR (CDCl$_3$, 100 MHz, 323 K): δ 156.5 (C), 148.9 (C), 148.3 (C), 146.5 (C), 146.2 (C), 140.7 (C), 140.3 (C), 136.9 (C), 112.0 (CH), 110.1 (CH), 108.4 (CH), 107.1 (CH), 82.0 (C), 70.3 (CH), 59.2 (CH$_2$), 57.3 (C), 52.2 (CH$_2$), 46.7 (CH$_2$), 43.5 (C), 31.5 (CH$_3$), 30.1 (CH$_3$), 28.2 (CH$_2$), 16.0 (CH$_2$), 15.9 (CH$_2$).

TZ$_{54}$-PA$_{54}$ PIM: A vigorously stirred mixture of finely ground Tz$_{54}$-NH PIM (3 g) in anhydrous DMAc (100 mL) was added 5-chloro-1-pentyne (4 mL, 37.6 mmol) and anhydrous K$_2$CO$_3$ (5.2 g, 37.6 mmol) and under N$_2$, the reaction was heated at 85° C. for 16 h. A light brown cloudy solution had formed over the course of the reaction. Upon completion, the reaction was diluted with H$_2$O (200 mL), the resulting precipitate was collected by vacuum filtration over a Buchner funnel. The filter cake was washed with distilled H$_2$O (3×100 mL), followed by MeOH (1×50 mL). The crude solid was dried thoroughly, then was redissolved in a minimum volume of CHCl$_3$, filtered over a plug of celite, then poured into MeOH. The resulting beige precipitate was filtered, and washed with MeOH. The crude was purified a second time by re-precipitation from CHCl$_3$/MeOH. The light brown solid was dried thoroughly in a vacuum oven at 60° C. for 3 hrs. yielding the product as a light beige/off-white solid (2.6 g). The title compound was isolated as a dark yellow solid (2.6 g). TZ$_{54}$-PA$_{54}$ PIM: $^1$H NMR (CDCl$_3$, 400 MHz, 323 K): δ 6.78 (s, 2H), 6.51 (s, 2H), 6.40 (s, 2H), 6.12 (s, 2H), 4.86 (m, 2H), 4.60-4.20 (m, 2H), 2.42-1.86 (m, 14H), 1.26 (s, 12H). $^{13}$C NMR (CDCl$_3$, 100 MHz, 323 K): δ 155.9 (C), 149.7 (C), 149.1 (C), 146.4 (C), 140.3 (C), 136.7 (C), 136.8 (C), 112.2 (CH), 110.4 (CH), 92.0 (C), 81.9 (C), 81.5 (C), 70.3 (CH), 59.3 (CH$_2$), 57.4 (C), 52.2 (CH$_2$), 46.7 (CH$_2$), 43.6 (C), 31.5 (CH$_3$), 30.2 (CH$_3$), 28.3 (CH$_2$), 28.2 (CH$_2$), 16.0 (CH$_2$), 15.9 (CH$_2$).

Example 19: TZ$_{33}$-PA$_{33}$

Example 20: TZ$_{100}$-PAz$_{100}$ PIM

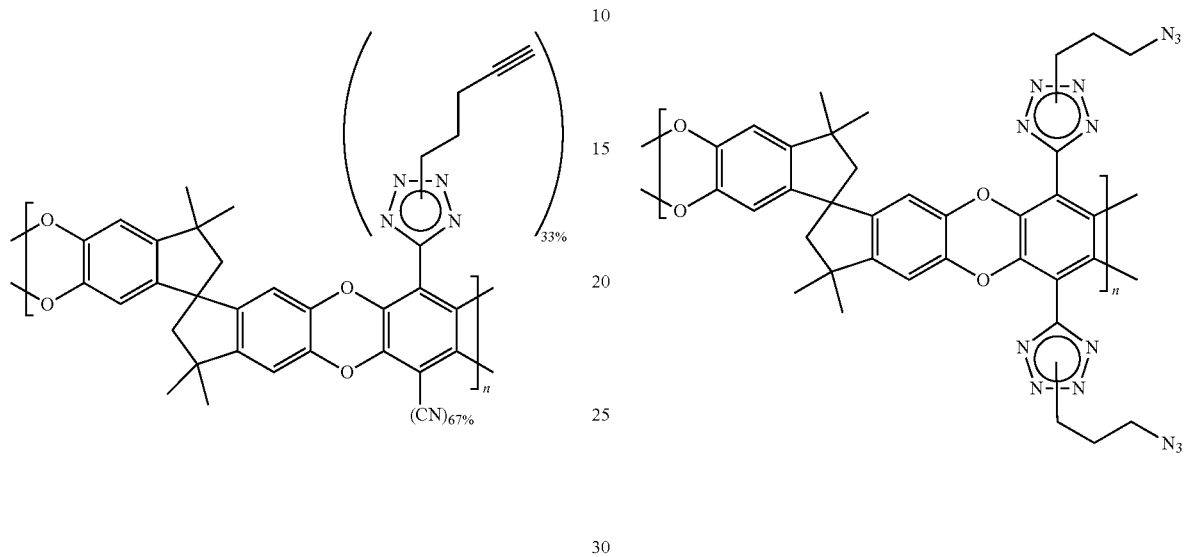

TZ$_{33}$-PA$_{33}$ PIM: A vigorously stirred mixture of finely ground Tz$_{33}$-NH PIM (3 g) in anhydrous DMAc (75 mL) was added 5-chloro-1-pentyne (3 mL, 28.3 mmol) and anhydrous K$_2$CO$_3$ (5.2 g, 38.6 mmol) and under N$_2$, the reaction was heated at 85° C. for 16 h. A light brown cloudy solution had formed over the course of the reaction. Upon completion, the reaction was diluted with H$_2$O (200 mL), the resulting precipitate was collected by vacuum filtration over a Buchner funnel. The filter cake was washed with H$_2$O (3×100 mL), followed by MeOH (1×50 mL). The crude solid was dried thoroughly, then was redissolved in a minimum volume of CHCl$_3$, filtered over a plug of celite, then poured into MeOH. The resulting beige precipitate was filtered, and washed with MeOH. The crude was purified a second time by re-precipitation from CHCl$_3$/MeOH. The yellow solid was dried thoroughly in a vacuum oven at 60° C. for 3 hrs. The title compound was isolated as a light beige/off-white solid (2.8 g). The title compound was isolated as an off-white solid (2.4 g). TZ$_{33}$-PA$_{33}$ PIM: $^1$H NMR (CDCl$_3$, 400 MHz, 323 K): δ 6.81 (s, 2H), 6.53 (s, 2H), 6.41 (s, 2H), 6.14 (s, 2H), 4.86 (m, 2H), 4.60-4.20 (m, 2H), 2.42-1.84 (m, 14H), 1.51-0.7 (m, 12H). $^{13}$C NMR (CDCl$_3$, 100 MHz, 323 K): δ 155.9 (C), 150.0 (C), 149.2 (C), 147.3 (C), 146.4 (C), 139.7 (C), 136.8 (C), 112.5 (CH), 110.4 (CH), 94.5 (C), 92.1 (C), 81.9 (C), 70.3 (CH), 59.4 (CH$_2$), 57.4 (C), 52.2 (CH$_2$), 43.6 (C), 31.6 (CH$_3$), 30.1 (CH$_3$), 28.4 (CH$_2$), 28.2 (CH$_2$), 16.0 (CH$_2$), 15.9 (CH$_2$).

TZ$_{100}$-PAz$_{100}$ PIM: A vigorously stirred mixture of finely ground Tz$_{100}$-NH PIM (3 g) in anhydrous DMAc (100 mL) was added propyl p-toluene sulfonate (9.6 g, 37.6 mmol) and anhydrous K$_2$CO$_3$ (5.2 g, 37.6 mmol) and under N$_2$, the reaction was heated at 85° C. for 16 h. A light brown/grey cloudy solution had formed over the course of the reaction. Added additional propyl p-toluene sulfonate (4.8 g, 18.8 mmol) and allowed to stir at 85° C. for 6 h. Upon completion, the reaction was diluted with H$_2$O (200 mL), the resulting precipitate was collected by vacuum filtration over a Buchner funnel. The filter cake was washed with H$_2$O (3×100 mL), followed by MeOH (1×50 mL). The crude solid was dried thoroughly, then was redissolved in a minimum volume of CHCl$_3$, filtered over a plug of celite, then poured into MeOH. The resulting light brown precipitate was filtered, and washed with MeOH. The filter cake purified by a second round of re-precipitation from CHCl$_3$/MeOH. The light brown solid was dried thoroughly in a vacuum oven at 60° C. for 3 hrs. The title compound was isolated as an light brown solid (2.3 g). $^1$H NMR (CDCl$_3$, 500 MHz, 323 K): δ 6.47 (s, 2H), 6.06 (s, 2H), 4.90-4.77 (m, 2H), 4.50-4.20 (m, 2H), 3.56-3.37 (m, 4H), 2.45-2.04 (m, 8H), 1.26 (s, 12H). $^{13}$C NMR (CDCl$_3$, 100 MHz, 323 K): δ 156.7 (C), 149.0 (C), 148.5 (C), 146.6 (C), 140.7 (C), 136.9 (C), 136.5 (C), 111.9 (CH), 110.2 (CH), 107.0 (CH), 102.7 (CH), 59.2 (CH$_2$), 57.3 (C), 50.6 (CH$_2$), 48.5 (CH$_2$), 48.4 (CH$_2$), 48.1 (CH$_2$), 45.2 (CH$_2$), 43.4 (C), 31.5 (CH$_3$), 30.1 (CH$_3$), 28.9 (CH$_2$), 28.8 (CH$_2$).

Example 21: TZ$_{84}$-PAz$_{84}$ PIM

Example 22: TZ$_{54}$-PAz$_{54}$ PIM

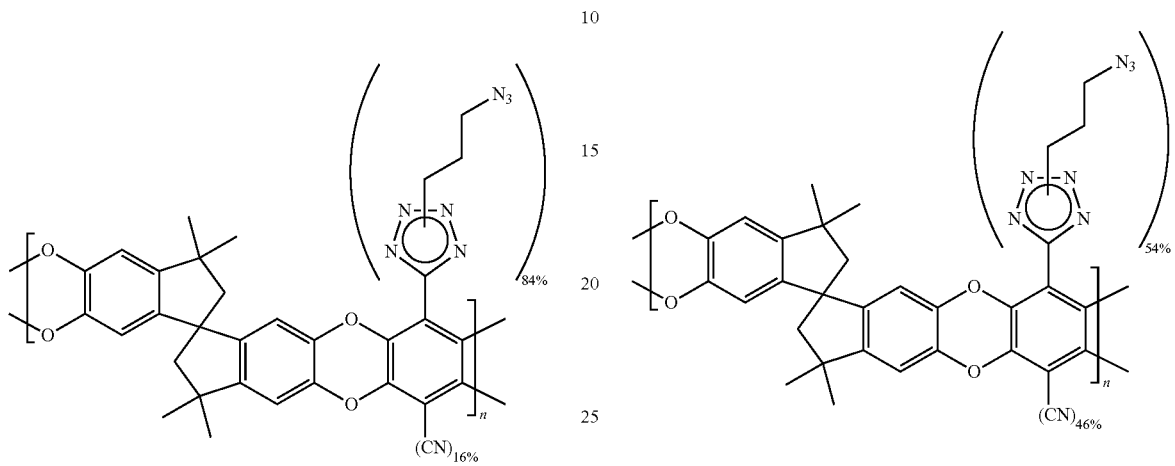

TZ$_{84}$-PAz$_{84}$ PIM: A vigorously stirred mixture of finely ground Tz$_{84}$-NH PIM (3 g) in anhydrous DMAc (100 mL) was added propyl p-toluene sulfonate$^2$ (9.6 g, 37.6 mmol) and anhydrous K$_2$CO$_3$ (5.2 g, 37.6 mmol) and under N$_2$, the reaction was heated at 85° C. for 16 h. A light brown/grey cloudy solution had formed over the course of the reaction. Upon completion, the reaction was diluted with H$_2$O (200 mL), the resulting precipitate was collected by vacuum filtration over a Buchner funnel. The filter cake was washed with H$_2$O (3×100 mL), followed by MeOH (1×50 mL). The crude solid was dried thoroughly, then was redissolved in a minimum volume of CHCl$_3$, filtered over a plug of celite, and poured into MeOH. The resulting light brown precipitate was filtered, and washed with MeOH. The filter cake was purified by a second round of re-precipitation from CHCl$_3$/MeOH. The light brown solid was dried thoroughly in a vacuum oven at 60° C. for 3 hrs. The title compound was isolated as an light brown solid (2.8 g). TZ$_{84}$-PAz$_{84}$ PIM: $^1$H NMR (CDCl$_3$, 500 MHz, 323 K): δ 6.76 (s, 2H), 6.60-6.30 (s, 4H), 6.07 (s, 2H), 4.91-4.77 (m, 2H), 4.52-4.20 (m, 2H), 3.56-3.37 (m, 4H), 2.44-2.04 (m, 8H), 1.23 (s, 12H). $^{13}$C NMR (CDCl$_3$, 100 MHz, 323 K): δ 156.7 (C), 148.9 (C), 148.4 (C), 146.5 (C), 146.1 (C), 145.8 (C), 140.7 (C), 140.2 (C), 136.8 (C), 136.9 (C), 136.5 (C), 112.0 (CH), 110.1 (CH), 107.0 (CH), 102.7 (CH). 59.2 (CH$_2$), 57.3 (C), 50.6 (CH$_2$), 48.4 (CH$_2$), 48.4 (CH$_2$), 48.0 (CH$_2$), 45.2 (CH$_2$), 43.5 (C), 31.5 (CH$_3$), 30.1 (CH$_3$), 28.8 (CH$_2$).

TZ$_{54}$-PAz$_{54}$ PIM: A vigorously stirred mixture of finely ground Tz$_{54}$-NH PIM (3 g) in anhydrous DMAc (100 mL) was added propyl p-toluene sulfonate 2 (9.6 g, 37.6 mmol) and anhydrous K$_2$CO$_3$ (5.2 g, 37.6 mmol) and under N$_2$, the reaction was heated at 85° C. for 16 h. A light brown/grey cloudy solution had formed over the course of the reaction. Upon completion, the reaction was diluted with H$_2$O (200 mL), the resulting precipitate was collected by vacuum filtration over a Buchner funnel. The filter cake was washed with H$_2$O (3×100 mL), followed by MeOH (1×50 mL). The crude solid was dried thoroughly, then was redissolved in a minimum volume of CHCl$_3$, filtered over a plug of celite, then poured into MeOH. The resulting light brown precipitate was filtered, and washed with MeOH. The filter cake purified by a second round of re-precipitation from CHCl$_3$/MeOH. The light brown solid was dried thoroughly in a vacuum oven at 60° C. for 3 hrs. The title compound was isolated as a beige solid (2.4 g). TZ$_{54}$-PAz$_{54}$ PIM: $^1$H NMR (CDCl$_3$, 500 MHz, 323 K): δ 6.79 (s, 2H), 6.50 (s, 2H), 6.40 (s, 2H), 6.10 (s, 2H), 4.91-4.76 (m, 2H), 4.52-4.22 (m, 2H), 3.55-3.36 (m, 4H), 2.43-2.07 (m, 8H), 1.26 (s, 12H). $^{13}$C NMR (CDCl$_3$, 100 MHz, 323 K): δ 156.0 (C), 149.8 (C), 149.2 (C), 147.1 (C), 146.5 (C), 145.8 (C), 139.7 (C), 136.8 (C), 136.4 (C), 112.2 (CH), 110.3 (CH), 109.8 (CH), 105.5 (CH). 93.5 (C), 92.1 (C), 59.2 (CH$_2$), 57.3 (C), 50.7 (CH$_2$), 48.4 (CH$_2$), 48.3 (CH$_2$), 48.2 (CH$_2$), 48.0 (CH$_2$), 45.2 (CH$_2$), 43.3 (C), 31.5 (CH$_3$), 30.1 (CH$_3$), 28.9 (CH$_2$), 28.8 (CH$_2$).

Example 23: TZ$_{33}$-PAz$_{33}$ PIM

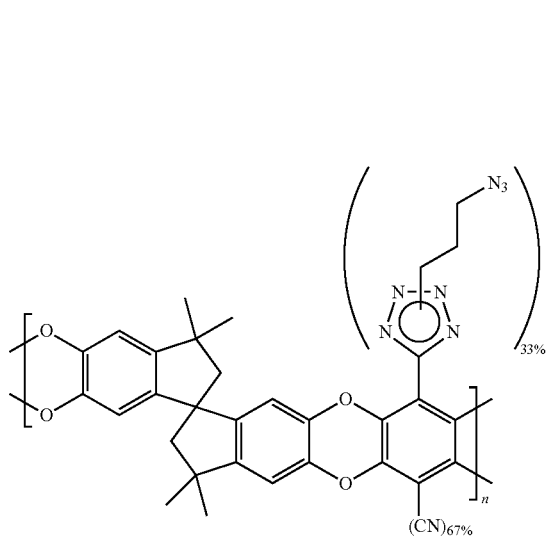

TZ$_{33}$-PAz$_{33}$ PIM: A vigorously stirred mixture of finely ground Tz$_{33}$-NH PIM (3 g) in anhydrous NMP (75 mL) was added 3 propyl p-toluene sulfonate[2] (7.2 g, 28.3 mmol) and anhydrous K$_2$CO$_3$ (5.2 g, 38.6 mmol) and under N$_2$, the reaction was heated at 85° C. for 16 h. A light brown/grey cloudy solution had formed over the course of the reaction. Upon completion, the reaction was diluted with H$_2$O (200 mL), the resulting precipitate was collected by vacuum filtration over a Buchner funnel. The filter cake was washed with H$_2$O (3×100 mL), followed by MeOH (1×50 mL). The crude solid was dried thoroughly, then was re-dissolved in a minimum volume of CHCl$_3$, filtered over a plug of celite, then poured into MeOH. The resulting light brown precipitate was filtered, and washed with MeOH. The crude was purified by a second round of re-precipitation from CHCl$_3$/MeOH. The light brown solid was dried thoroughly in a vacuum oven at 60° C. for 3 hrs. The title compound was isolated as an light brown solid (2.6 g). TZ$_{33}$-PAz$_{33}$ PIM: $^1$H NMR (CDCl$_3$, 400 MHz, 323 K): δ 6.81 (s, 2H), 6.52 (s, 2H), 6.41 (s, 2H), 6.11 (s, 2H), 4.91-4.75 (m, 2H), 4.52-4.20 (m, 2H), 3.55-3.36 (m, 4H), 2.43-2.00 (m, 8H), 1.30 (s, 12H). $^{13}$C NMR (CDCl$_3$, 100 MHz, 323 K): δ 156.0 (C), 149.9 (C), 149.2 (C), 147.1 (C), 146.4 (C), 145.8 (C), 139.4 (C), 136.7 (C), 136.3 (C), 112.4 (CH), 110.4 (CH), 109.8 (CH), 105.5 (CH). 93.4 (C), 92.1 (C), 59.2 (CH$_2$), 57.4 (C), 50.7 (CH$_2$), 48.4 (CH$_2$), 48.3 (CH$_2$), 48.0 (CH$_2$), 45.2 (CH$_2$), 43.7 (C), 31.5 (CH$_3$), 30.1 (CH$_3$), 28.8 (CH$_2$), 28.7 (CH$_2$).

Example 24: TZ$_{100}$-PA$_{70}$ PIM

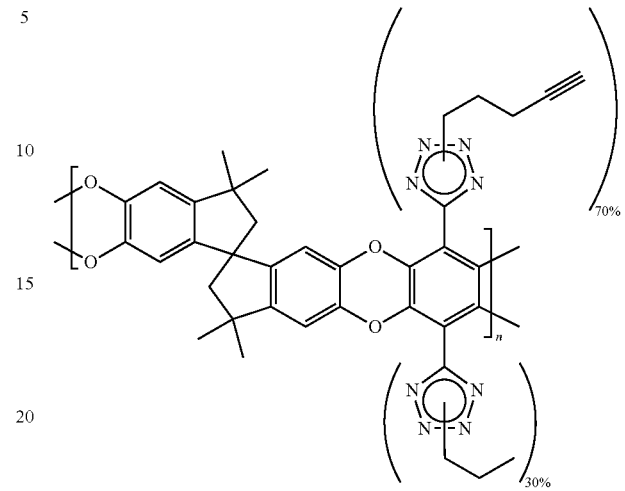

TZ$_{100}$-PA$_{70}$ PIM: Heated a mixture of NH$_{100}$-TZ PIM (1 g) in DMAc (50 mL) at 110° C. to partially solubilize the polymer, then added anhydrous K$_2$CO$_3$ (1.7 g, 12.5 mmol) and a pre-mixed solution of 5-chloro-1-pentyne (932 L, 8.8 mmol) and 1-chloro-propane (331.2 L, 3.76 mmol) and stirred the reaction at 110° C. for 16 h. Upon completion, the reaction was diluted with distilled water (100 mL), and the light-salmon colored precipitate was washed with water. Re-dissolved the solid in a minimum volume of CHCl$_3$, then poured into MeOH. The resultant precipitate was filtered and dried under vacuum. The title compound was isolated as a light pinkish-brown solid (966 mg). TZ$_{100}$-PA$_{70}$ PIM: $^1$H NMR (CDCl$_3$, 400 MHz, 323 K): δ 6.47 (s, 2H), 6.08 (s, 2H), 4.99-4.13 (m, 4H), 2.47-1.77 (m, 14H), 1.38-0.75 (s, 15H). $^{13}$C NMR (CDCl$_3$, 100 MHz, 323 K): δ 140.8 (C), 136.9 (C), 110.2 (CH), 82.0 (C), 70.2 (CH), 59.2 (CH$_2$), 57.3 (C), 55.1 (CH$_2$), 52.1 (CH$_2$), 43.4 (C), 31.5 (CH$_3$), 30.2 (CH$_3$), 28.3 (CH$_2$), 23.0, (CH$_2$) 15.9 (CH$_2$), 11.1 (CH$_3$).

Example 25: TZ$_{00}$-PA$_{30}$ PIM

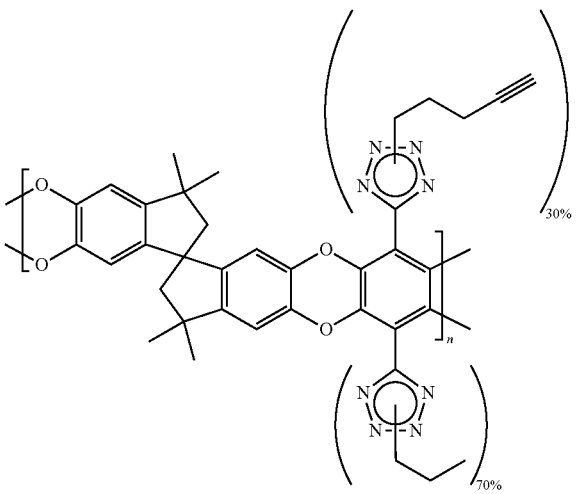

TZ$_{100}$-PA$_{30}$ PIM: Heated a mixture of NH$_{100}$-TZ PIM (1 g) in DMAc (50 mL) at 110° C. to partially solubilize the polymer, then added anhydrous K$_2$CO$_3$ (1.7 g, 12.5 mmol) and a pre-mixed solution of 5-chloro-1-pentyne (398 µL, 3.8 mmol) and 1-chloro-propane (775 µL, 8.8 mmol) and stirred the reaction at 85° C. for 16 h. A heterogeneous brown colored reaction was diluted with distilled water (100 mL), and the light brown precipitate was filtered and washed with water. Re-dissolved the solid in a minimum volume of CHCl$_3$ (12-20 mL), and poured into MeOH. The product was purified by a second re-precipitation from CHCl$_3$/MeOH, filtered and dried under vacuum. The title compound was isolated as a beige solid (755 mg). TZ$_{100}$-PA$_{30}$ PIM: $^1$H NMR (CDCl$_3$, 500 MHz, 323 K): δ 6.47 (s, 2H), 6.06 (s, 2H), 4.99-4.10 (m, 4H), 2.51-1.76 (m, 14H), 1.52-0.71 (s, 15H). $^{13}$C NMR (CDCl$_3$, 100 MHz, 323 K): δ 156.4 (C), 148.7 (C), 148.3 (C), 146.3 (C), 140.7 (C), 140.4 (C), 136.9 (C), 112.0 (CH), 110.1 (CH), 108.6 (CH), 107.3 (CH), 82.0 (C), 70.2 (CH), 59.3 (CH$_2$), 57.3 (C), 55.1 (CH$_2$), 52.2 (CH$_2$), 49.8 (CH$_2$), 46.7 (CH$_2$), 43.4 (C), 31.5 (CH$_3$), 30.2 (CH$_3$), 28.3 (CH$_2$), 23.0 (CH$_2$), 16.0 (CH$_2$), 11.1 (CH$_3$).

Example 26: TZ$_{100}$-PAz$_{70}$ PIM

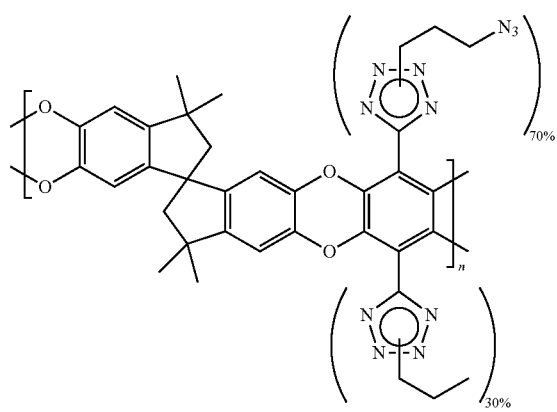

TZ$_{100}$-PAz$_{70}$ PIM: Heated a mixture of NH$_{100}$-TZ PIM (1 g) in DMAc (50 mL) at 110° C. to partially solubilize the polymer, then added anhydrous K$_2$CO$_3$ (1.7 g, 12.5 mmol) and a pre-mixed solution of 3-azidopropyl tosylate[2] (2.247 g, 8.8 mmol) and propyl p-toluene sulfonate (0.806 g, 3.8 mmol) and stirred the reaction at 85° C. for 16 h. Upon completion, the reaction was diluted with distilled water (100 mL), and the precipitate was washed with water. Re-dissolved the solid in a minimum volume of CHCl$_3$, then poured into MeOH. The resultant off-white precipitate was filtered and dried under vacuum. Repeated the re-precipitation from CHCl$_3$/MeOH. The title compound was isolated as a beige solid (629 mg). TZ$_{100}$-PAz$_{70}$ PIM: $^1$H NMR (CDCl$_3$, 400 MHz, 323 K): δ 6.47 (s, 2H), 6.08 (s, 2H), 5.00-4.11 (m, 4H), 3.55-3.38 (m, 4H), 2.53-1.82 (m, 8H), 1.48-0.73 (m, 15H). $^{13}$C NMR (CDCl$_3$, 100 MHz, 323 K): δ 148.4 (C), 146.3 (C), 140.7 (C), 136.9 (C), 111.9 (CH), 109.9 (C), 59.2 (C), 57.3 (C), 55.1 (CH$_2$), 50.6 (CH$_2$), 48.4 (CH$_2$), 48.1 (CH$_2$), 45.2 (CH$_2$), 43.4 (C), 31.1 (CH$_3$), 28.9 (CH$_3$), 22.9 (CH$_2$), 11.1 (CH$_3$).

Example 27: TZ$_{100}$-Paz$_{30}$ PIM

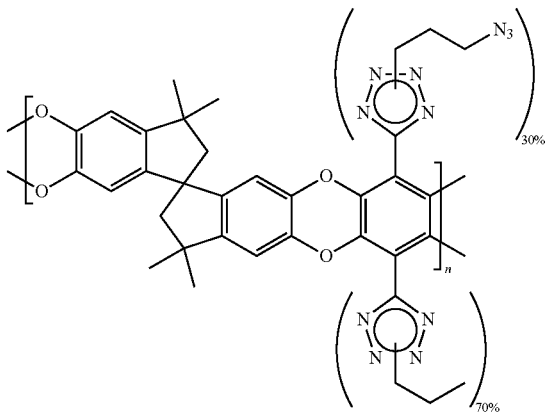

TZ$_{100}$-Paz$_{30}$ PIM: Heated a mixture of NH$_{100}$-TZ PIM (1 g) in DMAc (50 mL) at 110° C. to partially solubilize the polymer, then added anhydrous K$_2$CO$_3$ (1.7 g, 12.5 mmol) and a pre-mixed solution of 3-azidopropyl tosylate[2] (960 mg, 3.8 mmol) and propyl p-toluene sulfonate (1.886, 8.8 mmol) and stirred the reaction at 85° C. for 16 h. Upon completion, the reaction was diluted with distilled water (100 mL), and the precipitate was washed with water. Re-dissolved the solid in a minimum volume of CHCl$_3$, then poured into MeOH. The resultant precipitate was filtered and dried under vacuum. Repeated the re-precipitation from CHCl$_3$/MeOH. The title compound was isolated as a beige solid (661 mg). TZ$_{100}$-Paz$_{30}$ PIM: $^1$H NMR (CDCl$_3$, 400 MHz, 323 K): δ 6.46 (s, 2H), 6.06 (s, 2H), 4.99-4.10 (m, 4H), 3.61-3.23 (m, 2H), 2.51-1.81 (m, 8H), 1.21 (s, 12H), 1.20-0.72 (m, 3H). $^{13}$C NMR (CDCl$_3$, 100 MHz, 323 K): δ 156.4 (C), 149.1 (C), 148.9 (C), 146.3 (C), 140.7 (C), 136.9 (C), 111.9 (CH), 110.1 (C), 59.2 (C), 57.3 (C), 55.1 (CH$_2$), 50.6 (C), 48.5 (CH$_2$), 43.4 (C), 31.5 (CH$_3$), 30.1 (CH$_3$), 28.8 (CH$_2$), 23.0 (CH$_2$), 11.1 (CH$_3$).

Example 28: TZ$_{100}$-Bn$_{100}$ PIM

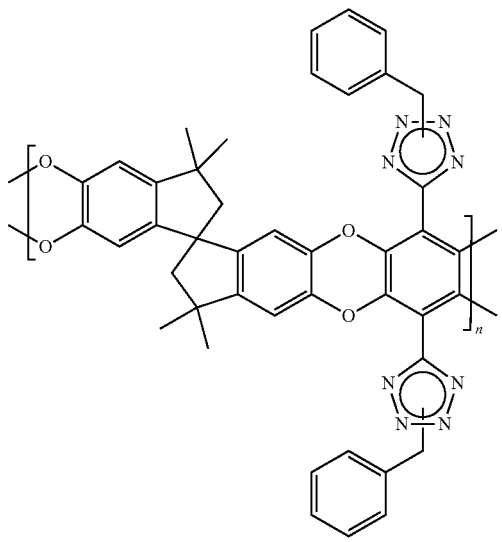

TZ$_{100}$-Bn$_{100}$ PIM: To a vigorously stirred suspension of Tz$_{100}$-NH PIM (32 g, 66.8 mmol) in anhydrous DMAc (200 mL) at 110° C., was added finely ground anhydrous K$_2$CO$_3$ (55.4 g, 401 mmol) and benzyl bromide (34.2 mL, 401 mmol) and allowed reaction to stir under N$_2$ for overnight. Diluted the reaction with H$_2$O (200 mL), filtered the precipitate, and washed the solid with H$_2$O (3×200 mL) and MeOH (200 mL). Redissolved in a minimum volume of CHCl$_3$, filtered over a pad of celite, then reprecipitated twice from CHCl$_3$/MeOH. The solid was dried in a vacuum oven at 65° C. for 24 h, yielding an off white solid (31.8 g). $^1$H NMR (CDCl$_3$, 500 MHz, 323 K): δ 7.55-6.87 (m, 10H), 6.37 (br s, 2H), 6.09-5.28 (m, 6H), 2.22 (br s, 2H), 2.03 (br s, 2H), 1.26 (s, 6H), 1.23 (s, 6H). $^{13}$C NMR (CDCl$_3$, 100 MHz, 323 K): δ 148.8 (C), 146.4 (C), 140.2 (C), 139.6 (C), 136.8 (C), 136.4 (C), 133.1 (C), 129.0 (CH), 128.7 (CH), 128.2 (CH), 111.8 (CH), 110.1 (CH), 59.2 (CH$_2$), 57.3 (C), 52.1 (CH$_2$), 43.5 (C), 31.6 (CH$_3$), 30.1 (CH$_3$).

Example 29: TA$_{72}$ PIM

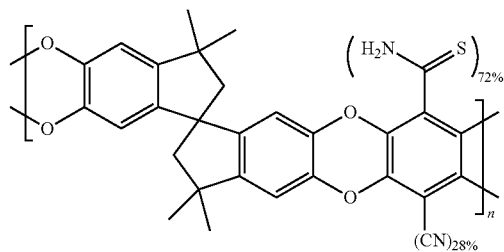

TA$_{72}$ PIM: A mixture of phosphorus pentasulfide (7.72 g, 17.4 mmol) and sodium sulfite (2.19 g, 17.4 mmol) in absolute ethanol (20 mL) was stirred under argon for 1 h at r.t. Then added PIM-1 (2 g, 4.4 mmol) and 1,4-dioxane (200 mL). Refluxed the mixture with vigorous stirring for 20 h. Cooled to r.t., then added distilled water (200 mL) and stirred for an addition 4 h at r.t. The light yellow mixture was filtered and the cake was stirred in chloroform, followed by warmed methanol. Filtered the solid, light yellow-orange solid dried in vacuo (1 g). $^1$H NMR (CDCl$_3$, 400 MHz, 373 K): δ 9.97-9.42 (m), 6.96 (s), 6.80 (s), 6.41 (s), 6.21 (s), 2.30-2.17 (m, 4H), 1.36 (s, 6H), 1.29 (s, 6H). $^{13}$C NMR (CDCl$_3$, 100 MHz, 373 K): δ 191.1 (C), 189.2 (C), 148.7 (C), 145.6 (C), 139.4 (C), 138.4 (C), 132.1 (C), 119.2 (C), 110.7 (CH), 109.6 (CH), 92.8 (CH), 87.7 (CH), 58.2 (CH$_2$), 56.3 (CH$_2$), 42.5 (CH$_2$), 40.1 (CH$_2$), 39.9 (CH$_2$), 39.1 (C), 30.5 (CH$_3$), 29.1 (CH$_3$).

Example 30: TZ$_{100}$-ρ-AzBn$_{100}$ PIM

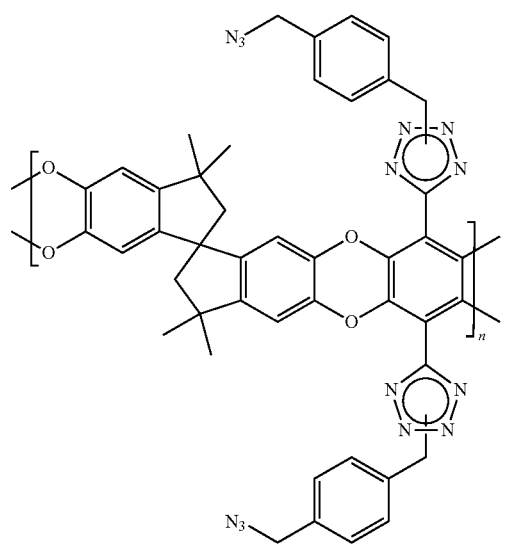

TZ$_{100}$-ρ-AzBn$_{100}$ PIM: A suspension of finely ground Tz$_{100}$-NH PIM (1 g) in anhydrous NMP (50 mL) was added 1-(azidomethyl)-4-(chloromethyl)benzene (1.14 g, 6.3 mmol) and anhydrous K$_2$CO$_3$ (1.7 g, 12.5 mmol) and the reaction was stirred under N$_2$, with heating at 110° C. for 16 hrs. Upon completion, the reaction was cooled to r.t., then added H$_2$O (100 mL), the resulting light brown precipitate was collected by vacuum filtration. The filter cake was washed with H$_2$O (3×50 mL), followed by MeOH (1×50 mL). The crude was re-dissolved in a minimum volume of CHCl$_3$, filtered over a plug of celite, then poured into MeOH. The resulting pale yellow precipitate was filtered, and washed with MeOH. The product was further purified by a second round of re-precipitation from CHCl$_3$/MeOH. The solid was dried thoroughly in a vacuum oven at 60° C. for 3 hrs yielding a solid (0.72 g). $^1$H NMR (CDCl$_3$, 400 MHz, 323 K): δ 7.58-6.91 (m, 8H), 6.40 (s, 2H), 6.19-5.20 (s, 6H), 4.46-3.87 (m, 4H), 2.25-2.06 (m, 4H), 1.25 (s, 12H). $^{13}$C NMR (CDCl$_3$, 100 MHz, 323 K): δ 149.4 (C), 146.0 (C), 140.1 (C), 139.6 (C), 136.9 (C), 136.2 (C), 132.8 (C), 128.8 (CH), 128.6 (CH), 111.9 (CH), 110.2 (CH), 104.4 (CH), 59.3 (CH$_2$), 57.4 (C), 56.8 (CH$_2$), 54.4 (CH$_2$), 54.1 (CH$_2$), 51.8 (CH$_2$), 43.5 (C), 31.5 (CH$_3$), 30.2 (CH$_3$).

Example 31: TZ$_{100}$-p-pgBn$_{100}$ PIM

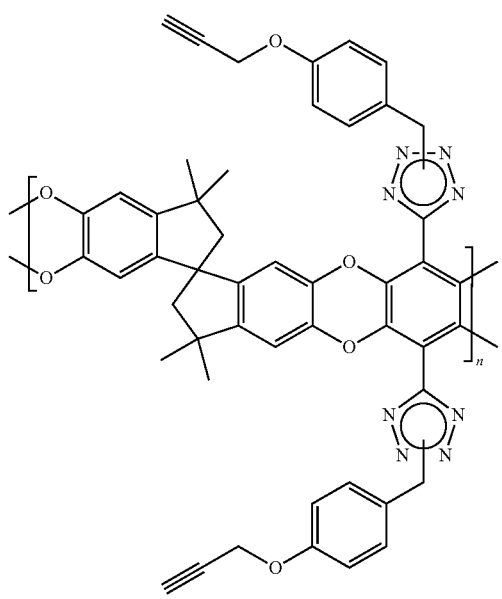

TZ$_{100}$-p-pgBn$_{100}$ PIM: A vigorously stirred mixture of finely ground Tz$_{100}$-NH PIM (1 g) in anhydrous NMP (50 mL) was added 1-(chloromethyl)-4-(prop-2-yn-1-yloxy)benzene (1.1 g, 6.3 mmol) and anhydrous K$_2$CO$_3$ (1.7 g, 12.5 mmol) and the reaction was heated at 100° C. for 15 hrs. Upon completion, the reaction was cooled to r.t. then was added H$_2$O (150 mL), the resulting light brown precipitate was collected by vacuum filtration. The filter cake was washed with H$_2$O (3×50 mL), followed by MeOH (1×50 mL). The crude was re-dissolved in a minimum volume of CHCl$_3$, filtered over a plug of celite, then poured into MeOH. The resulting pale yellow precipitate was filtered, and washed with MeOH. The product was purified by a second round of re-precipitation from CHCl$_3$/MeOH. The solid was dried thoroughly in a vacuum oven at 60° C. for 3 hrs yielding a pale yellow solid (0.99 g). $^1$H NMR (CDCl$_3$, 400 MHz, 323 K): δ 7.63-5.20 (m, 16H), 4.82-4.17 (m, 4H), 2.58-1.88 (m, 4H), 1.27 (s, 6H), 1.24 (s, 6H). $^{13}$C NMR (CDCl$_3$, 100 MHz, 323 K): δ 158.0 (C), 156.2 (C), 148.6 (C), 146.1 (C), 140.7 (C), 140.1 (C), 139.4 (C), 136.6 (C), 136.0 (C), 129.9 (CH), 126.4 (CH), 125.7 (C), 115.4 (CH), 111.9 (CH), 110.0 (CH), 108.1 (CH), 104.2 (CH), 103.0 (CH), 78.2 (C), 75.8 (CH), 59.1 (CH$_2$), 57.1 (C), 56.5 (CH$_2$), 55.9 (C), 51.7 (CH$_2$), 43.3 (C), 31.3 (CH$_3$), 29.9 (CH$_3$).

Example 32: Thz$_{72}$-pgPE PIM

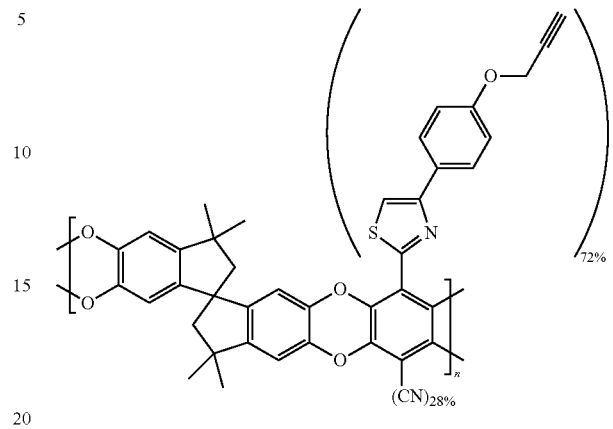

Thz$_{72}$-pgPE PIM: A solution of thioamide PIM (100 mg, 0.2 mmol) was dissolved in DMAc (10 mL). Then added propargyl bromide (172 uL, 2 mmol) and K2CO3 (276 mg, 2 mmol) and heated at 120 deg C. with stirring for 10 h. Upon completion, cooled the reaction to r.t. then added water (10 mL), a light brown precipitate formed. Filtered the solid and washed with 1M HCl, then water, then diethyl ether. Dissolved the crude in a minimal amount of hot THF, then added methanol to precipitate the produce. Filtered the solid and washed with methanol, dried the solid thoroughly in vacuo (85 mg). $^1$H NMR (CDCl$_3$, 400 MHz, 324 K): δ 8.01-6.25 (m), 4.76-4.67 (m), 2.53-2.09 (m), 1.27-1.26 (m). $^{13}$C NMR (CDCl$_3$, 100 MHz, 324 K): δ 158.0 (C), 155.8 (C), 141.2 (C), 136.6 (C), 128.0 (CH), 115.4 (CH), 113.8 (CH), 112.3 (CH), 110.8 (CH), 78.8 (C), 75.8 (CH), 59.5 (CH$_2$), 57.4 (CH$_2$), 56.3 (CH$_2$), 56.1 (CH$_2$), 43.5 (C), 31.6 (CH$_3$), 30.3 (CH$_3$).

As various changes can be made in the above-described subject matter without departing from the scope and spirit of the present invention, it is intended that all subject matter contained in the above description, or defined in the appended claims, be interpreted as descriptive and illustrative of the present invention. Many modifications and variations of the present invention are possible in light of the above teachings. Accordingly, the present description is intended to embrace all such alternatives, modifications, and variances which fall within the scope of the appended claims.

All patents, applications, publications, test methods, literature, and other materials cited herein are hereby incorporated by reference in their entirety as if physically present in this specification.

Additional embodiments of the disclosure are below.

Embodiment 1

A compound according to Formula I:

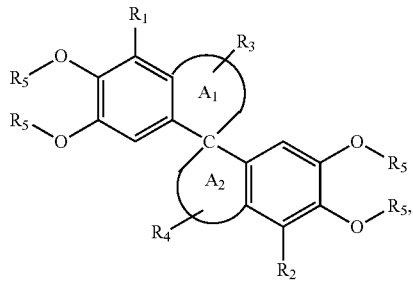

Formula I wherein:
the carbon indicated by "C" denotes a spiro-carbon;
$A_1$ and $A_2$ are each independently selected from:

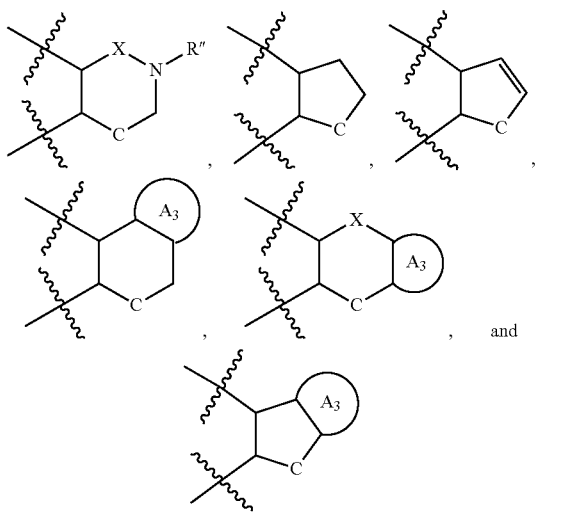

, and $A_3$ is a selected from substituted or unsubstituted $C_5$-$C_6$ aryl, substituted or unsubstituted $C_5$-$C_6$ heteroaryl, substituted or unsubstituted $C_5$-$C_6$ cycloalkyl and substituted or unsubstituted $C_5$-$C_6$ cyclic heterocycloalkyl;
X is —$CR_6$, —O—, —S—, $NR_6$, —C=O, —C=$NR_6$, —C=N—N($R_6$)$_2$, and C=N—$OR_6$;
$R_1$, $R_2$, $R_3$, and $R_4$ are each independently selected from H and Y—Z, wherein at least one of $R_1$, $R_2$, $R_3$, and $R_4$ is Y—Z;
$R_5$ is independently at each occurrence H, Si(OR$_6$)$_3$, or Si(R$_6$)$_3$;
$R_6$ is independently at each occurrence selected from H, substituted or unsubstituted alkyl, substituted or unsubstituted heteroalkyl, substituted or unsubstituted aryl, and substituted or unsubstituted heteroaryl;
Y is independently absent or selected from substituted or unsubstituted alkyl, substituted or unsubstituted heteroalkyl, substituted or unsubstituted aryl, substituted or unsubstituted heteroaryl, —NH—(C=O)—; =NO—$C_{1-6}$ alkyl-; and —(C=O)-phenyl-;
Z is independently selected from —N$_3$, —C≡CH, C≡C—R', —C≡N, —(C=O)—H, —SH, —CH=CH$_2$, halide, —SO$_3$R$_6$, —B(OR$_6$)$_2$, Sn(R$_6$)$_3$, and Zn(R$_6$)$_2$;

R' is selected from substituted or unsubstituted alkyl, substituted or unsubstituted heteroalkyl, substituted or unsubstituted aryl, substituted or unsubstituted heteroaryl, —CN, —CO$_2$R$_6$, —(C=O)—N(R$_6$)$_2$, and —(C=O)—R$_6$; and
R" is selected from $R_3$ and $R_4$.

Embodiment 2

The compound according to embodiment 1, wherein:
$A_1$ and $A_2$ are each independently selected from:

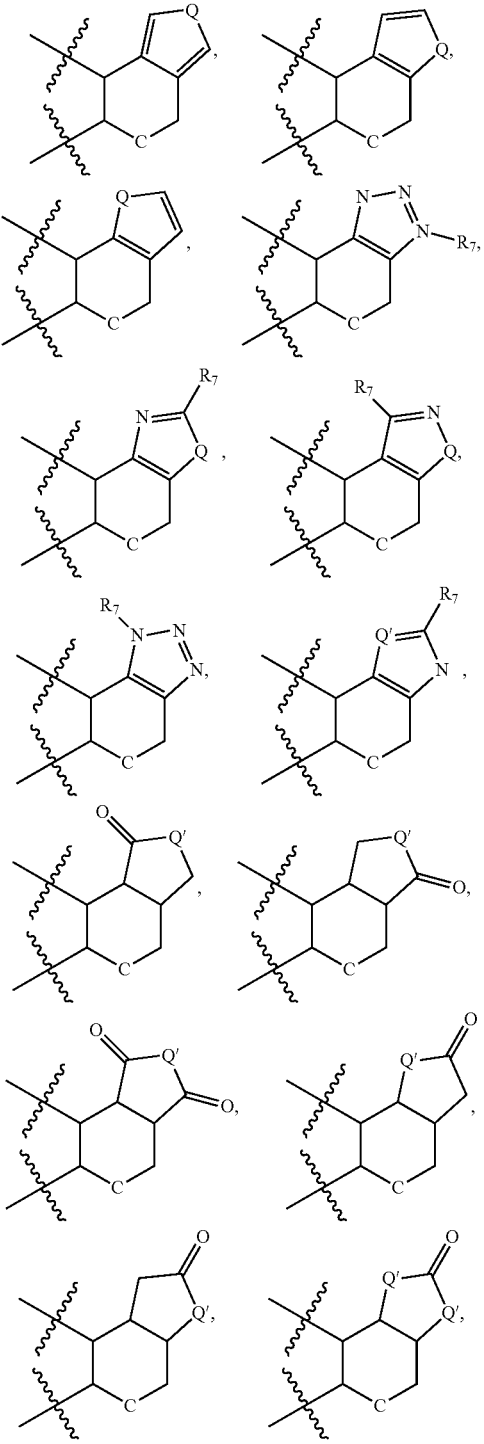

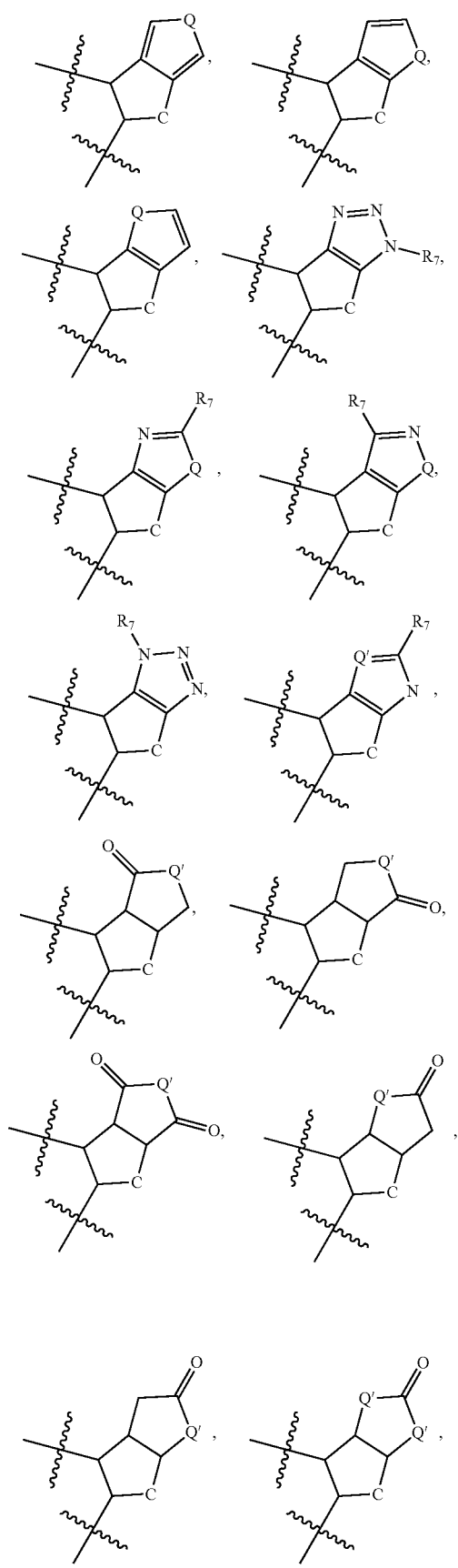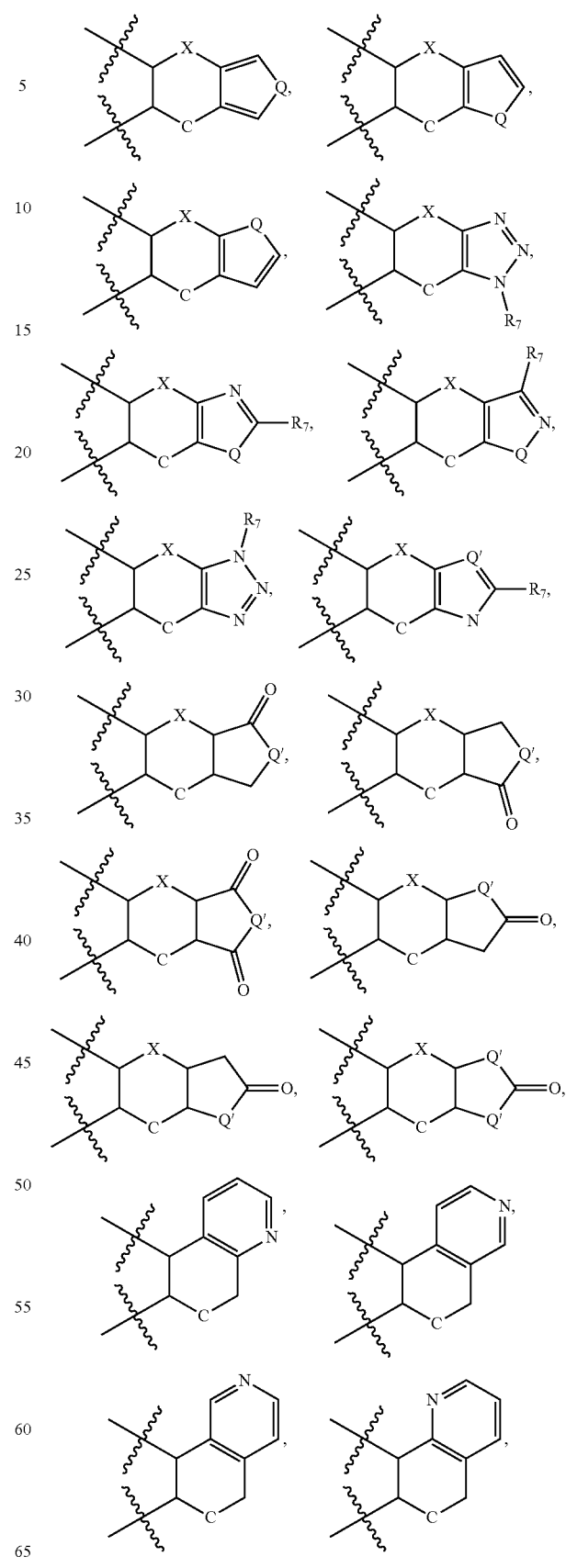

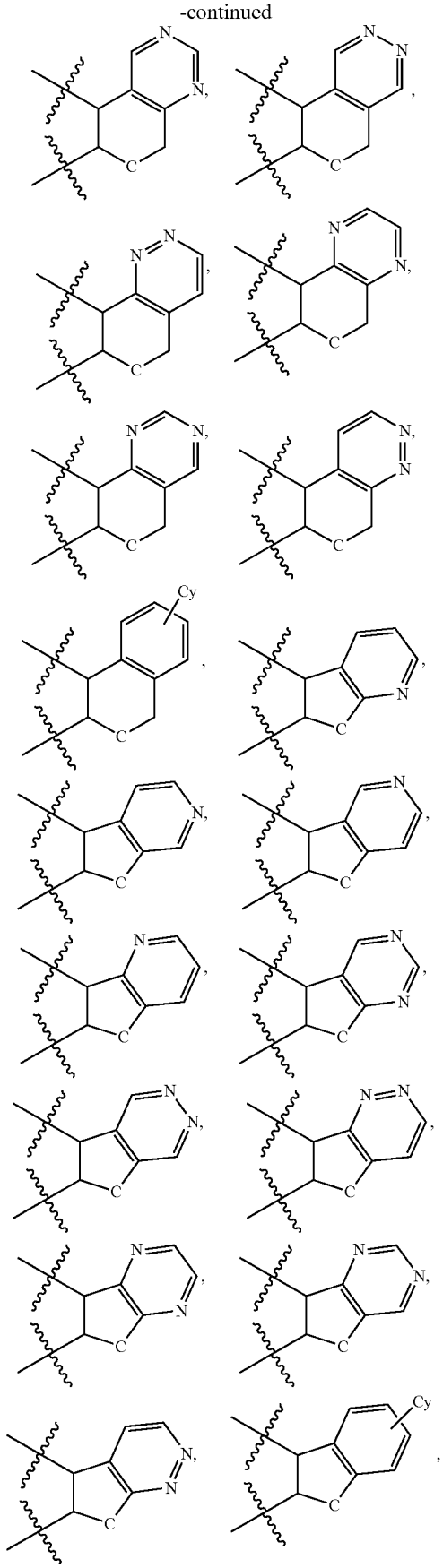

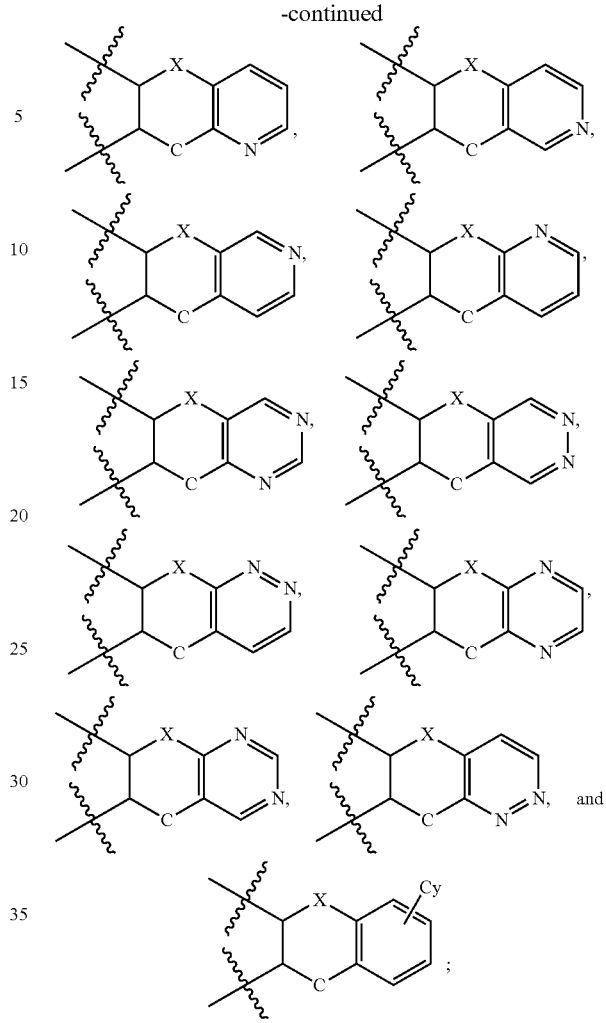

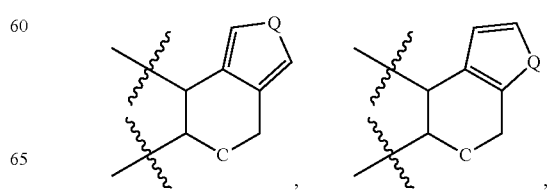

X is selected from —CR₆, —O—, —S—, NR₆, —C═O, —C═NR₆, —C═N—N(R₆)₂, and C═N—OR₆;

C_y is selected from substituted or unsubstituted C₅-C₆ aryl, substituted or unsubstituted C₅-C₆ heteroaryl, substituted or unsubstituted C₅-C₆ cycloalkyl and substituted or unsubstituted C₅-C₆ cyclic heterocycloalkyl;

Q is selected from —O—, —S—, —N—R₇, —C═O, —C═NR₇, —C═N—N(R₇)₂, and —C═N—OR₇;

Q' is independently at each occurrence selected from —O—, —S—, and —N—R₇; and

R₇ is independently at each occurrence selected from R₃ and R₄.

Embodiment 3

The compound according to embodiment 1, wherein:
A₁ and A₂ are each independently selected from:

-continued

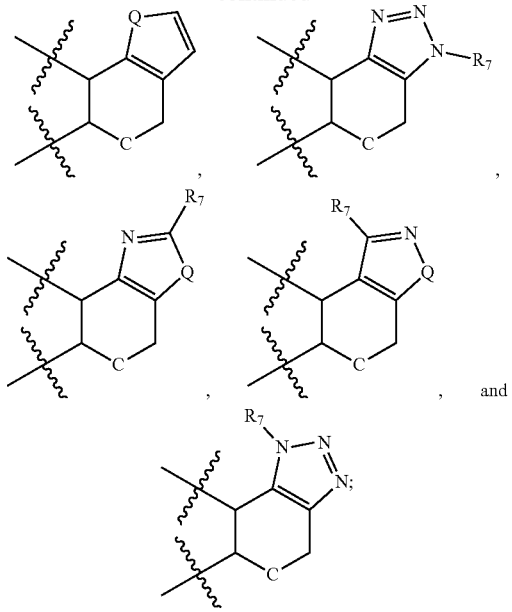

Z is independently selected from —N₃, —C≡CH, C≡C—R', —C≡N, —(C═O)—H, —SH, and —CH═CH₂;

Q is selected from —O—, —S—, —N—R₇, —C═O, —C═NR₇, —C═N—N(R₇)₂, and —C═N—OR₇;

R' is selected from substituted or unsubstituted alkyl, substituted or unsubstituted heteroalkyl, substituted or unsubstituted aryl, substituted or unsubstituted heteroaryl, —CN, —CO₂R₆, —(C═O)—N(R₆)₂, and —(C═O)—R₆;

R₆ is independently at each occurrence selected from H, substituted or unsubstituted alkyl, substituted or unsubstituted heteroalkyl, substituted or unsubstituted aryl, and substituted or unsubstituted heteroaryl, and R₇ is independently at each occurrence selected from R₃ and R₄.

Embodiment 4

The compound according to embodiment 1, wherein:
A₁ and A₂ are each independently selected from:

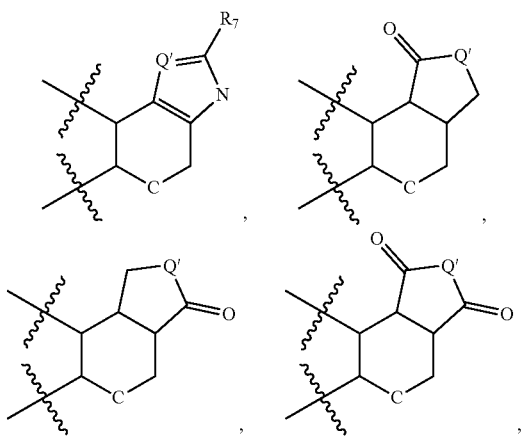

-continued

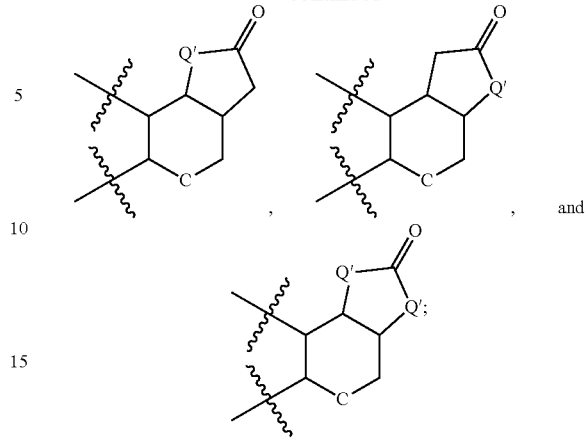

Z is independently selected from —N₃, —C≡CH, C≡C—R', —C≡N, —(C═O)—H, —SH, and —CH═CH₂;

Q' is independently at each occurrence selected from —O—, —S—, and —N—R₇;

R' is selected from substituted or unsubstituted alkyl, substituted or unsubstituted heteroalkyl, substituted or unsubstituted aryl, substituted or unsubstituted heteroaryl, —CN, —CO₂R₆, —(C═O)—N(R₆)₂, and —(C═O)—R₆;

R₆ is independently at each occurrence selected from H, substituted or unsubstituted alkyl, substituted or unsubstituted heteroalkyl, substituted or unsubstituted aryl, and substituted or unsubstituted heteroaryl, and R₇ is independently at each occurrence selected from R₃ and R₄.

Embodiment 5

The compound according to embodiment 1, wherein:
A₁ and A₂ are each independently selected from:

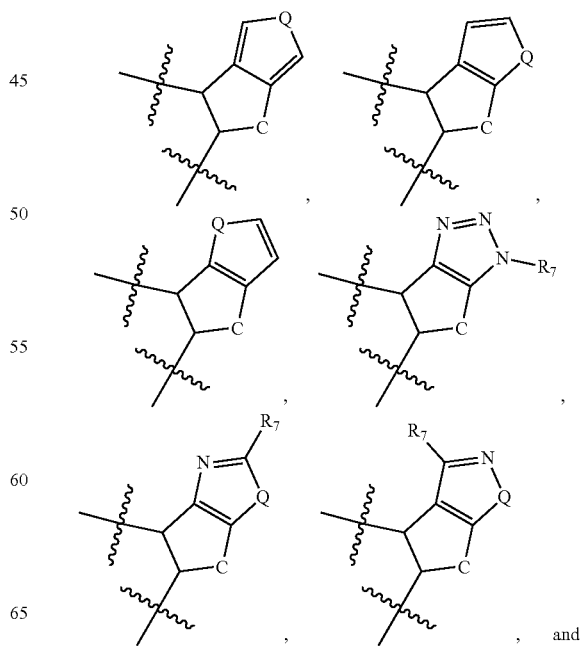

-continued

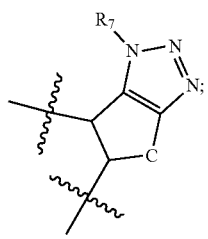

Z is independently selected from —N₃, —C≡CH, C≡C—R', —C≡N, —(C=O)—H, —SH, and —CH=CH₂;

Q is selected from —O—, —S—, —N—R₇, —C=O, —C=NR₇, —C=N—N(R₇)₂, and —C=N—OR₇;

R' is selected from substituted or unsubstituted alkyl, substituted or unsubstituted heteroalkyl, substituted or unsubstituted aryl, substituted or unsubstituted heteroaryl, —CN, —CO₂R₆, —(C=O)—N(R₆)₂, and —(C=O)—R₆;

R₆ is independently at each occurrence selected from H, substituted or unsubstituted alkyl, substituted or unsubstituted heteroalkyl, substituted or unsubstituted aryl, and substituted or unsubstituted heteroaryl, and R₇ is independently at each occurrence selected from R₃ and R₄.

Embodiment 6

The compound according to embodiment 1, wherein:
A₁ and A₂ are each independently selected from:

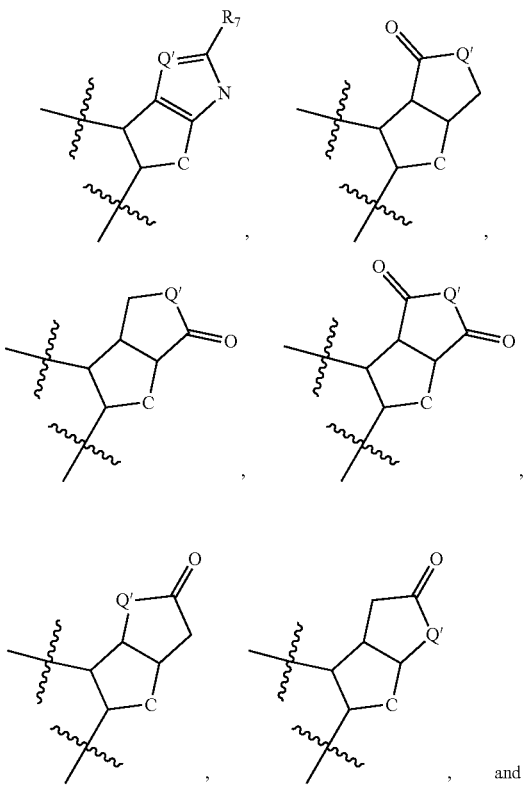

, and

-continued

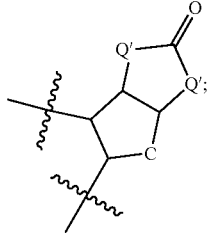

Z is independently selected from —N₃, —C≡CH, C≡C—R', —C≡N, —(C=O)—H, —SH, and —CH=CH₂;

Q' is independently at each occurrence selected from —O—, —S—, and —N—R₇;

R' is selected from substituted or unsubstituted alkyl, substituted or unsubstituted heteroalkyl, substituted or unsubstituted aryl, substituted or unsubstituted heteroaryl, —CN, —CO₂R₆, —(C=O)—N(R₆)₂, and —(C=O)—R₆;

R₆ is independently at each occurrence selected from H, substituted or unsubstituted alkyl, substituted or unsubstituted heteroalkyl, substituted or unsubstituted aryl, and substituted or unsubstituted heteroaryl, and R₇ is independently at each occurrence selected from R₃ and R₄.

Embodiment 7

The compound according to embodiment 1, wherein:
A₁ and A₂ are each independently selected from:

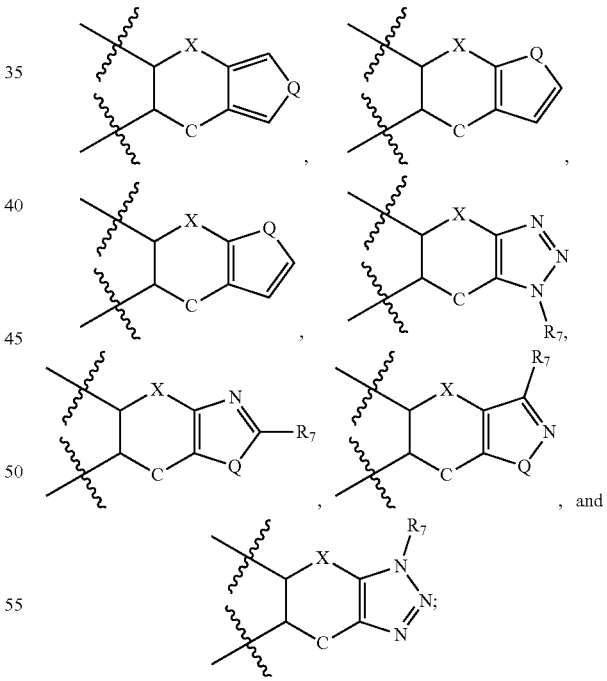

, and

Z is independently selected from —N₃, —C≡CH, C≡C—R', —C≡N, —(C=O)—H, —SH, and —CH=CH₂;

Q is selected from —O—, —S—, —N—R₇, —C=O, —C=NR₇, —C=N—N(R₇)₂, and —C=N—OR₇;

X is selected from —CR₆, —O—, —S—, NR₆, —C=O, —C=NR₆, —C=N—N(R₆)₂, and C=N—OR₆;

R' is selected from substituted or unsubstituted alkyl, substituted or unsubstituted heteroalkyl, substituted or unsubstituted aryl, substituted or unsubstituted heteroaryl, —CN, —CO$_2$R$_6$, —(C=O)—N(R$_6$)$_2$, and —(C=O)—R$_6$;

R$_6$ is independently at each occurrence selected from H, substituted or unsubstituted alkyl, substituted or unsubstituted heteroalkyl, substituted or unsubstituted aryl, and substituted or unsubstituted heteroaryl, and R$_7$ is independently at each occurrence selected from R$_3$ and R$_4$.

Embodiment 8

The compound according to embodiment 1, wherein:
A$_1$ and A$_2$ are each independently selected from:

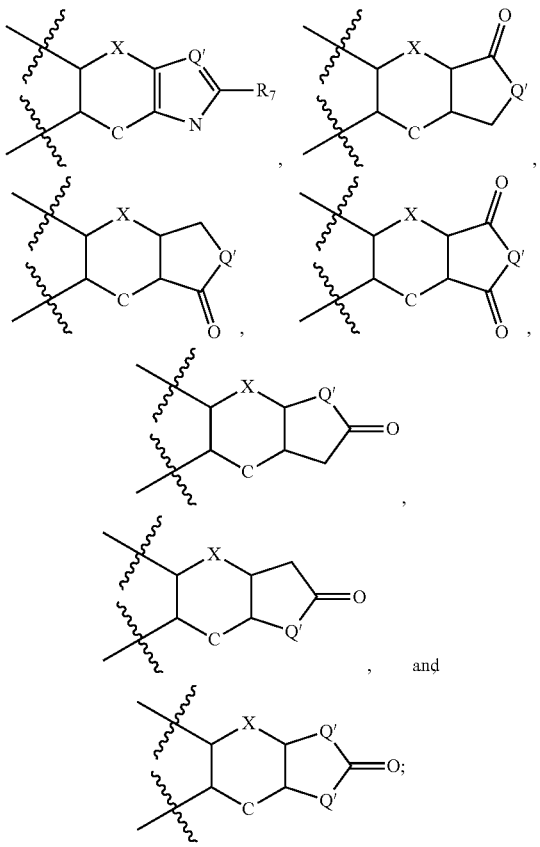

Z is independently selected from —N$_3$, —C≡CH, C≡C—R', —C≡N, —(C=O)—H, —SH, and —CH=CH$_2$;

X is selected from —CR$_6$, —O—, —S—, NR$_6$, —C=O, —C=NR$_6$, —C=N—N(R$_6$)$_2$, and C=N—OR$_6$;

Q' is independently at each occurrence selected from —O—, —S—, and —N—R$_7$;

R' is selected from substituted or unsubstituted alkyl, substituted or unsubstituted heteroalkyl, substituted or unsubstituted aryl, substituted or unsubstituted heteroaryl, —CN, —CO$_2$R$_6$, —(C=O)—N(R$_6$)$_2$, and —(C=O)—R$_6$;

R$_6$ is independently at each occurrence selected from H, substituted or unsubstituted alkyl, substituted or unsubstituted heteroalkyl, substituted or unsubstituted aryl, and substituted or unsubstituted heteroaryl, and R$_7$ is independently at each occurrence selected from R$_3$ and R$_4$.

Embodiment 9

The compound according to embodiment 1, wherein:
A$_1$ and A$_2$ are each independently selected from:

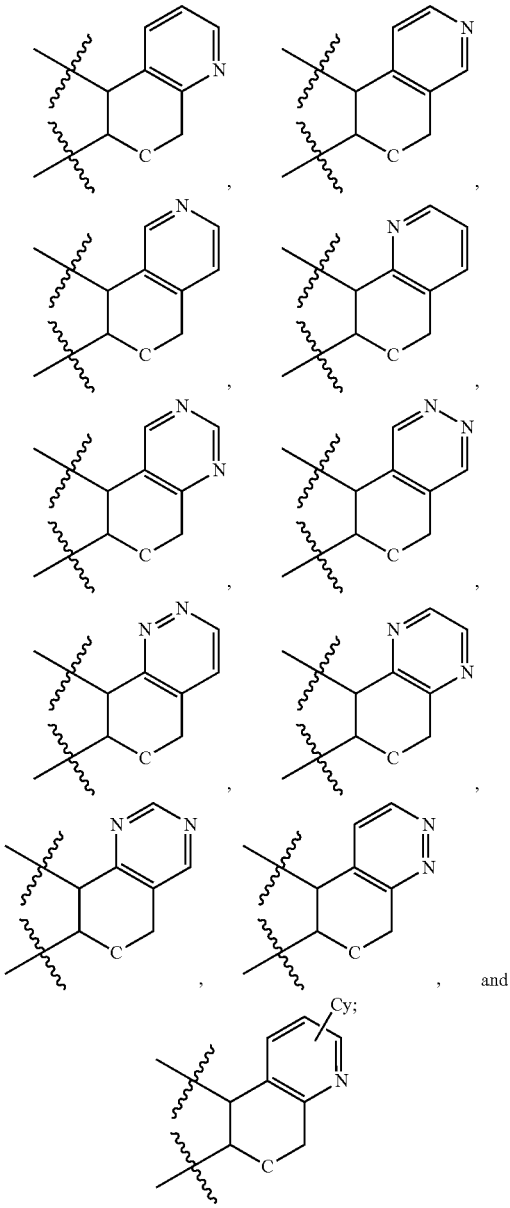

Z is independently selected from —N$_3$, —C≡CH, C≡C—R', —C≡N, —(C=O)—H, —SH, and —CH=CH$_2$;

R' is selected from substituted or unsubstituted alkyl, substituted or unsubstituted heteroalkyl, substituted or unsubstituted aryl, substituted or unsubstituted heteroaryl, —CN, —CO$_2$R$_6$, —(C=O)—N(R$_6$)$_2$, and —(C=O)—R$_6$;

R$_6$ is independently at each occurrence selected from H, substituted or unsubstituted alkyl, substituted or unsubstituted heteroalkyl, substituted or unsubstituted aryl, and substituted or unsubstituted heteroaryl, and C$_y$ is selected from substituted or unsubstituted C$_5$-C$_6$ aryl, substituted or unsubstituted C$_5$-C$_6$ heteroaryl, substituted or unsubstituted C$_5$-C$_6$ cycloalkyl and substituted or unsubstituted C$_5$-C$_6$ cyclic heterocycloalkyl.

131

Embodiment 10

The compound according to embodiment 1, wherein:

$A_1$ and $A_2$ are each independently selected from

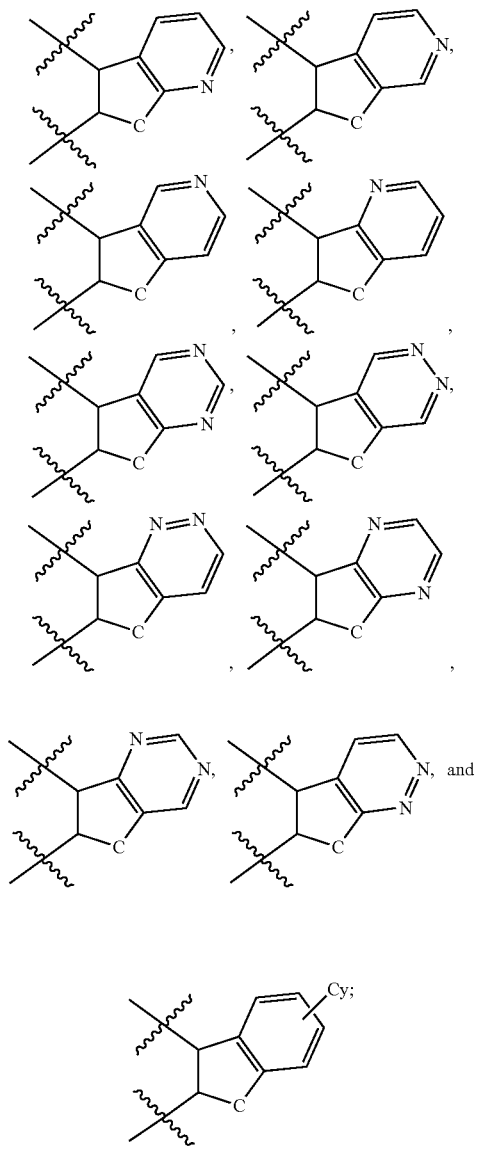

Z is independently selected from —$N_3$, —C≡CH, C≡C—R', —C≡N, —(C═O)—H, —SH, and —CH═$CH_2$;

R' is selected from substituted or unsubstituted alkyl, substituted or unsubstituted heteroalkyl, substituted or unsubstituted aryl, substituted or unsubstituted heteroaryl, —CN, —$CO_2R_6$, —(C═O)—$N(R_6)_2$, and —(C═O)—$R_6$;

$R_6$ is independently at each occurrence selected from H, substituted or unsubstituted alkyl, substituted or unsubstituted heteroalkyl, substituted or unsubstituted aryl, and substituted or unsubstituted heteroaryl, and $C_y$ is selected from substituted or unsubstituted $C_5$-$C_6$ aryl, substituted or unsubstituted $C_5$-$C_6$ heteroaryl, substituted or unsubstituted $C_5$-$C_6$ cycloalkyl and substituted or unsubstituted $C_5$-$C_6$ cyclic heterocycloalkyl.

132

Embodiment 11

The compound according to embodiment 1, wherein:

$A_1$ and $A_2$ are each independently selected from

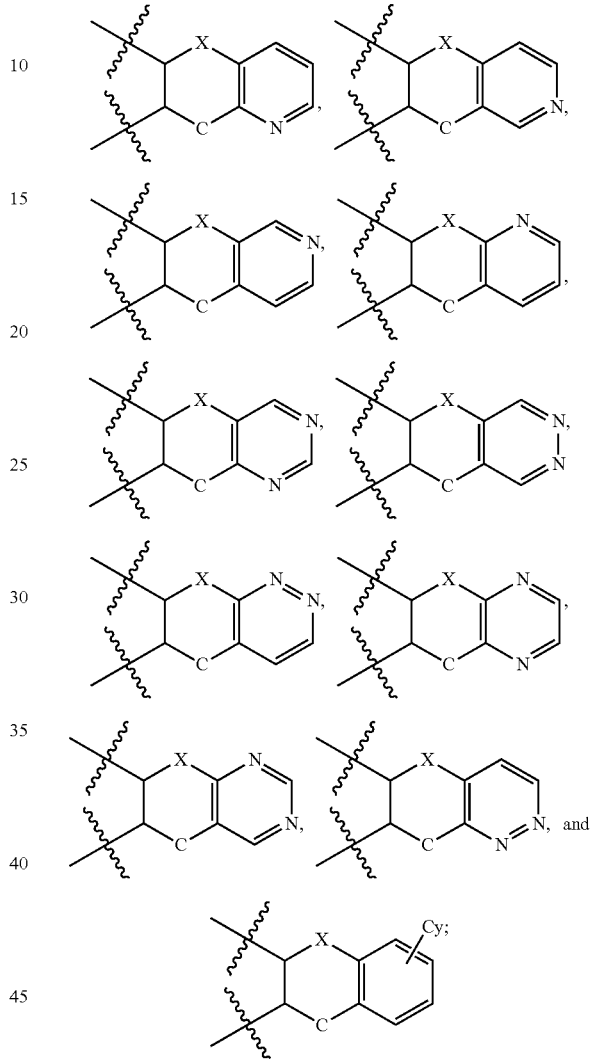

X is selected from —$CR_6$, —O—, —S—, $NR_6$, —C═O, —C═$NR_6$, —C═N—$N(R_6)_2$, and C═N—$OR_6$;

Z is independently selected from —$N_3$, —C≡CH, C≡C—R', —C≡N, —(C═O)—H, —SH, and —CH═$CH_2$;

R' is selected from substituted or unsubstituted alkyl, substituted or unsubstituted heteroalkyl, substituted or unsubstituted aryl, substituted or unsubstituted heteroaryl, —CN, —$CO_2R_6$, —(C═O)—$N(R_6)_2$, and —(C═O)—$R_6$;

$R_6$ is independently at each occurrence selected from H, substituted or unsubstituted alkyl, substituted or unsubstituted heteroalkyl, substituted or unsubstituted aryl, and substituted or unsubstituted heteroaryl, and Cy is selected from substituted or unsubstituted $C_5$-$C_6$ aryl, substituted or unsubstituted $C_5$-$C_6$ heteroaryl, substituted or unsubstituted $C_5$-$C_6$ cycloalkyl and substituted or unsubstituted $C_5$-$C_6$ cyclic heterocycloalkyl.

Embodiment 12

A compound according to embodiment 1, wherein Formula I is:

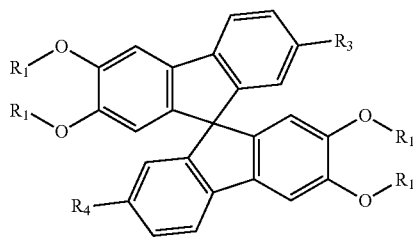

wherein:

$R_1$ is independently at each occurrence H or alkyl;

$R_3$ and $R_4$ are each independently selected from halide and $-B(OR_6)_2$.

Embodiment 13

The compound of embodiment 12, selected from the group consisting of:

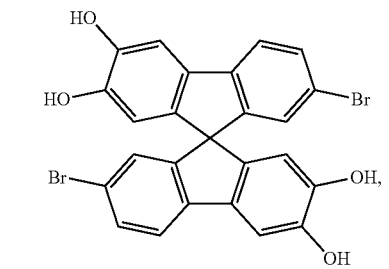

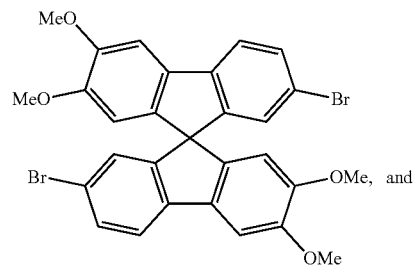

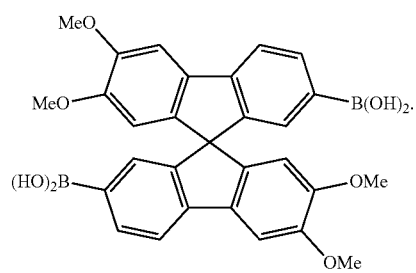

Embodiment 14

The compound according to embodiment 1 selected from the group consisting of:

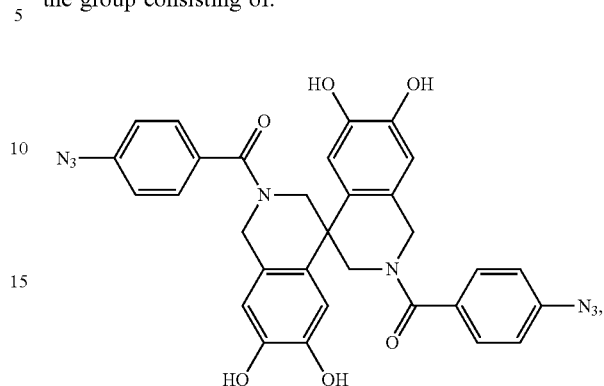

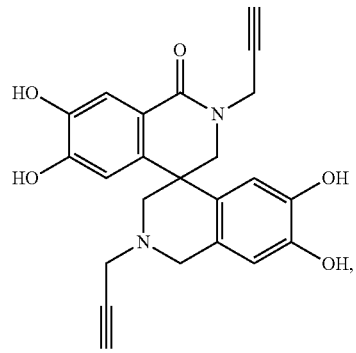

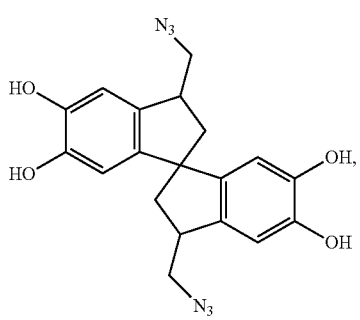

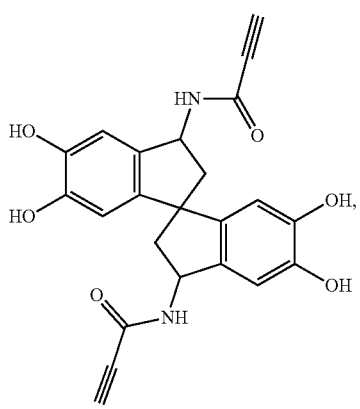

-continued
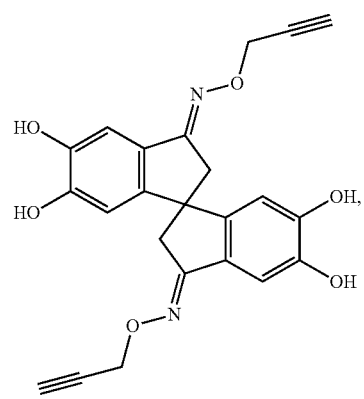
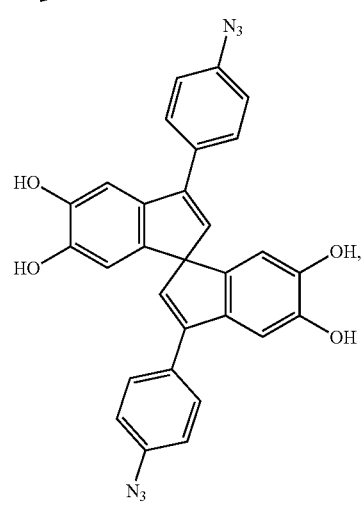
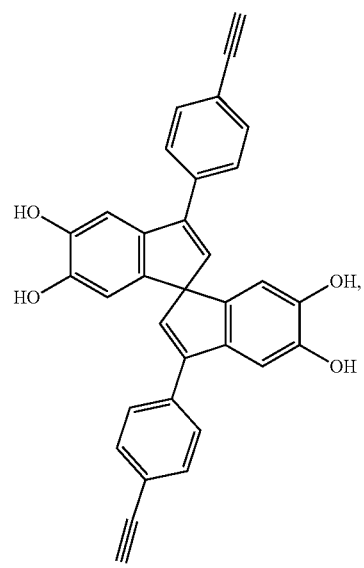
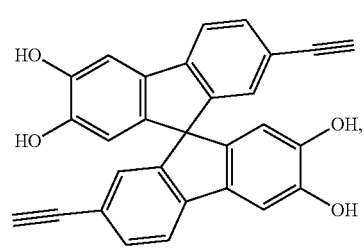
-continued
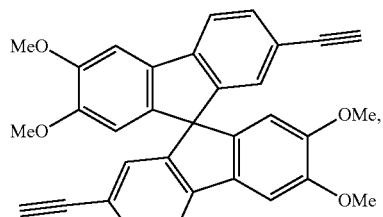
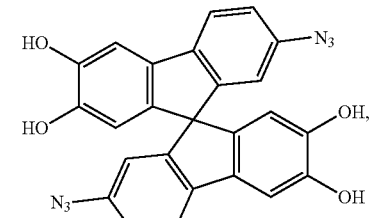
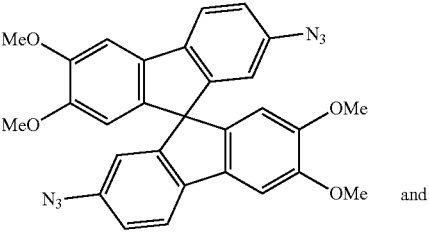
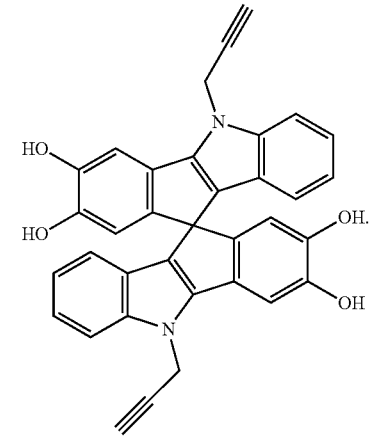
and
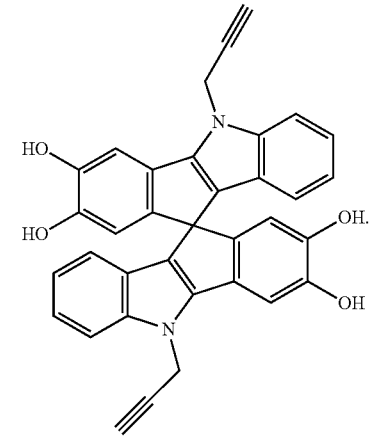
Embodiment 15
A compound according to Formula II:
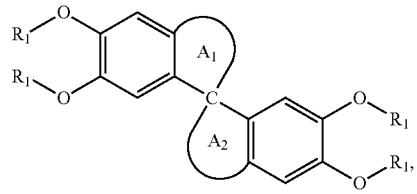
Formula II wherein: the carbon indicated by "C" denotes a spiro carbon;

A₁ is selected from

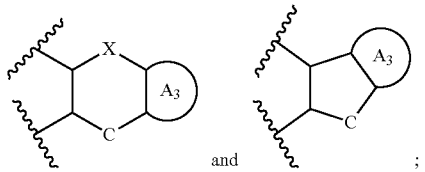

and

A₂ is

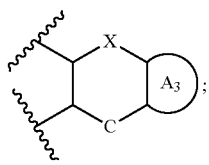

X is independently at each occurrence selected from O, or N—R₂;

R₁ is independently at each occurrence H or alkyl;

R₂ is selected from H, substituted or unsubstituted alkyl, and substituted or unsubstituted aryl, and A₃ is a selected from substituted or unsubstituted C₅-C₆ aryl, substituted or unsubstituted C₅-C₆ heteroaryl, substituted or unsubstituted C₅-C₆ cycloalkyl and substituted or unsubstituted C₅-C₆ cyclic heterocycloalkyl.

Embodiment 16

The compound according to embodiment 15, wherein: A₁ and A₂ are each independently selected from:

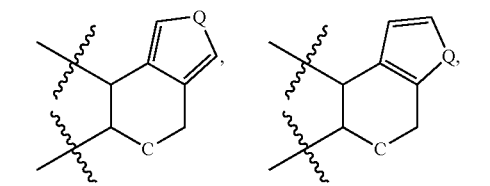

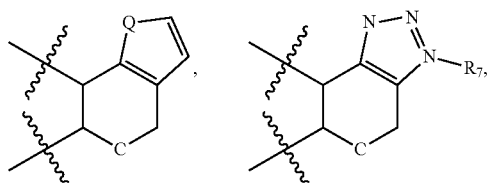

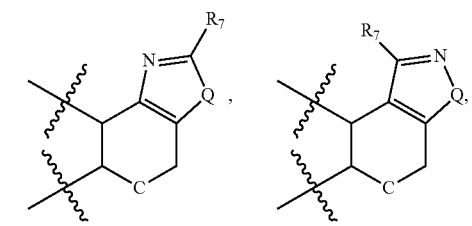

-continued

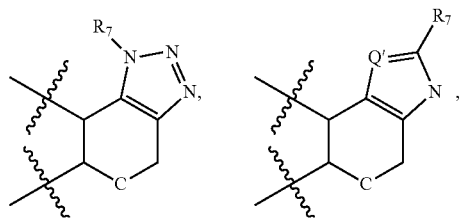

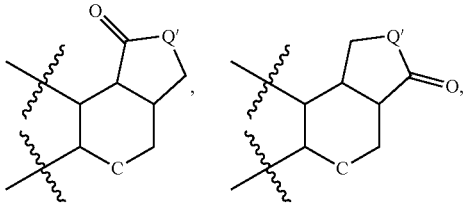

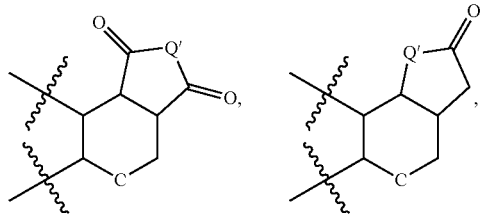

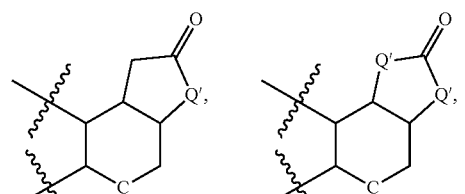

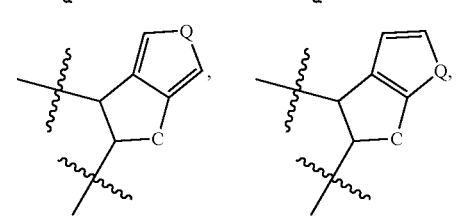

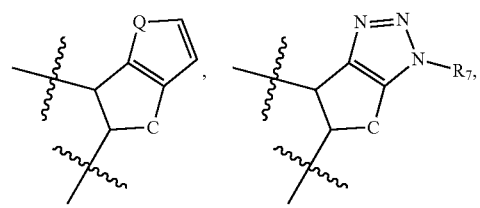

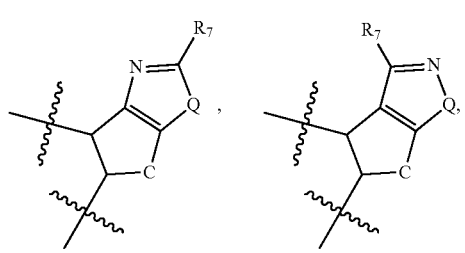

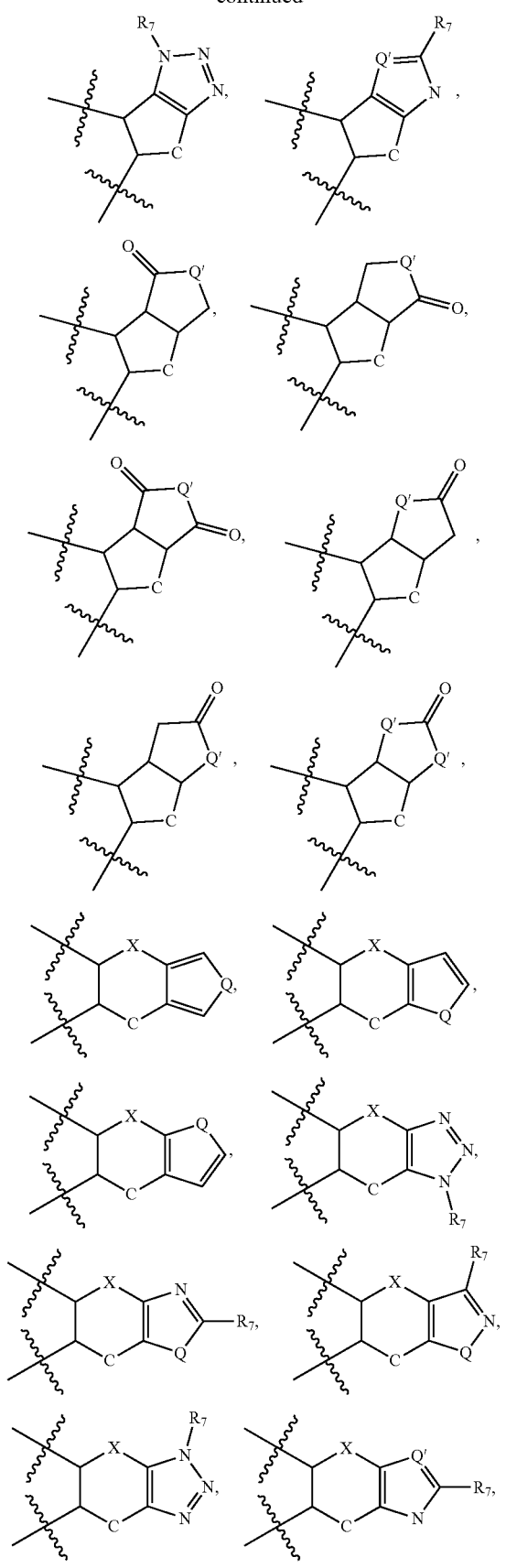
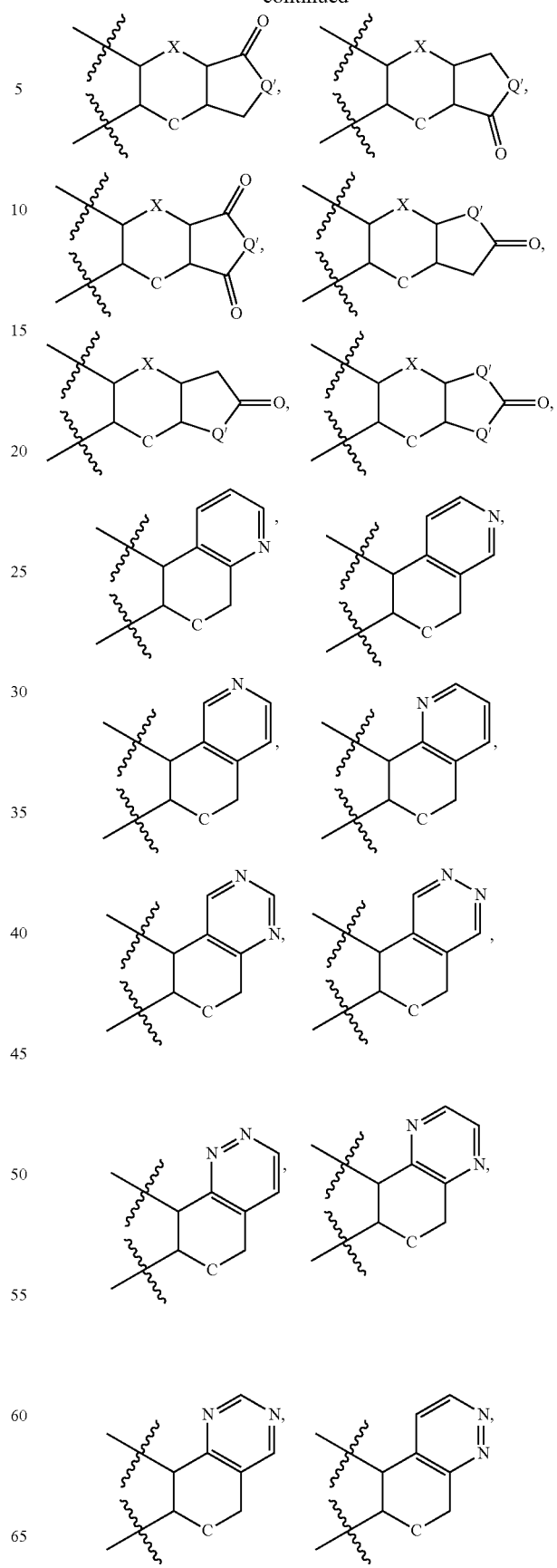

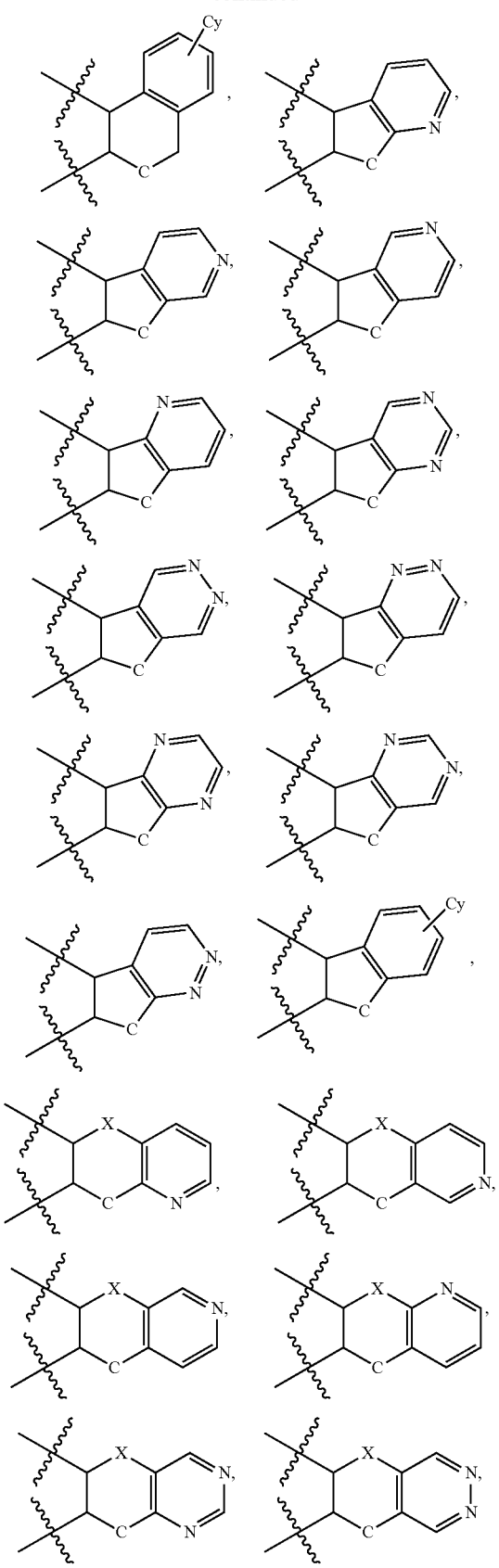

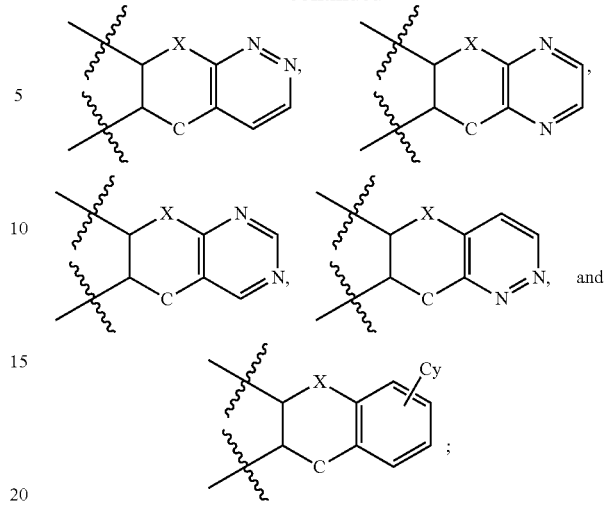

X is selected from —CR$_6$, —O—, —S—, NR$_6$, —C=O, —C=NR$_6$, —C=N—N(R$_6$)$_2$, and C=N—OR$_6$;

C$_y$ is selected from substituted or unsubstituted C$_5$-C$_6$ aryl, substituted or unsubstituted C$_5$-C$_6$ heteroaryl, substituted or unsubstituted C$_5$-C$_6$ cycloalkyl and substituted or unsubstituted C$_5$-C$_6$ cyclic heterocycloalkyl;

Q is selected from —O—, —S—, —N—R$_7$, —C=O, —C=NR$_7$, —C=N—N(R$_7$)$_2$, and —C=N—OR$_7$;

Q' is independently at each occurrence selected from —O—, —S—, and —N—R$_7$;

R$_6$ is independently at each occurrence selected from H, substituted or unsubstituted alkyl, substituted or unsubstituted heteroalkyl, substituted or unsubstituted aryl, and substituted or unsubstituted heteroaryl, and R$_7$ is independently at each occurrence selected from R$_3$ and R$_4$.

Embodiment 17

The compound according to embodiment 15 selected from the group consisting of:

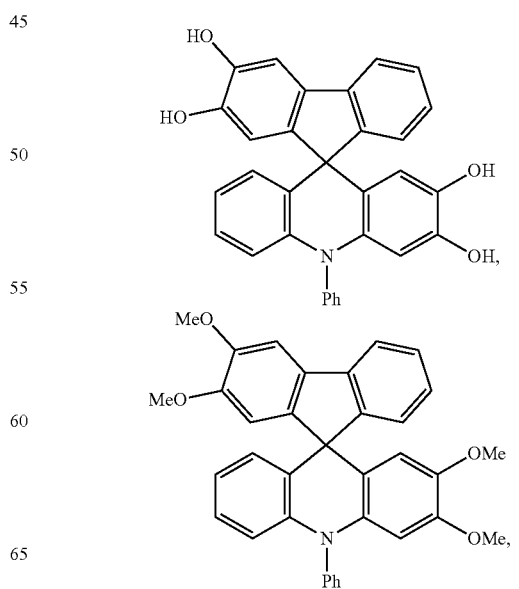

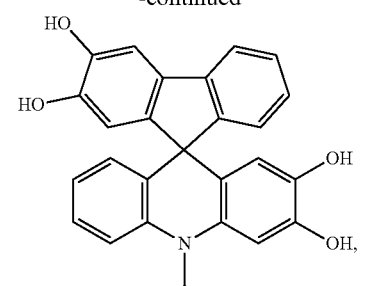
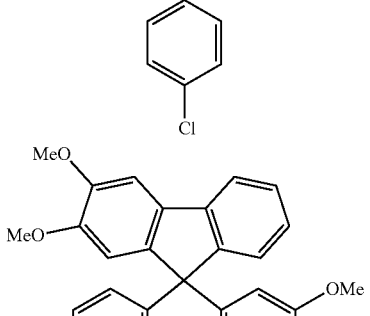
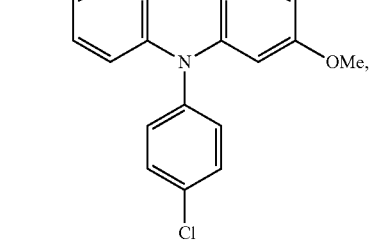
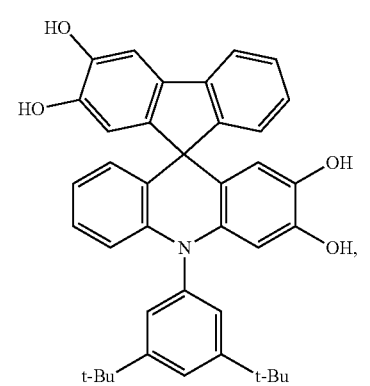
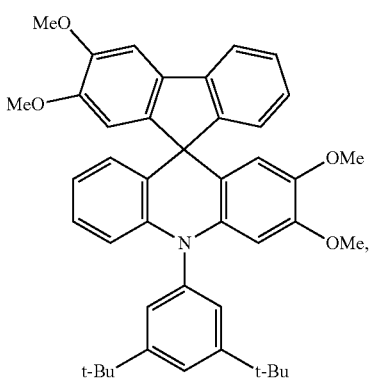
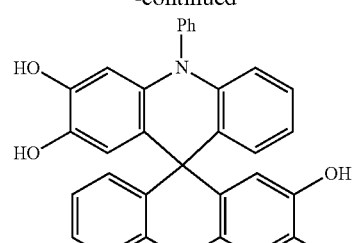
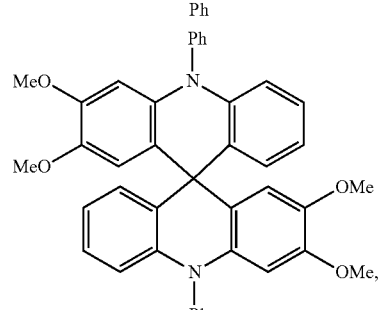
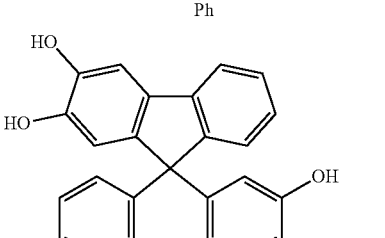
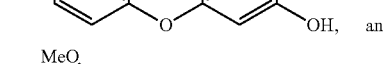
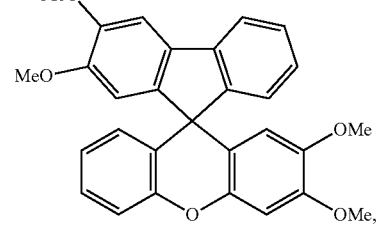
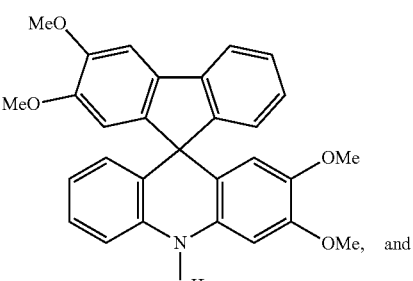
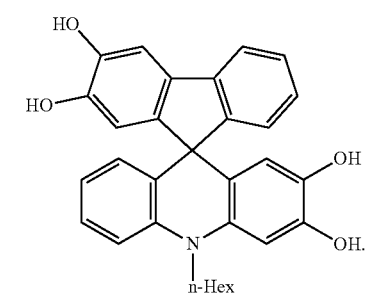

Embodiment 18

A compound according to Formula III:

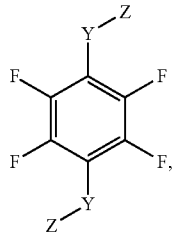

Formula III wherein:

Z is independently at each occurrence selected from —N$_3$, —C≡CH, C≡C—R', —C≡N, —(C=O)—H, —SH, and —CH=CH$_2$;

Y is independently at each occurrence absent, or selected from

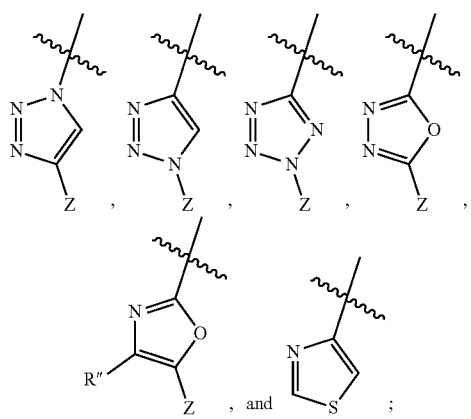

R' is selected from H, substituted or unsubstituted alkyl, substituted or unsubstituted heteroalkyl, substituted or unsubstituted aryl, substituted or unsubstituted heteroaryl, —CN, —CO$_2$R", —(C=O)—N(R")$_2$, and —(C=O)—R"; and R" is selected from H, substituted or unsubstituted alkyl, substituted or unsubstituted heteroalkyl, substituted or unsubstituted aryl, and substituted or unsubstituted heteroaryl.

Embodiment 19

The compound according to embodiment 18, wherein:

Z is selected from —N$_3$, —C≡CH, and C≡C—R';

R' is selected from H, substituted or unsubstituted alkyl, substituted or unsubstituted heteroalkyl, substituted or unsubstituted aryl, substituted or unsubstituted heteroaryl, —CN, —CO$_2$R", —(C=O)—N(R")$_2$, and —(C=O)—R"; and R" is selected from H, substituted or unsubstituted alkyl, substituted or unsubstituted heteroalkyl, substituted or unsubstituted aryl, and substituted or unsubstituted heteroaryl, and Y is the same at each occurrence.

Embodiment 20

A polymer according to Formula IV:

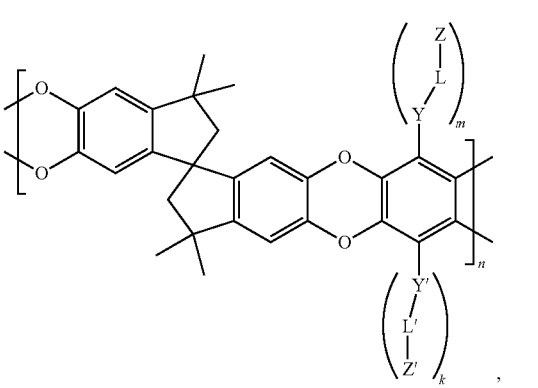

Formula IV wherein:

Y is absent or selected from tetrazole and thiazole;

L is absent or selected from substituted or unsubstituted C$_{1-12}$ alkyl, substituted or unsubstituted benzyl, and C$_{1-12}$ alkylcarbamate;

Z is absent or selected from —N$_3$, —C≡CH, C≡C—R', —C≡N, —(C=O)—H, —SH, and —CH=CH$_2$; wherein when Y and L are both absent, Z is not absent;

Y' is absent or selected from hydrogen, tetrazole, thiazole, and thioamide;

L' is absent or selected from substituted or unsubstituted C$_{1-12}$ alkyl, substituted or unsubstituted benzyl, and C$_{1-12}$ alkylcarbamate;

Z' is absent or selected from —N$_3$, —C≡CH, C≡C—R', —C≡N, —(C=O)—H, —SH, and —CH=CH$_2$; wherein when Y' and L' are both absent, Z' is not absent;

R' is independently at each occurrence selected from substituted or unsubstituted alkyl, substituted or unsubstituted heteroalkyl, substituted or unsubstituted aryl, substituted or unsubstituted heteroaryl, —CN, —CO$_2$R", —(C=O)—N(R")$_2$, and —(C=O)—R";

R" is selected from H, substituted or unsubstituted alkyl, substituted or unsubstituted heteroalkyl, substituted or unsubstituted aryl, and substituted or unsubstituted heteroaryl;

the ratio of m to n is from about 0:1 to about 1:1;

the ratio of k to n is from about 0:1 to about 1:1; and n is an integer from 5 to 100,000;

provided that when Z is absent, Y is not absent or hydrogen, and when Z' is absent, Y' is not absent or hydrogen.

Embodiment 21

The polymer according to embodiment 20, wherein:

Z is absent or selected from —N$_3$, —C≡CH, and C≡C—R';

R' is independently at each occurrence selected from substituted or unsubstituted alkyl, substituted or unsubstituted heteroalkyl, substituted or unsubstituted aryl, substituted or unsubstituted heteroaryl, —CN, —CO$_2$R", —(C=O)—N(R")$_2$, and —(C=O)—R";

R" is selected from H, substituted or unsubstituted alkyl, substituted or unsubstituted heteroalkyl, substituted or unsubstituted aryl, and substituted or unsubstituted heteroaryl;

147

Y' is selected from tetrazole, thiazole, and thioamide;
L' is selected from unsubstituted $C_{1-12}$ alkyl and unsubstituted benzyl; and
Z' is absent.

Embodiment 22

The polymer according to embodiment 20, wherein:
Z is selected from —$N_3$, —C≡CH, and C≡C—R';
R' is independently at each occurrence selected from substituted or unsubstituted alkyl, substituted or unsubstituted heteroalkyl, substituted or unsubstituted aryl, substituted or unsubstituted heteroaryl, —CN, —$CO_2$R", —(C═O)—N(R")$_2$, and —(C═O)—R";

148

R" is selected from H, substituted or unsubstituted alkyl, substituted or unsubstituted heteroalkyl, substituted or unsubstituted aryl, and substituted or unsubstituted heteroaryl;
Y' is selected from tetrazole, thiazole, and thioamide;
L' is selected from unsubstituted $C_{1-12}$ alkyl and unsubstituted benzyl;
Z' is absent;
the ratio of m to n is from about 0.3:1 to about 1:1; and
the ratio of k to n is from about 0:1 to about 0.7:1.

Embodiment 23

The polymer according to embodiment 20 selected from the group consisting of:

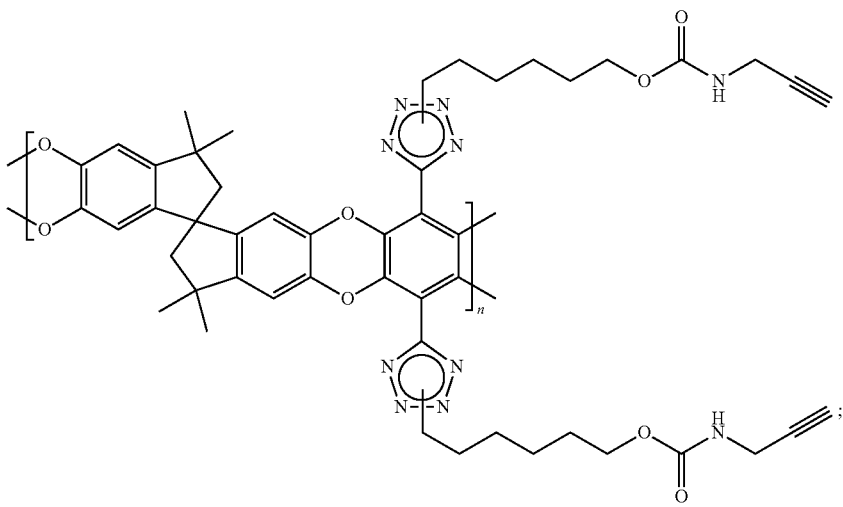

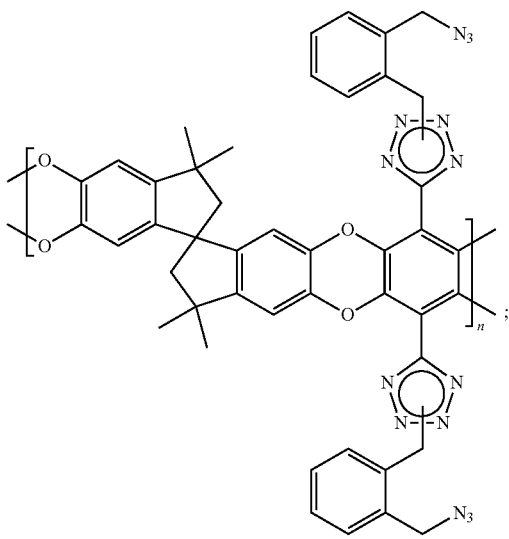

-continued
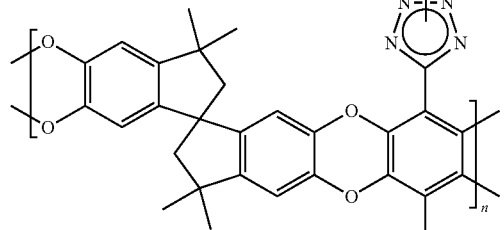
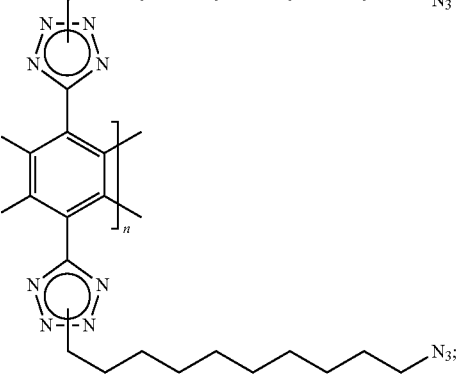
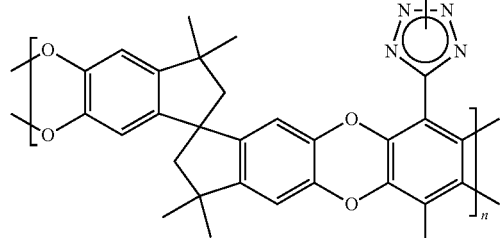
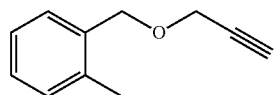
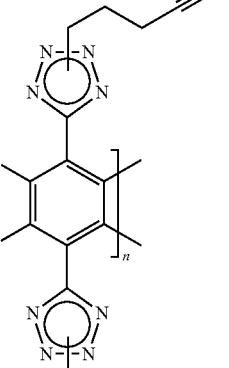
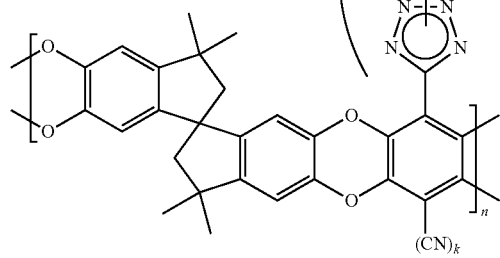
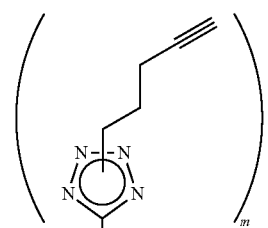
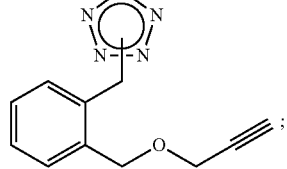
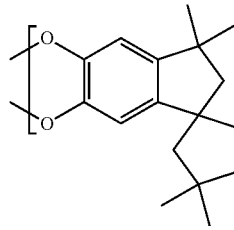
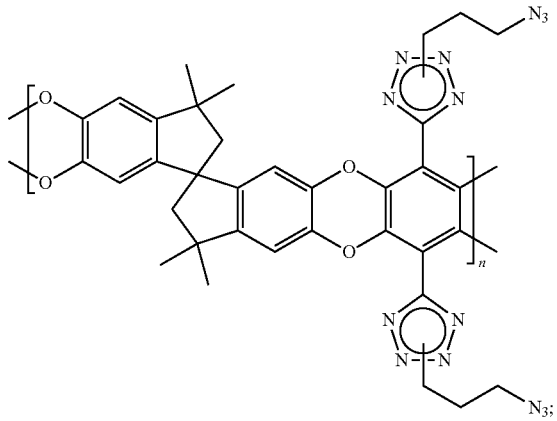

-continued
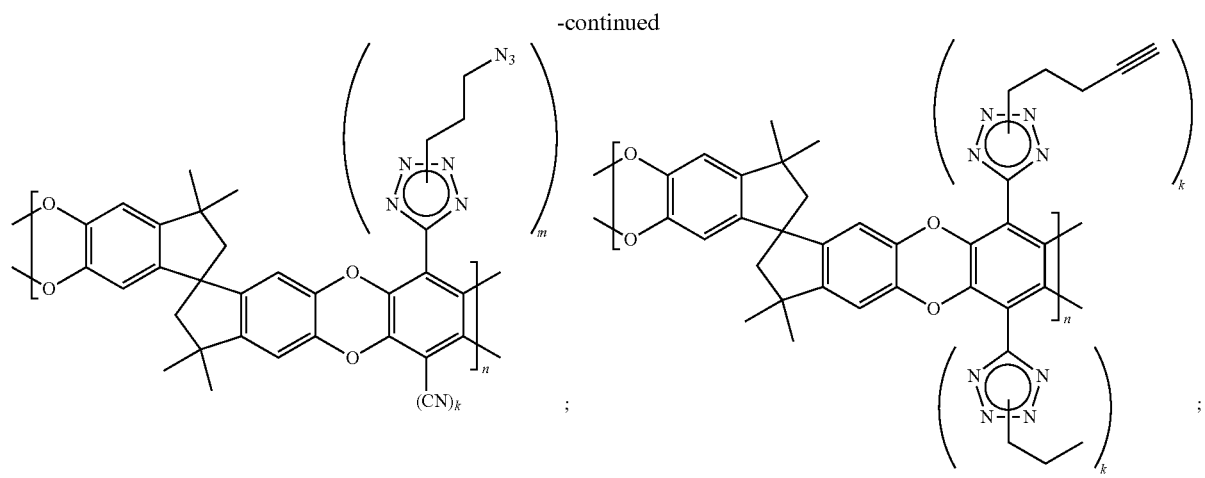
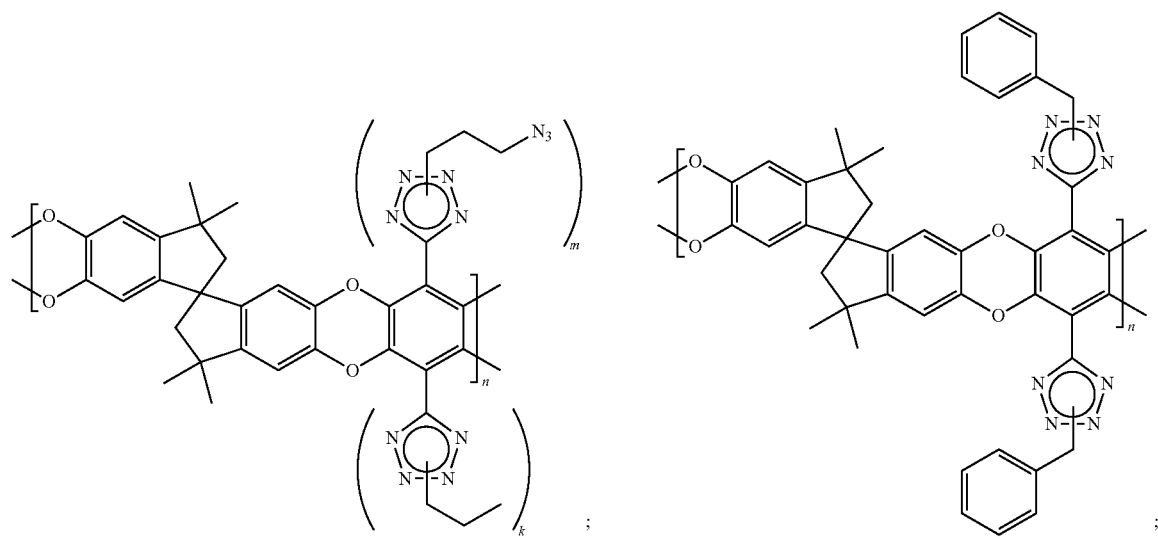
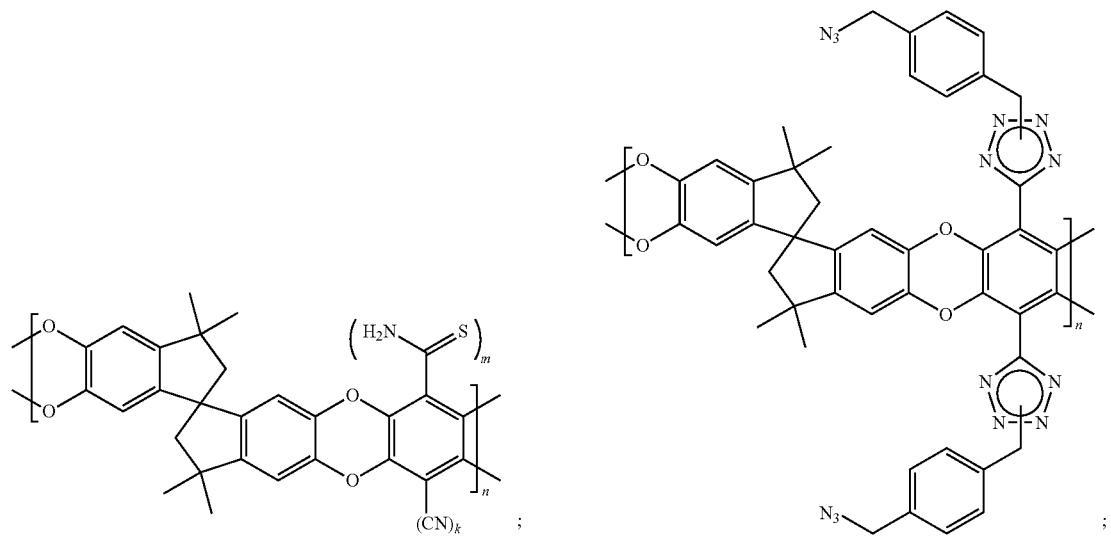

-continued
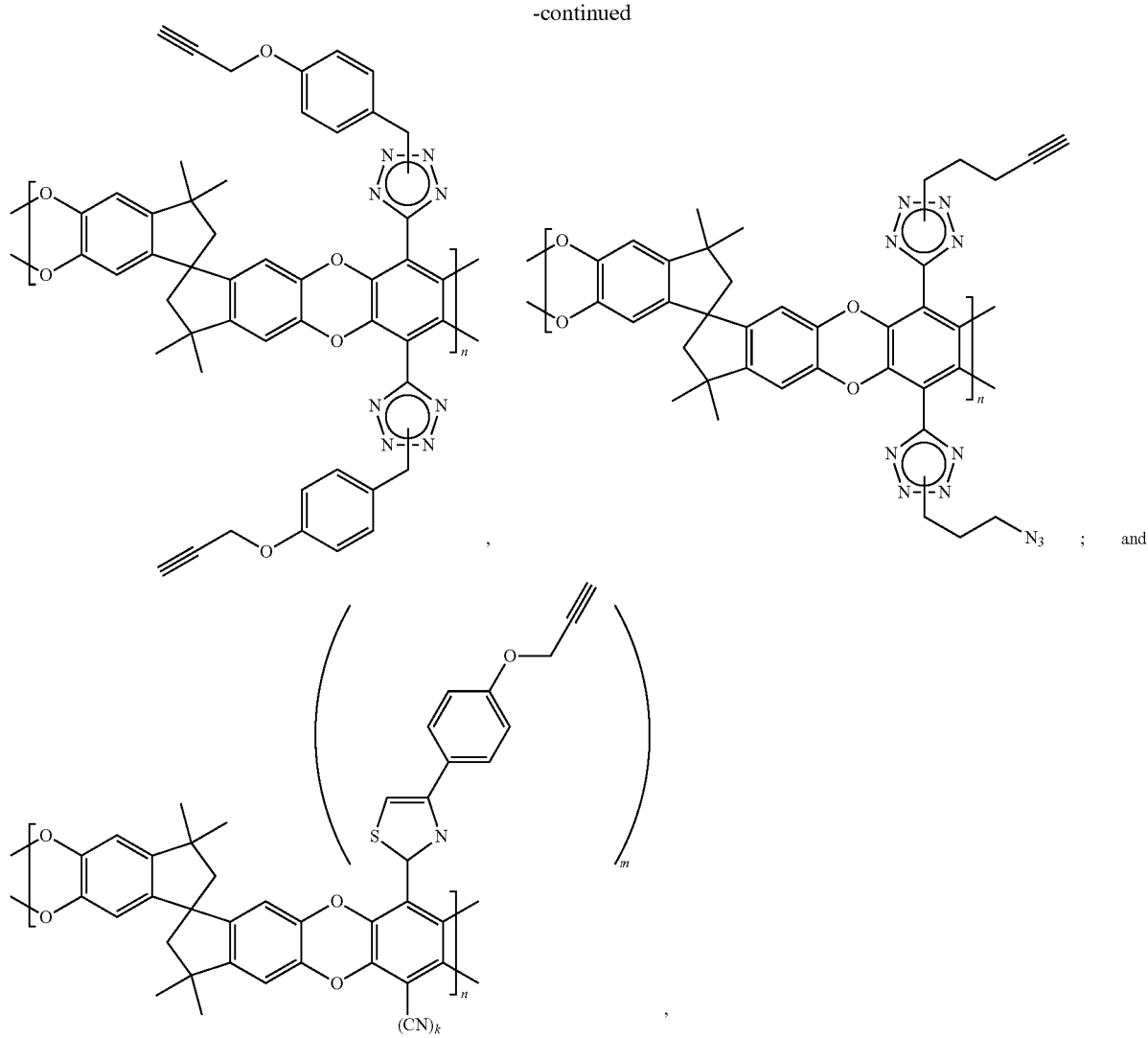
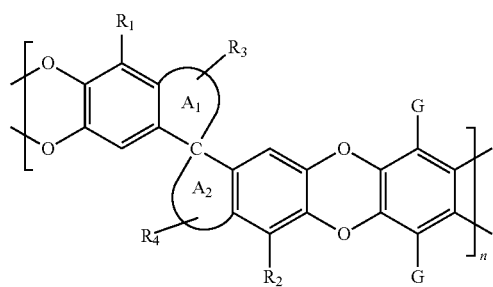
wherein the ratio of m to n is from about 0.1:1 to about 0.9:1; and
the ratio of k to n is from about 0.1:1 to about 0.9:1.
Embodiment 24
A polymer according to Formula V:
Formula V
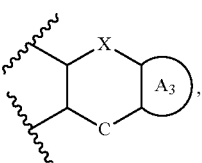
wherein: the carbon indicated by "C" denotes a spiro-carbon;
$A_1$ is selected from
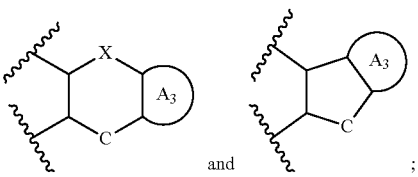
$A_2$ is X is independently at each occurrence selected from X is independently at each occurrence selected from —$CR_6$—, —O—, —S—, —$N(R_6)_2$, —C=O, —C=$NR_6$, —C=N—$N(R_6)_2$, and C=N—$OR_6$;

$R_1$, $R_2$, $R_3$, and $R_4$ are each independently selected from H and Y—Z;

$R_6$ is independently at each occurrence selected from H, substituted or unsubstituted alkyl, substituted or unsubstituted heteroalkyl, substituted or unsubstituted aryl, and substituted or unsubstituted heteroaryl;

$A_3$ is a selected from substituted or unsubstituted $C_5$-$C_6$ aryl, substituted or unsubstituted $C_5$-$C_6$ heteroaryl, substituted or unsubstituted $C_5$-$C_6$ cycloalkyl and substituted or unsubstituted $C_5$-$C_6$ cyclic heterocycloalkyl;

Y is independently absent or selected from substituted or unsubstituted alkyl, substituted or unsubstituted aryl, —NH—(C=O)—; =NO—$C_{1-6}$ alkyl-; and —(C=O)-phenyl-;

Z is independently absent or selected from —$N_3$, —C≡CH, C≡C—R', —C≡N, and —(C=O)—H, —SH, and —CH=$CH_2$;

R' is independently at each occurrence selected from substituted or unsubstituted alkyl, substituted or unsubstituted heteroalkyl, substituted or unsubstituted aryl, substituted or unsubstituted heteroaryl, —CN, —$CO_2$R", —(C=O)—N(R")$_2$, and —(C=O)—R";

R" is selected from H, substituted or unsubstituted alkyl, substituted or unsubstituted heteroalkyl, substituted or unsubstituted aryl, and substituted or unsubstituted heteroaryl;

G is selected from halogen, —CN, substituted or unsubstituted aryl, and substituted or unsubstituted heteroaryl; and n is an integer from 5 to 100,000.

Embodiment 25

The polymer according to embodiment 24, wherein:

$A_1$ and $A_2$ are each independently selected from:

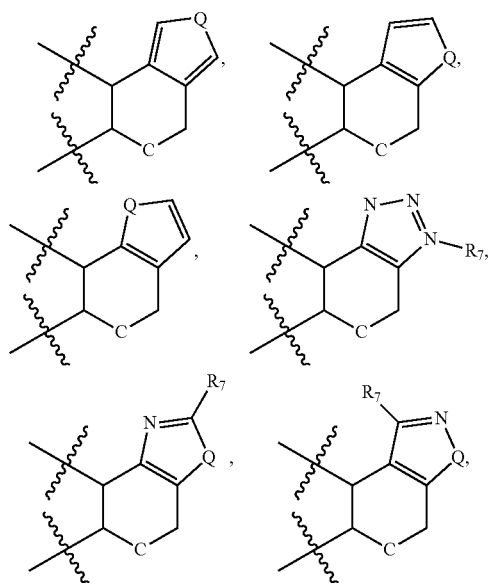

-continued

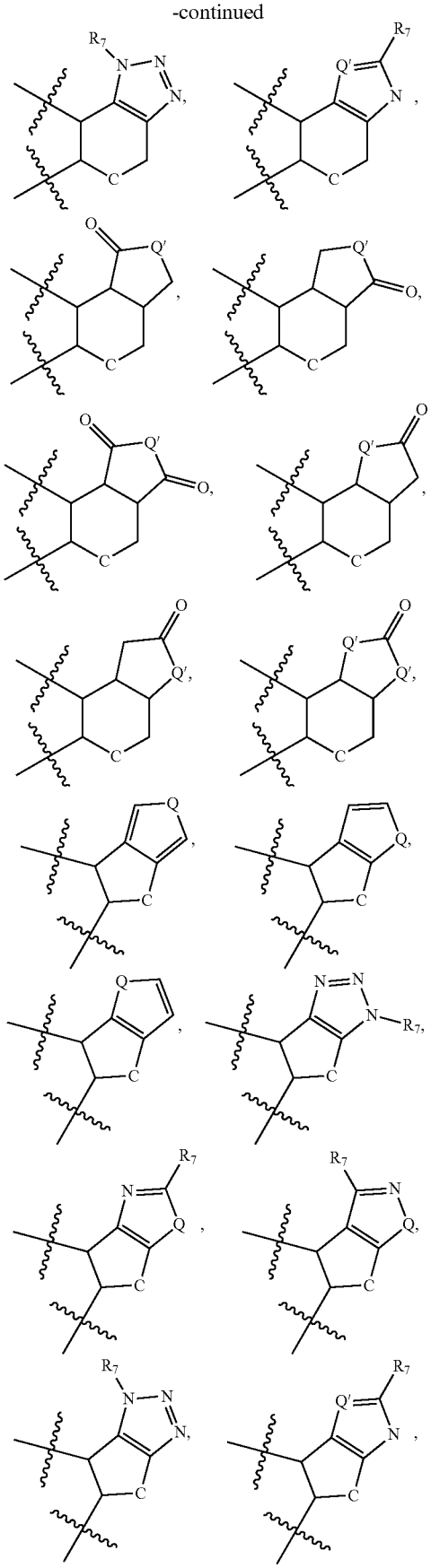

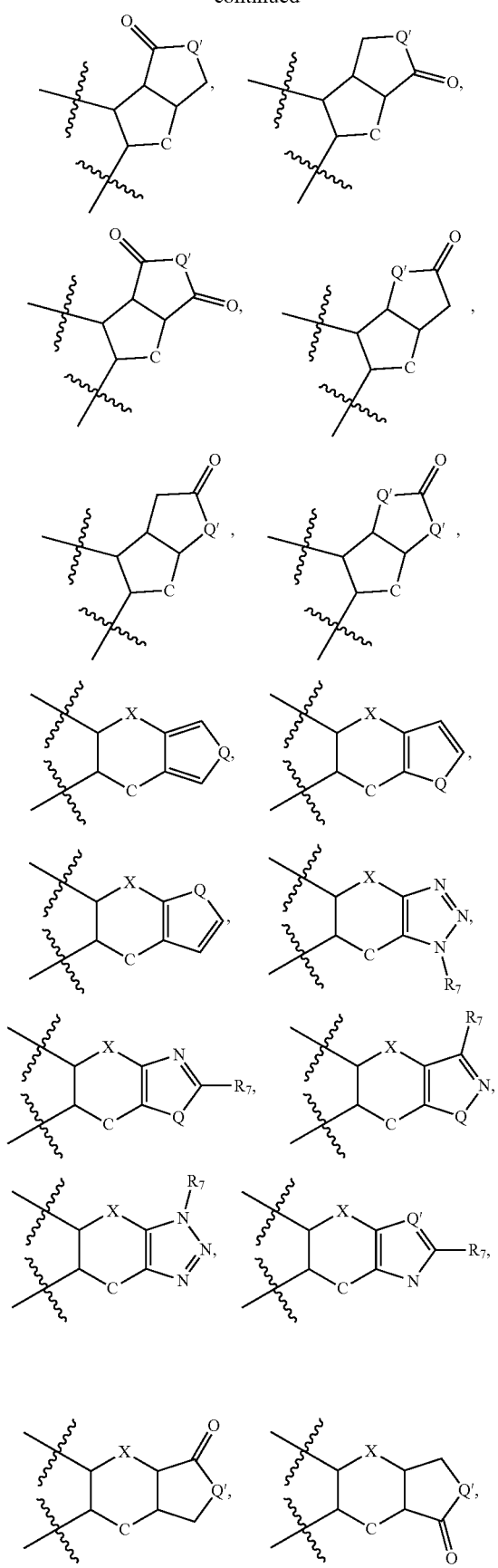
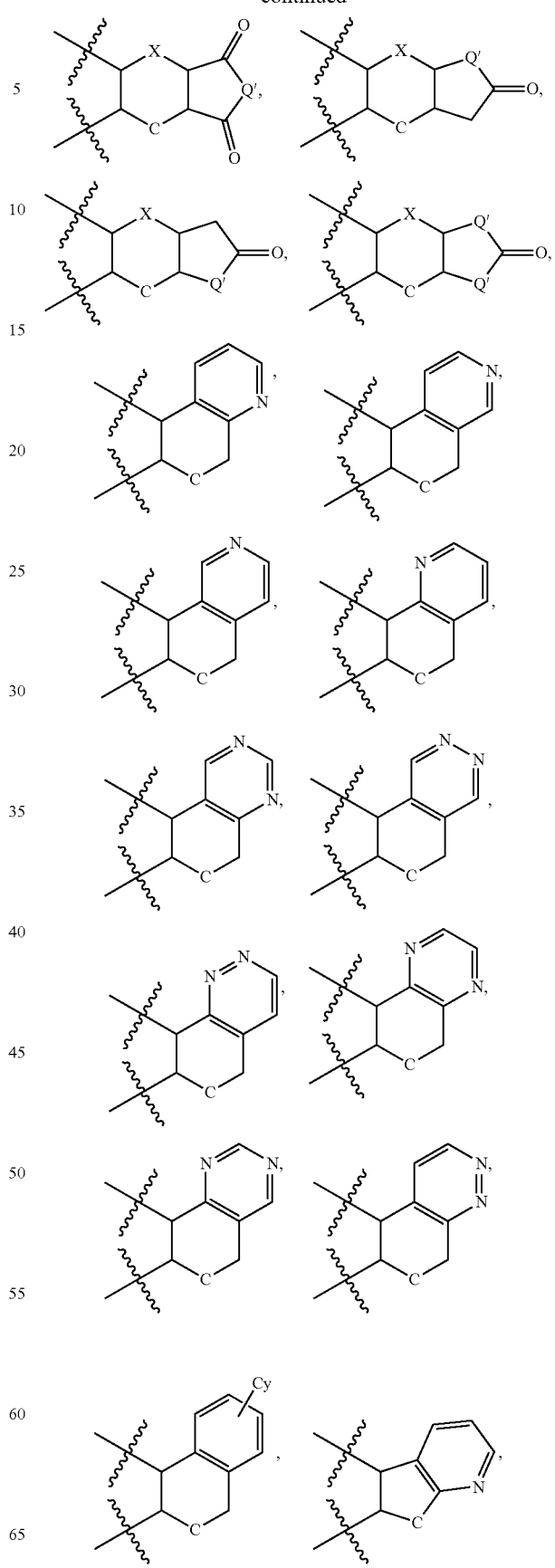

-continued

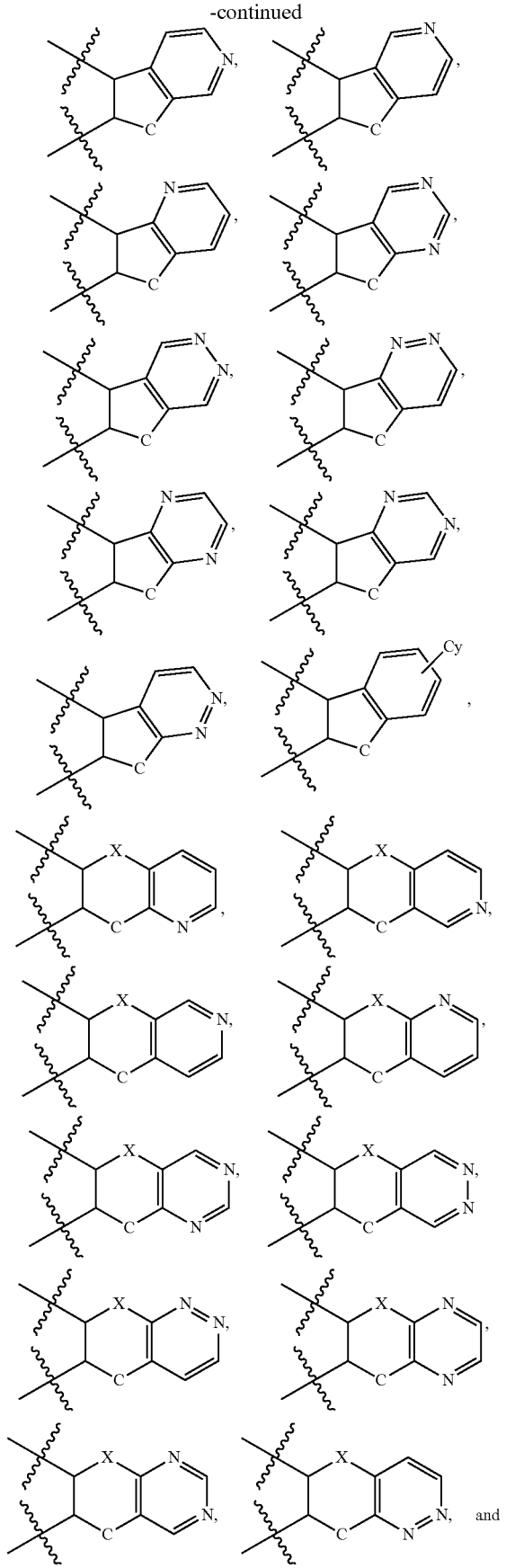

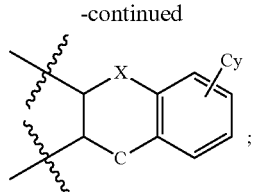

X is selected from —CR$_6$—, —O—, —S—, NR$_6$, —C═O, —C═NR$_6$, —C═N—N(R$_6$)$_2$, and C═N—OR$_6$;

C$_y$ is selected from substituted or unsubstituted C$_5$-C$_6$ aryl, substituted or unsubstituted C$_5$-C$_6$ heteroaryl, substituted or unsubstituted C$_5$-C$_6$ cycloalkyl and substituted or unsubstituted C$_5$-C$_6$ cyclic heterocycloalkyl;

Q is selected from —O—, —S—, —N—R$_7$, —C═O, —C═NR$_7$, —C═N—N(R$_7$)$_2$, and —C═N—OR$_7$;

Q' is independently at each occurrence selected from —O—, —S—, and —N—R$_7$;

R$_6$ is independently at each occurrence selected from H, substituted or unsubstituted alkyl, substituted or unsubstituted heteroalkyl, substituted or unsubstituted aryl, and substituted or unsubstituted heteroaryl, and R$_7$ is independently at each occurrence selected from R$_3$ and R$_4$.

Embodiment 26

The polymer according to embodiment 24, selected from the group consisting of:

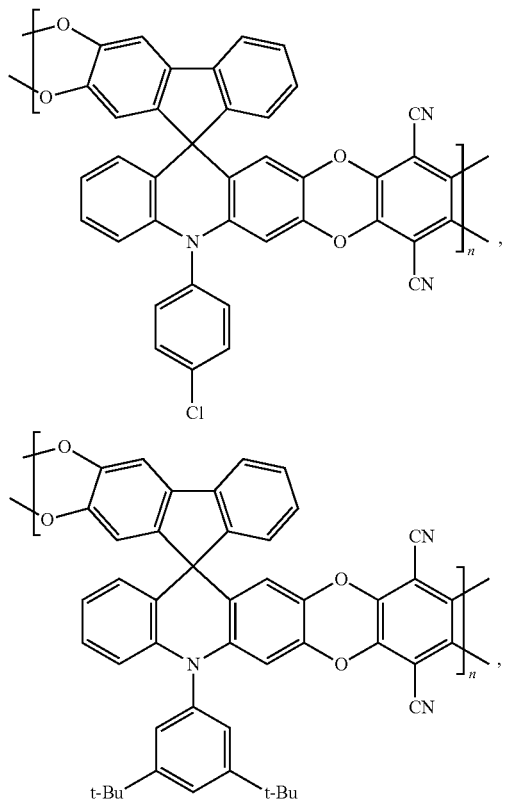

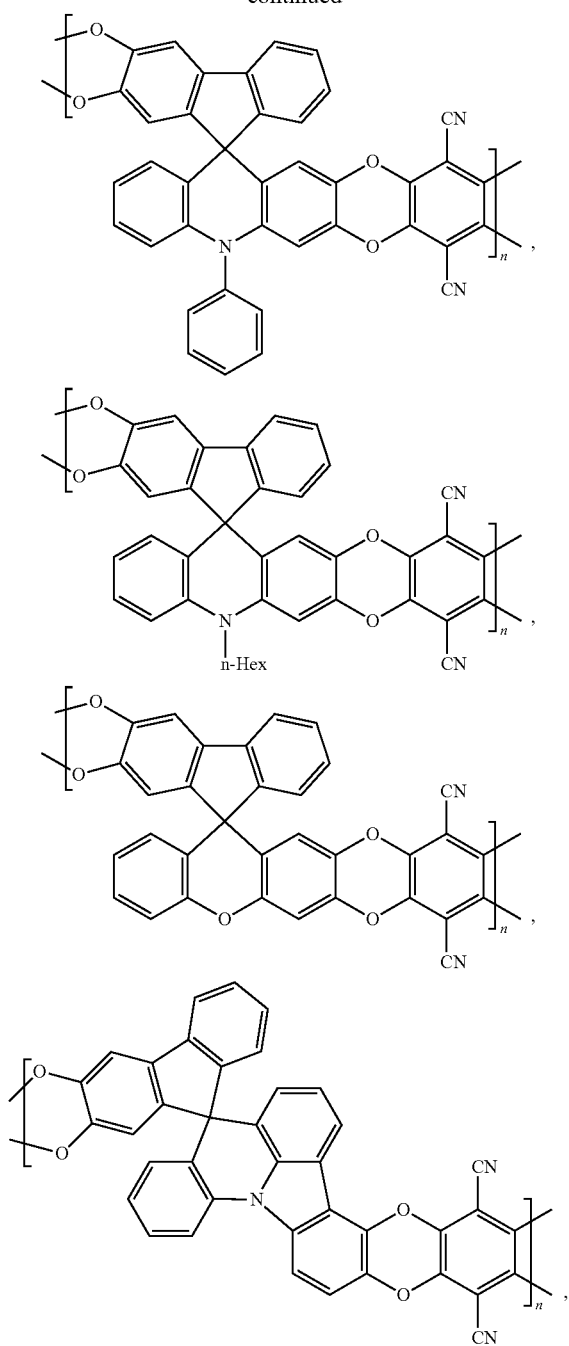
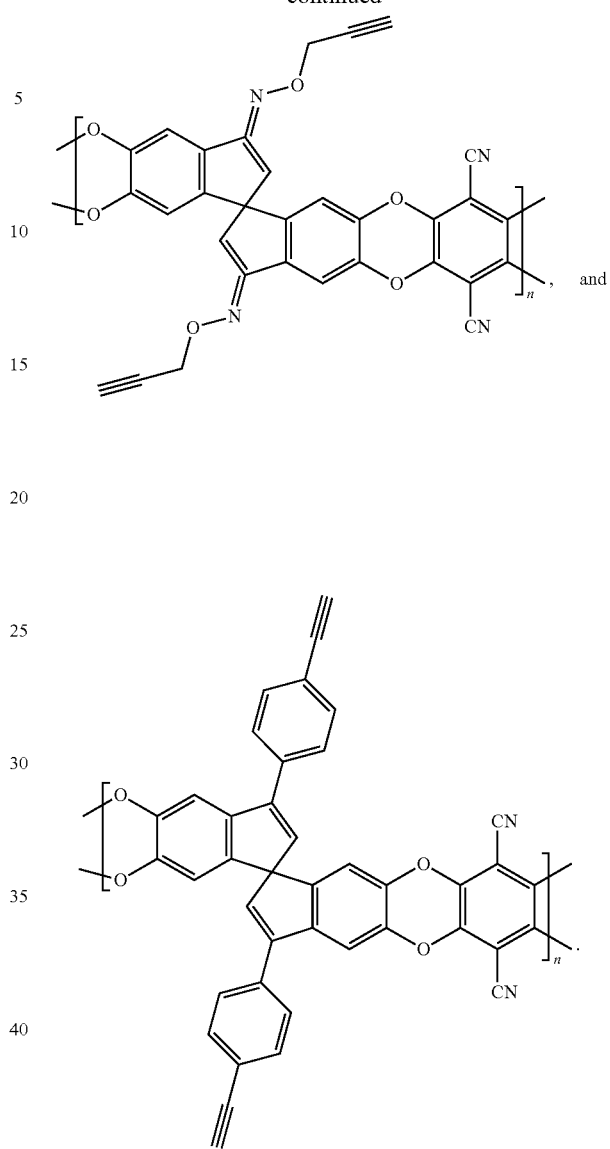
Embodiment 27
The polymer according to embodiment 24, selected from the group consisting of:
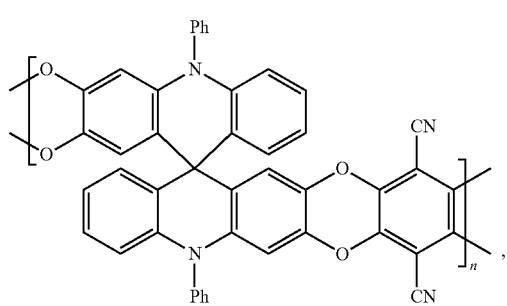
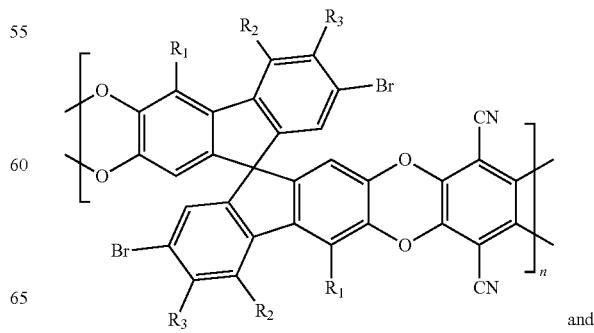
and -continued

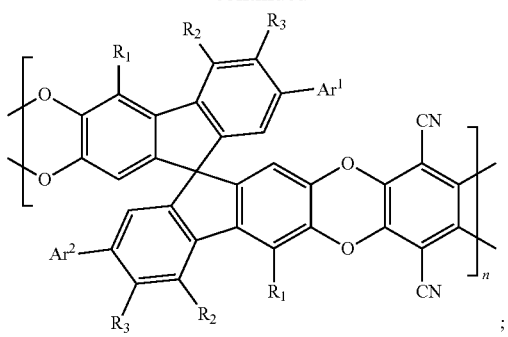

wherein at least one of $R_1$, $R_2$, and $R_3$ is substituted with Z;

Z is independently absent or selected from —$N_3$, —C≡CH, C≡C—R', —C≡N, and —(C=O)—H, —SH, and —CH=$CH_2$, and $Ar^1$ and $Ar^2$ are independently selected from substituted and unsubstituted aryl.

Embodiment 28

A polymer according to Formula VI:

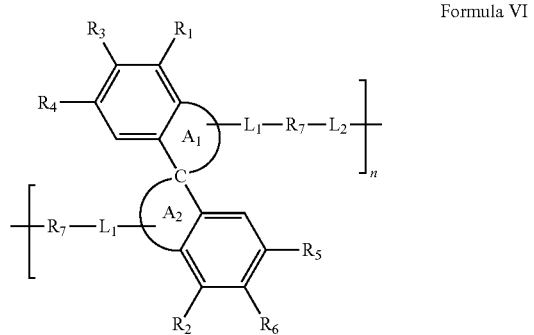

Formula VI wherein:

the carbon indicated by "C" denotes a spiro-carbon;

$A_1$ and $A_2$ are independently at each occurrence selected from:

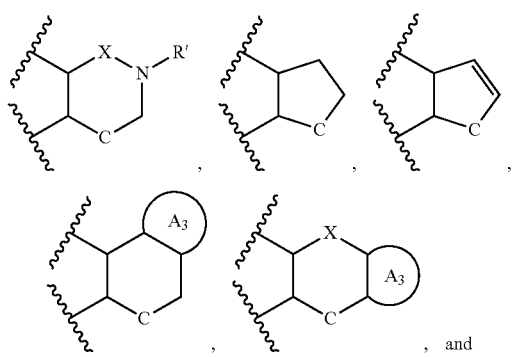

, and

-continued

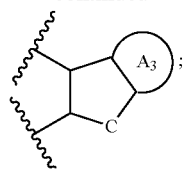

X is —$CR_2"$, —O—, —S—, $N(R")_2$, —C=O, —C=NR", —C=N—$N(R")_2$, and C=N—OR";

$R_1$, $R_2$, $R_3$, $R_4$, $R_5$, $R_6$ are independently selected from H, —OR", —$OSi(R")_3$, $Si(R")_3$, substituted or unsubstituted alkyl, substituted or unsubstituted heteroalkyl, substituted or unsubstituted aryl, substituted or unsubstituted heteroaryl, substituted or unsubstituted cycloalkyl and substituted or unsubstituted heterocycloalkyl, wherein at least one of $R_1$, $R_2$, $R_3$, $R_4$, $R_5$, $R_6$, is further substituted with Z;

$R_7$ is absent or selected from substituted or unsubstituted aryl, substituted or unsubstituted heteroaryl; substituted or unsubstituted arylamine, and imido;

$A_3$ is a selected from substituted or unsubstituted $C_5$-$C_6$ aryl, substituted or unsubstituted $C_5$-$C_6$ heteroaryl, substituted or unsubstituted $C_5$-$C_6$ cycloalkyl and substituted or unsubstituted $C_5$-$C_6$ cyclic heterocycloalkyl;

Z is independently selected from —$N_3$, —C≡CH, C≡C—R', —C≡N, —(C=O)—H, —SH, and —CH=$CH_2$;

R' is selected from substituted or unsubstituted alkyl, substituted or unsubstituted heteroalkyl, substituted or unsubstituted aryl, substituted or unsubstituted heteroaryl, —CN, —$CO_2R_6$, —(C=O)—$N(R")_2$, and —(C=O)—R";

R" is independently at each occurrence selected from H, substituted or unsubstituted alkyl, substituted or unsubstituted heteroalkyl, substituted or unsubstituted aryl, and substituted or unsubstituted heteroaryl; and $L_1$ and $L_2$ are independently selected from a bond, substituted or unsubstituted alkyl, substituted or unsubstituted cycloalkyl, substituted or unsubstituted alkynyl, substituted or unsubstituted aryl, and substituted or unsubstituted heteroaryl.

Embodiment 29

The polymer according to embodiment 28 wherein:

$A_1$ and $A_2$ are each independently selected from:

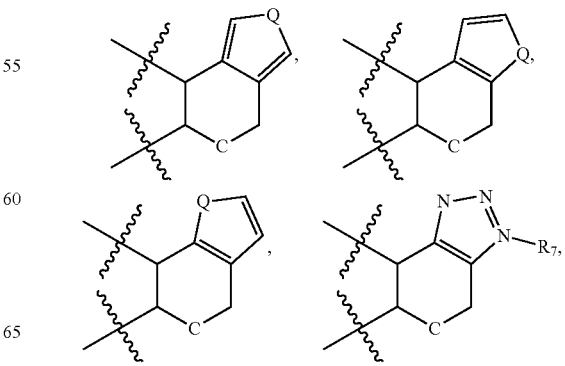

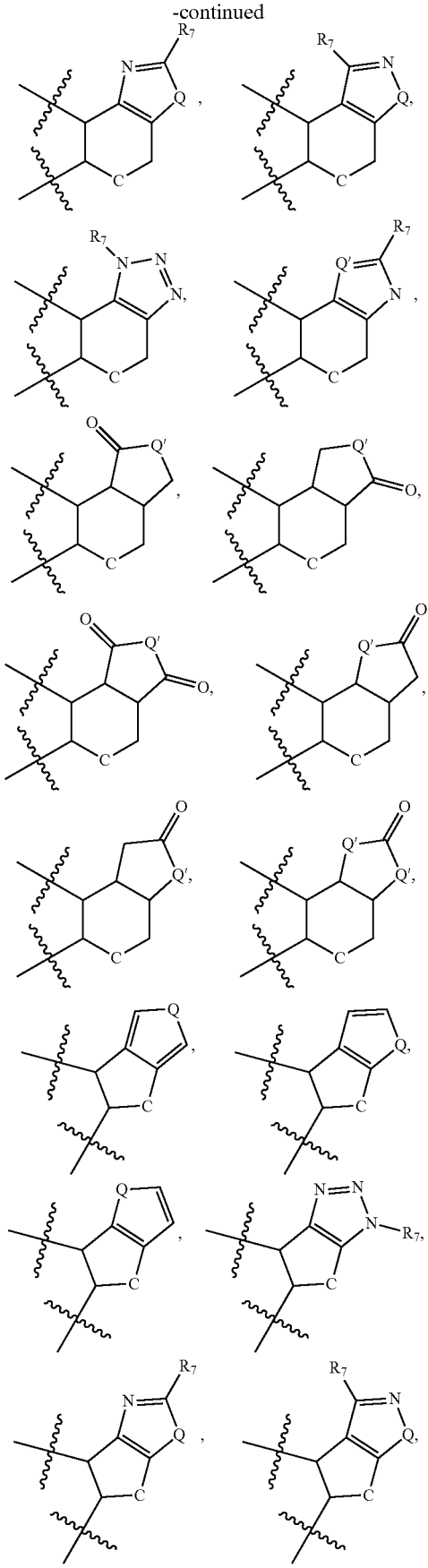
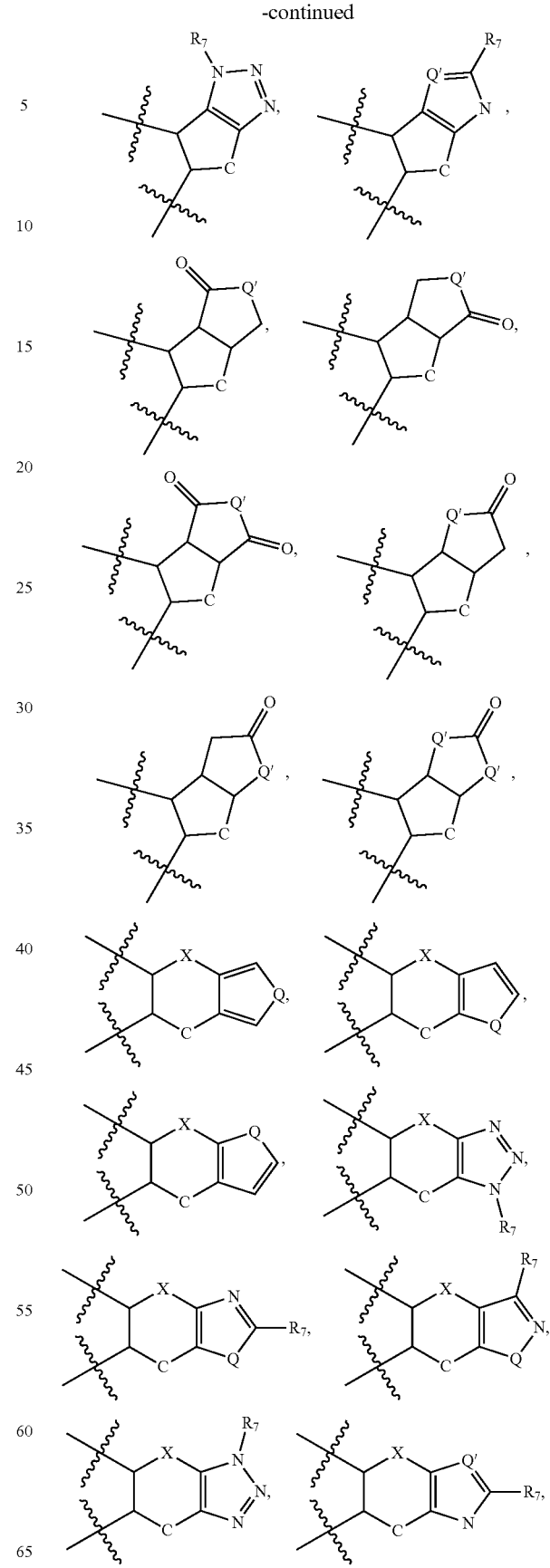

-continued
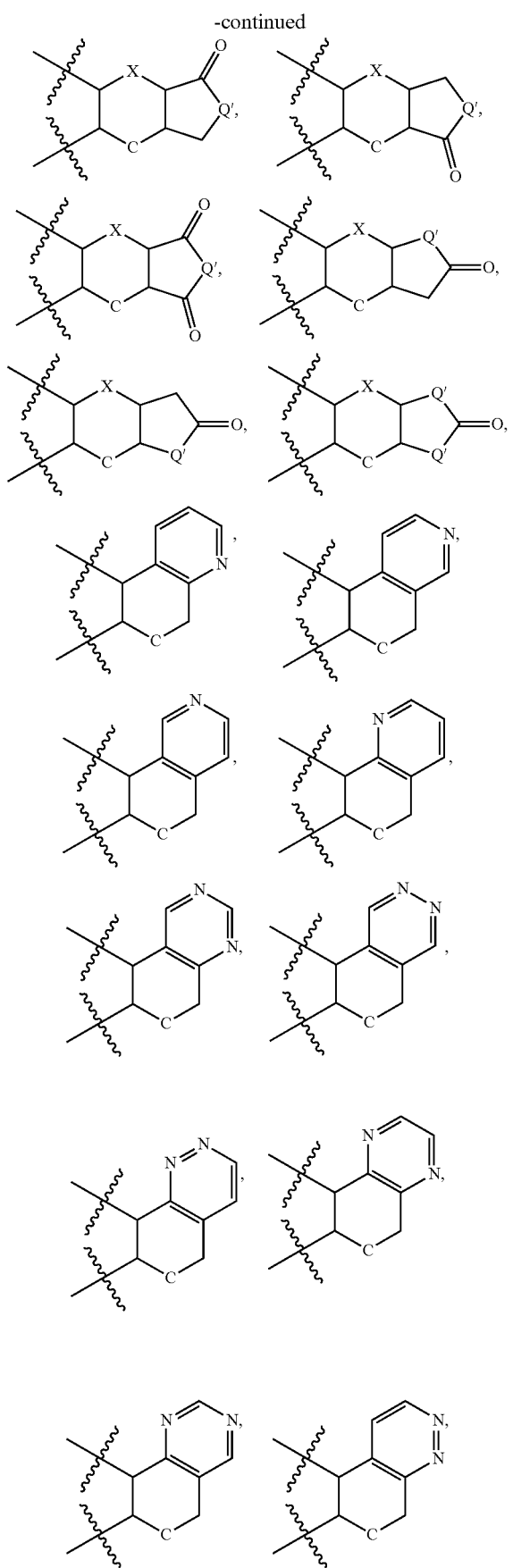
-continued
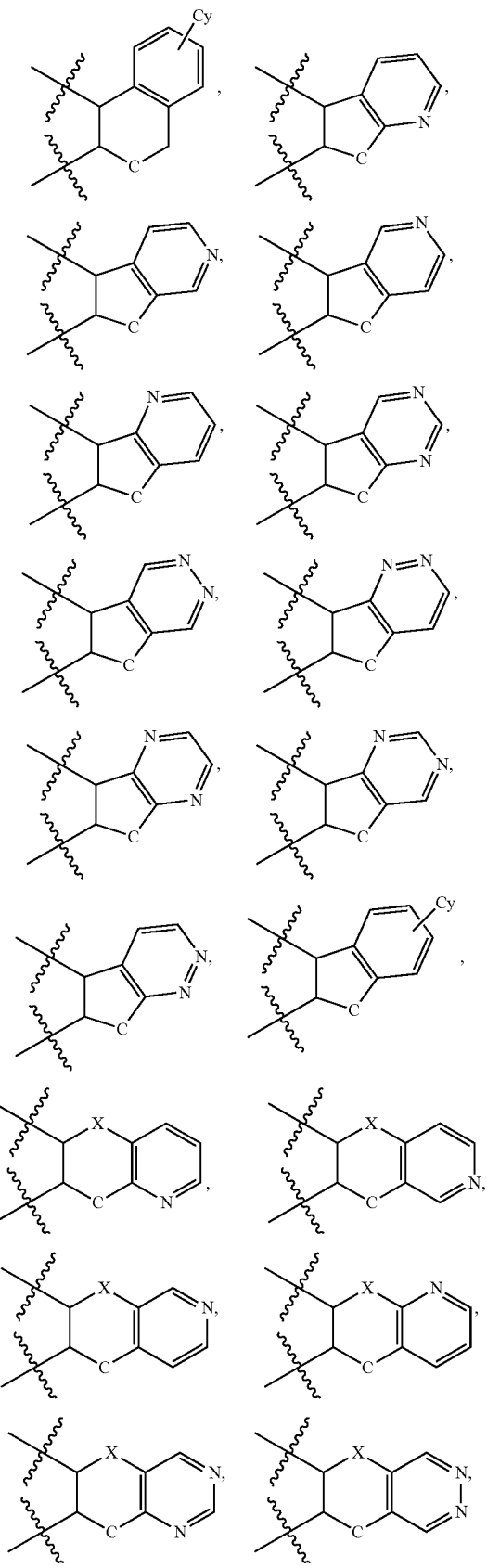

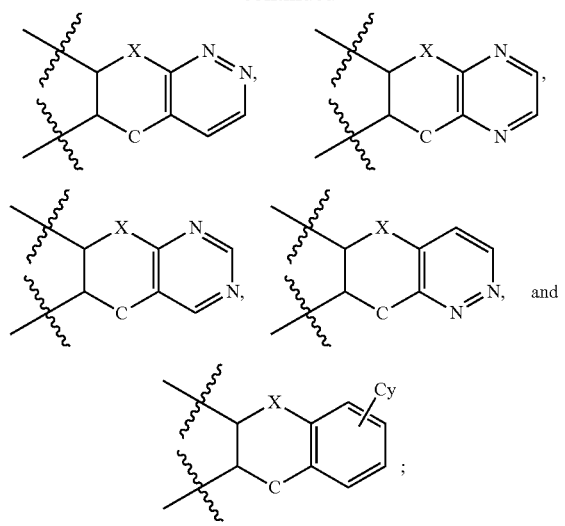

X is selected from —CR″, —O—, —S—, NR″, —C=O, —C=NR″, —C=N—N(R″)$_2$, and C=N—OR″;

C$_y$ is selected from substituted or unsubstituted C$_5$-C$_6$ aryl, substituted or unsubstituted C$_5$-C$_6$ heteroaryl, substituted or unsubstituted C$_5$-C$_6$ cycloalkyl and substituted or unsubstituted C$_5$-C$_6$ cyclic heterocycloalkyl;

Q is selected from —O—, —S—, —N—R$_7$, —C=O, —C=NR$_7$, —C=N—N(R$_7$)$_2$, and —C=N—OR$_7$;

Q' is independently at each occurrence selected from —O—, —S—, and —N—R$_7$; and R″ is independently at each occurrence selected from H, substituted or unsubstituted alkyl, substituted or unsubstituted heteroalkyl, substituted or unsubstituted aryl, and substituted or unsubstituted heteroaryl.

Embodiment 30

The polymer according to embodiment 28, selected from the group consisting of:

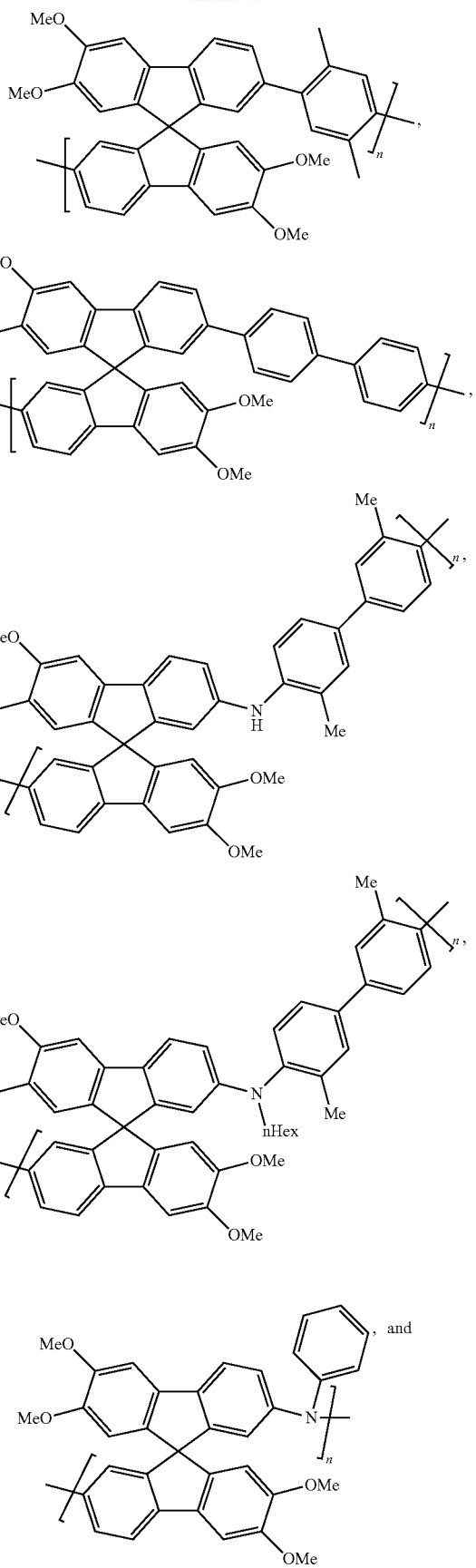

-continued

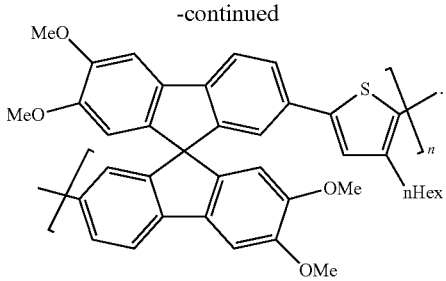

Embodiment 31

A polymer according to Formula VII:

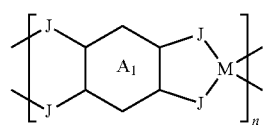

Formula VII wherein:
M is selected from —C—, —Si—, —Sn—, —Ti—, and —Zr—;
J is selected from —O— and —CH$_2$—;
A$_1$ is a selected from substituted or unsubstituted aryl and substituted or unsubstituted heteroaryl, and
n is an integer from 5 to 100,000.

Embodiment 32

The polymer according to embodiment 31, selected from the group consisting of:

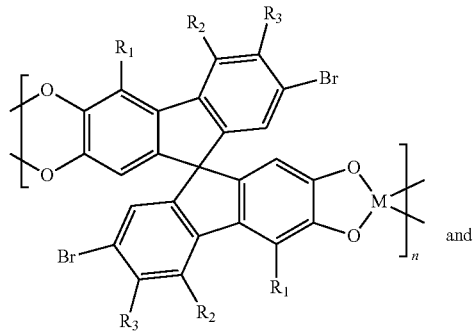

and

-continued

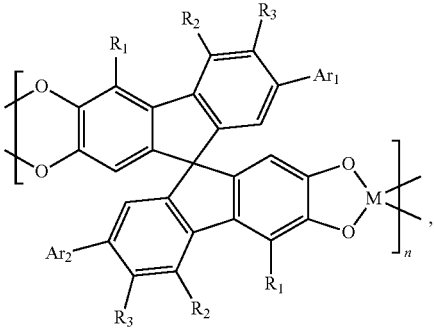

wherein R$_1$, R$_2$, and R$_3$ are independently selected from H, substituted or unsubstituted alkyl, substituted or unsubstituted heteroalkyl, substituted or unsubstituted aryl, substituted or unsubstituted heteroaryl, substituted or unsubstituted cycloalkyl and substituted or unsubstituted heterocycloalkyl, —OR', —SR', N(R")$_2$, and wherein at least one of R$_1$, R$_2$, and R$_3$ is substituted with Z; Z is independently selected from —N$_3$, —C≡CH, C≡C—R', —C≡N, —(C=O)—H, —SH, and —CH=CH$_2$;

R' is selected from substituted or unsubstituted alkyl, substituted or unsubstituted heteroalkyl, substituted or unsubstituted aryl, substituted or unsubstituted heteroaryl, —CN, —CO$_2$R", —(C=O)—N(R")$_2$, and —(C=O)—R";

R" is independently at each occurrence selected from H, substituted or unsubstituted alkyl, substituted or unsubstituted heteroalkyl, substituted or unsubstituted aryl, and substituted or unsubstituted heteroaryl, and Ar$^1$ and Ar$^2$ are independently selected from substituted and unsubstituted aryl.

Embodiment 33

A polymer according to Formula VIII:

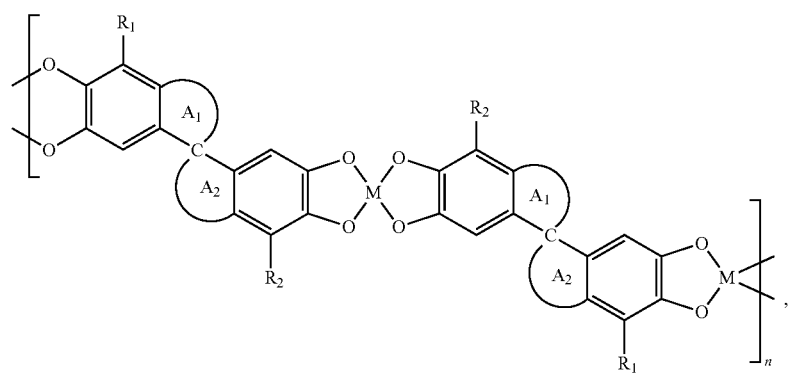

Formula VIII wherein: the carbon indicated by "C" denotes a spiro-carbon;

M is selected from —C—, —Si—, —Sn—, —Ti—, and —Zr—;

$A_1$ and $A_2$ are each independently selected from:

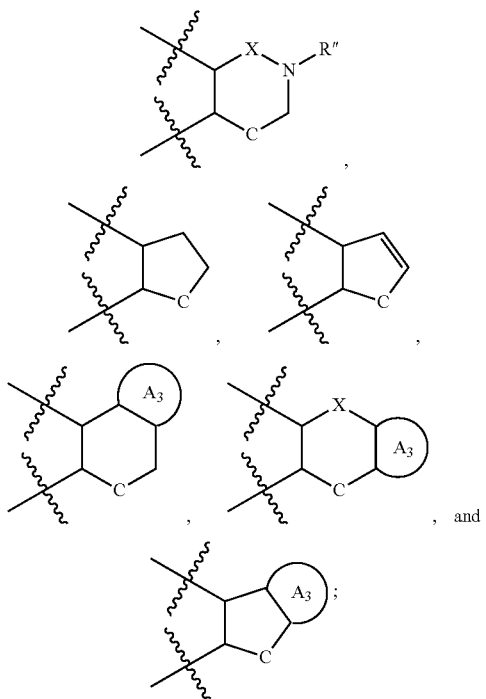

, and $A_3$ is a selected from substituted or unsubstituted $C_5$-$C_6$ aryl, substituted or unsubstituted $C_5$-$C_6$ heteroaryl, substituted or unsubstituted $C_5$-$C_6$ cycloalkyl and substituted or unsubstituted $C_5$-$C_6$ cyclic heterocycloalkyl;

X is —CR", —O—, —S—, NR", —C=O, —C=NR", —C=N—N(R")$_2$, and C=N—OR";

$R_1$, and $R_2$ are independently selected from H, substituted or unsubstituted alkyl, substituted or unsubstituted heteroalkyl, substituted or unsubstituted aryl, substituted or unsubstituted heteroaryl, substituted or unsubstituted cycloalkyl and substituted or unsubstituted heterocycloalkyl, wherein one or both of $R_1$, and $R_2$, are optionally further substituted with Z;

Z is independently selected from —N$_3$, —C≡CH, C≡C—R', —C≡N, —(C=O)—H, —SH, and —CH=CH$_2$;

R' is selected from substituted or unsubstituted alkyl, substituted or unsubstituted heteroalkyl, substituted or unsubstituted aryl, substituted or unsubstituted heteroaryl, —CN, —CO$_2$R", —(C=O)—N(R")$_2$, and —(C=O)—R"; and R" is independently at each occurrence selected from H, substituted or unsubstituted alkyl, substituted or unsubstituted heteroalkyl, substituted or unsubstituted aryl, and substituted or unsubstituted heteroaryl.

Embodiment 34

The polymer according to embodiment 33, wherein:

$A_1$ and $A_2$ are each independently selected from:

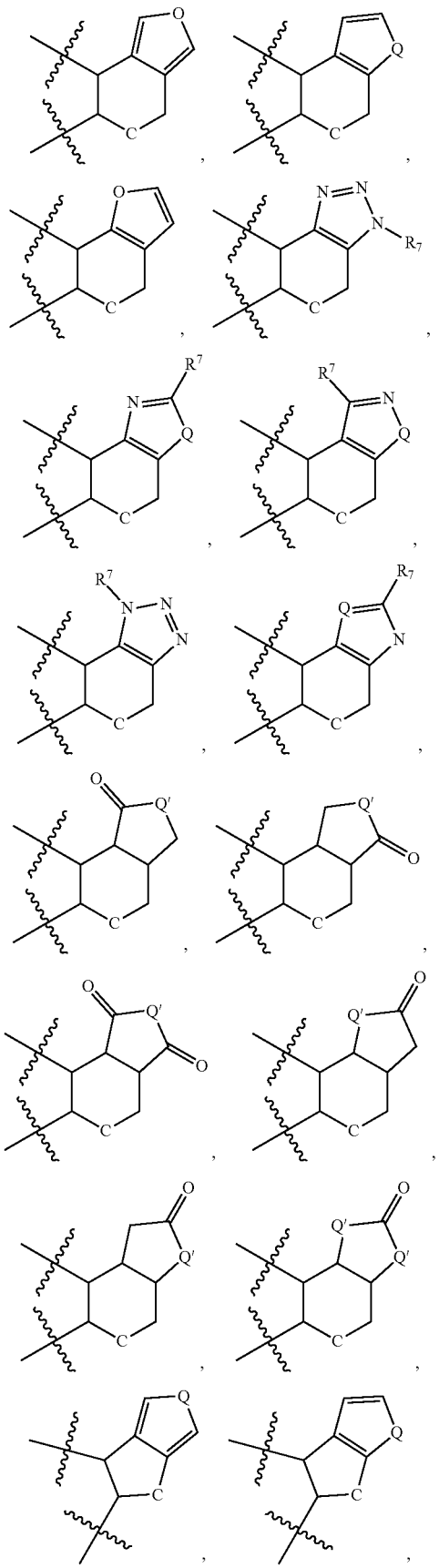

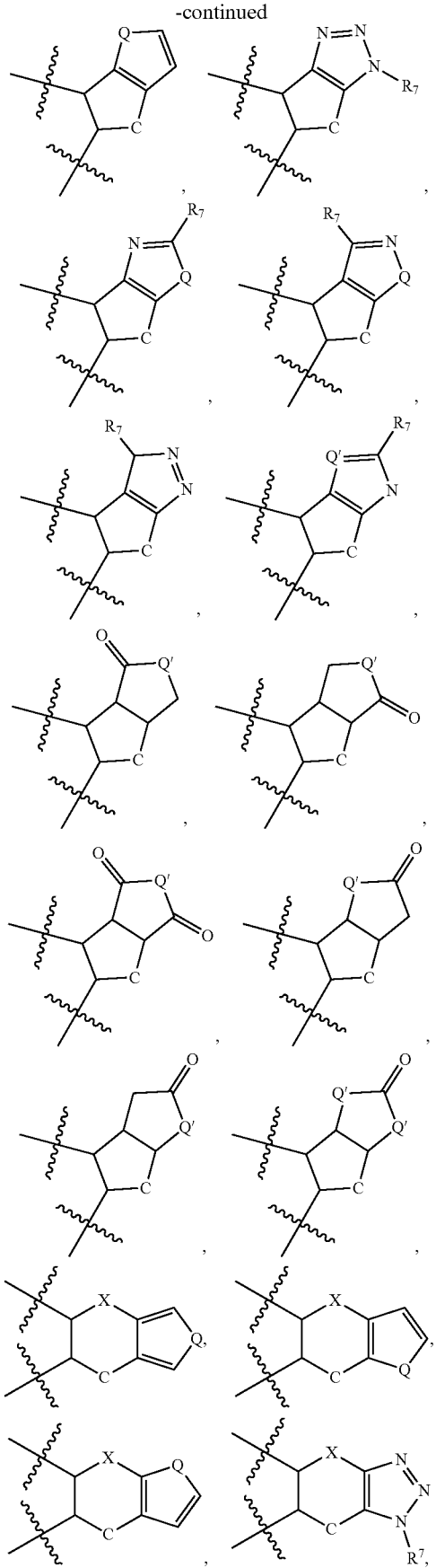
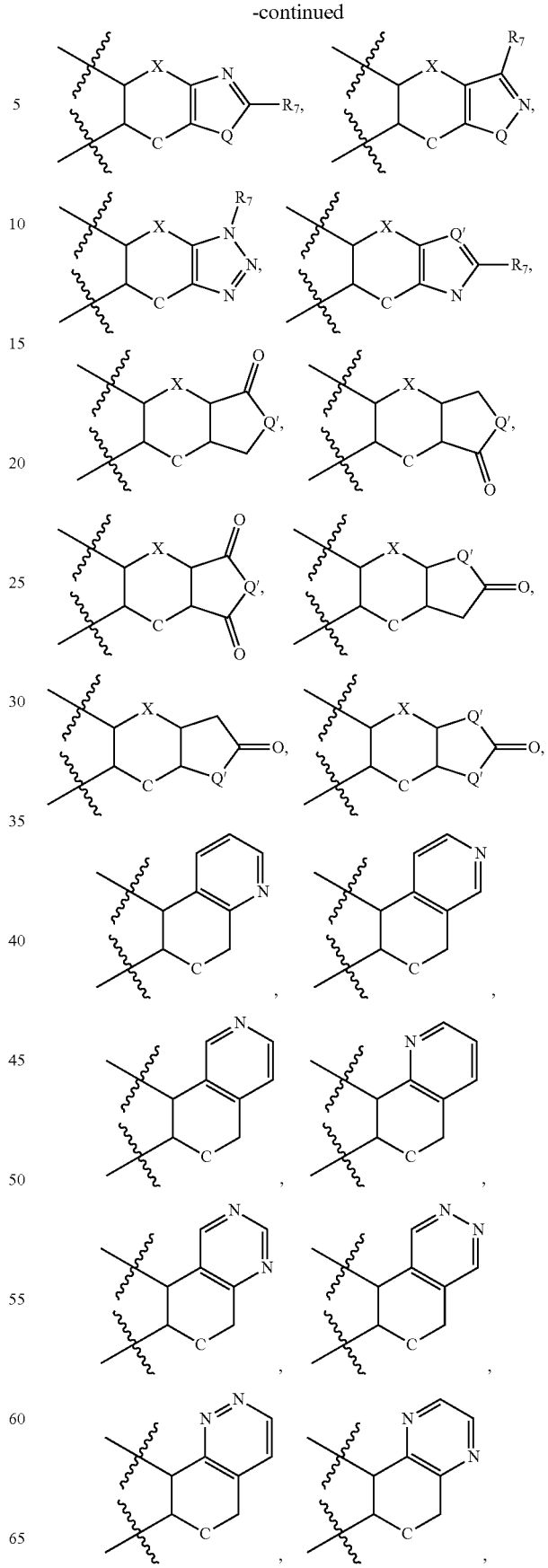

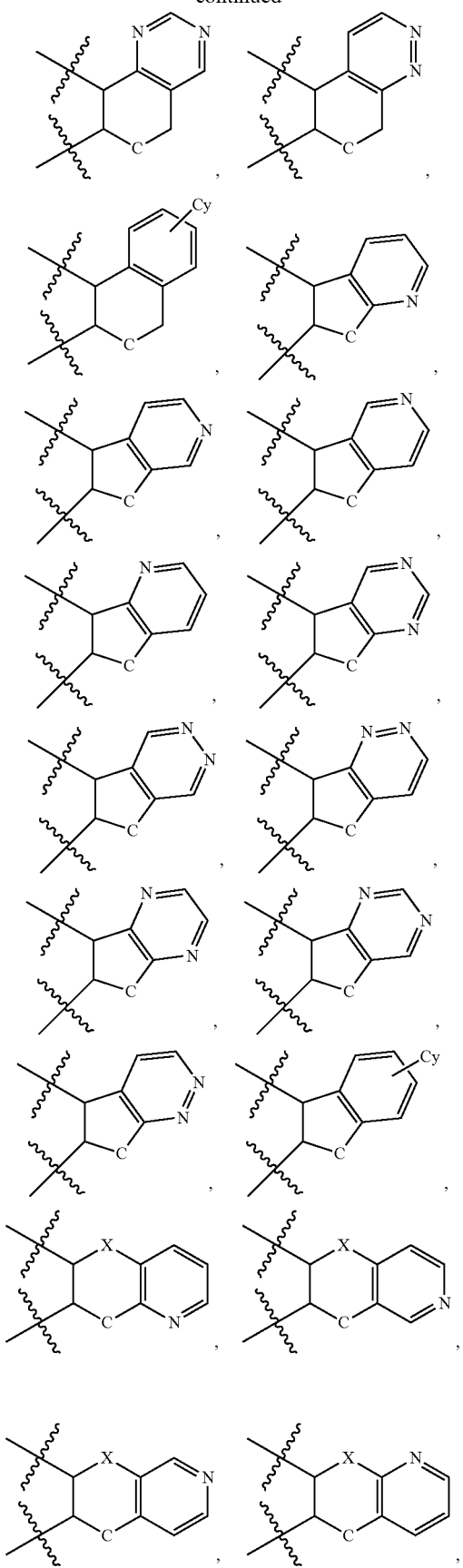

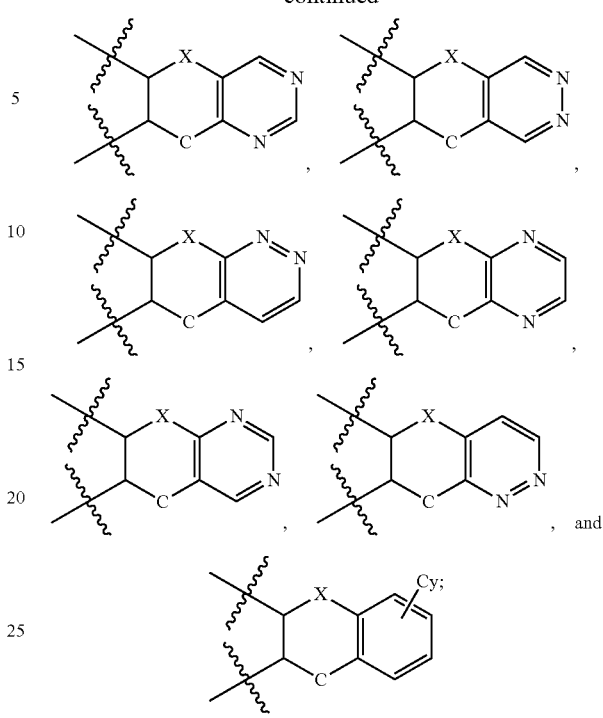

X is selected from —CR″, —O—, —S—, NR″, —C=O, —C=NR, —C=N—N(R″)₂, and C=N—OR″;

C_y is selected from substituted or unsubstituted C₅-C₆ substituted or unsubstituted C₅-C₆ heteroaryl, substituted or unsubstituted C₅-C₆ cycloalkyl and substituted or unsubstituted C₅-C₆ cyclic heterocycloalkyl;

Q is selected from —O—, —S—, —N—R₇, —C=O, —C=NR₇, —C=N—N(R₇)₂, and —C=N—OR₇;

Q' is independently at each occurrence selected from —O—, —S—, and —N—R₇;

R″ is independently at each occurrence selected from H, substituted or unsubstituted alkyl, substituted or unsubstituted heteroalkyl, substituted or unsubstituted aryl, and substituted or unsubstituted heteroaryl, and R₇ is absent or selected from substituted or unsubstituted aryl, substituted or unsubstituted heteroaryl; substituted or unsubstituted arylamine, and imido.

Embodiment 35

The polymer according to the formula:

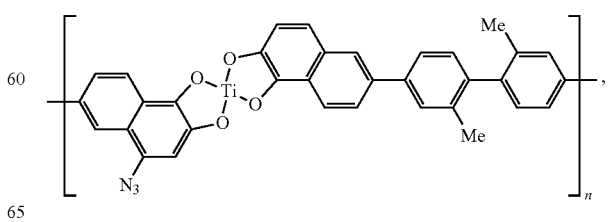

wherein n is an integer from 5 to 100,000.

Embodiment 36

A polymer according to the formula:

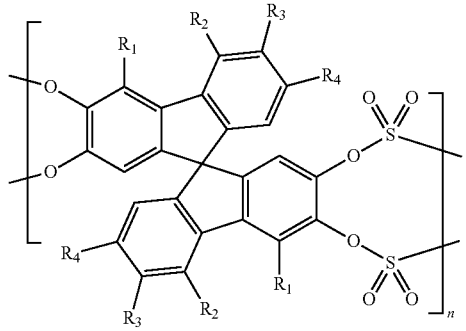

wherein:

R$_1$, R$_2$, R$_3$, and R$_4$ are independently selected from H, substituted or unsubstituted alkyl, substituted or unsubstituted heteroalkyl, substituted or unsubstituted aryl, substituted or unsubstituted heteroaryl, —OR', —SR', N(R")$_2$, wherein at least one of R$_1$, R$_2$, R$_3$, and R$_4$ is further substituted with Z;

Z is independently selected from —N$_3$, —C≡CH, C≡C—R', —C≡N, —(C=O)—H, —SH, and —CH=CH$_2$;

R' is selected from substituted or unsubstituted alkyl, substituted or unsubstituted heteroalkyl, substituted or unsubstituted aryl, substituted or unsubstituted heteroaryl, —CN, —CO$_2$R", —(C=O)—N(R")$_2$, and —(C=O)—R";

R" is independently at each occurrence selected from H, substituted or unsubstituted alkyl, substituted or unsubstituted heteroalkyl, substituted or unsubstituted aryl, and substituted or unsubstituted heteroaryl; and n is an integer from 5 to 100,000.

What is claimed is:

1. A compound according to Formula I:

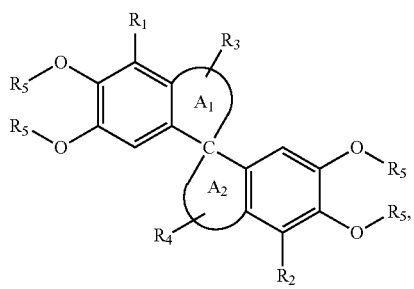

Formula I wherein:
the carbon indicated by "C" denotes a spiro-carbon;
A$_1$ and A$_2$ are each independently selected from:

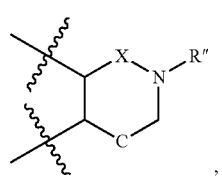

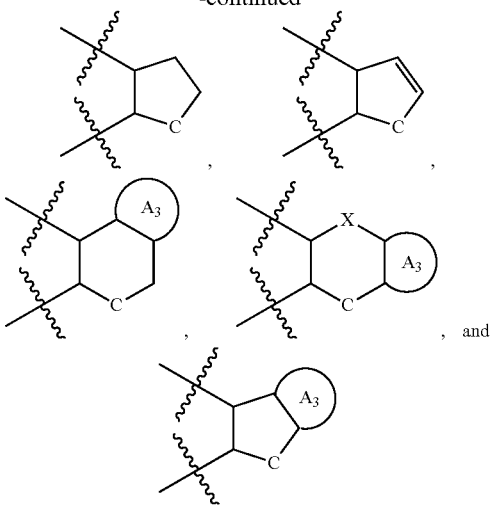

A$_3$ is a selected from substituted or unsubstituted C$_5$-C$_6$ aryl, substituted or unsubstituted C$_5$-C$_6$ heteroaryl, substituted or unsubstituted C$_5$-C$_6$ cycloalkyl and substituted or unsubstituted C$_5$-C$_6$ cyclic heterocycloalkyl;

X is —CR$_6$, —O—, —S—, NR$_6$, —C=O, —C=NR$_6$, —C=N—N(R$_6$)$_2$, and C=N—OR$_6$;

R$_1$, R$_2$, R$_3$, and R$_4$ are each independently selected from H and Y—Z, wherein at least one of R$_1$, R$_2$, R$_3$, and R$_4$ is Y—Z;

R$_5$ is independently at each occurrence H, Si(OR$_6$)$_3$, or Si(R$_6$)$_3$;

R$_6$ is independently at each occurrence selected from H, substituted or unsubstituted alkyl, substituted or unsubstituted heteroalkyl, substituted or unsubstituted aryl, and substituted or unsubstituted heteroaryl;

Y is independently absent or selected from substituted or unsubstituted alkyl, substituted or unsubstituted heteroalkyl, substituted or unsubstituted aryl, substituted or unsubstituted heteroaryl, —NH—(C=O)—; =NO—C$_{1-6}$ alkyl-; and —(C=O)-phenyl-;

Z is independently selected from —N$_3$, —C≡CH, C≡C—R', —C≡N, —(C=O)—H, —SH, —CH=CH$_2$, halide, —SO$_3$R$_6$, —B(OR$_6$)$_2$, Sn(R$_6$)$_3$, and Zn(R$_6$)$_2$;

R' is selected from substituted or unsubstituted alkyl, substituted or unsubstituted heteroalkyl, substituted or unsubstituted aryl, substituted or unsubstituted heteroaryl, —CN, —CO$_2$R$_6$, —(C=O)—N(R$_6$)$_2$, and —(C=O)—R$_6$; and R" is selected from R$_3$ and R$_4$.

2. The compound according to claim 1, wherein:
A$_1$ and A$_2$ are each independently selected from:

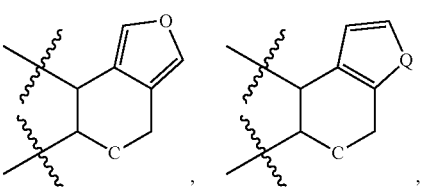

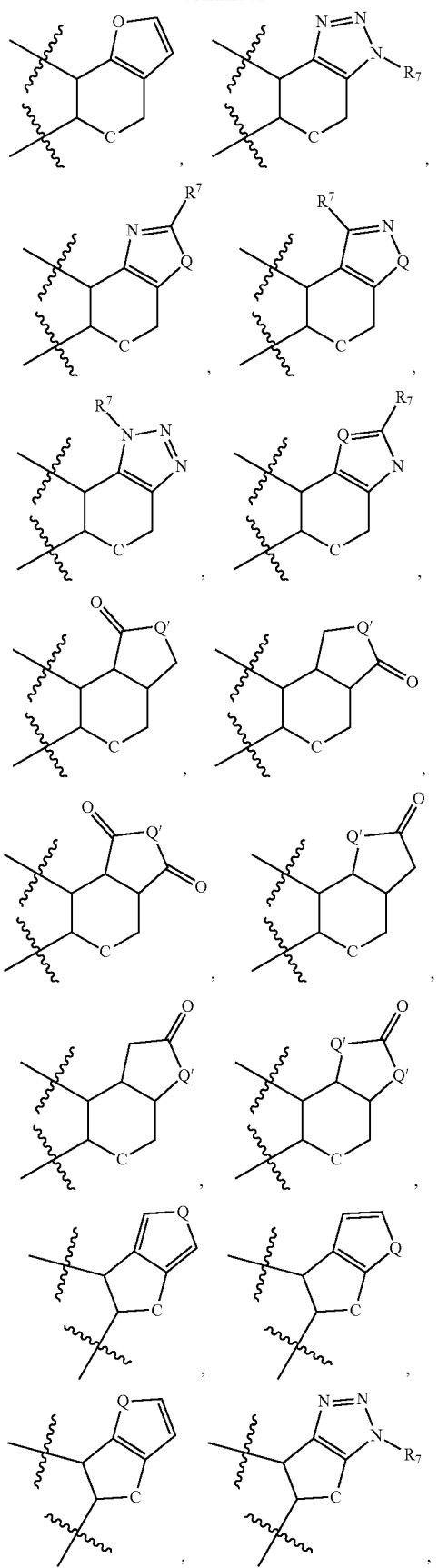
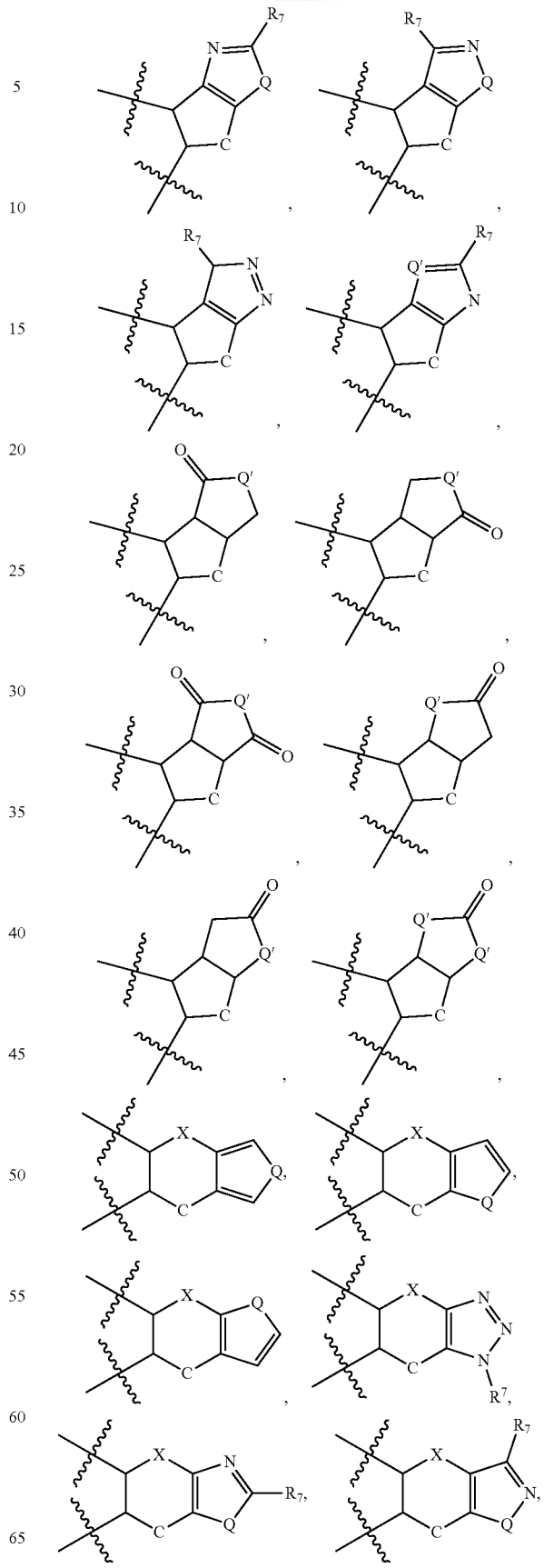

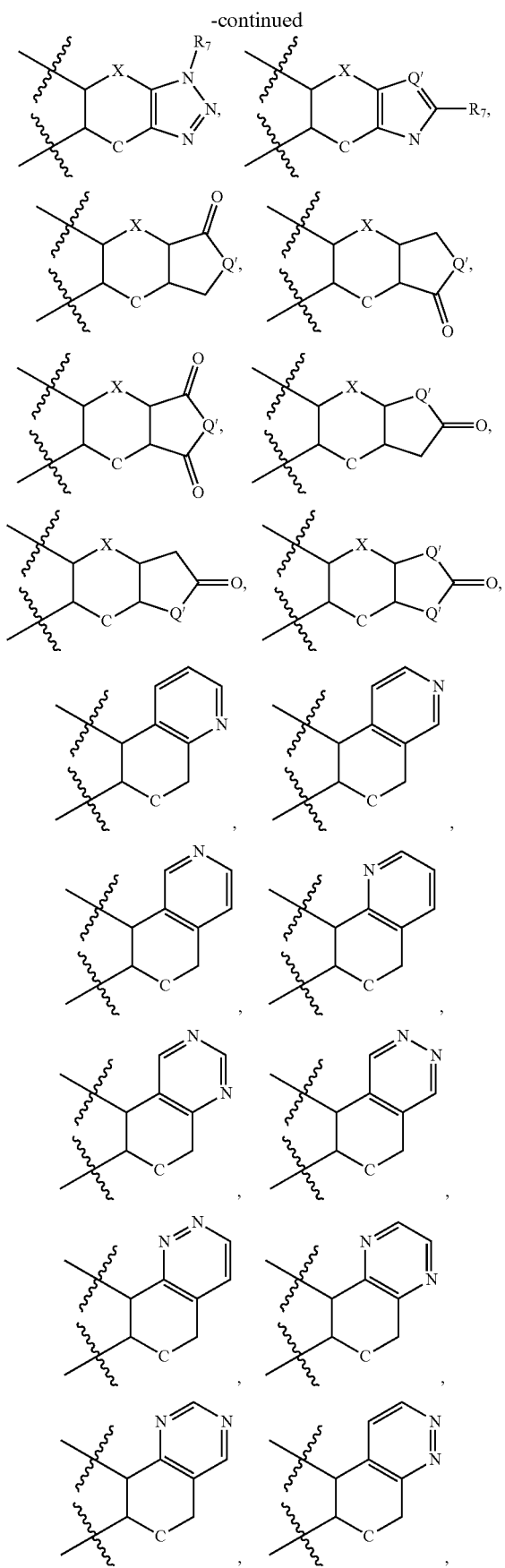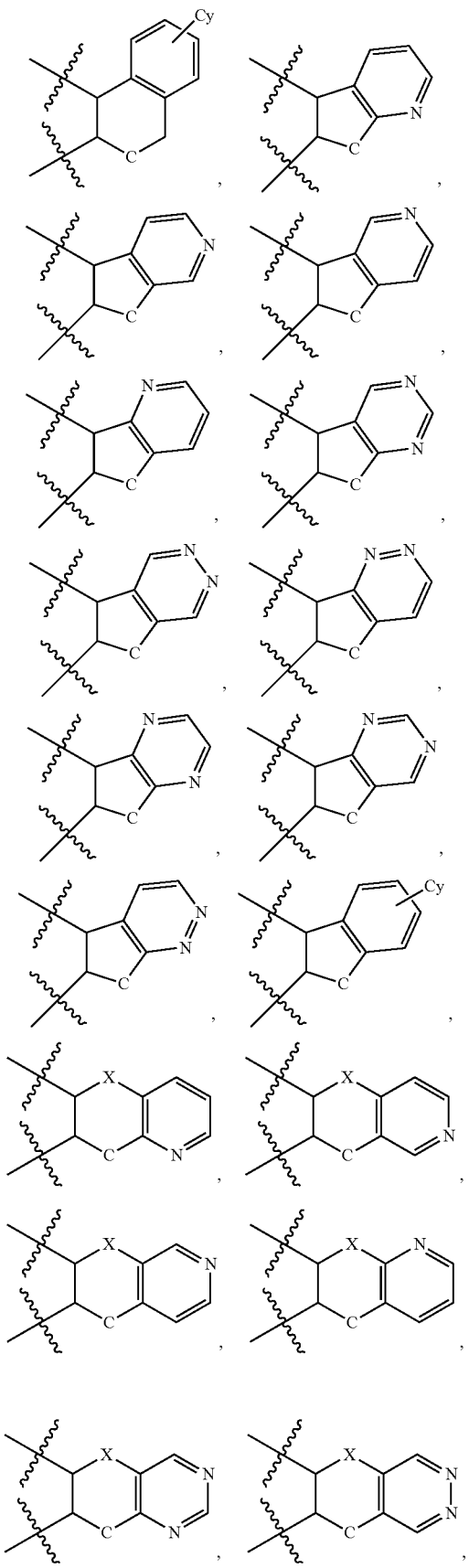

-continued

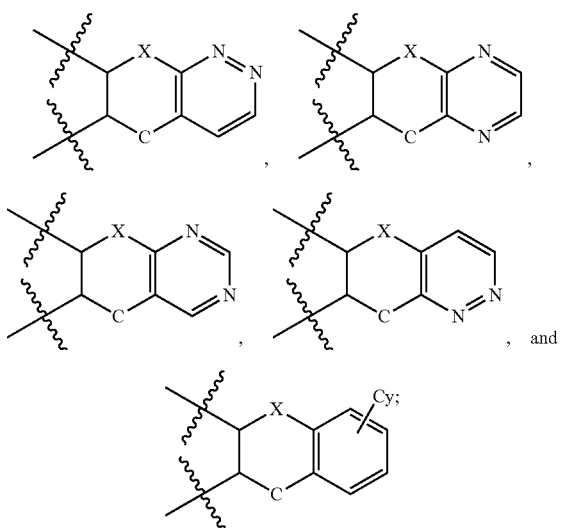

X is selected from —CR$_6$, —O—, —S—, NR$_6$, —C═O, —C═NR$_6$, —C═N—N(R$_6$)$_2$, and C═N—OR$_6$;

C$_y$ is selected from substituted or unsubstituted C$_5$-C$_6$ aryl, substituted or unsubstituted C$_5$-C$_6$ heteroaryl, substituted or unsubstituted C$_5$-C$_6$ cycloalkyl and substituted or unsubstituted C$_5$-C$_6$ cyclic heterocycloalkyl;

Q is selected from —O—, —S—, —N—R$_7$, —C═O, —C═NR$_7$, —C═N—N(R$_7$)$_2$, and —C═N—OR$_7$;

Q' is independently at each occurrence selected from —O—, —S—, and —N—R$_7$; and R$_7$ is independently at each occurrence selected from R$_3$ and R$_4$.

3. The compound according to claim 1, wherein:

A$_1$ and A$_2$ are each independently selected from:

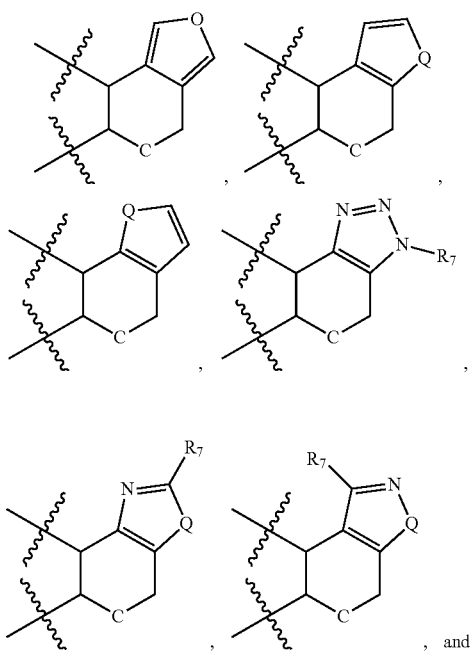

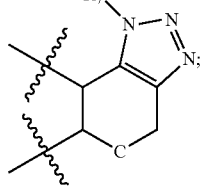

Z is independently selected from —N$_3$, —C≡CH, C═C—R', —C≡N, —(C═O)—H, —SH, and —CH═CH$_2$;

Q is selected from —O—, —S—, —N—R$_7$, —C═O, —C═NR$_7$, —C═N—N(R$_7$)$_2$, and —C═N—OR$_7$;

R' is selected from substituted or unsubstituted alkyl, substituted or unsubstituted heteroalkyl, substituted or unsubstituted aryl, substituted or unsubstituted heteroaryl, —CN, —CO$_2$R$_6$, —(C═O)—N(R$_6$)$_2$, and —(C═O)—R$_6$;

R$_6$ is independently at each occurrence selected from H, substituted or unsubstituted alkyl, substituted or unsubstituted heteroalkyl, substituted or unsubstituted aryl, and substituted or unsubstituted heteroaryl, and R$_7$ is independently at each occurrence selected from R$_3$ and R$_4$.

4. The compound according to claim 1, wherein:

A$_1$ and A$_2$ are each independently selected from:

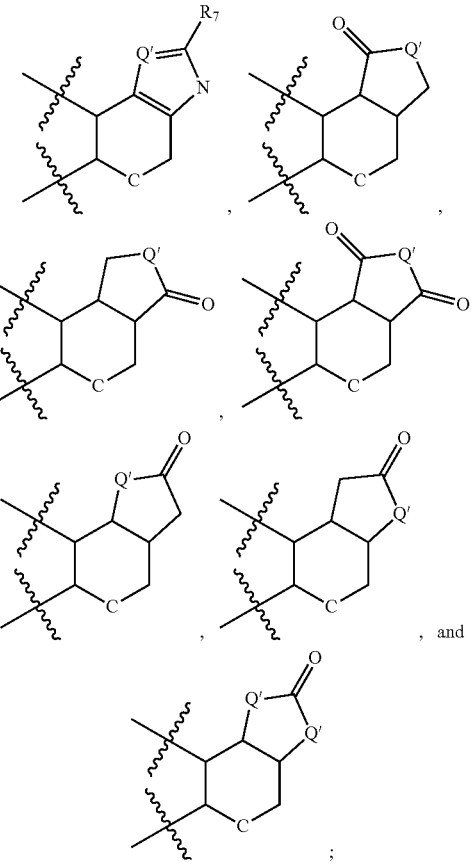

Z is independently selected from —N$_3$, —C≡CH, C═C—R', —C≡N, —(C═O)—H, —SH, and —CH═CH$_2$;

Q' is independently at each occurrence selected from —O—, —S—, and —N—R$_7$;

R' is selected from substituted or unsubstituted alkyl, substituted or unsubstituted heteroalkyl, substituted or unsubstituted aryl, substituted or unsubstituted heteroaryl, —CN, —CO$_2$R$_6$, —(C=O)—N(R$_6$)$_2$, and —(C=O)—R$_6$;

R$_6$ is independently at each occurrence selected from H, substituted or unsubstituted alkyl, substituted or unsubstituted heteroalkyl, substituted or unsubstituted aryl, and substituted or unsubstituted heteroaryl, and R$_7$ is independently at each occurrence selected from R$_3$ and R$_4$.

5. The compound according to claim 1, wherein:
A$_1$ and A$_2$ are each independently selected from:

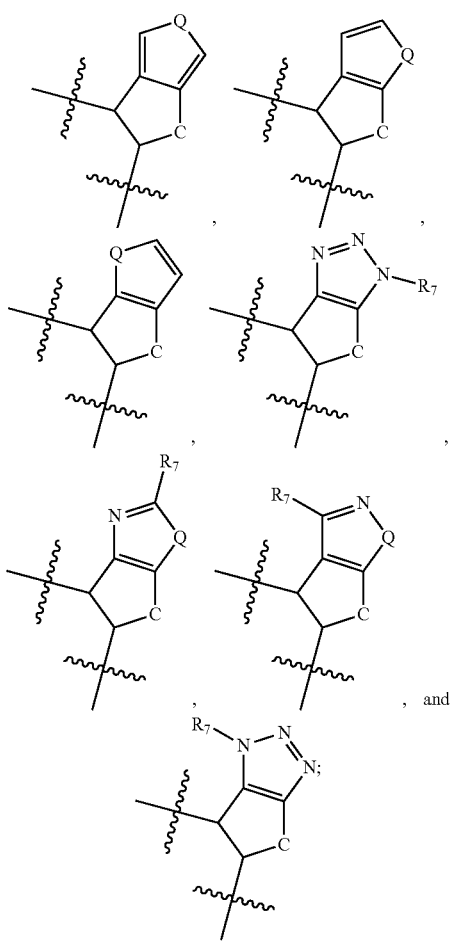

Z is independently selected from —N$_3$, —C≡CH, C≡C—R', —C≡N, —(C=O)—H, —SH, and —CH=CH$_2$;

Q is selected from —O—, —S—, —N—R$_7$, —C=O, —C=NR$_7$, —C=N—N(R$_7$)$_2$, and —C=N—OR$_7$;

R' is selected from substituted or unsubstituted alkyl, substituted or unsubstituted heteroalkyl, substituted or unsubstituted aryl, substituted or unsubstituted heteroaryl, —CN, —CO$_2$R$_6$, —(C=O)—N(R$_6$)$_2$, and —(C=O)—R$_6$;

R$_6$ is independently at each occurrence selected from H, substituted or unsubstituted alkyl, substituted or unsubstituted heteroalkyl, substituted or unsubstituted aryl, and substituted or unsubstituted heteroaryl, and R$_7$ is independently at each occurrence selected from R$_3$ and R$_4$.

6. The compound according to claim 1, wherein:
A$_1$ and A$_2$ are each independently selected from:

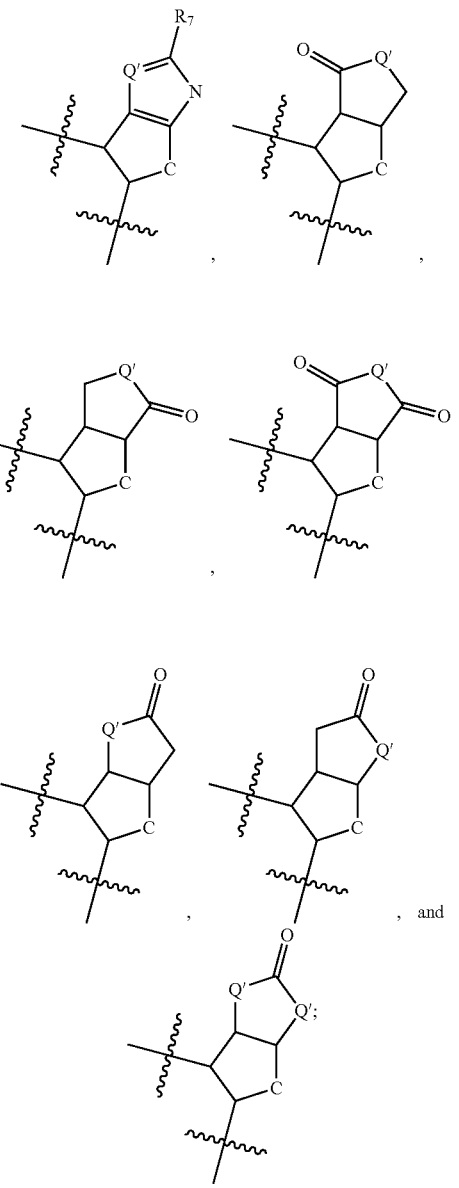

Z is independently selected from —N$_3$, —C≡CH, C≡C—R', —C≡N, —(C=O)—H, —SH, and —CH=CH$_2$;

Q' is independently at each occurrence selected from —O—, —S—, and —N—R$_7$;

R' is selected from substituted or unsubstituted alkyl, substituted or unsubstituted heteroalkyl, substituted or unsubstituted aryl, substituted or unsubstituted heteroaryl, —CN, —CO$_2$R$_6$, —(C=O)—N(R$_6$)$_2$, and —(C=O)—R$_6$;

R$_6$ is independently at each occurrence selected from H, substituted or unsubstituted alkyl, substituted or unsubstituted heteroalkyl, substituted or unsubstituted aryl, and substituted or unsubstituted heteroaryl, and R$_7$ is independently at each occurrence selected from R$_3$ and R$_4$.

7. The compound according to claim 1, wherein:
A₁ and A₂ are each independently selected from:

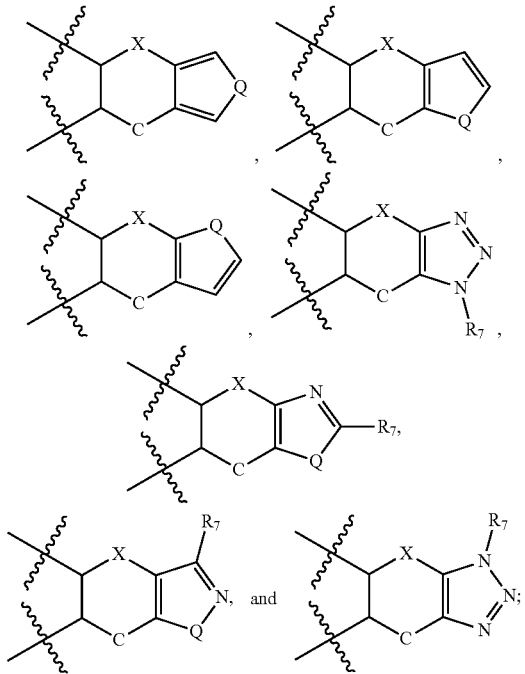

Z is independently selected from —N₃, —C≡CH, C≡C—R', —C≡N, —(C═O)—H, —SH, and —CH═CH₂;
Q is selected from —O—, —S—, —N—R₇, —C═O, —C═NR₇, —C═N—N(R₇)₂, and —C═N—OR₇;
X is selected from —CR₆, —O—, —S—, NR₆, —C═O, —C═NR₆, —C═N—N(R₆)₂, and C═N—OR₆;
R' is selected from substituted or unsubstituted alkyl, substituted or unsubstituted heteroalkyl, substituted or unsubstituted aryl, substituted or unsubstituted heteroaryl, —CN, —CO₂R₆, —(C═O)—N(R₆)₂, and —(C═O)—R₆;
R₆ is independently at each occurrence selected from H, substituted or unsubstituted alkyl, substituted or unsubstituted heteroalkyl, substituted or unsubstituted aryl, and substituted or unsubstituted heteroaryl, and
R₇ is independently at each occurrence selected from R₃ and R₄.

8. The compound according to claim 1, wherein:
A₁ and A₂ are each independently selected from:

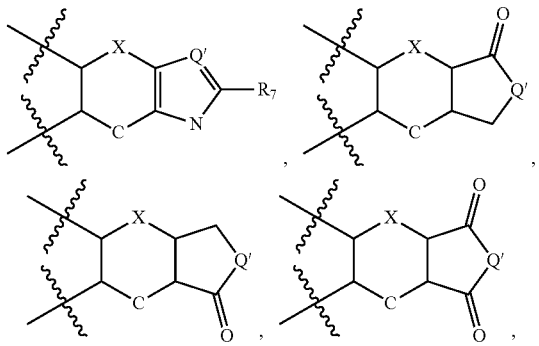

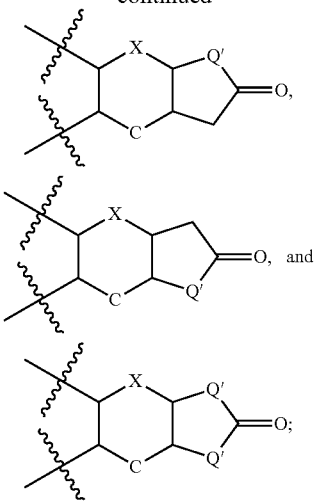

Z is independently selected from —N₃, —C≡CH, C≡C—R', —C≡N, —(C═O)—H, —SH, and —CH═CH₂;
X is selected from —CR₆, —O—, —S—, NR₆, —C═O, —C═NR₆, —C═N—N(R₆)₂, and C═N—OR₆;
Q' is independently at each occurrence selected from —O—, —S—, and —N—R₇;
R' is selected from substituted or unsubstituted alkyl, substituted or unsubstituted heteroalkyl, substituted or unsubstituted aryl, substituted or unsubstituted heteroaryl, —CN, —CO₂R₆, —(C═O)—N(R₆)₂, and —(C═O)—R₆;
R₆ is independently at each occurrence selected from H, substituted or unsubstituted alkyl, substituted or unsubstituted heteroalkyl, substituted or unsubstituted aryl, and substituted or unsubstituted heteroaryl, and
R₇ is independently at each occurrence selected from R₃ and R₄.

9. The compound according to claim 1, wherein:
A₁ and A₂ are each independently selected from:

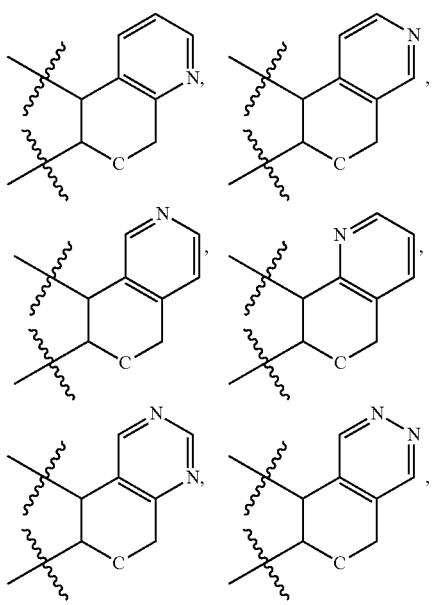

191

-continued

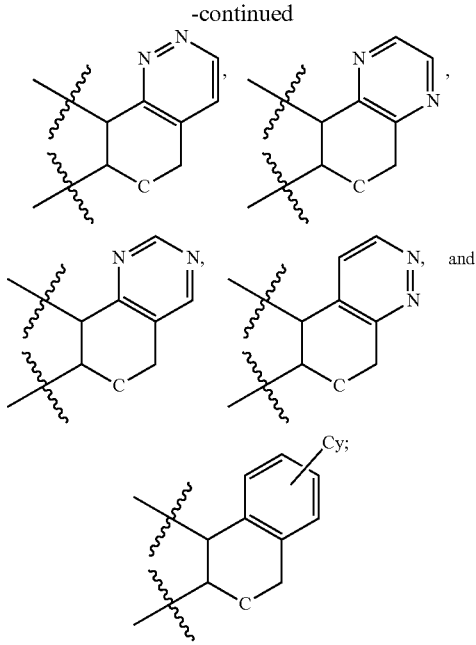

Z is independently selected from —N$_3$, —C≡CH, C≡C—R', —C≡N, —(C=O)—H, —SH, and —CH=CH$_2$;

R' is selected from substituted or unsubstituted alkyl, substituted or unsubstituted heteroalkyl, substituted or unsubstituted aryl, substituted or unsubstituted heteroaryl, —CN, —CO$_2$R$_6$, —(C=O)—N(R$_6$)$_2$, and —(C=O)—R$_6$;

R$_6$ is independently at each occurrence selected from H, substituted or unsubstituted alkyl, substituted or unsubstituted heteroalkyl, substituted or unsubstituted aryl, and substituted or unsubstituted heteroaryl, and C$_y$ is selected from substituted or unsubstituted C$_5$-C$_6$ aryl, substituted or unsubstituted C$_5$-C$_6$ heteroaryl, substituted or unsubstituted C$_5$-C$_6$ cycloalkyl and substituted or unsubstituted C$_5$-C$_6$ cyclic heterocycloalkyl.

10. The compound according to claim 1, wherein:
A$_1$ and A$_2$ are each independently selected from

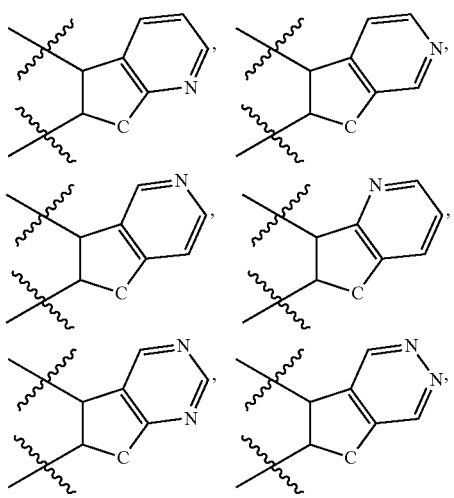

192

-continued

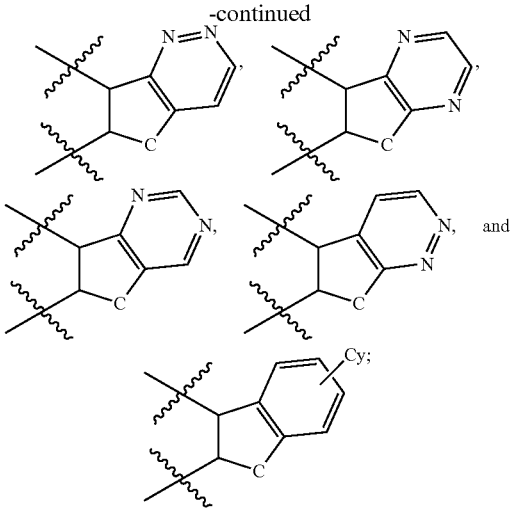

Z is independently selected from —N$_3$, —C≡CH, C≡C—R', —C≡N, —(C=O)—H, —SH, and —CH=CH$_2$;

R' is selected from substituted or unsubstituted alkyl, substituted or unsubstituted heteroalkyl, substituted or unsubstituted aryl, substituted or unsubstituted heteroaryl, —CN, —CO$_2$R$_6$, —(C=O)—N(R$_6$)$_2$, and —(C=O)—R$_6$;

R$_6$ is independently at each occurrence selected from H, substituted or unsubstituted alkyl, substituted or unsubstituted heteroalkyl, substituted or unsubstituted aryl, and substituted or unsubstituted heteroaryl, and C$_y$ is selected from substituted or unsubstituted C$_5$-C$_6$ aryl, substituted or unsubstituted C$_5$-C$_6$ heteroaryl, substituted or unsubstituted C$_5$-C$_6$ cycloalkyl and substituted or unsubstituted C$_5$-C$_6$ cyclic heterocycloalkyl.

11. The compound according to claim 1, wherein:
A$_1$ and A$_2$ are each independently selected from

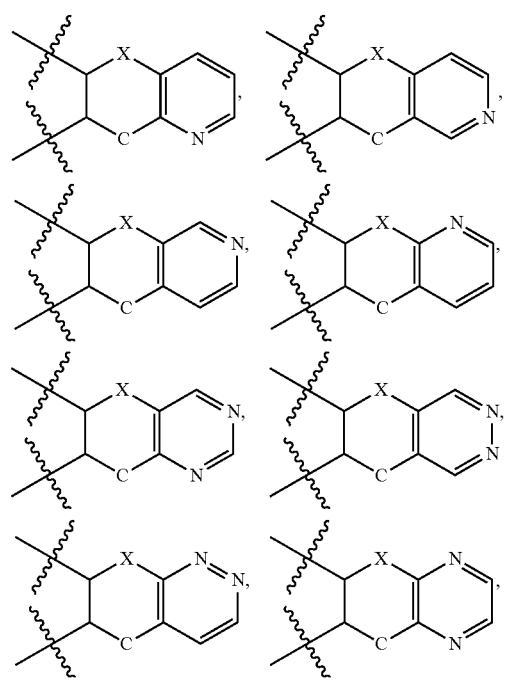

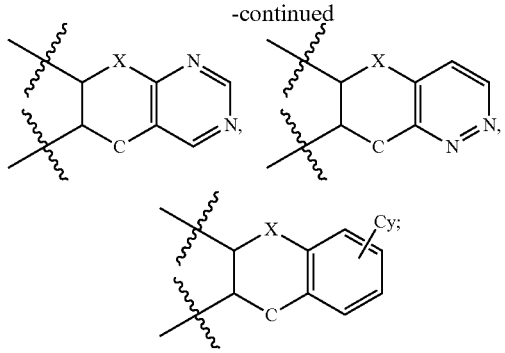

X is selected from —CR$_6$, —O—, —S—, NR$_6$, —C=O, —C=NR$_6$, —C=N—N(R$_6$)$_2$, and C=N—OR$_6$;

Z is independently selected from —N$_3$, —C=CH, C≡C—R', —C≡N, —(C=O)—H, —SH, and —CH=CH$_2$;

R' is selected from substituted or unsubstituted alkyl, substituted or unsubstituted heteroalkyl, substituted or unsubstituted aryl, substituted or unsubstituted heteroaryl, —CN, —CO$_2$R$_6$, —(C=O)—N(R$_6$)$_2$, and —(C=O)—R$_6$;

R$_6$ is independently at each occurrence selected from H, substituted or unsubstituted alkyl, substituted or unsubstituted heteroalkyl, substituted or unsubstituted aryl, and substituted or unsubstituted heteroaryl, and C$_y$ is selected from substituted or unsubstituted C$_5$-C$_6$ aryl, substituted or unsubstituted C$_5$-C$_6$ heteroaryl, substituted or unsubstituted C$_5$-C$_6$ cycloalkyl and substituted or unsubstituted C$_5$-C$_6$ cyclic heterocycloalkyl.

12. A compound according to claim 1, wherein Formula I is:

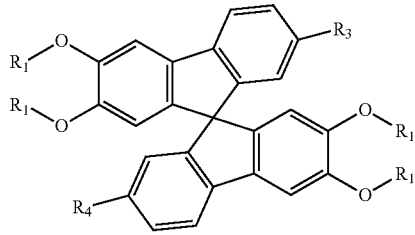

wherein:
   R$_1$ is independently at each occurrence H or alkyl;
   R$_3$ and R$_4$ are each independently selected from halide and —B(OR$_6$)$_2$.

13. The compound of claim 12, selected from the group consisting of:

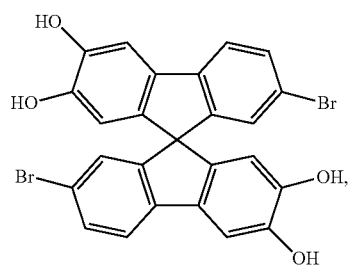

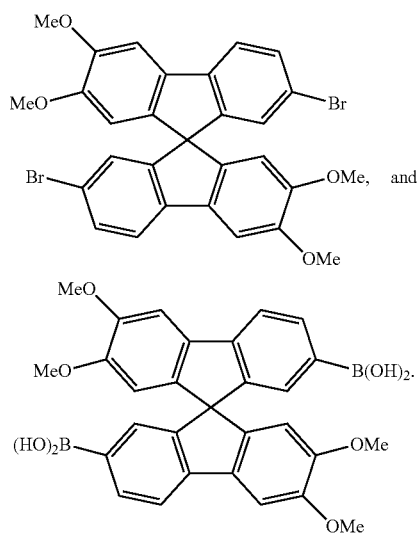

14. The compound according to claim 1 selected from the group consisting of:

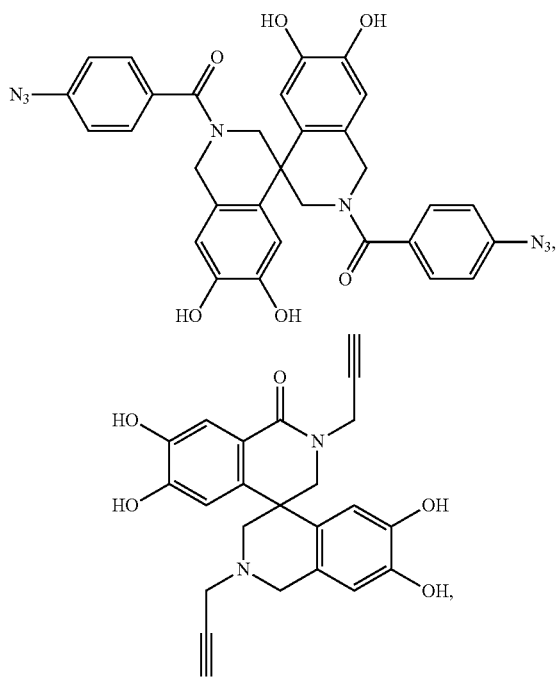

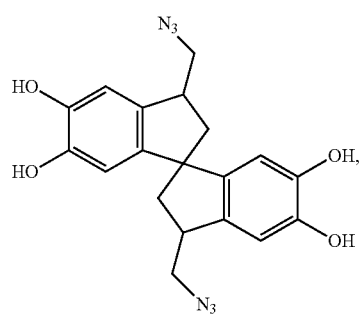

195
-continued
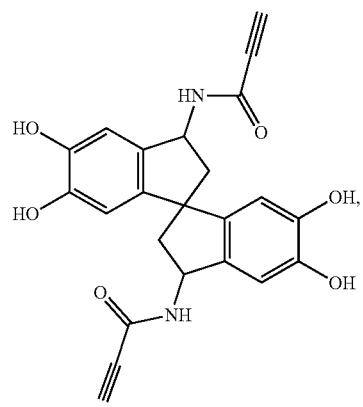
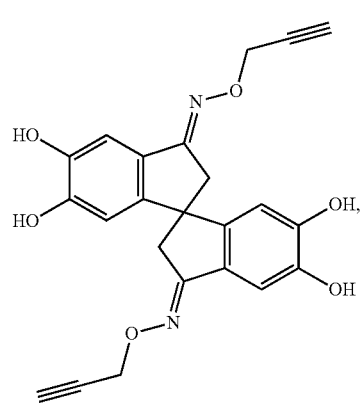
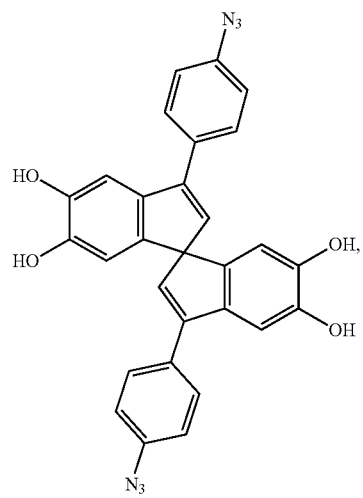
196
-continued
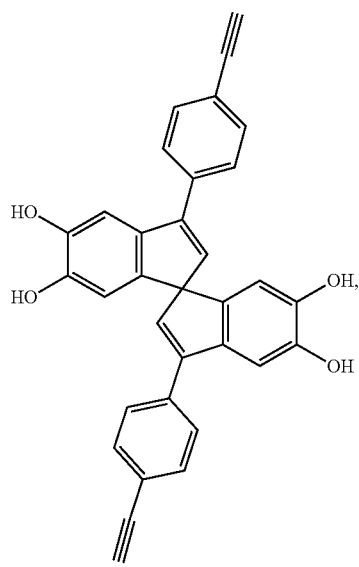
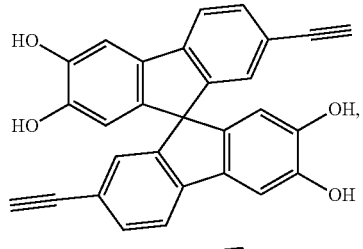
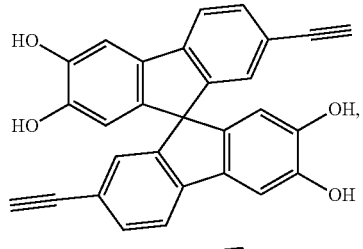
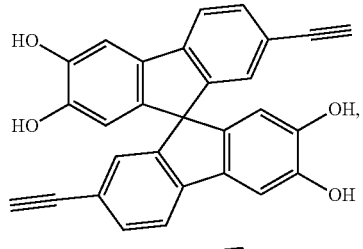
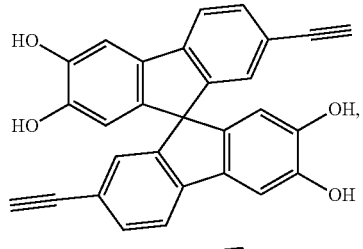
and -continued

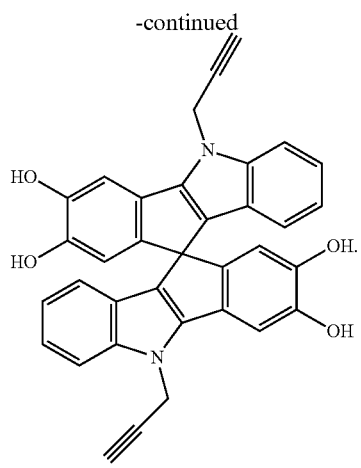

15. A compound according to Formula II:

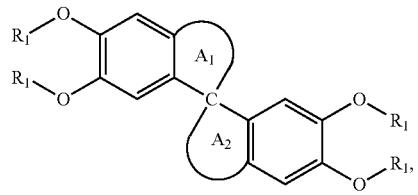

Formula II wherein: the carbon indicated by "C" denotes a spiro carbon;

$A_1$ is selected from

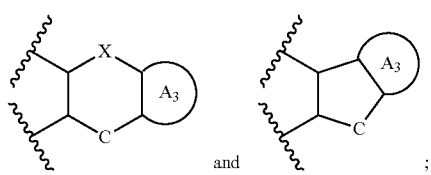

and $A_2$ is

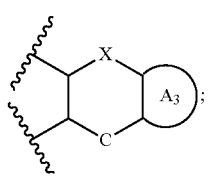

X is independently at each occurrence selected from O, or N—$R_2$;

$R_1$ is independently at each occurrence H or alkyl;

$R_2$ is selected from H, substituted or unsubstituted alkyl, and substituted or unsubstituted aryl, and $A_3$ is a selected from substituted or unsubstituted $C_5$-$C_6$ aryl, substituted or unsubstituted $C_5$-$C_6$ heteroaryl, substituted or unsubstituted $C_5$-$C_6$ cycloalkyl and substituted or unsubstituted $C_5$-$C_6$ cyclic heterocycloalkyl.

16. The compound according to claim 15, wherein:

$A_1$ and $A_2$ are each independently selected from:

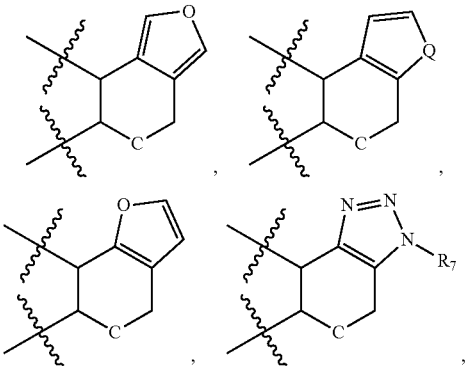

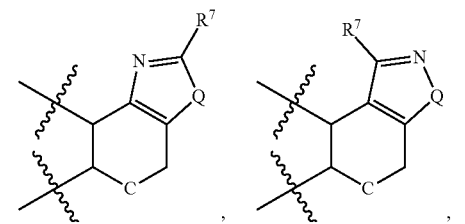

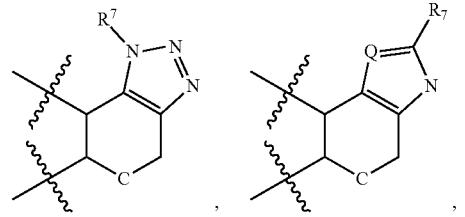

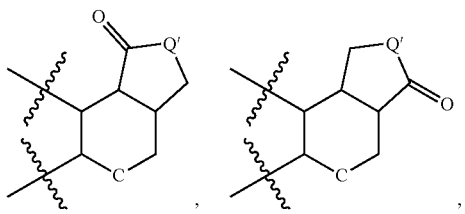

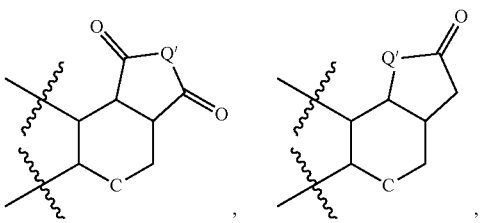

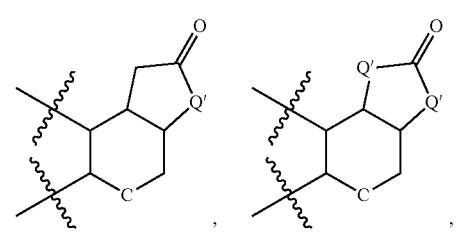

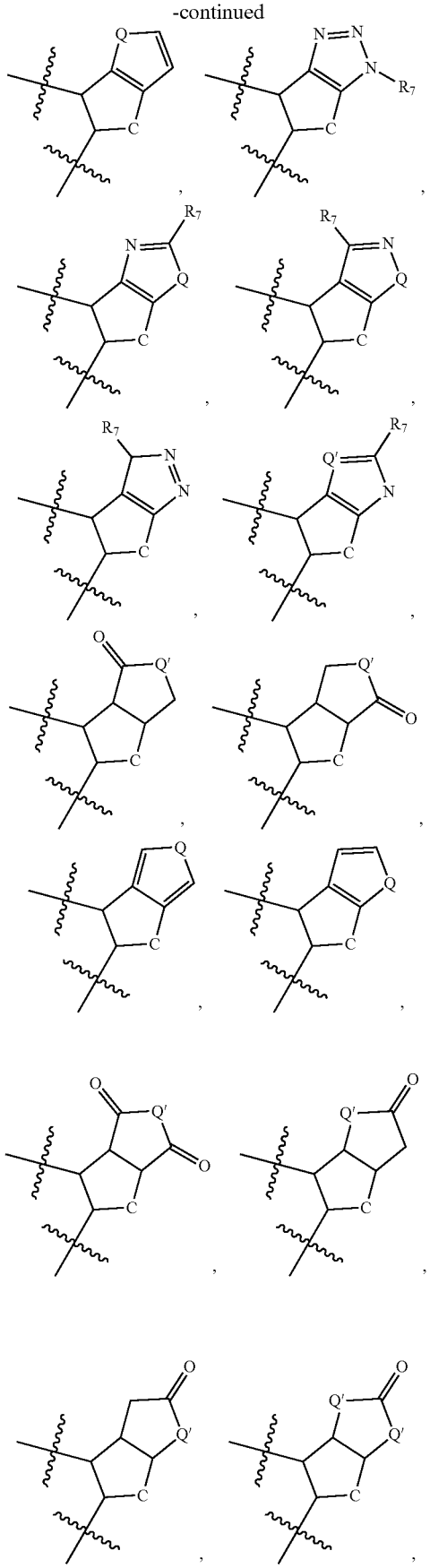
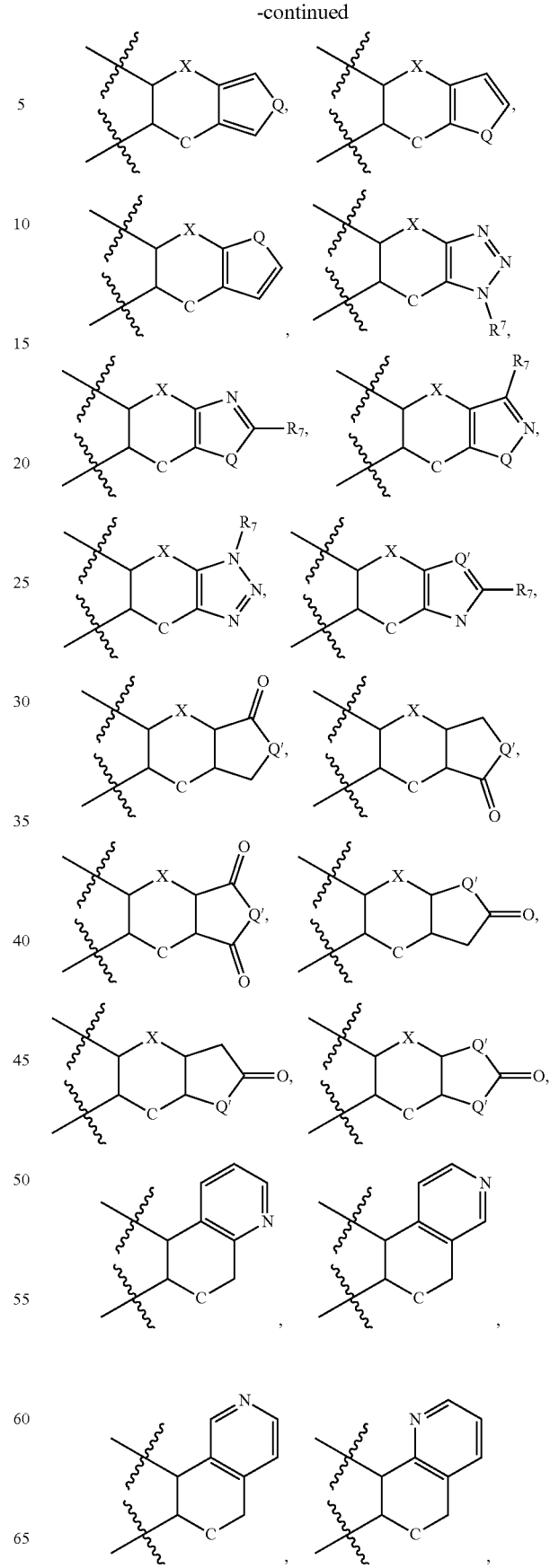

201

-continued

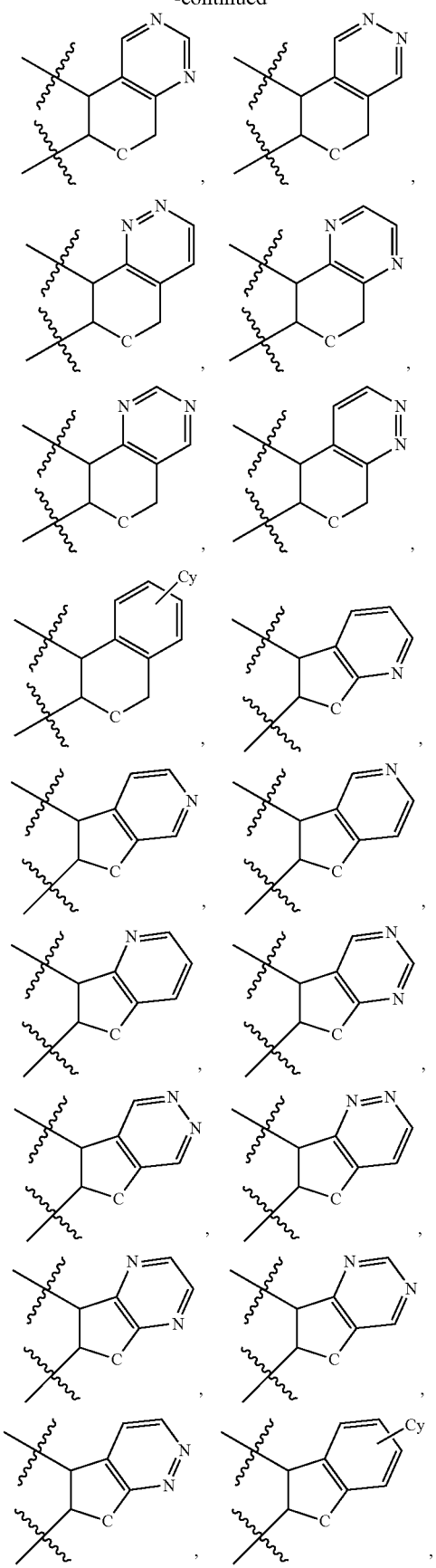

202

-continued

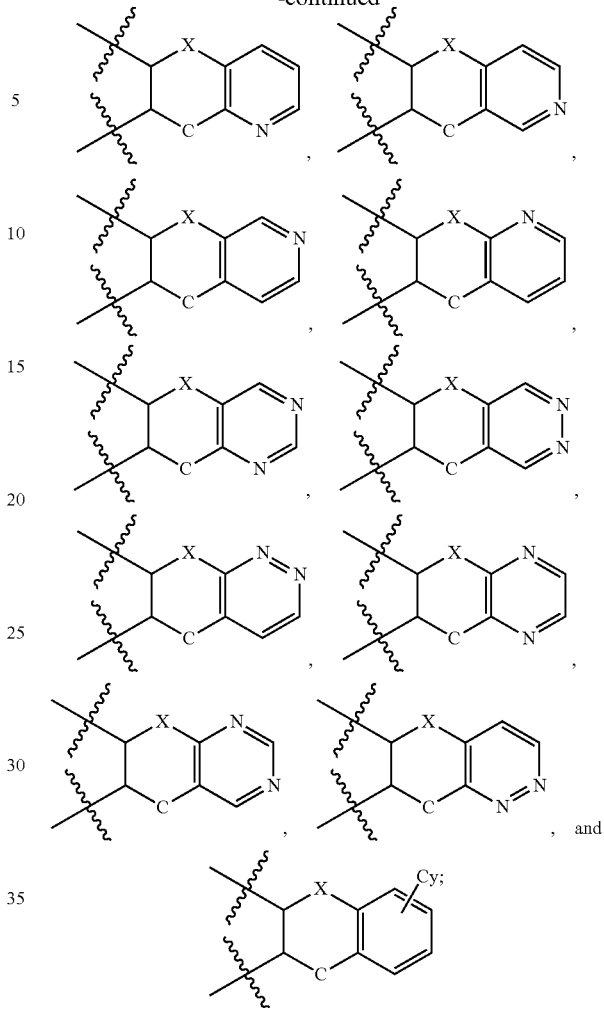

, and

X is selected from —CR$_6$, —O—, —S—, NR$_6$, —C=O, —C=NR$_6$, —C=N—N(R$_6$)$_2$, and C=N—OR$_6$;

C$_y$ is selected from substituted or unsubstituted C$_5$-C$_6$ aryl, substituted or unsubstituted C$_5$-C$_6$ heteroaryl, substituted or unsubstituted C$_5$-C$_6$ cycloalkyl and substituted or unsubstituted C$_5$-C$_6$ cyclic heterocycloalkyl;

Q is selected from —O—, —S—, —N—R$_7$, —C=O, —C=NR$_7$, —C=N—N(R$_7$)$_2$, and —C=N—OR$_7$;

Q' is independently at each occurrence selected from —O—, —S—, and —N—R$_7$;

R$_6$ is independently at each occurrence selected from H, substituted or unsubstituted alkyl, substituted or unsubstituted heteroalkyl, substituted or unsubstituted aryl, and substituted or unsubstituted heteroaryl, and R$_7$ is independently at each occurrence selected from H and Y—Z, wherein Y is independently absent or selected from substituted or unsubstituted alkyl, substituted or unsubstituted heteroalkyl, substituted or unsubstituted aryl, substituted or unsubstituted heteroaryl, —NH—(C=O)—; =NO—C$_{1-6}$ alkyl-; and —(C=O)-phenyl-; and Z is independently selected from —N$_3$, —C≡CH, C≡C—R', —C≡N, —(C=O)—H, —SH, —CH=CH$_2$, halide, —SO$_3$R$_6$, —B(OR$_6$)$_2$, Sn(R$_6$)$_3$, and Zn(R$_6$)$_2$.

17. The compound according to claim 15 selected from the group consisting of

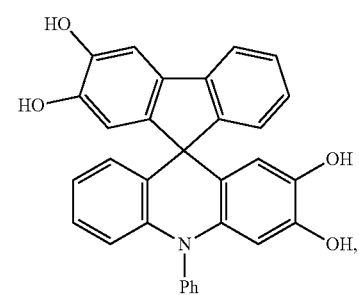
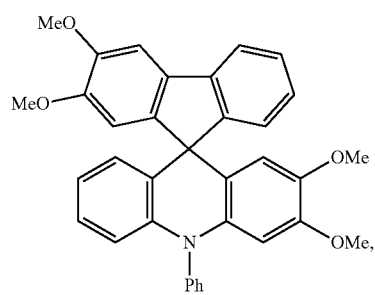
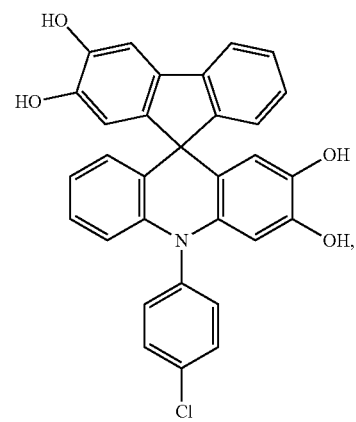
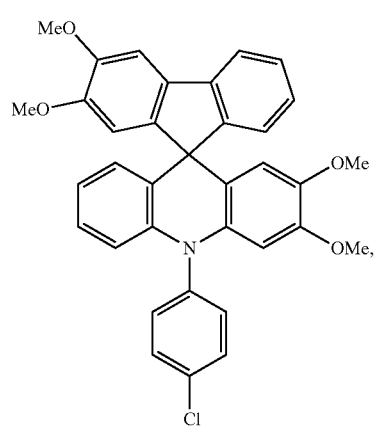
-continued
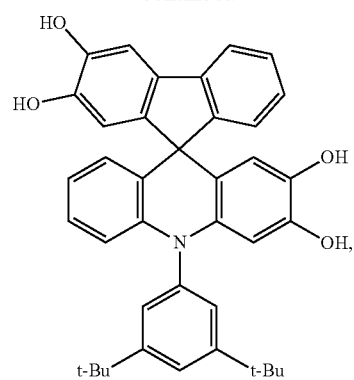
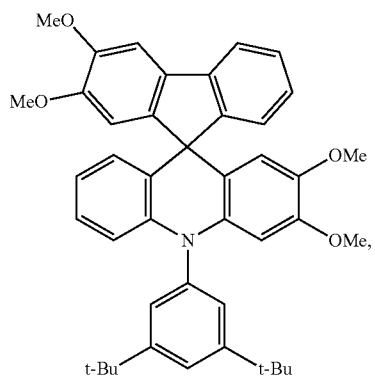
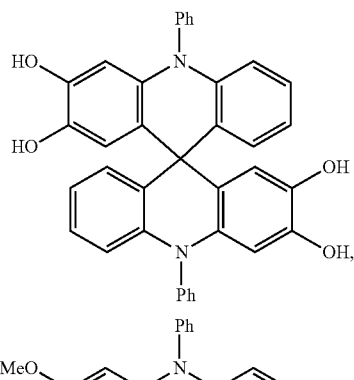
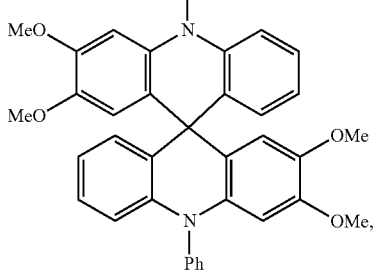
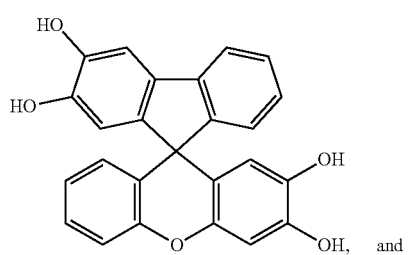, and 205
-continued
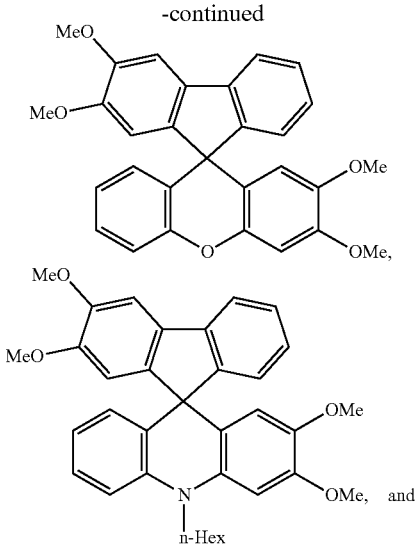
and
206
-continued
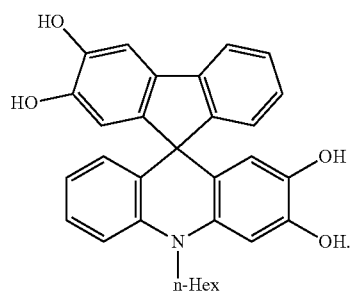
* * * * *